United States Patent
Dunaway et al.

(10) Patent No.: US 12,281,356 B2
(45) Date of Patent: *Apr. 22, 2025

(54) CHEMICAL COMPOSITIONS AND METHODS OF USING SAME

(71) Applicant: Bruker Spatial Biology, Inc., Seattle, WA (US)

(72) Inventors: Dwayne Dunaway, Seattle, WA (US); Elizabeth A. Manrao, Lake Forest Park, WA (US); Joseph M. Beechem, Piedmont, CA (US); Rustem Khafizov, Seattle, WA (US); Sanghamithra Korukonda, Seattle, WA (US); Yi Deng, Seattle, WA (US); Dae Kim, Bellevue, WA (US); Mark Gregory, Boise, ID (US); Margaret Hoang, Seattle, WA (US); Matthew Walsh, Seattle, WA (US); Gavin Meredith, Seattle, WA (US); Mark McElwain, Seattle, WA (US); Peter Skene, Issaquah, WA (US); Cassandra Burke, Seattle, WA (US)

(73) Assignee: Bruker Spatial Biology, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,565

(22) Filed: Dec. 21, 2022

(65) Prior Publication Data

US 2023/0220461 A1 Jul. 13, 2023

Related U.S. Application Data

(63) Continuation of application No. 16/411,394, filed on May 14, 2019, now Pat. No. 11,549,139.

(Continued)

(51) Int. Cl.
*C12Q 1/68* (2018.01)
*C12Q 1/6839* (2018.01)
(Continued)

(52) U.S. Cl.
CPC ......... *C12Q 1/6869* (2013.01); *C12Q 1/6839* (2013.01); *C12Q 1/6876* (2013.01)

(58) Field of Classification Search
CPC ... C12Q 1/6876; C12Q 1/6869; C12Q 1/6839
See application file for complete search history.

(56) References Cited

U.S. PATENT DOCUMENTS 5,320,814 A 6/1994 Walt et al.
5,432,272 A 7/1995 Benner
(Continued)

FOREIGN PATENT DOCUMENTS

CN 101432439 A 5/2009
CN 101932729 A 12/2010
(Continued)

OTHER PUBLICATIONS

Alfano, et al., Optical sensing, imaging, and manipulation for biological and biomedical applications, The International Society for Optical Engineering, Jul. 2000, 342 pages.

(Continued)

*Primary Examiner* — Jezia Riley
(74) *Attorney, Agent, or Firm* — Shay Glenn LLP

(57) ABSTRACT

The present disclosure relates to chemical compositions, kits, and apparatuses and methods for using these compositions, kits and apparatuses in various assays.

19 Claims, 72 Drawing Sheets
(68 of 72 Drawing Sheet(s) Filed in Color)
Specification includes a Sequence Listing.

Related U.S. Application Data

(60) Provisional application No. 62/836,327, filed on Apr. 19, 2019, provisional application No. 62/671,091, filed on May 14, 2018.

(51) Int. Cl.
*C12Q 1/6869* (2018.01)
*C12Q 1/6876* (2018.01)

(56) References Cited

U.S. PATENT DOCUMENTS

| | | |
|---|---|---|
| 5,543,838 A | 8/1996 | Hosier et al. |
| 5,635,352 A | 6/1997 | Urdea et al. |
| 5,665,540 A | 9/1997 | Lebo |
| 5,681,697 A | 10/1997 | Urdea et al. |
| 5,710,264 A | 1/1998 | Urdea et al. |
| 5,763,167 A | 6/1998 | Conrad |
| 5,776,688 A | 7/1998 | Bittner et al. |
| 5,780,227 A | 7/1998 | Sheridan et al. |
| 5,783,387 A | 7/1998 | Lucas et al. |
| 5,853,993 A | 12/1998 | Dellinger et al. |
| 5,871,928 A | 2/1999 | Fodor et al. |
| 5,888,778 A | 3/1999 | Shuber |
| 5,945,515 A | 8/1999 | Chomczynski |
| 5,981,180 A | 11/1999 | Chandler et al. |
| 5,985,549 A | 11/1999 | Singer et al. |
| 6,037,120 A | 3/2000 | Benner |
| 6,140,496 A | 10/2000 | Benner |
| 6,207,392 B1 | 3/2001 | Weiss et al. |
| 6,225,285 B1 | 5/2001 | Luo et al. |
| 6,238,869 B1 | 5/2001 | Kris et al. |
| 6,242,184 B1 | 6/2001 | Singer et al. |
| 6,277,569 B1 | 8/2001 | Bittner et al. |
| 6,306,643 B1 | 10/2001 | Gentalen et al. |
| 6,316,200 B1 | 11/2001 | Nadeau et al. |
| 6,365,362 B1 | 4/2002 | Terstappen et al. |
| 6,368,800 B1 | 4/2002 | Smith et al. |
| 6,379,888 B1 | 4/2002 | Nadeau et al. |
| 6,428,957 B1 | 8/2002 | Delenstarr |
| 6,429,027 B1 | 8/2002 | Chee et al. |
| 6,440,667 B1 | 8/2002 | Fodor et al. |
| 6,449,562 B1 | 9/2002 | Chandler et al. |
| 6,506,563 B1 | 1/2003 | Ward et al. |
| 6,511,824 B1 | 1/2003 | Buchman et al. |
| 6,534,266 B1 | 3/2003 | Singer |
| 6,548,259 B2 | 4/2003 | Ward et al. |
| 6,569,626 B2 | 5/2003 | Bittner et al. |
| 6,610,475 B1 | 8/2003 | Kacian et al. |
| 6,673,914 B1 | 1/2004 | Hoon |
| 6,727,356 B1 | 4/2004 | Reed et al. |
| 6,750,016 B2 | 6/2004 | Mirkin et al. |
| 6,803,200 B2 | 10/2004 | Xia et al. |
| 6,942,968 B1 | 9/2005 | Dickinson et al. |
| 7,033,754 B2 | 4/2006 | Chee et al. |
| 7,033,758 B2 | 4/2006 | Kenny et al. |
| 7,052,841 B2 | 5/2006 | Delenstarr |
| 7,064,197 B1 | 6/2006 | Rabbani et al. |
| 7,250,371 B2 | 7/2007 | Kang et al. |
| 7,255,999 B2 | 8/2007 | Singh et al. |
| 7,285,384 B2 | 10/2007 | Fan et al. |
| 7,385,043 B1 | 6/2008 | Kramer |
| 7,462,475 B2 | 12/2008 | Kermekchiev et al. |
| 7,473,767 B2 | 1/2009 | Dimitrov |
| 7,524,631 B2 | 4/2009 | Patterson |
| 7,582,415 B2 | 9/2009 | Straus |
| 7,608,396 B2 | 10/2009 | Delenstarr |
| 7,615,351 B2 | 11/2009 | McMaster et al. |
| 7,709,198 B2 | 5/2010 | Luo et al. |
| 7,741,046 B2 | 6/2010 | Larsen et al. |
| 7,745,129 B1 | 6/2010 | Schatz |
| 7,763,421 B2 | 7/2010 | Farrell |
| 7,771,949 B2 | 8/2010 | Kramer |
| 7,803,541 B2 | 9/2010 | Luo et al. |
| 7,807,352 B2 | 10/2010 | Rabbani et al. |
| 7,829,278 B2 | 11/2010 | Selvin et al. |
| 7,863,012 B2 | 1/2011 | Rao et al. |
| 7,906,072 B2 | 3/2011 | Unger et al. |
| 7,919,237 B2 | 4/2011 | Dimitrov et al. |
| 7,927,798 B2 | 4/2011 | Zheng et al. |
| 7,941,279 B2 | 5/2011 | Hwang et al. |
| 7,951,539 B2 | 5/2011 | McMaster et al. |
| 7,955,794 B2 | 6/2011 | Shen et al. |
| 7,968,327 B2 | 6/2011 | McMaster et al. |
| 8,017,360 B2 | 9/2011 | Luo et al. |
| 8,048,378 B2 | 11/2011 | Unger et al. |
| 8,049,893 B2 | 11/2011 | Moon et al. |
| 8,055,034 B2 | 11/2011 | Dube et al. |
| 8,063,196 B2 | 11/2011 | Zheng et al. |
| 8,114,681 B2 | 2/2012 | Martin et al. |
| 8,148,075 B2 | 4/2012 | Farrell |
| 8,148,512 B2 | 4/2012 | Dimitrov |
| 8,173,785 B2 | 5/2012 | Stender et al. |
| 8,288,522 B2 | 10/2012 | Luo et al. |
| 8,309,306 B2 | 11/2012 | Nolan et al. |
| 8,394,944 B2 | 3/2013 | Zheng et al. |
| 8,404,444 B2 | 3/2013 | Zhang et al. |
| 8,405,970 B2 | 3/2013 | Sun |
| 8,415,102 B2 | 4/2013 | Geiss et al. |
| 8,492,094 B2 | 7/2013 | Dimitrov et al. |
| 8,501,459 B2 | 8/2013 | Chen et al. |
| 8,501,490 B2 | 8/2013 | Chen et al. |
| 8,519,115 B2 | 8/2013 | Webster et al. |
| 8,604,182 B2 | 12/2013 | Luo et al. |
| 8,628,918 B2 | 1/2014 | Luo et al. |
| 8,658,361 B2 | 2/2014 | Wu et al. |
| 8,685,646 B2 | 4/2014 | Battersby et al. |
| 8,715,926 B2 | 5/2014 | Duerksen-Hughes et al. |
| 8,741,566 B2 | 6/2014 | Winther et al. |
| 8,790,878 B2 | 7/2014 | Hayes |
| 8,865,404 B2 | 10/2014 | Wu et al. |
| 8,951,726 B2 | 2/2015 | Luo et al. |
| 9,046,477 B2 | 6/2015 | Empedocles et al. |
| 9,096,902 B2 | 8/2015 | Weier |
| 9,150,910 B2 | 10/2015 | Hu et al. |
| 9,228,948 B2 | 1/2016 | Empedocles et al. |
| 9,297,762 B2 | 3/2016 | Empedocles et al. |
| 9,304,084 B2 | 4/2016 | Empedocles et al. |
| 9,315,854 B2 | 4/2016 | Wu et al. |
| 10,138,509 B2 | 11/2018 | Church et al. |
| 10,227,639 B2 | 3/2019 | Levner et al. |
| 10,415,080 B2 | 9/2019 | Dunaway et al. |
| 10,457,980 B2 | 10/2019 | Cai et al. |
| 10,549,139 B2 | 2/2020 | Zanyk |
| 10,597,719 B2 | 3/2020 | Kuwahara |
| 10,844,426 B2 | 11/2020 | Daugharthy et al. |
| 11,021,737 B2 | 6/2021 | Church et al. |
| 11,098,303 B2 | 8/2021 | Zhuang et al. |
| 11,111,521 B2 | 9/2021 | Church et al. |
| 11,118,220 B2 | 9/2021 | Daugharthy et al. |
| 11,193,163 B2 | 12/2021 | Daugharthy et al. |
| 11,279,969 B2 | 3/2022 | Dunaway et al. |
| 11,293,054 B2 | 4/2022 | Levner et al. |
| 11,542,554 B2 | 1/2023 | Daugharthy et al. |
| 11,549,139 B2 | 1/2023 | Dunaway et al. |
| 11,821,026 B2 | 11/2023 | Dunaway |
| 12,049,666 B2 | 7/2024 | Dunaway |
| 2001/0002315 A1 | 5/2001 | Schultz et al. |
| 2001/0007775 A1 | 7/2001 | Seul et al. |
| 2001/0023078 A1 | 9/2001 | Bawendi et al. |
| 2001/0029049 A1 | 10/2001 | Walt et al. |
| 2001/0034034 A1 | 10/2001 | Bruchez et al. |
| 2001/0053334 A1 | 12/2001 | Chen et al. |
| 2002/0028457 A1 | 3/2002 | Empedocles et al. |
| 2002/0034737 A1 | 3/2002 | Drmanac |
| 2002/0034827 A1 | 3/2002 | Singh et al. |
| 2002/0039728 A1 | 4/2002 | Kain et al. |
| 2002/0051971 A1 | 5/2002 | Stuelpnagel et al. |
| 2002/0068018 A1 | 6/2002 | Pepper et al. |
| 2002/0102574 A1 | 8/2002 | Nadeau et al. |
| 2002/0177141 A1 | 11/2002 | Chee et al. |
| 2002/0187515 A1 | 12/2002 | Chee et al. |
| 2003/0008323 A1 | 1/2003 | Ravkin et al. |
| 2003/0028981 A1 | 2/2003 | Chandler et al. |
| 2003/0148335 A1 | 8/2003 | Shen et al. |

(56) References Cited

U.S. PATENT DOCUMENTS

| | | |
|---|---|---|
| 2003/0186426 A1 | 10/2003 | Brewer et al. |
| 2004/0248144 A1 | 12/2004 | Mir |
| 2005/0037397 A1 | 2/2005 | Mirkin et al. |
| 2005/0048498 A1 | 3/2005 | Woudenberg et al. |
| 2005/0064435 A1 | 3/2005 | Su et al. |
| 2005/0131006 A1 | 6/2005 | Mukherjee et al. |
| 2005/0147981 A1 | 7/2005 | Yamakawa et al. |
| 2005/0170439 A1 | 8/2005 | Chan-Hui et al. |
| 2005/0233318 A1 | 10/2005 | Chee et al. |
| 2005/0239084 A1 | 10/2005 | Nadeau et al. |
| 2006/0014191 A1 | 1/2006 | Lao et al. |
| 2006/0063196 A1 | 3/2006 | Akeson et al. |
| 2006/0088872 A1 | 4/2006 | Ahmadian et al. |
| 2006/0134917 A1 | 6/2006 | Huang et al. |
| 2006/0210982 A1 | 9/2006 | Yanagawa et al. |
| 2007/0048759 A1 | 3/2007 | Luo et al. |
| 2007/0117109 A1 | 5/2007 | Rothemund |
| 2007/0148690 A1 | 6/2007 | Shao et al. |
| 2007/0154889 A1 | 7/2007 | Wang |
| 2008/0085509 A1 | 4/2008 | Knoll et al. |
| 2008/0108073 A1 | 5/2008 | Nautiyal et al. |
| 2009/0220978 A1 | 9/2009 | Dimitrov |
| 2009/0246879 A1 | 10/2009 | Drmanac et al. |
| 2009/0299640 A1 | 12/2009 | Ellis et al. |
| 2009/0318298 A1 | 12/2009 | Kim et al. |
| 2010/0015607 A1 | 1/2010 | Geiss et al. |
| 2010/0047924 A1 | 2/2010 | Webster et al. |
| 2010/0151472 A1 | 6/2010 | Nolan et al. |
| 2010/0261026 A1 | 10/2010 | Ferree et al. |
| 2010/0268478 A1 | 10/2010 | Andregg et al. |
| 2011/0021369 A1 | 1/2011 | Mhlanga et al. |
| 2011/0086774 A1 | 4/2011 | Dunaway |
| 2011/0145176 A1 | 6/2011 | Perou et al. |
| 2011/0195864 A1 | 8/2011 | Ma |
| 2011/0201515 A1 | 8/2011 | Webster et al. |
| 2011/0229888 A1 | 9/2011 | Hengen et al. |
| 2012/0003648 A1 | 1/2012 | Ma et al. |
| 2012/0004132 A1 | 1/2012 | Zhang et al. |
| 2012/0052498 A1 | 3/2012 | Nguyen et al. |
| 2012/0071343 A1 | 3/2012 | Ma et al. |
| 2012/0100540 A1 | 4/2012 | Wu et al. |
| 2012/0122712 A1 | 5/2012 | Goldstein |
| 2012/0172246 A1 | 7/2012 | Nguyen et al. |
| 2012/0178081 A1 | 7/2012 | Nguyen et al. |
| 2012/0214152 A1 | 8/2012 | Ma et al. |
| 2012/0295801 A1 | 11/2012 | Wu et al. |
| 2012/0301886 A1 | 11/2012 | Farrell et al. |
| 2012/0316082 A1 | 12/2012 | Pregibon et al. |
| 2013/0004482 A1 | 1/2013 | Perou et al. |
| 2013/0017971 A1 | 1/2013 | Geiss et al. |
| 2013/0023433 A1 | 1/2013 | Luo et al. |
| 2013/0065780 A1 | 3/2013 | He et al. |
| 2013/0171621 A1 | 7/2013 | Luo et al. |
| 2013/0178372 A1 | 7/2013 | Geiss et al. |
| 2013/0203055 A1 | 8/2013 | Aurich-Costa |
| 2013/0230851 A1 | 9/2013 | Geiss et al. |
| 2013/0237437 A1 | 9/2013 | Russell et al. |
| 2013/0274117 A1 | 10/2013 | Church et al. |
| 2013/0337444 A1 | 12/2013 | Ferree et al. |
| 2013/0345161 A1 | 12/2013 | Perou et al. |
| 2014/0005067 A1 | 1/2014 | Webster et al. |
| 2014/0017688 A1 | 1/2014 | Webster et al. |
| 2014/0030698 A1 | 1/2014 | Wang |
| 2014/0037620 A1 | 2/2014 | Ferree et al. |
| 2014/0087959 A1 | 3/2014 | Ellis et al. |
| 2014/0120083 A1 | 5/2014 | Stern et al. |
| 2014/0154681 A1 | 6/2014 | Wallden |
| 2014/0162251 A1 | 6/2014 | Dimitrov et al. |
| 2014/0178869 A1 | 6/2014 | Ma et al. |
| 2014/0227706 A1 | 8/2014 | Kato et al. |
| 2014/0249040 A1 | 9/2014 | Wu et al. |
| 2014/0302042 A1 | 10/2014 | Chin et al. |
| 2014/0349294 A1 | 11/2014 | Church et al. |
| 2014/0357509 A1 | 12/2014 | Ma et al. |
| 2014/0357660 A1 | 12/2014 | Mock et al. |
| 2014/0371088 A1 | 12/2014 | Webster |
| 2014/0377258 A1 | 12/2014 | Stern et al. |
| 2015/0011435 A1 | 1/2015 | Wu et al. |
| 2015/0018231 A1 | 1/2015 | Vallabhaneni |
| 2015/0038556 A1 | 2/2015 | Heartlein et al. |
| 2015/0051117 A1 | 2/2015 | Church et al. |
| 2015/0086981 A1 | 3/2015 | Cherkasov et al. |
| 2015/0105298 A1 | 4/2015 | Czaplinski |
| 2015/0110857 A1 | 4/2015 | DeRosa et al. |
| 2015/0140070 A1 | 5/2015 | Heartlein et al. |
| 2015/0232935 A1 | 8/2015 | Deshpande et al. |
| 2015/0247204 A1 | 9/2015 | Deshpande et al. |
| 2015/0247205 A1 | 9/2015 | Gandhi et al. |
| 2015/0267251 A1 | 9/2015 | Cai et al. |
| 2015/0283142 A1 | 10/2015 | Stern et al. |
| 2015/0292007 A1 | 10/2015 | Church et al. |
| 2016/0054308 A1 | 2/2016 | Guo |
| 2016/0194701 A1 | 7/2016 | Beechem et al. |
| 2017/0212986 A1 | 7/2017 | Zhuang et al. |
| 2017/0220733 A1 | 8/2017 | Zhuang et al. |
| 2017/0327876 A1 | 11/2017 | Khafizov et al. |
| 2018/0142286 A1 | 5/2018 | Dunaway et al. |
| 2019/0055594 A1 | 2/2019 | Samusik et al. |
| 2019/0119742 A1 | 4/2019 | Zhang et al. |
| 2019/0161796 A1 | 5/2019 | Hauling et al. |
| 2019/0271028 A1 | 9/2019 | Khafizov et al. |
| 2019/0345548 A1 | 11/2019 | Dunaway et al. |
| 2019/0360025 A1 | 11/2019 | Persson et al. |
| 2019/0390258 A1 | 12/2019 | Dunaway et al. |
| 2020/0010891 A1 | 1/2020 | Beechem et al. |
| 2020/0071751 A1 | 3/2020 | Daugharthy et al. |
| 2021/0164039 A1 | 6/2021 | Wang et al. |
| 2021/0403992 A1 | 12/2021 | Pinard et al. |
| 2022/0040346 A1 | 2/2022 | Phillips et al. |
| 2022/0213532 A1 | 7/2022 | Dunaway et al. |
| 2022/0243260 A1 | 8/2022 | Rothmann et al. |
| 2022/0282313 A1 | 9/2022 | Khafizov et al. |
| 2022/0298559 A1 | 9/2022 | Daugharthy et al. |
| 2022/0333186 A1 | 10/2022 | Brown |
| 2022/0356519 A1 | 11/2022 | Shen et al. |
| 2022/0364160 A1 | 11/2022 | Nolan et al. |
| 2022/0403462 A1 | 12/2022 | Meyer et al. |
| 2022/0411862 A1 | 12/2022 | Spiecker et al. |
| 2023/0039899 A1 | 2/2023 | Larman et al. |
| 2023/0160004 A1 | 5/2023 | Beechem et al. |
| 2023/0183800 A1 | 6/2023 | Beechem et al. |
| 2023/0257800 A1 | 8/2023 | Dunaway et al. |
| 2024/0084361 A1 | 3/2024 | Dunaway |

FOREIGN PATENT DOCUMENTS

| | | |
|---|---|---|
| CN | 102439177 A | 5/2012 |
| CN | 102858995 A | 1/2013 |
| CN | 103635594 A | 3/2014 |
| CN | 107208144 A | 9/2017 |
| EP | 1672082 A2 | 6/2006 |
| EP | 2722388 A1 | 4/2014 |
| EP | 2766498 A2 | 8/2014 |
| EP | 2794928 A1 | 10/2014 |
| EP | 2971184 A1 | 1/2016 |
| EP | 3458601 A1 | 3/2019 |
| EP | 3472359 A1 | 4/2019 |
| EP | 4001432 A1 | 5/2022 |
| EP | 4039822 A1 | 8/2022 |
| JP | 2002537858 A | 11/2002 |
| JP | 2003517283 A | 5/2003 |
| JP | 2003523935 A | 8/2003 |
| JP | 2004298082 A | 10/2004 |
| JP | 2006129866 A | 5/2006 |
| JP | 2008512129 A | 4/2008 |
| JP | 2009519717 A | 5/2009 |
| JP | 2010539982 A | 12/2010 |
| JP | 2011525111 A | 9/2011 |
| JP | 2012500007 A | 1/2012 |
| JP | 2014531908 A | 12/2014 |
| JP | 2017535269 A | 11/2017 |

(56) References Cited

FOREIGN PATENT DOCUMENTS

| | | |
|---|---|---|
| JP | 2019522463 A | 8/2019 |
| JP | 2020500514 A | 1/2020 |
| KR | 20050044668 A | 5/2005 |
| KR | 20060129469 A | 12/2006 |
| WO | WO-9707245 A1 | 2/1997 |
| WO | WO-9714028 A2 | 4/1997 |
| WO | WO-9918434 A1 | 4/1999 |
| WO | WO-0053805 A1 | 9/2000 |
| WO | WO-0057701 A1 | 10/2000 |
| WO | WO-0061807 A1 | 10/2000 |
| WO | WO-0073777 A1 | 12/2000 |
| WO | WO-0100875 A2 | 1/2001 |
| WO | WO-03003810 A2 | 1/2003 |
| WO | WO-03019141 A2 | 3/2003 |
| WO | WO-03048387 A2 | 6/2003 |
| WO | WO-03054214 A2 | 7/2003 |
| WO | WO-2004067742 A1 | 8/2004 |
| WO | WO-2005079462 A2 | 9/2005 |
| WO | WO-2006031745 A2 | 3/2006 |
| WO | WO-2006084132 A2 | 8/2006 |
| WO | WO-2007070869 A2 | 6/2007 |
| WO | WO-2007121489 A2 | 10/2007 |
| WO | WO-2007133831 A2 | 11/2007 |
| WO | WO-2008039998 A2 | 4/2008 |
| WO | WO-2008069973 A2 | 6/2008 |
| WO | WO-2009046149 A1 | 4/2009 |
| WO | WO-2009076238 A2 | 6/2009 |
| WO | WO-2009155181 A1 | 12/2009 |
| WO | WO-2010019826 A1 | 2/2010 |
| WO | WO-2010080134 A1 | 7/2010 |
| WO | WO-2010081114 A2 | 7/2010 |
| WO | WO-2010115154 A1 | 10/2010 |
| WO | WO-2011032040 A1 | 3/2011 |
| WO | WO-2011047087 A2 | 4/2011 |
| WO | WO-2011106583 A1 | 9/2011 |
| WO | WO-2011156434 A2 | 12/2011 |
| WO | WO-2012049316 A1 | 4/2012 |
| WO | WO-2012058638 A2 | 5/2012 |
| WO | WO-2012150035 A1 | 11/2012 |
| WO | WO-2012154876 A1 | 11/2012 |
| WO | WO-2012157684 A1 | 11/2012 |
| WO | WO-2012173274 A1 | 12/2012 |
| WO | WO-2013053901 A1 | 4/2013 |
| WO | WO-2013055995 A2 | 4/2013 |
| WO | WO-2013096851 A1 | 6/2013 |
| WO | WO-2013102108 A2 | 7/2013 |
| WO | WO-2013184754 A2 | 12/2013 |
| WO | WO-2014152321 A1 | 9/2014 |
| WO | WO-2014153052 A2 | 9/2014 |
| WO | WO-2014163886 A1 | 10/2014 |
| WO | WO-2014165232 A1 | 10/2014 |
| WO | WO-2014182598 A1 | 11/2014 |
| WO | WO-2014186411 A1 | 11/2014 |
| WO | WO-2014201232 A2 | 12/2014 |
| WO | WO-2015031541 A1 | 3/2015 |
| WO | WO-2015089449 A2 | 6/2015 |
| WO | WO-2015095766 A2 | 6/2015 |
| WO | WO-2015100459 A2 | 7/2015 |
| WO | WO-2015108972 A1 | 7/2015 |
| WO | WO-2015124738 A1 | 8/2015 |
| WO | WO-2015127407 A1 | 8/2015 |
| WO | WO-2015136509 A2 | 9/2015 |
| WO | WO-2015143078 A1 | 9/2015 |
| WO | WO-2015148531 A1 | 10/2015 |
| WO | WO-2015148606 A2 | 10/2015 |
| WO | WO-2016081740 A1 | 5/2016 |
| WO | WO-2016168584 A1 | 10/2016 |
| WO | WO-2017201073 A1 | 11/2017 |
| WO | WO-2017222453 A1 | 12/2017 |
| WO | WO-2018094385 A1 | 5/2018 |
| WO | WO-2019222178 A1 | 11/2019 |
| WO | WO-2022197801 A1 | 9/2022 |

OTHER PUBLICATIONS

Bolzer, et al., Three-dimensional maps of all chromosomes in human male fibroblast nuclei and prometaphase rosettes, PloS Biology, May 2005, 17 pages.

CDC Centers for Disease Control and Prevention, COVID-19 SARS-CoV-2 Variant Classifications and Definitions, Jan. 2023, 7 pages.

Chen, et al., Expansion microscopy, Science, Jan. 2015, pp. 543-548.

Chen, et al., Spatially resolved, highly multiplexed RNA profiling in single cells, Science, Apr. 2015, 16 pages.

Collins M. L. et al., A branched DNA signal amplification assay for quantification of nucleic acid targets below 100 molecules/ml, Nucleic Acids Research, Aug. 1997, pp. 2979-2984.

De Capoa et al., Computer-assisted analysis of methylation status of individual interphase nuclei in human cultured cells, Cytometry, Feb. 1998, pp. 85-92.

Duose, et al., Multiplexed and reiterative fluorescence labeling via DNA circuitry, Bioconjugate chemistry, Dec. 2010, pp. 2327-2331.

Duowei, et al., Molecular Biology, Nanjing Normal University Press, Jul. 31, 2007, p. 149, 7 total pages (with English translation).

Eid, et al., Real-time DNA sequencing from single polymerase molecules, Science, Jan. 2009, pp. 133-138.

Emanuel, et al., Using MERSCOPE to generate a cell atlas of the mouse brain that includes lowly expressed genes, Microscopy Today, Nov. 2021, pp. 16-19.

Fang, et al., Conservation and divergence in cortical cellular organization between human and mouse revealed by single-cell transcriptome imaging, bioRxiv, Nov. 2021, pp. 2021-11.

Femino, et al., Visualization of single RNA transcripts in situ, Science, Apr. 1998, pp. 585-590.

Ferguson, et al., High-density fiber-optic DNA random microsphere array, Analytical Chemistry, Nov. 2000, pp. 5618-5624.

Geiss et al., Direct multiplexed measurement of gene expression with color-coded probe pairs, Nature biotechnology, Mar. 2008, pp. 317-325.

Göransson, et al., A single molecule array for digital targeted molecular analyses, Nucleic Acids Research, Jan. 2009, 9 pages.

Gunderson, et al., Decoding Randomly Ordered DNA Arrays, Genome Res, May 2004, pp. 870-877.

Hauser et al Utilising the left-helical conformation of L-DNA for analysing different marker types on a single universal microarray platform, Nucleic Acids Research, Sep. 2006, pp. 5101-5111.

Itzkovitz, et al., Validating transcripts with probes and imaging technology, Nature Methods Supplement, Apr. 2011, pp. S12-S19.

Jungmann, R. et al., Multiplexed 3D Cellular Super-Resolution Imaging with DNA-PAINT and Exchange-PAINT, Nature methods, Mar. 2014, pp. 313-318.

Ke, et al., In situ sequencing for RNA analysis in preserved tissue and cells, Nature methods, Sep. 2013, pp. 857-860.

Kosman et al., Multiplex detection of RNA expression in *Drosophila* embryos, Science, Aug. 2004, p. 846.

Kosman, et al., Multiplex detection of RNA expression in *Drosophila* embryos, Science, Aug. 2004, Supporting Online Material, 13 pages.

Lee, et al., Fluorescent in situ sequencing (FISSEQ) of RNA for gene expression profiling in intact cells and tissues, Nature protocols, Mar. 2015, pp. 442-458.

Lee, et al., Highly multiplexed subcellular RNA sequencing in situ, Science, Mar. 2014, pp. 1360-1363.

Levsky et al., Single-Cell Gene Expression Profiling, Science, Aug. 2002, pp. 836-840.

Lin, et al., Submicrometre geometrically encoded fluorescent barcodes self-assembled from DNA, Nature chemistry, Oct. 2012, pp. 832-839.

Liu, et al., Comparative analysis of MERFISH spatial transcriptomics with bulk and single-cell RNA sequencing, BioRxiv, Mar. 7, 2022, 48 pages.

(56) References Cited

OTHER PUBLICATIONS

Lu, et al., Spatial transcriptome profiling by MERFISH reveals fetal liver hematopoietic stem cell niche architecture, Cell Discovery, Jun. 2021, 17 pages.
Lubeck, et al., Single-cell in situ RNA profiling by sequential hybridization, Nature methods, Apr. 2014, pp. 360-361.
Lubeck, et al., Single-cell systems biology by super-resolution imaging and combinatorial labeling, Nature methods, Jul. 2012, pp. 743-748.
Marbleston, et al., Rosetta Brains: A Strategy for Molecularly-Annotated Connectomics, Apr. 2014, 18 pages.
McElwain, et al., NanoString: Single-molecule long read sequencing using Hyb & Seq™, Chemistry, Feb. 13, 2017, 1 page.
MERSCOPE™ Instrument User Guide, Document No. 91600001, Document Revision: Rev B, Revision Date Oct. 2021, 39 pages.
MERSCOPE™ User Guide, Fresh and Fixed Frozen Tissue Sample Preparation, Document No. 91600002, Document Revision Rev B, Revision Date Oct. 2021, 28 pages.
Müller, et al., Towards unlimited colors for fluorescence in-situ hybridization (FISH), Chromosome Research, Mar. 2002, pp. 223-232.
Moffitt, et al., High-throughput single-cell gene-expression profiling with multiplexed error-robust fluorescence in situ hybridization, PNAS, Sep. 2016, pp. 11046-11051.
Moffitt, et al., RNA imaging with multiplexed error-robust fluorescence in situ hybridization (MERFISH), Methods in Enzymology, Jan. 2016, pp. 1-49 pages.
Olejnik, et al., Photocleavable aminotag phosphoramidites for 5'-termini DNA/RNA labeling, Nucleic Acids Research, Aug. 1998, pp. 3572-3576.
Player, et al., Single-copy gene detection using branched DNA (bDNA) in situ hybridization, The Journal of Histochemistry & Cytochemistry, May 2001, pp. 603-611.
Press Release, Wyss Institute Launches New Company To Provide Inexpensive Access To Super-Resolution Microscopy, published online Oct. 13, 2015, 6 pages.
Raj, et al., Imaging individual mRNA molecules using multiple singly labeled probes, Nature Methods, Oct. 2008, pp. 877-879.
Söderberg, et al., Characterizing proteins and their interactions in cells and tissues using the in situ proximity ligation assay, Methods, Jul. 2008, pp. 227-232.
Söderberg, et al., Direct observation of individual endogenous protein complexes in situ by proximity ligation, Nature Methods, Dec. 2006, pp. 995-1000.
Seelig, et al., Catalyzed relaxation of a metastable DNA fuel, J. Am. Chem. Soc. Sep. 2006, pp. 12211-12220.
Seo, et al., Four-color DNA sequencing by synthesis on a chip using photocleavable fluorescent nucleotides, PNAS, Apr. 2005, pp. 5926-5931.
Shendure, et al., Accurate multiplex polony sequencing of an evolved bacterial genome Science, 2005, pp. 1728-1732.
Shendure, et al., Accurate Multiplex Polony Sequencing of an Evolved Bacterial Genome, Supporting Online Material, Science, 2005, 41 pages.
Sinnamon, et al., RNA detection in situ with FISH-STICs, RNA, Feb. 2014, pp. 260-266.
Steemers et al., Screening unlabeled DNA targets with randomly ordered fiber-optic gene arrays, Nature biotechnology, Jan. 2000, pp. 91-94.
Sweeney, et al., Quantitative multiplexed quantum dot immunohistochemistry, Biochemical and biophysical research communications, Sep. 2008, pp. 181-186.
Swoboda, et al., Enzymatic oxygen scavenging for photostability without pH drop in single-molecule experiments, ACS nano, Jul. 2012, pp. 6364-6369.
Voelkerding, et al., Next-Generation Sequencing: From Basic Research to Diagnostics, Clinical Chemistry, Apr. 2009, pp. 641-658.
Wang, et al., Multiplexed imaging of high-density libraries of RNAs with MERFISH and expansion microscopy, Scientific Reports, Mar. 2018, 13 pages.
Wang, et al., NAscope: a novel in situ RNA analysis platform for formalin-fixed, paraffin-embedded tissues, The Journal of Molecular Diagnostics, Jan. 2012, pp. 22-29.
Wang, et al., Spatial organization of the transcriptome in individual neurons, BioRxiv, Dec. 2020, pp. 2020-12.
Wei, et al., Complex shapes self-assembled from single-stranded DNA tiles, Nature, May 2012, pp. 623-626.
Werner, et al., Current status of DNA sequencing by single molecule detection, Advances in Fluorescence Sensing Technology IV, May 1999, pp. 355-366.
Wikipedia, ABI Solid Sequencing, downloaded on Feb. 23, 2023, 3 pages.
Xia, et al., Multiplexed detection of RNA using MERFISH and branched DNA amplification, Scientific reports, May 2019, 13 pages.
Xia, et al., Spatial transcriptome profiling by MERFISH reveals subcellular RNA compartmentalization and cell cycle-dependent gene expression, PNAS, 2019, pp. 19490-19499.
Xia, et al., Spatial transcriptome profiling by MERFISH reveals subcellular RNA compartmentalization and cell cycle-dependent gene expression, PNAS, Supplementary Information, Sep. 2019, 32 pages.
Castro et al., "Adaptation of laser microdissection technique for the study of a spontaneous metastatic mammary carcinoma mouse model by NanoString technologies," PLOS One, 2016 pp. 1-15.
Pichon, et al., A growing toolbox to image gene expression in single cells: sensitive approaches for demanding challenges, Molecular cell, Aug. 2018, pp. 468-480.
Co-pending U.S. Appl. No. 18/668,982, inventor Khafizov; Rustem, filed May 20, 2024.

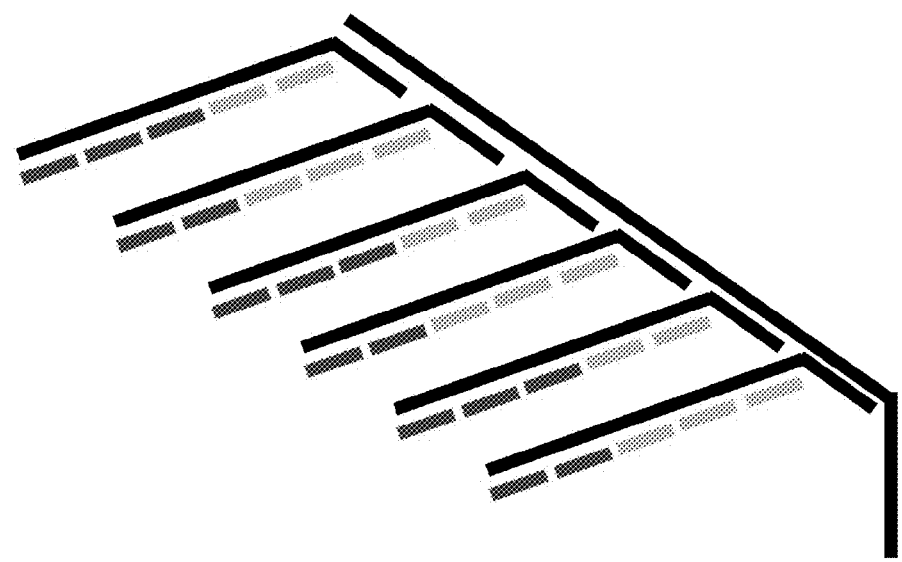
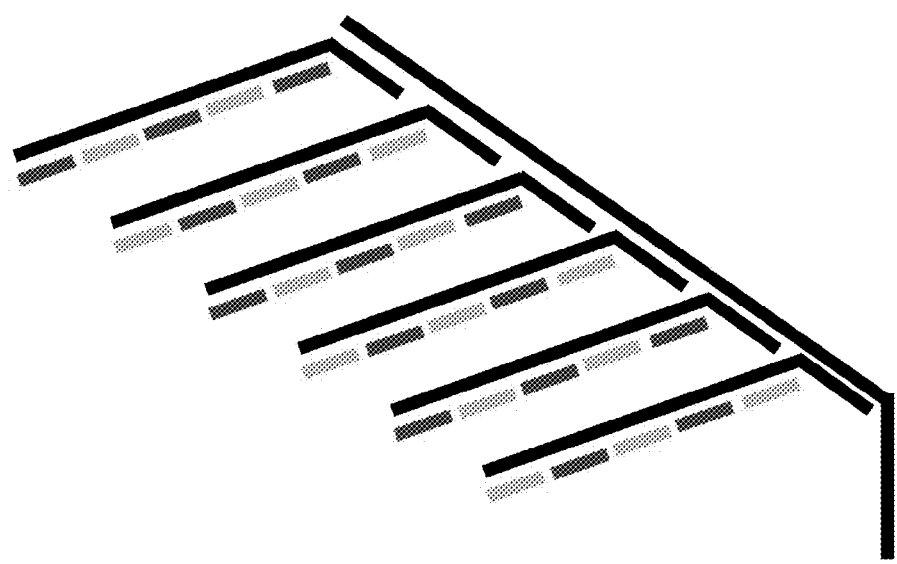
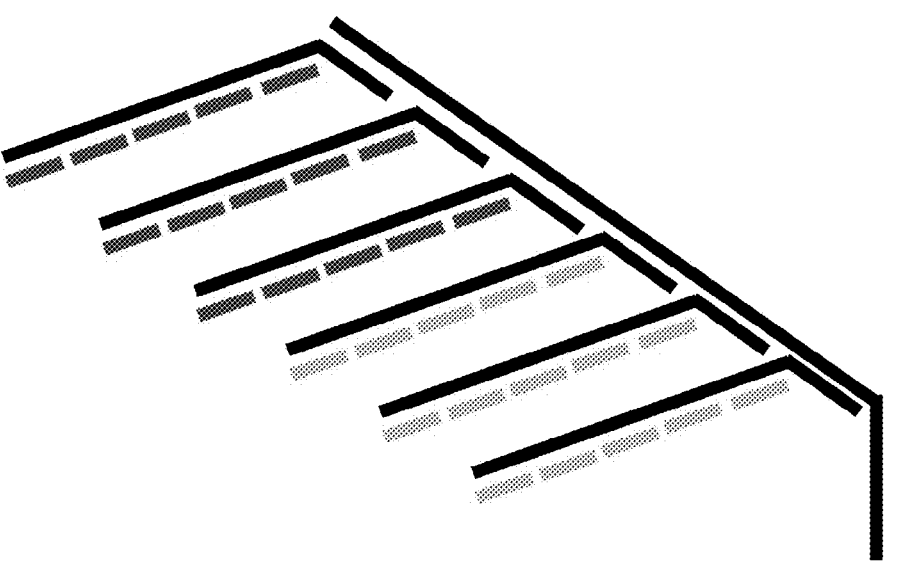
FIG. 5

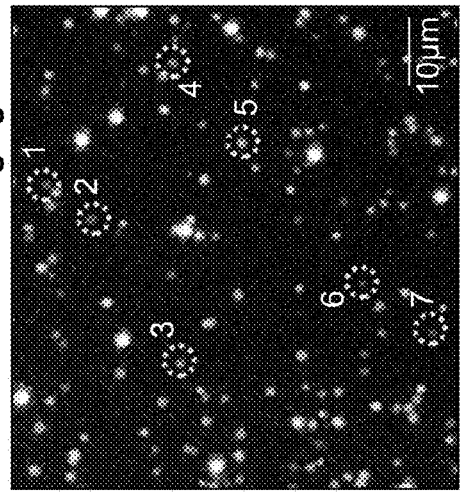
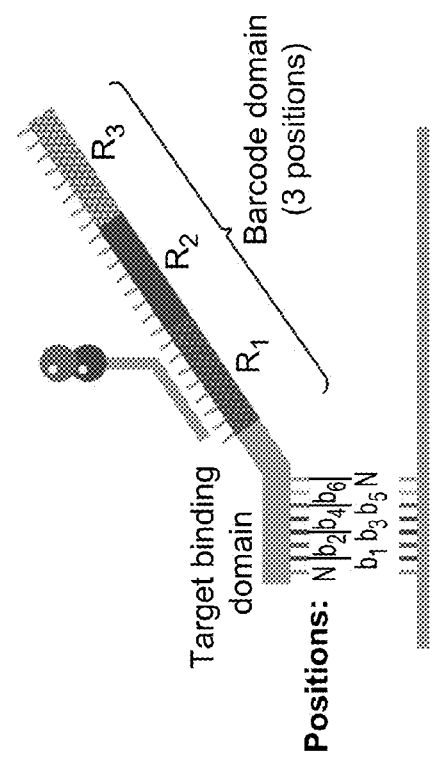
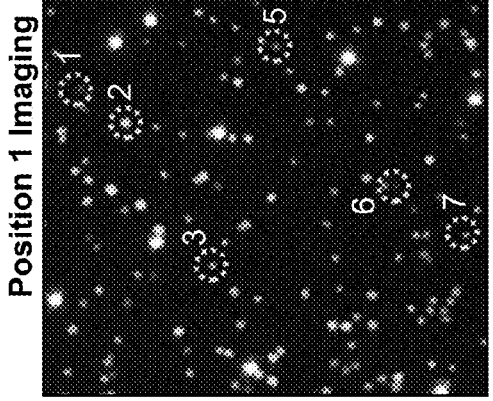
FIG. 11A

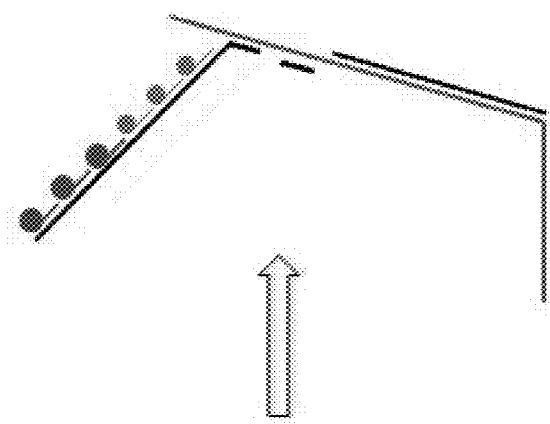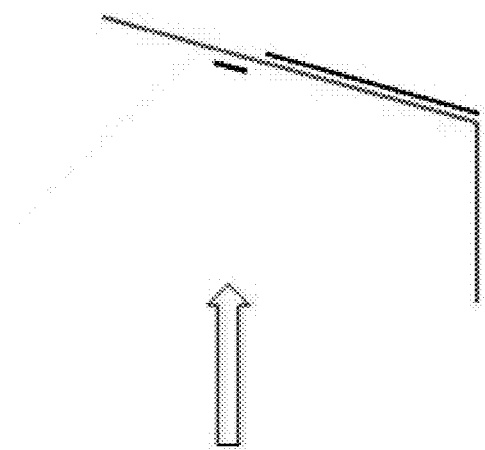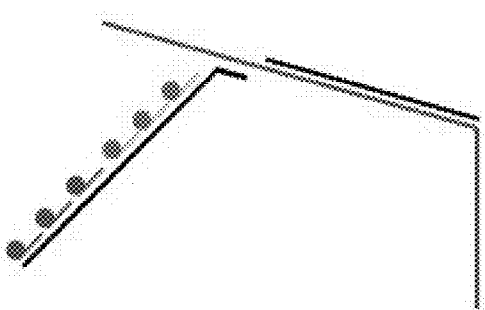
FIG. 15

```
       CACCT            Four calls of C
       CACCT            Two different probes observed
    AACACC              Voting High Quality Call
    AACACC
3'-AACACCACCT-5' consensus
         (SEQ ID NO: 2)

ACACCT              Six calls of C from two different
     CACCT              probes
     CACCT              One Call of A
   AACACC               Two different probes observed
   AACACC               calling C
   AACACC               Voting High Quality Call
   AACAAC
3'-AACACCACCT-5' consensus
         (SEQ ID NO: 2)

CACCT              Three calls of C from two different Probes
    ACACCT              Two Calls of A from a single probe
    ACACCT              Voting Medium Quality Call
     CACCT
   AACACC
3'-AACACCACCT-5' consensus
         (SEQ ID NO: 2)
```

FIG. 17

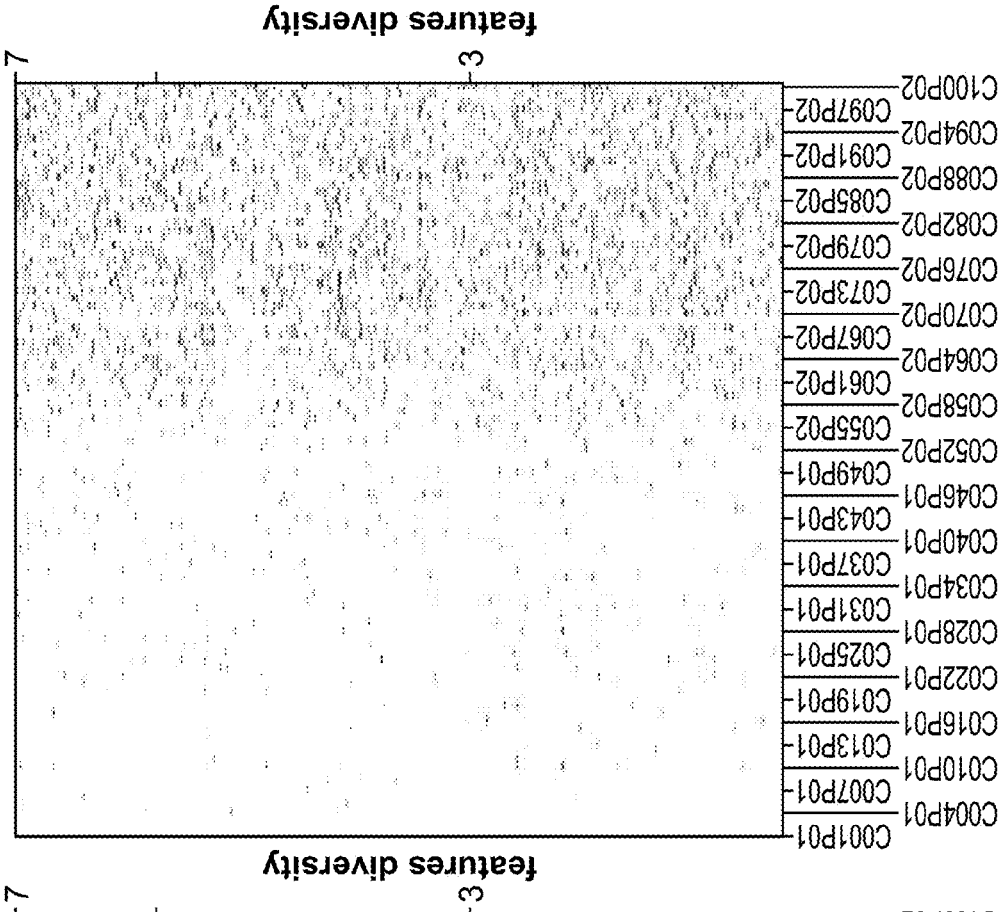
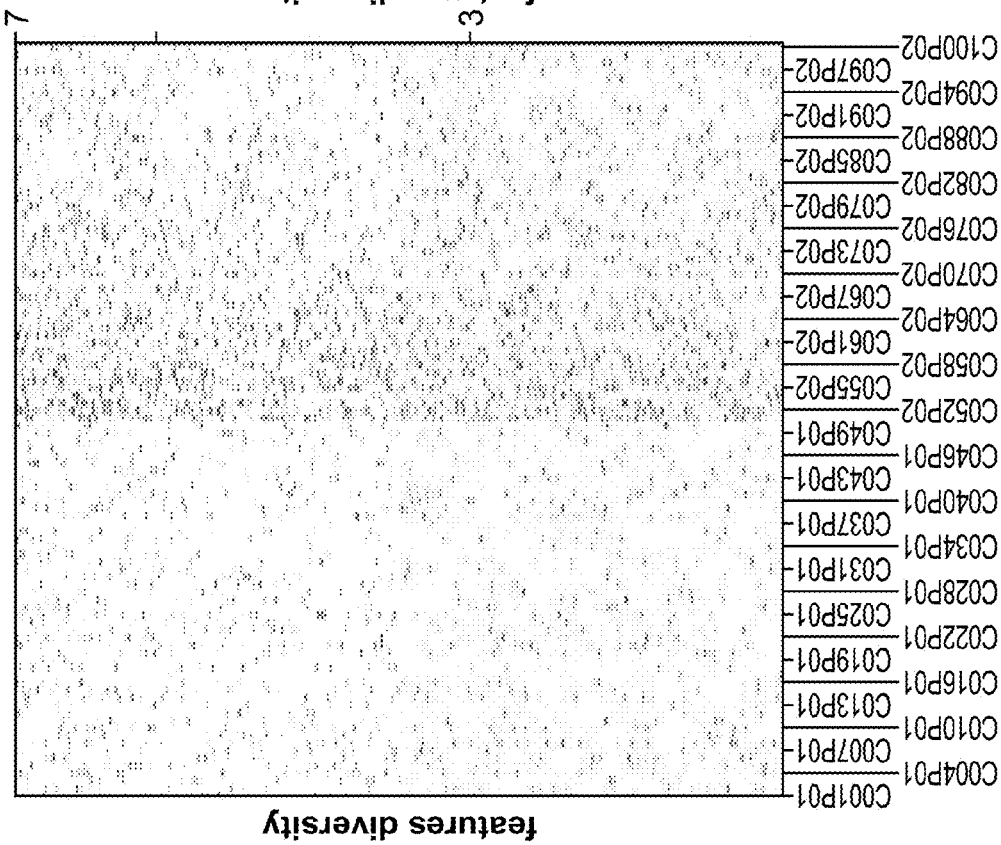
FIG. 66B

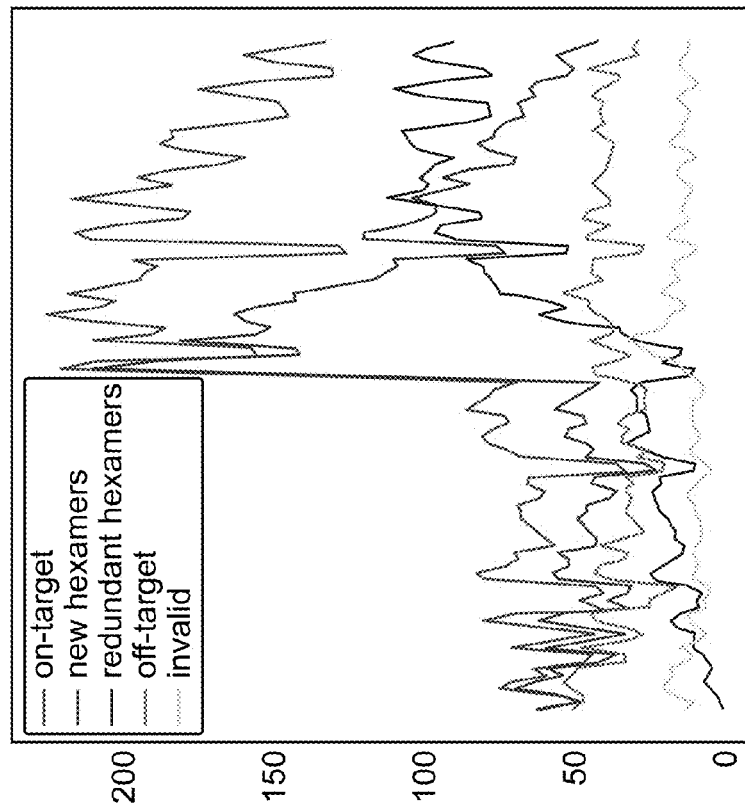
FIG. 66C

SEQUENCE LISTING

```
Sequence total quantity: 114
SEQ ID NO: 1            moltype = DNA  length = 38
FEATURE                 Location/Qualifiers
source                  1..38
                        mol_type = other DNA
                        organism = Homo sapiens
SEQUENCE: 1
accgtgacat gagaagaaca ggtcgacata ggtcatac                                  38

SEQ ID NO: 2            moltype = DNA  length = 10
FEATURE                 Location/Qualifiers
misc_feature            1..10
                        note = Example Consensus
source                  1..10
                        mol_type = other DNA
                        organism = synthetic construct
```

```
SEQUENCE: 2
aacaccacct                                                              10

SEQ ID NO: 3            moltype = DNA   length = 24
FEATURE                 Location/Qualifiers
source                  1..24
                        mol_type = other DNA
                        organism = Homo sapiens
SEQUENCE: 3
gtctagctac agtgaaatct cgat                                              24

SEQ ID NO: 4            moltype = DNA   length = 23
FEATURE                 Location/Qualifiers
source                  1..23
                        mol_type = other DNA
                        organism = Homo sapiens
SEQUENCE: 4
tcaaagtgct gggctccggt gcg                                               23

SEQ ID NO: 5            moltype = DNA   length = 27
FEATURE                 Location/Qualifiers
source                  1..27
                        mol_type = other DNA
                        organism = Homo sapiens
SEQUENCE: 5
tagttggagc tggtggcgta ggcaaga                                           27

SEQ ID NO: 6            moltype = DNA   length = 23
FEATURE                 Location/Qualifiers
source                  1..23
                        mol_type = other DNA
                        organism = Homo sapiens
SEQUENCE: 6
gaatgatgca catcatggtg gct                                               23

SEQ ID NO: 7            moltype = DNA   length = 23
FEATURE                 Location/Qualifiers
source                  1..23
                        mol_type = other DNA
                        organism = Homo sapiens
SEQUENCE: 7
gcagctcatc acgcagctca tgc                                               23

SEQ ID NO: 8            moltype = DNA   length = 23
FEATURE                 Location/Qualifiers
source                  1..23
                        mol_type = other DNA
                        organism = Homo sapiens
SEQUENCE: 8
atacagctgg acaagaagag tac                                               23

SEQ ID NO: 9            moltype = DNA   length = 25
FEATURE                 Location/Qualifiers
source                  1..25
                        mol_type = other DNA
                        organism = Homo sapiens
SEQUENCE: 9
tggctcgaga tatcatgagt gattc                                             25

SEQ ID NO: 10           moltype = DNA   length = 23
FEATURE                 Location/Qualifiers
source                  1..23
                        mol_type = other DNA
                        organism = Homo sapiens
SEQUENCE: 10
tcatcatagg tcgtcatgct tat                                               23

SEQ ID NO: 11           moltype = DNA   length = 23
FEATURE                 Location/Qualifiers
source                  1..23
                        mol_type = other DNA
                        organism = Homo sapiens
SEQUENCE: 11
atggagtatg tgtctgtgga gac                                               23

SEQ ID NO: 12           moltype = DNA   length = 23
FEATURE                 Location/Qualifiers
source                  1..23
                        mol_type = other DNA
```

```
                            organism = Homo sapiens
SEQUENCE: 12
gtgcaactct ccgtacatcg tgg                                           23

SEQ ID NO: 13           moltype = DNA   length = 23
FEATURE                 Location/Qualifiers
source                  1..23
                        mol_type = other DNA
                        organism = Homo sapiens
SEQUENCE: 13
cagccgcgtg ctgcacacca acg                                           23

SEQ ID NO: 14           moltype = RNA   length = 30
FEATURE                 Location/Qualifiers
source                  1..30
                        mol_type = other RNA
                        organism = Homo sapiens
SEQUENCE: 14
gcttcagcac cactccactc cacattctca                                    30

SEQ ID NO: 15           moltype = RNA   length = 30
FEATURE                 Location/Qualifiers
source                  1..30
                        mol_type = other RNA
                        organism = Homo sapiens
SEQUENCE: 15
tgtcctcatg tattggtctc tcatggcact                                    30

SEQ ID NO: 16           moltype = RNA   length = 30
FEATURE                 Location/Qualifiers
source                  1..30
                        mol_type = other RNA
                        organism = Homo sapiens
SEQUENCE: 16
ctttcgccaa agtggaggag accatcgccg                                    30

SEQ ID NO: 17           moltype = RNA   length = 30
FEATURE                 Location/Qualifiers
source                  1..30
                        mol_type = other RNA
                        organism = Homo sapiens
SEQUENCE: 17
gaaggtgatg tttgggtcag gtgccttagt                                    30

SEQ ID NO: 18           moltype = DNA   length = 50
FEATURE                 Location/Qualifiers
source                  1..50
                        mol_type = other DNA
                        organism = Homo sapiens
SEQUENCE: 18
caaactggtg gtggttggag caggtggtgt tgggaaaagc gcactgacaa               50

SEQ ID NO: 19           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 19
aggacagatg ac                                                       12

SEQ ID NO: 20           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 20
gtatcggatg ac                                                       12

SEQ ID NO: 21           moltype = DNA   length = 12
FEATURE                 Location/Qualifiers
misc_feature            1..12
                        note = 12-mer attachment position
source                  1..12
                        mol_type = other DNA
                        organism = synthetic construct
```

```
SEQUENCE: 21
aggagtgatg ac                                                                    12

SEQ ID NO: 22        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 22
aggggtgagg ag                                                                    12

SEQ ID NO: 23        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 23
agagggatg ac                                                                     12

SEQ ID NO: 24        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 24
agtgggagg ag                                                                     12

SEQ ID NO: 25        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 25
agccgagatg ac                                                                    12

SEQ ID NO: 26        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 26
agggtggatg ac                                                                    12

SEQ ID NO: 27        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 27
tggatggaaa ag                                                                    12

SEQ ID NO: 28        moltype = DNA  length = 12
FEATURE              Location/Qualifiers
misc_feature         1..12
                     note = 12-mer attachment position
source               1..12
                     mol_type = other DNA
                     organism = synthetic construct
SEQUENCE: 28
gaaggagaaa ag                                                                    12

SEQ ID NO: 29        moltype = DNA  length = 12
FEATURE              Location/Qualifiers
misc_feature         1..12
                     note = 12-mer attachment position
source               1..12
                     mol_type = other DNA
```

```
                         organism = synthetic construct
SEQUENCE: 29
ggggatgaaa ag                                                              12

SEQ ID NO: 30            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 30
gtgagggaaa ag                                                              12

SEQ ID NO: 31            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 31
agccgagaaa ag                                                              12

SEQ ID NO: 32            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 32
cgagaggaaa ag                                                              12

SEQ ID NO: 33            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 33
gagggcgaaa ag                                                              12

SEQ ID NO: 34            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 34
agcgtggaaa ag                                                              12

SEQ ID NO: 35            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 35
tgagaagggt ag                                                              12

SEQ ID NO: 36            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 36
gttgttattg tg                                                              12

SEQ ID NO: 37            moltype = DNA  length = 12
FEATURE                  Location/Qualifiers
misc_feature             1..12
                         note = 12-mer attachment position
source                   1..12
```

```
                        mol_type = other DNA
                        organism = synthetic construct
SEQUENCE: 37
tttgggttta gg                                                                       12

SEQ ID NO: 38           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 38
gttagtggga aa                                                                       12

SEQ ID NO: 39           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 39
atgggaaaaa gt                                                                       12

SEQ ID NO: 40           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 40
gagttggatg ag                                                                       12

SEQ ID NO: 41           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 41
atgttgtggg ta                                                                       12

SEQ ID NO: 42           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 42
gagggtttta ag                                                                       12

SEQ ID NO: 43           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 43
atcttttccc cact                                                                     14

SEQ ID NO: 44           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 44
ccccactatt tctt                                                                     14

SEQ ID NO: 45           moltype = DNA   length = 14
FEATURE                 Location/Qualifiers
misc_feature            1..14
                        note = 14-mer attachment position
```

```
source                         1..14
                               mol_type = other DNA
                               organism = synthetic construct
SEQUENCE: 45
ctacccacaa cata                                                              14

SEQ ID NO: 46                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 46
ccatataaac ccca                                                              14

SEQ ID NO: 47                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 47
aaactccaat ctcc                                                              14

SEQ ID NO: 48                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 48
ctattctcaa ccta                                                              14

SEQ ID NO: 49                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 49
cccctctttt aaa                                                               14

SEQ ID NO: 50                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 50
ccaatcttac ctca                                                              14

SEQ ID NO: 51                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 51
ccctcacata actt                                                              14

SEQ ID NO: 52                  moltype = DNA   length = 14
FEATURE                        Location/Qualifiers
misc_feature                   1..14
                               note = 14-mer attachment position
source                         1..14
                               mol_type = other DNA
                               organism = synthetic construct
SEQUENCE: 52
ctcctctact ttcc                                                              14

SEQ ID NO: 53                  moltype = DNA   length = 14
FEATURE                        Location/Qualifiers
misc_feature                   1..14
```

```
                        note = 14-mer attachment position
source                  1..14
                        mol_type = other DNA
                        organism = synthetic construct
SEQUENCE: 53
ccctaaaccc aaaa                                                       14

SEQ ID NO: 54           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 54
cacttttcc catc                                                        14

SEQ ID NO: 55           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 55
catctgattc ctcc                                                       14

SEQ ID NO: 56           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 56
ctaaaccccc tact                                                       14

SEQ ID NO: 57           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 57
cctttacaaa caca                                                       14

SEQ ID NO: 58           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 58
ataccaccct cttt                                                       14

SEQ ID NO: 59           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 59
tattcttcta cccc                                                       14

SEQ ID NO: 60           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 60
tctacccttc tcat                                                       14

SEQ ID NO: 61           moltype = DNA  length = 14
FEATURE                 Location/Qualifiers
```

```
                        -continued misc_feature            1..14
                        note = 14-mer attachment position
source                  1..14
                        mol_type = other DNA
                        organism = synthetic construct
SEQUENCE: 61
ccacaataac aacc                                                         14

SEQ ID NO: 62           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 62
accttaacat tccc                                                         14

SEQ ID NO: 63           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 63
atttcccact aacc                                                         14

SEQ ID NO: 64           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 64
acttaaaacc ctcc                                                         14

SEQ ID NO: 65           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 65
tacctattcc tcca                                                         14

SEQ ID NO: 66           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 66
cccctttctc taag                                                         14

SEQ ID NO: 67           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 67
gatgatggta ggtg                                                         14

SEQ ID NO: 68           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 68
atgagaaggg taga                                                         14

SEQ ID NO: 69           moltype = DNA   length = 14
```

```
FEATURE                  Location/Qualifiers
misc_feature             1..14
                         note = 14-mer attachment position
source                   1..14
                         mol_type = other DNA
                         organism = synthetic construct SEQUENCE: 69
gttttgttgg tgag                                                          14

SEQ ID NO: 70            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 70
ttagtgtgtt ggag                                                          14

SEQ ID NO: 71            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 71
atgtaggaga gaga                                                          14

SEQ ID NO: 72            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 72
gggaatgtta aggt                                                          14

SEQ ID NO: 73            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 73
ggttagtggg aaat                                                          14

SEQ ID NO: 74            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 74
ggagggtttt aagt                                                          14

SEQ ID NO: 75            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 75
gtagtgtgga tgtt                                                          14

SEQ ID NO: 76            moltype = DNA   length = 14
FEATURE                  Location/Qualifiers
misc_feature             1..14
                         note = 14-mer attachment position
source                   1..14
                         mol_type = other DNA
                         organism = synthetic construct SEQUENCE: 76
cttagagaaa gggg                                                          14
```

-continued

```
SEQ ID NO: 77           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 77
ggaagaggat gaaa                                                          14

SEQ ID NO: 78           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 78
aagttatgtg aggg                                                          14

SEQ ID NO: 79           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 79
ggaaagtaga ggag                                                          14

SEQ ID NO: 80           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 80
ttttgggttt aggg                                                          14

SEQ ID NO: 81           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 81
agatgtatgg gtga                                                          14

SEQ ID NO: 82           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 82
gatgggaaaa agtg                                                          14

SEQ ID NO: 83           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 83
ggaggaatca gatg                                                          14

SEQ ID NO: 84           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 84
agagggattg atga                                                          14
```

-continued

```
SEQ ID NO: 85              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 85
tgtgtttgta aagg                                                               14

SEQ ID NO: 86              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 86
aaggagtgat agga                                                               14

SEQ ID NO: 87              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 87
tggtgattta gagg                                                               14

SEQ ID NO: 88              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 88
ggggtagaag aata                                                               14

SEQ ID NO: 89              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 89
aagaaatagt gggg                                                               14

SEQ ID NO: 90              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 90
tatgttgtgg gtag                                                               14

SEQ ID NO: 91              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 91
gttaaaggga ggtt                                                               14

SEQ ID NO: 92              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 92
```

```
tggggtttat atgg                                                                     14

SEQ ID NO: 93              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 93
agggaatatg gaga                                                                     14

SEQ ID NO: 94              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 94
taggttgaga atag                                                                     14

SEQ ID NO: 95              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 95
tttaaaagag gggg                                                                     14

SEQ ID NO: 96              moltype = DNA   length = 14
FEATURE                    Location/Qualifiers
misc_feature               1..14
                           note = 14-mer attachment position
source                     1..14
                           mol_type = other DNA
                           organism = synthetic construct
SEQUENCE: 96
tgaggtaaga ttgg                                                                     14

SEQ ID NO: 97              moltype = DNA   length = 10
FEATURE                    Location/Qualifiers
misc_feature               1..10
                           note = Target binding domain
source                     1..10
                           mol_type = other DNA
                           organism = synthetic construct
SEQUENCE: 97
agcttcttat                                                                          10

SEQ ID NO: 98              moltype = DNA   length = 50
FEATURE                    Location/Qualifiers
misc_feature               1..50
                           note = Target nucleic acid
source                     1..50
                           mol_type = other DNA
                           organism = synthetic construct
SEQUENCE: 98
gagactagca gaataggagg ataagaagct cgaagagtga ggacaaatgg                               50

SEQ ID NO: 99              moltype = DNA   length = 10
FEATURE                    Location/Qualifiers
misc_feature               1..10
                           note = Target binding domain
source                     1..10
                           mol_type = other DNA
                           organism = synthetic construct
SEQUENCE: 99
ttcactgtag                                                                          10

SEQ ID NO: 100             moltype = DNA   length = 35
FEATURE                    Location/Qualifiers
misc_feature               1..35
                           note = exemplary lawn oligonucleotide
misc_feature               1
                           note = Modified with a 5' amine with a 6 carbon linker
source                     1..35
```

```
                        mol_type = other DNA
                        organism = synthetic construct
SEQUENCE: 100
tggtgaggtt gttggtagta gtgagtttgt agggt                              35

SEQ ID NO: 101          moltype = DNA   length = 25
FEATURE                 Location/Qualifiers
misc_feature            1..25
                        note = exemplary lawn oligonucleotide
misc_feature            1
                        note = Modified with a 5' amine with a 6 carbon linker
source                  1..25
                        mol_type = other DNA
                        organism = synthetic construct
SEQUENCE: 101
tggtgaggtt gttggtagta gtgag                                         25

SEQ ID NO: 102          moltype = DNA   length = 35
FEATURE                 Location/Qualifiers
misc_feature            1..35
                        note = exemplary lawn oligonucleotide
misc_feature            1
                        note = Modified with a 5' amine with a 6 carbon linker
source                  1..35
                        mol_type = other DNA
                        organism = synthetic construct
SEQUENCE: 102
tttttttttt tttttttttt tttttttttt ttttt                              35

SEQ ID NO: 103          moltype = DNA   length = 36
FEATURE                 Location/Qualifiers
misc_feature            1..36
                        note = exemplary lawn oligonucleotide
misc_feature            1
                        note = Modified with a 5' amine with a 6 carbon linker
source                  1..36
                        mol_type = other DNA
                        organism = synthetic construct
SEQUENCE: 103
catctcaaac accttctaca atatgaccta acacac                             36

SEQ ID NO: 104          moltype = DNA   length = 36
FEATURE                 Location/Qualifiers
misc_feature            1..36
                        note = exemplary lawn oligonucleotide
misc_feature            1
                        note = Modified with a 5' amine with a 6 carbon linker
source                  1..36
                        mol_type = other DNA
                        organism = synthetic construct
SEQUENCE: 104
gtgatggtta taagaggtgt tgatatattt atagta                             36

SEQ ID NO: 105          moltype = DNA   length = 36
FEATURE                 Location/Qualifiers
misc_feature            1..36
                        note = exemplary lawn oligonucleotide
misc_feature            1
                        note = Modified with a 5' amine with a 6 carbon linker
source                  1..36
                        mol_type = other DNA
                        organism = synthetic construct
SEQUENCE: 105
tattgatatt gagaaagcgt ttgatgatgt attgat                             36

SEQ ID NO: 106          moltype = DNA   length = 36
FEATURE                 Location/Qualifiers
misc_feature            1..36
                        note = exemplary lawn oligonucleotide
misc_feature            1
                        note = Modified with a 5' amine with a 6 carbon linker
source                  1..36
                        mol_type = other DNA
                        organism = synthetic construct
SEQUENCE: 106
tagttatgta gtagtttgcg aaagagttat agttat                             36

SEQ ID NO: 107          moltype = DNA   length = 36
FEATURE                 Location/Qualifiers
```

```
misc_feature            1..36
                        note = exemplary lawn oligonucleotide
misc_feature            1
                        note = Modified with a 5' amine with a 6 carbon linker
source                  1..36
                        mol_type = other DNA
                        organism = synthetic construct
SEQUENCE: 107
actaccctac tctacccttc taagatatac atatac                                 36

SEQ ID NO: 108          moltype = DNA   length = 35
FEATURE                 Location/Qualifiers
misc_feature            1..35
                        note = exemplary lawn oligonucleotide
misc_feature            1
                        note = Modified with a 5' amine with a 6 carbon linker
misc_feature            3
                        note = Comprises isoguanine base
misc_feature            7
                        note = Comprises isoguanine base
misc_feature            11
                        note = Comprises isoguanine base
misc_feature            15
                        note = Comprises isoguanine base
misc_feature            18
                        note = Comprises isoguanine base
misc_feature            21
                        note = Comprises isoguanine base
misc_feature            25
                        note = Comprises isoguanine base
misc_feature            29
                        note = Comprises isoguanine base
misc_feature            33
                        note = Comprises isoguanine base
source                  1..35
                        mol_type = other DNA
                        organism = synthetic construct
SEQUENCE: 108
tggtgaggtt gttggtagta gtgagtttgt agggt                                  35

SEQ ID NO: 109          moltype = DNA   length = 25
FEATURE                 Location/Qualifiers
misc_feature            1..25
                        note = OA-sequence
source                  1..25
                        mol_type = other DNA
                        organism = synthetic construct
SEQUENCE: 109
cgaaagccat gacctccgat cactc                                             25

SEQ ID NO: 110          moltype = DNA   length = 60
FEATURE                 Location/Qualifiers
misc_feature            1..60
                        note = adapter oligonucleotide
misc_feature            28
                        note = Comprises 5-methyl-isocytosine base
misc_feature            32
                        note = Comprises 5-methyl-isocytosine base
misc_feature            36
                        note = Comprises 5-methyl-isocytosine base
misc_feature            40
                        note = Comprises 5-methyl-isocytosine base
misc_feature            43
                        note = Comprises 5-methyl-isocytosine base
misc_feature            46
                        note = Comprises 5-methyl-isocytosine base
misc_feature            50
                        note = Comprises 5-methyl-isocytosine base
misc_feature            54
                        note = Comprises 5-methyl-isocytosine base
misc_feature            58
                        note = Comprises 5-methyl-isocytosine base
source                  1..60
                        mol_type = other DNA
                        organism = synthetic construct
SEQUENCE: 110
gagtgatcgg aggtcatggc tttcgaccct acaaactcac tactaccaac aacctcacca       60

SEQ ID NO: 111          moltype = DNA   length = 63
```

```
FEATURE              Location/Qualifiers
misc_feature         1..63
                     note = capture probe
source               1..63
                     mol_type = other DNA
                     organism = synthetic construct
SEQUENCE: 111
ccggtcaacc gttttgtaga acaactcccg tcccctcact cactagcctc cagtaccgaa    60
agc                                                                  63

SEQ ID NO: 112       moltype = DNA  length = 15
FEATURE              Location/Qualifiers
misc_feature         1..15
                     note = Single stranded purification sequence
source               1..15
                     mol_type = other DNA
                     organism = synthetic construct
SEQUENCE: 112
aacatcacac agacc                                                     15

SEQ ID NO: 113       moltype = DNA  length = 15
FEATURE              Location/Qualifiers
misc_feature         1..15
                     note = Single stranded purification sequence
source               1..15
                     mol_type = other DNA
                     organism = synthetic construct
SEQUENCE: 113
gtctatcatc acagc                                                     15

SEQ ID NO: 114       moltype = DNA  length = 34
FEATURE              Location/Qualifiers
misc_feature         1..34
                     note = lawn oligonucleotide
misc_feature         1..34
                     note = L-DNA
source               1..34
                     mol_type = other DNA
                     organism = synthetic construct
SEQUENCE: 114
tttttttttt tttttttttt tttttttttt tttt                                34
```

CHEMICAL COMPOSITIONS AND METHODS OF USING SAME

CROSS-REFERENCE TO RELATED APPLICATIONS

This application is a continuation of U.S. application Ser. No. 16/411,394, filed May 14, 2019, now U.S. Pat. No. 11,549,139, which claims priority to, and the benefit of, U.S. Provisional Application No. 62/671,091, filed May 14, 2018 and U.S. Provisional Application No. 62/836,327, filed Apr. 19, 2019. The contents of each of the aforementioned patent applications are incorporated herein by reference in their entireties.

SEQUENCE LISTING

The Sequence Listing XML associated with this application is provided electronically in XML format and is hereby incorporated by reference into the specification. The name of the XML file containing the Sequence Listing XML is "NATE-039_C01US_SeqList.xml". The XML file is 150,001 bytes, created on Nov. 10, 2022, and is being submitted electronically via USPTO Patent Center.

BACKGROUND OF THE INVENTION

There are currently a variety of methods for nucleic acid sequencing, i.e., the process of determining the precise order of nucleotides within a nucleic acid molecule. Current methods require amplifying a nucleic acid enzymatically, e.g., PCR, and/or by cloning. Further enzymatic polymerizations are required to produce a detectable signal by a light detection means. Such amplification and polymerization steps are costly and/or time-consuming. Thus, there is a need in the art for a method of nucleic acid sequencing that is rapid and amplification- and enzyme-free. The present disclosure addresses these needs.

SUMMARY OF THE INVENTION

The present disclosure provides sequencing probes, methods, kits, and apparatuses that provide rapid enzyme-free, amplification-free, and library-free nucleic acid sequencing that has long-read-lengths and with low error rate. The sequencing probes described herein include barcode domains in which each position in the barcode domain corresponds to at least two nucleotides in the target binding domain. Moreover, the methods, kits, and apparatuses have rapid sample-to-answer capability. These features are particularly useful for sequencing in a clinical setting. The present disclosure is an improvement of the disclosure disclosed in Patent Publication No. U.S. 2016/0194701, the contents of which are herein incorporated by reference is their entirety.

The present disclosure provides a probe comprising a target binding domain and a barcode domain; wherein the target binding domain comprises at least eight nucleotides and hybridizes to a target nucleic acid, wherein at least six nucleotides in the target binding domain identify a corresponding nucleotide in the target nucleic acid molecule and wherein at least two nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment position comprising at least one nucleic acid sequence that hybridizes to a complementary nucleic acid molecule, and wherein the synthetic backbone comprises L-DNA, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain; and a first complementary primary nucleic acid molecule hybridized to a first attachment position of the at least three attachment positions, wherein the first primary complementary nucleic acid molecule comprises at least two domains and a cleavable linker, wherein the first domain is hybridized to the first attachment position of the barcode domain and the second domain capable of hybridizing to at least one complementary secondary nucleic acid molecule, and wherein the linker modification is

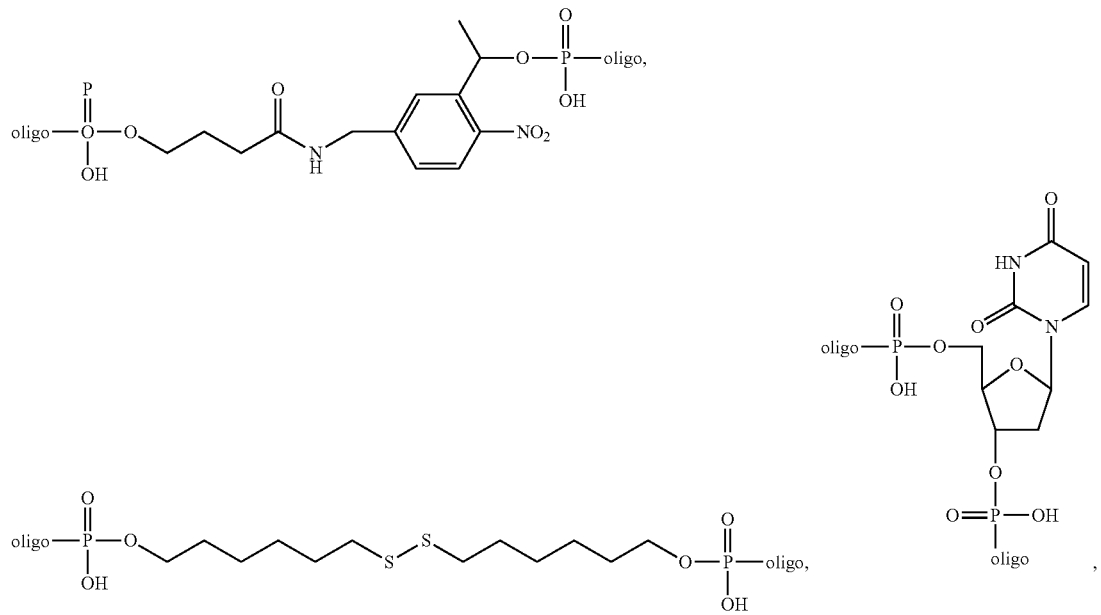

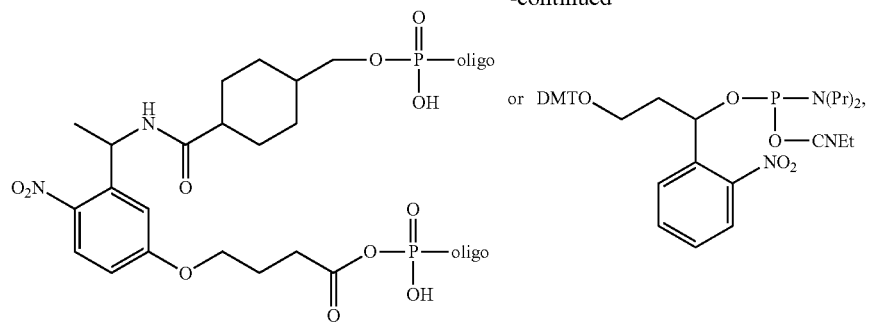

and wherein the linker modification is located between the first and second domains.

A probe can comprise about 60 nucleotides. A probe can comprise a single-stranded DNA synthetic backbone and a double-stranded DNA spacer between the target binding domain and the barcode domain. A single-stranded DNA synthetic backbone can comprise L-DNA. A single-stranded DNA synthetic backbone can comprise about 27 nucleotides. A double-stranded DNA spacer can comprise L-DNA. A double-stranded DNA spacer can comprise about 25 nucleotides in length.

The number of nucleotides in a target binding domain of a probe can be greater than the number of attachment positions in the barcode domain of the probe. A target binding domain can comprise eight nucleotides and a barcode domain can comprise three attachment positions. At least one of the nucleotides in the target binding domain that does not identify a corresponding nucleotide in the target nucleic acid molecule can precede the at least six nucleotides in the target binding domain and wherein at least one of the nucleotides in the target binding domain that does not identify a corresponding nucleotide in the target nucleic acid molecule can follow the at least six nucleotides in the target binding domain.

An attachment position in the barcode domain can comprise one attachment region. At least one nucleic acid sequence of each attachment position in the barcode domain can comprise about 9 nucleotides. At least one nucleic acid sequence of an attachment position can comprise a 3' terminal guanosine nucleotide. At least one nucleic acid sequence of each attachment position can comprise at least one adenine nucleotide, at least one thymine nucleotide, at least one cytosine nucleotide or any combination thereof and a 3' terminal guanosine nucleotide. Each nucleotide of an at least one nucleic acid sequence of an attachment position can be L-DNA. Each nucleotide of the at least eight nucleotides of the target binding domain can be D-DNA.

A complementary nucleic acid molecule can be a primary nucleic acid molecule, wherein the primary nucleic acid molecule directly can bind to at least one attachment region within at least one attachment position of a barcode domain. A primary nucleic acid molecule can comprise at least two domains, a first domain capable of binding to at least one attachment region within at least one attachment position of the barcode domain and a second domain capable of binding to at least one complementary secondary nucleic acid molecule. The first domain of a primary nucleic acid molecule can comprise L-DNA. The second domain of the primary nucleic acid molecule can comprise D-DNA. The first domain of the primary nucleic acid molecule can comprise a 5' terminal cytosine nucleotide. The first domain of the primary nucleic acid molecule can comprise at least one adenine nucleotide, at least one thymine nucleotide, at least one guanine nucleotide or any combination thereof and a 5' terminal cytosine nucleotide. A cleavable linker can be located between the first domain of a primary nucleic acid molecule and the second domain of a primary nucleic acid molecule. The cleavable linker can comprises at least one cleavable moiety. The cleavable moiety can be a photocleavable moiety.

A primary nucleic molecule cam ne hybridized to at least one attachment region within at least one attachment position of a barcode domain and can be hybridized to at least one secondary nucleic acid molecule. A primary nucleic molecule can be hybridized to four secondary nucleic acid molecules.

A secondary nucleic acid molecule can comprise at least two domains, a first domain capable of binding to a complementary sequence in at least one primary nucleic acid molecule; and a second domain capable of binding to (a) a first detectable label and an at least second detectable label, (b) to at least one complementary tertiary nucleic acid molecule, or (c) a combination thereof. A secondary nucleic acid molecule can comprise a cleavable linker. The cleavable linker can be located between the first domain and the second domain. The cleavable linker can be photo-cleavable. A secondary nucleic molecule can be hybridized to at least one primary nucleic acid molecule and hybridized to at least one tertiary nucleic acid molecule. A secondary nucleic molecule can be hybridized to (a) at least one primary nucleic acid molecule, (b) at least one tertiary nucleic acid molecule, and (c) a first detectable label and an at least second detectable label. Each secondary nucleic molecule can be hybridized to one tertiary nucleic acid molecule. A first and at least second detectable labels can have the same emission spectrum or can have different emission spectra.

A tertiary nucleic acid molecule can comprise at least two domains, a first domain capable of binding to a complementary sequence in a secondary nucleic acid molecule; and a second domain capable of binding to a first detectable label and an at least second detectable label. A tertiary nucleic acid molecule comprises a cleavable linker. A cleavable linker can be located between the first domain and the second domain. The cleavable linker can be photo-cleavable. A tertiary nucleic molecule can be hybridized to at least one secondary nucleic acid molecule and can comprise a first detectable label and an at least second detectable label. The first and at least second detectable labels can have the same emission spectrum or can have different emission spectra.

The at least first and second detectable labels located on the secondary nucleic acid molecule can have the same emission spectra and the at least first and second detectable labels located on the tertiary nucleic acid molecule can have the same emission spectra, and wherein the emission spectra of the detectable labels on the secondary nucleic acid molecule can be different than the emission spectra of the detectable labels on the tertiary nucleic acid molecule.

A primary nucleic acid molecule can be hybridized to four secondary nucleic acid molecules, wherein each of the four secondary nucleic acid molecules comprises four first detectable labels, and wherein each of the four secondary nucleic acid molecules is hybridized to one tertiary nucleic acid molecule, wherein the tertiary nucleic acid molecule comprises five detectable labels. The emission spectra of the first detectable labels of the secondary nucleic acid molecules can be different than the emission spectra of the second detectable labels on the tertiary nucleic acid molecules.

The present disclosure provides a method for determining a nucleotide sequence of a nucleic acid comprising: (1) hybridizing the target binding domain of at least one first probe of claim 1 to a first region of a target nucleic acid that is optionally immobilized to a substrate at one or more positions; (2) hybridizing a first complementary nucleic acid molecule comprising at least one first detectable label and at least one second detectable label to a first attachment position of the at least three attachment positions of the barcode domain; (3) identifying the at least one first and the at least one second detectable label of the first complementary nucleic acid molecule hybridized to the first attachment position; (4) removing the at least one first and the at least one second detectable label hybridized to the first attachment position; (5) hybridizing a second complementary nucleic acid molecule comprising at least one third detectable label and at least one fourth detectable label to a second attachment position of the at least three attachment positions of the barcode domain; (6) identifying the at least one third and the at least one fourth detectable label of the second complementary nucleic acid molecule hybridized to the second attachment position; (7) removing the at least one third and the at least one fourth detectable label hybridized to the second attachment position; (8) hybridizing a third complementary nucleic acid molecule comprising at least one fifth detectable label and at least one sixth detectable label to a third attachment position of the at least three attachment positions of the barcode domain; (9) identifying the at least one fifth and the at least one sixth detectable label of the third complementary nucleic acid molecule hybridized to the third attachment position; and (10) determining the nucleotide sequence of at least six nucleotides of the optionally immobilized target nucleic acid hybridized to the at least six nucleotides of the target binding domain of the at least one first probe based on the identity of the at least one first detectable label, the at least one second detectable label, the at least one third detectable label, the at least one fourth detectable label, the at least one fifth detectable label and the at least one sixth detectable label.

The preceding method can further comprise (11) removing the at least one first probe from the first region of the optionally immobilized target nucleic acid; (12) hybridizing the target binding domain of a least one second probe of claim 1 to a second region of the optionally immobilized target nucleic acid and wherein the target binding domain of the first probe and the at least second probe are different; (13) hybridizing a fourth complementary nucleic acid molecule comprising at least one seventh detectable label and at least one eighth detectable label to a first attachment position of the at least three attachment positions of the barcode domain of the at least one second probe; (14) identifying the at least one seventh and the at least one eighth detectable label of the fourth complementary nucleic acid molecule hybridized to the first attachment position; (15) removing the at least one seventh and the at least one eighth detectable label hybridized to the first attachment position; (16) hybridizing a fifth complementary nucleic acid molecule comprising at least one ninth detectable label and at least one tenth detectable label to a second attachment position of the at least three attachment positions of the barcode domain of the at least second probe; (17) identifying the at least one ninth and the at least one tenth detectable label of the fifth complementary nucleic acid molecule hybridized to the second attachment position; (18) removing the at least one ninth and the at least one tenth detectable label hybridized to the second attachment position; (19) hybridizing a sixth complementary nucleic acid molecule comprising at least one eleventh detectable label and at least one twelfth detectable label to a third attachment position of the at least three attachment positions of the barcode domain of the at least second probe; (20) identifying the at least one eleventh and the at least one twelfth detectable label of the sixth complementary nucleic acid molecule hybridized to the third attachment position; and (21) determining the nucleotide sequence of at least six nucleotides of the optionally immobilized target nucleic acid hybridized to the at least six nucleotides of the target binding domain of the at least one second probe based on the identity of the at least one seventh detectable label, the at least one eighth detectable label, the at least one ninth detectable label, the at least one tenth detectable label, the at least one eleventh detectable label and the at least one twelfth detectable label.

The preceding method can further comprise assembling each identified linear order of nucleotides in the at least first region and at least second region of the optionally immobilized target nucleic acid, thereby identifying a sequence for the optionally immobilized target nucleic acid.

Steps (4) and (5) can occur sequentially or concurrently. Steps (7) and (8) can occur sequentially or concurrently.

The first and second detectable labels can have the same emission spectrum or have different emission spectra. The third and fourth detectable labels can have the same emission spectrum or have different emission spectra. The fifth and sixth detectable labels can have the same emission spectrum or have different emission spectra.

A first complementary nucleic acid molecule, a second complementary nucleic acid molecule and a third complementary nucleic acid molecule can comprise a cleavable linker. A cleavable linker can be photo-cleavable.

A first complementary nucleic acid molecule can comprise a primary nucleic acid, four secondary nucleic acid molecules and four tertiary nucleic acid molecules, wherein the primary nucleic acid is hybridized to four secondary nucleic acid molecules, wherein each of the four secondary nucleic acid molecules comprises four first detectable labels, and wherein each of the four secondary nucleic acid molecules is hybridized to one tertiary nucleic molecule, wherein each of the four tertiary nucleic acid molecules comprises five second detectable labels.

A primary nucleic acid molecule can comprise at least two domains, a first domain that hybridizes to a first attachment position of the barcode domain and a second domain that hybridizes to four secondary nucleic acid molecules. A primary nucleic acid molecule can comprise a cleavable linker located between the first domain and the second domain.

A secondary nucleic acid molecule can comprise at least two domains, a first domain that hybridizes to the second domain of the primary nucleic acid molecule; and a second domain that comprises four first detectable labels and that hybridizes to one tertiary nucleic acid molecule. A secondary nucleic acid molecule can comprise a cleavable linker located between the first domain and the second domain.

Removing at least one first and the at least one second detectable label hybridized to a first attachment position can comprise cleaving the cleavable linker between the first domain and the second domain of the primary nucleic acid, cleaving the cleavable linker between the first domain and the second domain of each secondary nucleic acid or any combination thereof.

The present disclosure provides A composition comprising at least one molecular complex, wherein the at least one molecular complex comprises: (A) a target nucleic acid molecule obtained from a biological sample, and (B) at least two nucleic acid molecule complexes, wherein a first complex comprises a first partially double-stranded nucleic acid molecule, wherein one strand of the first partially double-stranded nucleic acid molecule comprises: a target specific domain hybridized to a first portion of the target nucleic acid molecule, a duplex domain annealed to the other strand of the first partially double-stranded nucleic acid molecule, and at least one first affinity moiety, wherein the other strand of the first partially double-stranded nucleic acid molecule comprises: a duplex domain that is annealed to the other strand of the first partially double-stranded nucleic acid molecule, a substrate specific domain that hybridizes to a complementary nucleic acid attached to a substrate, and at least one second affinity moiety wherein the second complex comprises a second partially double-stranded nucleic acid molecule, wherein one strand of the second partially double-stranded nucleic acid molecule comprises: a target specific domain hybridized to a second portion of the target nucleic acid, wherein the first and the second portion do not overlap, and a duplex domain annealed to the other strand of the second partially double-stranded nucleic acid molecule, wherein the other strand of the second partially double-stranded nucleic acid molecule comprises: a duplex domain annealed to the other strand of the second partially double-stranded nucleic acid molecule, a sample specific domain that identifies the biological sample from which the target nucleic acid was obtained, a first single-stranded purification sequence, a first cleavable moiety located between the duplex domain and the sample specific domain, and a second cleavable moiety located between the sample specific domain and the first single-stranded purification sequence.

The present disclosure provides a composition comprising at least one molecular complex, wherein the at least one molecular complex comprises: (A) a target nucleic acid molecule obtained from a biological sample, and (B) at least two nucleic acid molecule complexes, wherein a first complex comprises a first partially double-stranded nucleic acid molecule, wherein one strand of the first partially double-stranded nucleic acid molecule comprises: a target specific domain hybridized to a first portion of the target nucleic acid molecule, a duplex domain annealed to the other strand of the first partially double-stranded nucleic acid molecule, and at least one first affinity moiety, wherein the other strand of the first partially double-stranded nucleic acid molecule comprises: a duplex domain that is annealed to the other strand of the first partially double-stranded nucleic acid molecule and that is operably linked to the 3' end of the target nucleic acid molecule, a substrate specific domain that hybridizes to a complementary nucleic acid attached to a substrate, and at least one second affinity moiety, wherein the second complex comprises a second partially double-stranded nucleic acid molecule, wherein one strand of the second partially double-stranded nucleic acid molecule comprises: a target specific domain hybridized to a second portion of the target nucleic acid, wherein the first and the second portion do not overlap, and a duplex domain annealed to the other strand of the second partially double-stranded nucleic acid molecule, wherein the other strand of the second partially double-stranded nucleic acid molecule comprises: a duplex domain annealed to the other strand of the second partially double-stranded nucleic acid molecule and that is operably linked to the 5' end of the target nucleic acid molecule, a sample specific domain that identifies the biological sample from which the target nucleic acid was obtained, and a first cleavable moiety located between the duplex domain and the sample specific domain.

The present disclosure provides a composition comprising at least one molecular complex, wherein the at least one molecular complex comprises: (A) a target nucleic acid molecule obtained from a biological sample, and (B) at least two nucleic acid molecule complexes, wherein a first complex comprises a first partially double-stranded nucleic acid molecule, wherein one strand of the first partially double-stranded nucleic acid molecule comprises: a target specific domain hybridized to a first portion of the target nucleic acid molecule, a duplex domain annealed to the other strand of the first partially double-stranded nucleic acid molecule, and at least one first affinity moiety wherein the other strand of the first partially double-stranded nucleic acid molecule comprises: a duplex domain that is annealed to the other strand of the first partially double-stranded nucleic acid molecule and that is operably linked to the 3' end of the target nucleic acid molecule, a substrate specific domain that hybridizes to a complementary nucleic acid attached to a substrate, and at least one second affinity moiety, wherein the second complex comprises a second partially double-stranded nucleic acid molecule, wherein one strand of the second partially double-stranded nucleic acid molecule comprises: a target specific domain hybridized to a second portion of the target nucleic acid, wherein the first and the second portion do not overlap, and a duplex domain annealed to the other strand of the second partially double-stranded nucleic acid molecule, wherein the other strand of the second partially double-stranded nucleic acid molecule comprises: a duplex domain annealed to the other strand of the second partially double-stranded nucleic acid molecule and that is operably linked to the 5' end of the target nucleic acid molecule.

The present disclosure also provide a composition comprising: a planar solid support substrate; a first layer on the planar solid support substrate; a second layer on the first layer; wherein the second layer comprises a plurality of nanowells, wherein each nanowell provides access to an exposed portion of the first layer, wherein each nanowell comprises a plurality of first oligonucleotides covalently attached to the exposed portion of the first layer.

The present disclosure provides a sequencing probe comprising a target binding domain and a barcode domain; wherein the target binding domain comprises at least eight nucleotides and hybridizes to a target nucleic acid, wherein at least six nucleotides in the target binding domain identify a corresponding nucleotide in the target nucleic acid molecule and wherein at least two nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence that hybridizes to a complementary nucleic acid molecule, wherein the nucleic acid sequences of the at least three attachment positions determine the position and identity of the at least six nucleotides in the target nucleic acid that are bound by the target binding domain, and wherein each of the at least three attachment positions have a different nucleic acid sequence The present disclosure also provides a sequencing probe comprising a target binding domain and a barcode domain; wherein the target binding domain comprises at least eight nucleotides and hybridizes to a target nucleic acid, wherein at least six nucleotides in the target binding domain identify a corresponding nucleotide in the target nucleic acid molecule and wherein at least two nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment position comprising at least one nucleic acid sequence that hybridizes to a complementary nucleic acid molecule, wherein each attachment position of the at least three attachment positions nucleic acid, wherein at least six nucleotides in the target binding domain identify a corresponding nucleotide in the target nucleic acid molecule and wherein at least two nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence that hybridizes to a complementary nucleic acid molecule, wherein the nucleic acid sequences of the at least three attachment positions determine the position and identity of the at least six nucleotides in the target nucleic acid that are bound by the target binding domain, and wherein each of the at least three attachment positions have a different nucleic acid sequence; and a first complementary primary nucleic acid molecule hybridized to a first attachment position of the at least three attachment positions, wherein the first primary complementary nucleic acid molecule comprises at least two domains and a cleavable linker, wherein the first domain is hybridized to the first attachment position of the barcode domain and the second domain is capable of hybridizing to at least one complementary secondary nucleic acid molecule, and wherein the cleavable linker is

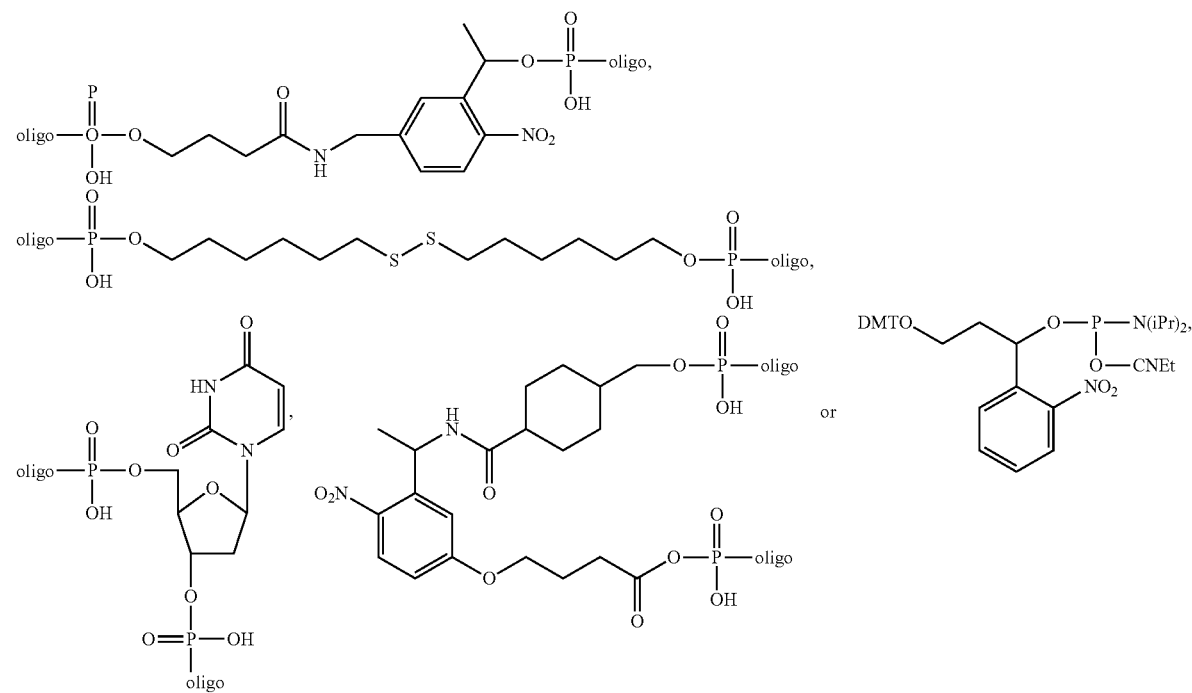

corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The present disclosure provides a complex comprising: a) a composition comprising a target binding domain and a barcode domain; wherein the target binding domain comprises at least eight nucleotides and hybridizes to a target and wherein the cleavable linker is located between the first and second domains.

The present disclosure provides a method for determining a nucleotide sequence of a nucleic acid comprising: (1) hybridizing the target binding domain of a first sequencing probe of the present disclosure to a first region of a target nucleic acid that is optionally immobilized to a substrate at one or more positions; (2) hybridizing a first complementary nucleic acid molecule comprising at least one first detectable label and at least one second detectable label to a first attachment position of the at least three attachment positions of the barcode domain; (3) identifying the at least one first and the at least one second detectable label of the first complementary nucleic acid molecule hybridized to the first attachment position; (4) removing the at least one first and the at least one second detectable label hybridized to the first attachment position; (5) hybridizing a second complementary nucleic acid molecule comprising at least one third detectable label and at least one fourth detectable label to a second attachment position of the at least three attachment positions of the barcode domain; (6) identifying the at least one third and the at least one fourth detectable label of the second complementary nucleic acid molecule hybridized to the second attachment position; (7) removing the at least one third and the at least one fourth detectable label hybridized to the second attachment position; (8) hybridizing a third complementary nucleic acid molecule comprising at least one fifth detectable label and at least one sixth detectable label to a third attachment position of the at least three attachment positions of the barcode domain; (9) identifying the at least one fifth and the at least one sixth detectable label of the third complementary nucleic acid molecule hybridized to the third attachment position; and (10) determining the nucleotide sequence of at least six nucleotides of the optionally immobilized target nucleic acid hybridized to the at least six nucleotides of the target binding domain of the first sequencing probe based on the identity of the at least one first detectable label, the at least one second detectable label, the at least one third detectable label, the at least one fourth detectable label, the at least one fifth detectable label and the at least one sixth detectable label.

The present disclosure provides a method for determining a nucleotide sequence of a nucleic acid comprising: (1) hybridizing the target binding domain of a first sequencing probe to a target nucleic acid that is optionally immobilized to a substrate at one or more positions; (2) hybridizing a first complementary nucleic acid molecule comprising at least one first detectable label and at least one second detectable label to a first attachment position of the at least three attachment positions of the barcode domain; (3) identifying the at least one first and the at least one second detectable label of the first complementary nucleic acid molecule hybridized to the first attachment position; (4) identifying the position and identity of a first nucleotide and a second nucleotide in the optionally immobilized target nucleic acid hybridized to two of the at least six nucleotides of the target binding domain based on the identity of the at least one first detectable label and the at least one second detectable label; (5) removing the at least one first and the at least one second detectable label hybridized to the first attachment position; (6) hybridizing a second complementary nucleic acid molecule comprising at least one third detectable label and at least one fourth detectable label to a second attachment position of the at least three attachment positions of the barcode domain; (7) identifying the at least one third and the at least one fourth detectable label of the second complementary nucleic acid molecule hybridized to the second attachment position; (8) identifying the position and identity of a third nucleotide and a fourth nucleotide in the optionally immobilized target nucleic acid hybridized to two of the at least six nucleotides of the target binding domain based on the identity of the at least one third detectable label and the at least one fourth detectable label; (9) removing the at least one third and the at least one fourth detectable label hybridized to the second attachment position; (10) hybridizing a third complementary nucleic acid molecule comprising at least one fifth detectable label and at least one sixth detectable label to a third attachment position of the at least three attachment positions of the barcode domain; (11) identifying the at least one fifth and the at least one sixth detectable label of the third complementary nucleic acid molecule hybridized to the third attachment position; and (12) identifying the position and identity of a fifth nucleotide and a sixth nucleotide in the optionally immobilized target nucleic acid hybridized to two of the at least six nucleotides of the target binding domain based on the identity of the at least one fifth detectable label and the at least one sixth detectable label; thereby determining the nucleotide sequence of at least six nucleotides of the optionally immobilized target nucleic acid hybridized to the at least six nucleotides of the target binding domain of the first sequencing probe.

The present disclosure also provides a method for identifying the presence of a predetermined nucleotide sequence in a target nucleic acid comprising: (1) hybridizing the target binding domain of a first sequencing probe of the present disclosure to a first region of a target nucleic acid that is optionally immobilized to a substrate at one or more positions; (2) hybridizing a first complementary nucleic acid molecule comprising at least one first detectable label and at least one second detectable label to a first attachment position of the at least three attachment positions of the barcode domain; (3) identifying the at least one first and the at least one second detectable label of the first complementary nucleic acid molecule hybridized to the first attachment position; (4) removing the at least one first and the at least one second detectable label hybridized to the first attachment position; (5) hybridizing a second complementary nucleic acid molecule comprising at least one third detectable label and at least one fourth detectable label to a second attachment position of the at least three attachment positions of the barcode domain; (6) identifying the at least one third and the at least one fourth detectable label of the second complementary nucleic acid molecule hybridized to the second attachment position; (7) removing the at least one third and the at least one fourth detectable label hybridized to the second attachment position; (8) hybridizing a third complementary nucleic acid molecule comprising at least one fifth detectable label and at least one sixth detectable label to a third attachment position of the at least three attachment positions of the barcode domain; (9) identifying the at least one fifth and the at least one sixth detectable label of the third complementary nucleic acid molecule hybridized to the third attachment position, thereby determining the presence of the predetermined nucleotide sequence based on the identity of the at least one first detectable label, the at least one second detectable label, the at least one third detectable label, the at least one fourth detectable label, the at least one fifth detectable label and the at least one sixth detectable label.

The present disclosure provides a kit comprising: (A) a first nucleic acid molecule complex comprising a first partially double-stranded nucleic acid molecule, wherein one strand of the first partially double-stranded nucleic acid molecule comprises: a target specific domain that hybridizes to a first portion of a target nucleic acid molecule, a duplex domain annealed to the other strand of the first partially double-stranded nucleic acid molecule, at least one first affinity moiety, wherein the other strand of the first partially double-stranded nucleic acid molecule comprises: a duplex domain that is annealed to the other strand of the first partially double-stranded nucleic acid molecule, substrate specific domain that hybridizes to a complementary nucleic acid attached to a substrate, and at least one second affinity moiety; (B) a second nucleic acid molecule complex comprising a second partially double-stranded nucleic acid molecule, wherein one strand of the second partially double-stranded nucleic acid molecule comprises: a target specific domain that hybridizes to a second portion of the target nucleic acid, wherein the first and the second portion do not overlap, and a duplex domain annealed to the other strand of the second partially double-stranded nucleic acid molecule, and wherein the other strand of the second partially double-stranded nucleic acid molecule comprises: a duplex domain annealed to the other strand of the second partially double-stranded nucleic acid molecule, a sample specific domain that identifies the biological sample from which a target nucleic acid was obtained, a substrate specific domain that hybridizes to a complementary nucleic acid attached to a substrate, a first single-stranded purification sequence, a first cleavable moiety located between the duplex domain and the sample specific domain, and a second cleavable moiety located between the sample specific domain and the first single-stranded purification sequence.

The present disclosure also provides a kit comprising: a first single-stranded nucleic acid molecule comprising: a target specific domain that hybridizes to a first portion of a target nucleic acid molecule, a duplex domain that anneals to the duplex domain of a second single-stranded nucleic acid molecule, and at least one first affinity moiety, (B) a second single-stranded nucleic acid molecule comprising: a duplex domain that anneals to the duplex domain of the first single-stranded nucleic acid molecule, a substrate specific domain that hybridizes to a complementary nucleic acid attached to a substrate, and at least one second affinity moiety, (C) a third single-stranded nucleic acid molecule comprising: a target specific domain that hybridizes to a second portion of a target nucleic acid, wherein the first and the second portion do not overlap, and a duplex domain that anneals to the duplex domain of a fourth single-stranded nucleic acid molecule, (D) a fourth single-stranded nucleic acid molecule comprising: a duplex domain that anneals to the duplex domain of the third single-stranded nucleic acid molecule, a sample specific domain that identifies the biological sample from which a target nucleic acid was obtained, a first single-stranded purification sequence, a first cleavable moiety located between the duplex domain and the sample specific domain, and a second cleavable moiety located between the sample specific domain and the first single-stranded purification sequence.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and further features will be more clearly appreciated from the following detailed description when taken in conjunction with the accompanying drawings.

FIG. 5 is a schematic illustration of several exemplary reporter probes of the present disclosure comprising different arrangements of tertiary nucleic acids.

FIGS. 11A and 11B are schematic illustrations of one cycle of the sequencing method of the present disclosure and the corresponding imaging data collected during this cycle.

FIG. 15 is an illustrative example of an exemplary sequencing cycle of the present disclosure in which a position within a barcode domain is darkened by displacement of the primary nucleic acids.

FIG. 17 shows how multiple base calls for a specific nucleotide position on the target nucleic acid, recorded from one or more sequencing probes, can be combined to create a consensus sequence, thereby increasing the accuracy of the final base call.

FIGS. 66A, 66B, 66C and 66D are a series of charts showing the results of sequencing experiments using LG-spaced sequencing probes and D-pocket sequencing probes of the present disclosure. The leftmost panels of FIG. 66A and FIG. 66C show the number of on-target, new hexamer, redundant hexamer, off-target and invalid events recorded in each cycle of the sequencing experiments. Cycles 1-50 were performed using D-pocket sequencing probes and cycles 51-100 were performed using LG-spaced sequencing probes of the present disclosure.

DETAILED DESCRIPTION OF THE INVENTION

Figure 1:
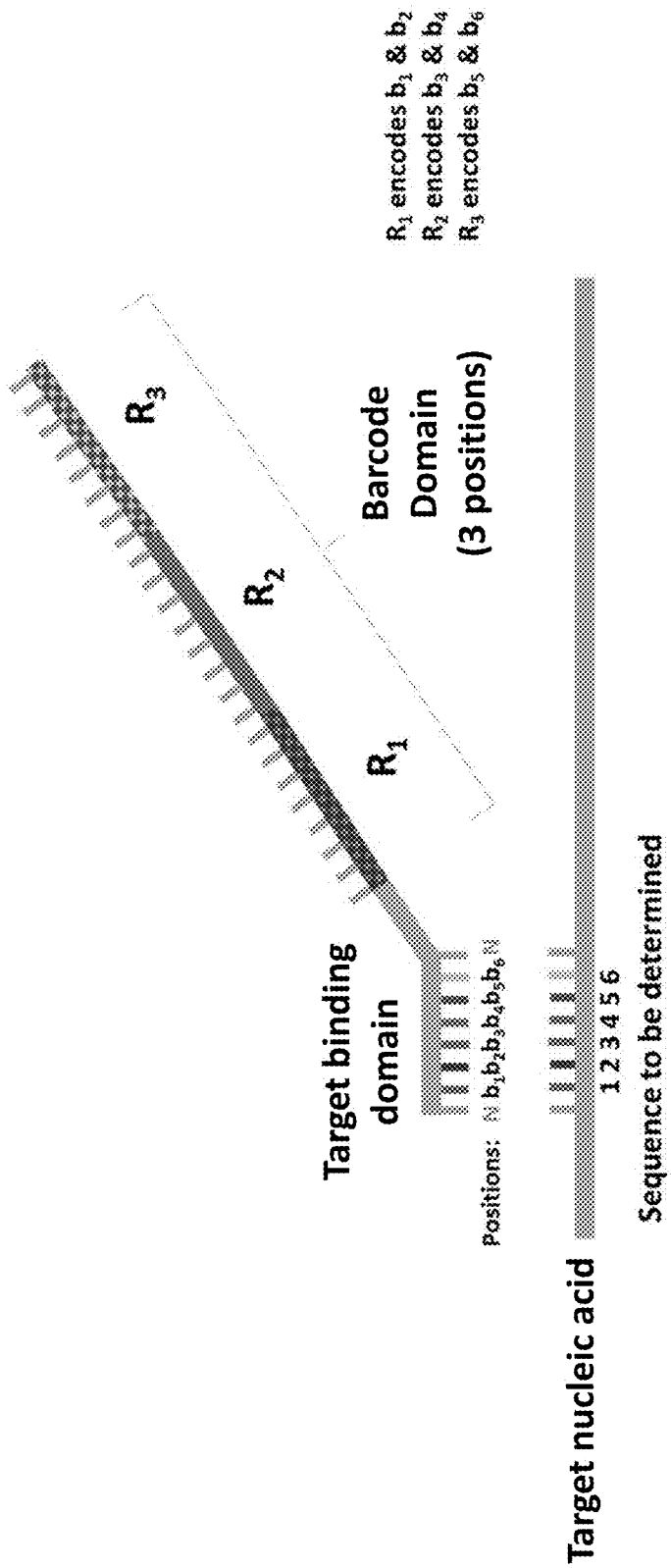
FIG. 1 is an illustration of one exemplary sequencing probe of the present disclosure.

The present disclosure provides sequencing probes, reporter probes, methods, kits, and apparatuses that provide rapid, enzyme-free, amplification-free, and library-free nucleic acid sequencing that has long-read-lengths and with low error rate.

Compositions of the Present Disclosure

The present disclosure provides a sequencing probe comprising a target binding domain and a barcode domain; wherein the target binding domain comprises any of the constructs recited in Table 1. An exemplary target binding domain comprises at least eight nucleotides and is capable of hybridizing to a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein any of the at least six nucleotides in the target binding domain can be modified nucleotides or nucleotide analogues and wherein the at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases. An exemplary barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

In other aspects, an exemplary target binding domain can comprise at least six nucleotides capable of hybridizing to a target nucleic acid, wherein the at least six nucleotides in the target binding domain are capable of identifying a corresponding (complementary) nucleotide in the target nucleic acid molecule; wherein any of the at least six nucleotides in the target binding domain can be modified nucleotides or nucleotide analogues.

The present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The present disclosure also provides a population of sequencing probes comprising a plurality of any of the sequencing probes disclosed herein.

The target binding domain, barcode domain, and backbone of the disclosed sequencing probes, as well as, the complementary nucleic acid molecule (e.g., reporter molecules or reporter complexes) are described in more detail below.

A sequencing probe of the present disclosure comprises a target binding domain and a barcode domain. FIG. 1 is a schematic illustration of an exemplary sequencing probe of the present disclosure. FIG. 1 shows that the target binding domain is capable of binding a target nucleic acid. A target nucleic acid can be any nucleic acid to which the sequencing probe of the present disclosure can hybridize. The target nucleic acid can be DNA or RNA. The target nucleic acid can be obtained from a biological sample from a subject. The terms "target binding domain" and "sequencing domain" are used interchangeably herein.

The target binding domain can comprise a series of nucleotides (e.g. is a polynucleotide). The target binding domain can comprise DNA, RNA, or a combination thereof. In the case when the target binding domain is a polynucleotide, the target binding domain binds to a target nucleic acid by hybridizing to a portion of the target nucleic acid that is complementary to the target binding domain of the sequencing probe, as shown in FIG. 1.

The target binding domain of the sequencing probe can be designed to control the likelihood of sequencing probe hybridization and/or de-hybridization and the rates at which these occur. Generally, the lower a probe's Tm, the faster and more likely that the probe will de-hybridize to/from a target nucleic acid. Thus, use of lower Tm probes will decrease the number of probes bound to a target nucleic acid.

The length of a target binding domain, in part, affects the likelihood of a probe hybridizing and remaining hybridized to a target nucleic acid. Generally, the longer (greater number of nucleotides) a target binding domain is, the less likely that a complementary sequence will be present in the target nucleotide. Conversely, the shorter a target binding domain is, the more likely that a complementary sequence will be present in the target nucleotide. For example, there is a 1/256 chance that a four-mer sequence will be located in a target nucleic acid versus a 1/4096 chance that a six-mer sequence will be located in the target nucleic acid. Consequently, a collection of shorter probes will likely bind in more locations for a given stretch of a nucleic acid when compared to a collection of longer probes.

In circumstances, it is preferable to have probes having shorter target binding domains to increase the number of reads in the given stretch of the nucleic acid, thereby enriching coverage of a target nucleic acid or a portion of the target nucleic acid, especially a portion of particular interest, e.g., when detecting a mutation or SNP allele.

The target binding domain can be any amount or number of nucleotides in length. The target binding domain can be at least 12 nucleotides in length, at least 10 nucleotides in length, at least 8 nucleotides in length, at least 6 nucleotides in length or at least three nucleotides in length.

Each nucleotide in the target binding domain can identify (or code for) a complementary nucleotide of the target molecule. Alternatively, some nucleotides in the target binding domain identify (or code for) a complementary nucleotide of the target molecule and some nucleotides in the target binding domain do not identify (or code for) a complementary nucleotide of the target molecule.

The target binding domain can comprise at least one natural base. The target binding domain can comprise no natural bases. The target binding domain can comprise at least one modified nucleotide or nucleic acid analog. The target binding domain can comprise no modified nucleotides or nucleic acid analogs. The target binding domain can comprise at least one universal base. The target binding domain can comprise no universal bases. The target binding domain can comprise at least one degenerate base. The target binding domain can comprise no degenerate bases.

The target domain can comprise any combination natural bases (e.g. 0, 1, 2, 3, 4, 5, 6, 7, 8, 9, 10, or more natural bases), modified nucleotides or nucleic acid analogs (e.g. 0, 1, 2, 3, 4, 5, 6, 7, 8, 9, 10, or more modified nucleotides or nucleic acid analogs), universal bases (e.g. 0, 1, 2, 3, 4, 5, 6, 7, 8, 9, 10, or more universal bases), or degenerate bases (e.g. 0, 1, 2, 3, 4, 5, 6, 7, 8, 9, 10, or more degenerative bases). When present in a combination, the natural bases, modified nucleotides or nucleic acid analogs, universal bases and degenerate bases of a particular target binding domain can be arranged in any order.

The terms "modified nucleotides" or "nucleic acid analogues" include, but are not limited to, locked nucleic acids (LNA), bridged nucleic acids (BNA), propyne-modified nucleic acids, zip nucleic acids (ZNA®), isoguanine, isocytosine 6-amino-1-(4-hydroxy-5-hydroxy methyl-tetrahydrofuran-2-yl)-1,5-dihydro-pyrazolo[3,4-d]pyrimidin-4-one (PPG) and 2'-modified nucleic acids such as 2'-O-methyl nucleic acids. The target binding domain can include zero to six (e.g. 0, 1, 2, 3, 4, 5 or 6) modified nucleotides or nucleic acid analogues. Preferably, the modified nucleotides or nucleic acid analogues are locked nucleic acids (LNAs).

The term "locked nucleic acids (LNA)" as used herein includes, but is not limited to, a modified RNA nucleotide in which the ribose moiety comprises a methylene bridge connecting the 2' oxygen and the 4' carbon. This methylene bridge locks the ribose in the 3'-endo confirmation, also known as the north confirmation, that is found in A-form RNA duplexes. The term inaccessible RNA can be used interchangeably with LNA. The term "bridged nucleic acids (BNA)" as used herein includes, but is not limited to, modified RNA molecules that comprise a five-membered or six-membered bridged structure with a fixed 3'-endo confirmation, also known as the north confirmation. The bridged structure connects the 2' oxygen of the ribose to the 4' carbon of the ribose. Various different bridge structures are possible containing carbon, nitrogen, and hydrogen atoms. The term "propyne-modified nucleic acids" as used herein includes, but is not limited to, pyrimidines, namely cytosine and thymine/uracil, that comprise a propyne modification at the C5 position of the nucleic acid base. The term "zip nucleic acids) (ZNA®)" as used herein includes, but is not limited to, oligonucleotides that are conjugated with cationic spermine moieties.

The term "universal base" as used herein includes, but is not limited to, a nucleotide base does not follow Watson-Crick base pair rules but rather can bind to any of the four canonical bases (A, T/U, C, G) located on the target nucleic acid. The term "degenerate base" as used herein includes, but is not limited to, a nucleotide base that does not follow Watson-Crick base pair rules but rather can bind to at least two of the four canonical bases A, T/U, C, G), but not all four. A degenerate base can also be termed a Wobble base; these terms are used interchangeably herein.

The exemplary sequencing probe depicted in FIG. 1 illustrates a target binding domain that comprises a six nucleotide long (6-mer) sequence ($b_1$-$b_2$-$b_3$-$b_6$) that hybridizes specifically to complementary nucleotides 1-6 of the target nucleic acid that is to be sequenced. This 6-mer portion of the target binding domain ($b_1$-$b_2$-$b_3$-$b_6$) identifies (or codes for) the complementary nucleotides in the target sequence (1-2-3-4-5-6). This 6-mer sequence is flanked on either side by a base (N). The bases indicated by (N) may independently be a universal or degenerate base. Typically, the bases indicated by (N) are independently one of the canonical bases. The bases indicated by (N) do not identify (or code for) the complementary nucleotide it binds in the target sequence and are independent of the nucleic acid sequence of the (6-mer) sequence ($b_1$-$b_2$-$b_3$-$b_6$).

The sequencing probe depicted in FIG. 1 can be used in conjugation with the sequencing methods of the present disclosure to sequence target nucleic acids using only hybridization reactions, no covalent chemistry, enzymes or amplification is needed. To sequence all possible 6-mer sequences in a target nucleic acid molecule, a total of 4096 sequencing probes are needed (4^6=4096).

FIG. 1 is exemplary for one configuration of a target binding domain of the sequence probe of the present disclosure. Table 1 provides several other configurations of target binding domains of the present disclosure. One preferred target binding domain, called the "6 LNA" target binding domain, comprises 6 LNAs at positions b1 to b6 of the target binding domain. These 6 LNAs are flanked on either side by a base (N). As used herein, an (N) base can be a universal/degenerate base or a canonical base that is independent of the nucleic acid sequence of the (6-mer) sequence ($b_1$-$b_2$-$b_3$-$b_4$-$b_5$-$b_6$). In other words, while the bases $b_1$-$b_2$-$b_3$-$b_4$-$b_5$-$b_6$ may be specific to any given target sequence, the (N) bases can be a universal/degenerate base or composed of any of the four canonical bases that is not specific to the target dictated by bases $b_1$-$b_2$-$b_3$-$b_4$-$b_5$-$b_6$. For example, if the target sequence to be interrogated is CAGG-CATA bases $b_1$-$b_2$-$b_3$-$b_4$-$b_5$-$b_6$ of the target binding domain would be TCCGTA while each of the (N) bases of the target binding domain could independently be A, C, T or G such that a resulting target binding domain could have the sequence ATCCGTAG, TTCCGTAC, GTCCGTAG or any of the other 16 possible iterations. Alternatively, the two (N) bases could proceed the 6 LNAs. Alternatively still, the two (N) bases could follow the 6 LNAs.

TABLE 1

| Target Binding Domain Bases | | B1 | B2 | B3 | B4 | B5 | B6 | | |
|---|---|---|---|---|---|---|---|---|---|
| "6mer" | | b | b | b | b | b | b | | |
| "8mer" | b | b | b | b | b | b | b | | |
| "10mer" | b | b | b | b | b | b | b | b | b |
| "Natural I" | N | N | b | b | b | b | b | b | N | N |
| "Natural II" | | N | b | b | b | b | b | b | N |
| "2 LNA" | | N | b | b | + | + | b | b | N |
| | | N | b | + | b | b | + | b | N |
| | | N | + | b | b | b | b | + | N |
| "4 LNA" | | N | + | + | b | b | + | + | N |
| | | N | + | b | + | + | b | + | N |
| | | N | b | + | + | + | + | b | N |
| "6 LNA" | | | + | + | + | + | + | + | |
| | | N | + | + | + | + | + | + | N |
| "8mer with LNA" | | N | b/+ | b/+ | b/+ | b/+ | b/+ | b/+ | N |
| "MGB" | | Q | b | b | b | b | b | b | |
| | Q | b | b | b | b | b | b | b | | b = natural base;
+ = modified nucleotide or nucleotide analog (e.g. LNA, 2-O'-methyl-modified bases, 6-amino-1-(4-hydroxy-5-hydroxy methyl-tetrahydro-furan-2-yl)-1,5-dihydro-pyrazolo[3,4-d]pyrimidin-4-one (PPG));
N = natural, universal or degenerate base; Q is a minor groove binder (e.g. Twisted Intercalating Nucleic Acid, MGB-BP3, Brostallicin)

Table 1 also describes a "10 mer" target binding domain that comprises 10 natural, target-specific bases. Table 1 also describes an "8 mer" target binding domain that comprises 8 natural, target-specific bases.

Table 1 further describes the "Natural I" target binding domain that comprises 6 natural bases at positions b1 to b6. These 6 natural bases are flanked on either side by 2 (N) bases. Alternatively, all four (N) bases could proceed the 6 natural bases. Alternatively still, all four (N) bases could follow the 6 natural bases. Any number of the four (N) bases (i.e. 1, 2, 3 or 4) could proceed the 6 natural bases while the remaining (N) bases would follow the 6 natural bases.

Table 1 further describes the "Natural II" target binding domain that comprises 6 natural bases at positions b1 to b6. These 6 natural bases are flanked on either side by an (N) base. Alternatively, both (N) bases could proceed the 6 natural bases. Alternatively still, both (N) bases could follow the 6 natural bases. Typically the (N) bases of the Natural II binding domain are degenerate bases.

Table 1 also describes a "2 LNA" target binding domain that comprises a combination of 2 LNAs and 4 natural bases at positions b1 to b6 of the target binding domain. The 2 LNAs and 4 natural bases can occur in any order. For example, the positions b3 and b4 can be LNAs while positions b1, b2, b5 and b6 are natural bases. Bases b1 to b6 are flanked on either side by a (N) base. Alternatively, bases b1 to b6 can be proceeded by two (N) bases. Alternatively still, bases b1 to b6 can be followed by two (N) bases.

Table 1 further describes a "4 LNA" target binding domain that comprises a combination of 4 LNAs and 2 natural bases at positions b1 to b6 of the target binding domain. The 4 LNAs and 2 natural bases can occur in any order. For example, the positions b2 to b5 can be LNAs while positions b1 and b6 are natural bases. Bases b1 to b6 are flanked on either side by a (N) base. Alternatively, bases b1 to b6 can be proceeded by two (N) bases. Alternatively still, bases b1 to b6 can be followed by two (N) bases.

Table 1 further describes a "6 LNA" target binding domain that comprises 6 LNAs at positions b1 to b6 of the target binding domain. Bases b1 to b6 can be flanked on either side by a (N) base.

Table 1 further describes a "8mer with LNA" target binding domain that individually comprises either a natural base or an LNA at any of the positions b1 to b6 of the target binding domain. Bases b1 to b6 can be flanked on either side by a (N) base.

The target binding domain can also comprise a minor-groove binder moiety. A minor-groove binder moiety is a chemical modification of an oligonucleotide that adds a chemical moiety that can bind to the minor groove of the target nucleotide to which the oligonucleotide is hybridized. Without being bound by theory, the inclusion of a minor-groove binder moiety increases the affinity of a target binding domain for a target nucleic acid, increasing the melting temperature of the target binding domain-target nucleic acid duplex. The higher binding affinity can allow for use of a smaller target binding domain.

The target binding domain can also comprise one or more twisted intercalating nucleic acids (TINAs). A TINA is a nucleic acid molecule that stabilizes the formation of Hoogsteen triplex DNA from double-stranded oligonucleotides and triplex-forming oligonucleotides. TINAs can be used to stabilize a double-stranded oligonucleotides, thereby improving the specificity and sensitivity of an oligonucleotide probe to a target nucleic acid.

The target binding domain can also comprise nucleic acid molecules comprising a 2'-O-methyl-modified base. A 2'-O-methyl-modified base is a nucleoside modification of RNA in which a methyl group is added to the 2' hydroxyl group of the ribose to produce a 2' methoxy group. A 2'-O-methyl-modified base offers superior protection against base hydrolysis and digestion by nucleases. Without being bound by theory, the addition of a 2'-O-methyl-modified base also increases the melting temperature of a nucleic acid duplex.

The target binding domain can also comprise a covalently linked stilbene modification. A stilbene modification can increase the stability of a nucleic acid duplex.

The sequencing probe of the present disclosure comprises a synthetic backbone. The target binding domain, also described herein as the sequencing domain, and the barcode domain are operably linked. The target binding domain and barcode domain can be covalently attached, as part of one synthetic backbone. The target binding domain and barcode domain can be attached via a linker (e.g., nucleic acid linker, chemical linker). The synthetic backbone can comprise any material, e.g., polysaccharide, polynucleotide, polymer, plastic, fiber, peptide, peptide nucleic acid, or polypeptide. Preferably, the synthetic backbone is rigid. The synthetic backbone can comprise a single-stranded DNA molecule. The backbone can comprise "DNA origami" of six DNA double helices (See, e.g., Lin et al, "Submicrometre geometrically encoded fluorescent barcodes self-assembled from DNA." *Nature Chemistry*; 2012 October; 4(10): 832-9). A barcode can be made of DNA origami tiles (Jungmann et al, "Multiplexed 3D cellular super-resolution imaging with DNA-PAINT and Exchange-PAINT", *Nature Methods*, Vol. 11, No. 3, 2014).

The sequencing probe of the present disclosure can comprise a partially double-stranded synthetic backbone. The sequencing probe can comprise a single-stranded DNA synthetic backbone and a double-stranded DNA spacer between the target binding domain and the barcode domain. The double-stranded DNA spacer can comprise at least one modified nucleotide or nucleic acid analogue. Typical modified nucleotides or nucleic acid analogues useful in the double-stranded DNA spacer are isoguanine and isocytosine. Alternatively still, each of the nucleic acids comprising the double-stranded DNA spacer can independently be L-DNA. In some aspects, a double-stranded DNA spacer can comprise L-DNA. A double-stranded DNA spacer can consist of L-DNA. A double-stranded DNA spacer can consist essentially of L-DNA.

A double-stranded DNA spacer can comprise about 1 nucleotide to about 100 nucleotides in length. A double-stranded DNA spacer can comprise about 25 nucleotides in length.

A synthetic backbone can comprise L-DNA. A synthetic backbone can consist of L-DNA. A synthetic backbone can consist essentially of L-DNA. A single-stranded DNA synthetic backbone can comprise about 10 nucleotides to about 100 nucleotides in length. A single-stranded DNA synthetic backbone can comprise about 52 nucleotides in length. A single-stranded DNA synthetic backbone can comprise about 27 nucleotides in length.

A barcode domain can comprise L-DNA. A barcode domain can consist of L-DNA. A barcode domain can consist essentially of L-DNA. A barcode domain can comprise about 27 nucleotides, or about 52 nucleotides, or about 99 nucleotides, or about 74 nucleotides. A barcode domain can be about 27 nucleotides, or about 52 nucleotides, or about 99 nucleotide or about 74 nucleotides in length.

The sequencing probe can comprise a single-stranded DNA synthetic backbone and a polymer-based spacer, with similar mechanical properties as double-stranded DNA, between the target binding domain and the barcode domain. Typical polymer-based spacers include polyethylene glycol (PEG) type polymers.

The double-stranded DNA spacer can be from about 1 nucleotide to about 100 nucleotides in length; from about 2 nucleotides to about 50 nucleotides in length; from about 20 nucleotides to about 40 nucleotides in length. Preferably, the double-stranded DNA spacer is about 36 nucleotides in length.

Figure 2:
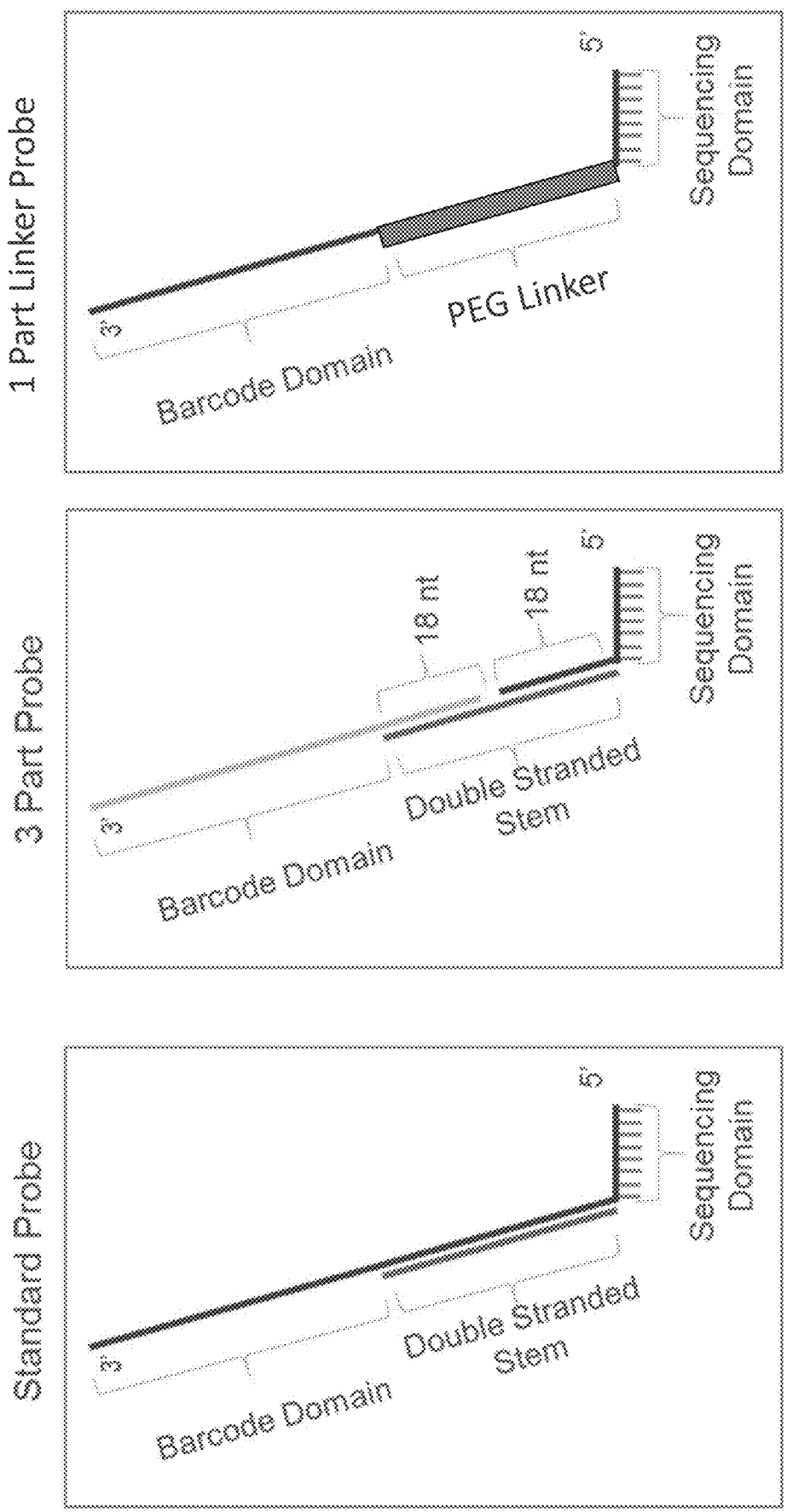
FIG. 2 shows the design of standard, three-part sequencing and one-part linker probes of the present disclosure.

One sequencing probe of the present disclosure, termed a "standard probe" is illustrated in the left panel of FIG. 2. The standard probe of FIG. 2 comprises a barcode domain covalently attached to the target binding domain, such that the target binding and barcode domains are present within the same single stranded oligonucleotide. In FIG. 2, left panel, the single stranded oligonucleotide binds to a stem oligonucleotide to create a 36 nucleotide long double-stranded spacer region called the stem. Using this architecture, each sequencing probe in a pool of probes can hybridize to the same stem sequence.

In alternative aspects, each of the nucleic acids comprising the barcode domain and the region that binds to the stem oligo nucleotide of a standard probe can be a canonical base or a modified nucleotide or nucleic acid analogue. Typical modified nucleotides or nucleic acid analogues useful in the barcode domain and the region that binds to the stem oligo nucleotide of a standard probe are isoguanine and isocytosine. Alternatively still, each of the nucleic acids comprising the barcode domain and the region that binds to the stem oligo nucleotide of a standard probe can independently be L-DNA. For example, the barcode domain and the region that binds to the stem oligo nucleotide of a standard probe can be comprised entirely of L-DNA. In other examples, the barcode domain and the region that binds to the stem oligo nucleotide of a standard probe can be comprised of segments of L-DNA separated by segments of single-stranded nucleic acid that is abasic or segments of a polymer with similar mechanical properties as double-stranded DNA such as PEG further described below.

Another sequencing probe of the present disclosure, termed a "3 Part Probe" is illustrated in the middle panel of FIG. 2. The 3 Part Probe of FIG. 2 comprises a barcode domain that is attached to the target binding domain via a linker. In this example, the linker is a single stranded stem oligonucleotide that hybridizes to the single stranded oligonucleotide that contains the target binding domain and the single stranded oligonucleotide that contains the barcode domain, creating a 36 nucleotide long double stranded spacer region that bridges the barcode domain (18 nucleotides) and target binding domain (18 nucleotides). Using this exemplary probe configuration, in order to prevent the exchange of barcode domains, each barcode can be designed such that it hybridizes to a unique stem sequence. Furthermore, each barcode domain can also be hybridized to its corresponding stem oligonucleotide prior to pooling together different sequencing probes.

In alternative aspects, each of the nucleic acids comprising the single stranded stem oligonucleotide can be a canonical base or a modified nucleotide or nucleic acid analogue. Typical modified nucleotides or nucleic acid analogues useful in the single stranded stem oligonucleotide are isoguanine and isocytosine. Alternatively still, each of the nucleic acids comprising the single stranded stem oligonucleotide can independently be L-DNA.

In alternative aspects, each of the nucleic acids comprising the region on the barcode domain to which the single stranded stem oligonucleotide hybridizes can be a canonical base or a modified nucleotide or nucleic acid analogue. Typical modified nucleotides or nucleic acid analogues useful in the single stranded stem oligonucleotide are isoguanine and isocytosine. Alternatively still, each of the nucleic acids comprising the region on the barcode domain to which the single stranded stem oligonucleotide hybridizes can independently be L-DNA.

In alternative aspects, each of the nucleic acids comprising the region on the single stranded oligonucleotide that contains the target binding domain to which the single stranded stem oligonucleotide hybridizes can be a canonical base or a modified nucleotide or nucleic acid analogue. Typical modified nucleotides or nucleic acid analogues useful in the single stranded stem oligonucleotide are isoguanine and isocytosine. Alternatively still, each of the nucleic acids comprising the region on the single stranded oligonucleotide that contains the target binding domain to which the single stranded stem oligonucleotide hybridizes can independently be L-DNA.

Another sequencing probe of the present disclosure, termed a "1-Part Linker Probe" is illustrated in the right panel of FIG. 2. The 1-Part Linker Probe of FIG. 2 comprises a barcode domain that is attached to the target binding domain via a linker. In this example, the linker is a PEG molecule. Alternatively, the linker could be trans-stilbene. Alternatively still, the linker can be any polymer with similar mechanical properties as double-stranded DNA. Typical polymer-based spacers include polyethylene glycol (PEG) type polymers.

A sequencing probe of the present disclosure can comprise about 60 nucleotides. A sequencing probe of the present disclosure can comprise about 107 nucleotides. A sequencing probe of the present disclosure can be about 60 nucleotides in length, or about 107 nucleotides in length. The nucleotides comprising a sequencing probe can each individually be a canonical base a modified nucleotide or nucleic acid analogue including L-DNA and D-DNA.

A barcode domain comprises a plurality of attachment positions, e.g., one, two, three, four, five, six, seven, eight, nine, ten, or more attachment positions. The number of attachment positions can be less than, equal to, or more than the number of nucleotides in the target binding domain. The target binding domain can comprise more nucleotides than number of attachment positions in the backbone domain, e.g., one, two, three, four, five, six, seven, eight, nine, ten, or more nucleotides. The target binding domain can comprise eight nucleotides and the barcode domain comprises three attachment positions. The target binding domain can comprise ten nucleotides and the barcode domain comprises three attachment positions The length of the barcode domain is not limited as long as there is sufficient space for at least three attachment positions, as described below. The terms "attachment positions," "positions" and "spots," are used interchangeably herein. The terms "barcode domain" and "reporting domain," are used interchangeably herein.

Each attachment position in the barcode domain corresponds to two nucleotides (a dinucleotide) in the target binding domain and, thus, to the complementary dinucleotide in the target nucleic acid that is hybridized to the dinucleotide in the target binding domain. As a non-limiting example, the first attachment position in the barcode domain corresponds to the first and second nucleotides in the target binding domain (e.g., FIG. 1 where R1 is the first attachment position in the barcode domain and R1 corresponds to dinucleotide b1 and b2 in the target binding domain—which in turn identifies dinucleotides 1 and 2 of the target nucleic acid); the second attachment position in the barcode domain corresponds to the third and fourth nucleotides in the target binding domain (e.g., FIG. 1 where R2 is the second attachment position in the barcode domain and R2 corresponds to dinucleotide b3 and b4 in the target binding domain—which in turn identifies dinucleotides 3 and 4 of the target nucleic acid); and the third attachment position in the barcode domain corresponds to the fifth and sixth nucleotides in the target binding domain (e.g., FIG. 1 where R3 is the third attachment position in the barcode domain and R3 corresponds to dinucleotide b5 and b6 in the target binding domain—which in turn identifies dinucleotide 5 and 6 of the target nucleic acid). In a further non-limiting example, the first attachment position in the barcode domain, the second attachment position in the barcode domain and the third attachment position in the barcode domain collectively correspond to the first through sixth nucleotides in the target binding domain (e.g., FIG. 1 where nucleotides b1 to b6 in the target binding domain—which in turn identifies six nucleotides of the target nucleic acid).

Each attachment position in the barcode domain comprises at least one attachment region, e.g., one to 50, or more, attachment regions. Certain positions in a barcode domain can have more attachment regions than other positions (e.g., a first attachment position can have three attachment regions whereas a second attachment position can have two attachment positions); alternately, each position in a barcode domain has the same number of attachment regions. Each attachment position in the barcode domain can comprise one attachment region. Each attachment position in the barcode domain can comprise more than one attachment region. At least one of the at least three attachment positions in the barcode domain can comprise a different number of attachment regions than the other two attachments positions in the barcode domain. In some aspects, each attachment position in a barcode domain can comprise one attachment region.

Each attachment region comprises at least one (i.e., one to fifty, e.g., ten to thirty) copies of a nucleic acid sequence(s) capable of being reversibly bound by a complementary nucleic acid molecule (e.g., DNA or RNA). The nucleic acid sequences of attachment regions at a single attachment position can be identical; thus, the complementary nucleic acid molecules that bind those attachment regions are identical. Alternatively, the nucleic acid sequences of attachment regions at a position are not identical; thus, the complementary nucleic acid molecules that bind those attachment regions are not identical.

The nucleic acid sequence comprising each attachment region in a barcode domain can be about 6 nucleotides to about 20 nucleotides in length. The nucleic acid sequence comprising each attachment region in a barcode domain can be about 12 nucleotides in length. The nucleic acid sequence comprising each attachment region in a barcode domain can be about 16 nucleotides in length. The nucleic acid sequence comprising each attachment region in a barcode domain can be about 14 nucleotides in length. The nucleic acid sequence comprising each attachment region in a barcode domain can be about 8 nucleotides in length. The nucleic acid sequence comprising each attachment region in a barcode domain can be about 9 nucleotides in length.

An attachment position, an attachment region or at least one nucleic acid sequence of an attachment region can comprise at least one super T base (5-hydroxybutynl-2'-deoxyuridine). An attachment position, an attachment region or at least one nucleic acid sequence of an attachment region can comprise at least one 3' terminal super T base (5-hydroxybutynl-2'-deoxyuridine). An attachment position, an attachment region or at least one nucleic acid sequence of an attachment region can comprise at least one 5' terminal super T base (5-hydroxybutynl-2'-deoxyuridine).

Each of the nucleic acids comprising each attachment region in a barcode domain can independently be a canonical base or a modified nucleotide or nucleic acid analogue. At least one, at least two, at least three, at least four, at least five, or at least six nucleotides in the attachment region in a barcode domain can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the attachment region in a barcode domain are isoguanine and isocytosine. The use of modified nucleotides or nucleotide analogues such as isoguanine and isocytosine, for example, can improve binding efficiency and accuracy of the reporter to the appropriate attachment region in a barcode domain while minimizing binding elsewhere, including to the target.

One or more attachment regions within a barcode domain can comprise L-DNA. L-DNA is the left-turning and mirror image version of naturally occurring, right-turning D-DNA. L-DNA is more stable and resistant to enzymatic digestion. Since L-DNA cannot hybridize to D-DNA, L-DNA can improve binding efficiency and binding accuracy of the reporter to the appropriate attachment region in the barcode domain and prevent binding of the reporter elsewhere on the sequencing probe. In some aspects, each nucleotide of the at least one nucleic acid sequence of an attachment position can be L-DNA.

Each of the nucleic acids comprising each attachment region in a barcode domain can independently comprise an Adenine, a Cytosine, a Guanine, or a Thymine base. Alternatively, each of the nucleic acids comprising each attachment region in a barcode domain can independently comprise an Adenine, a Guanine or a Thymine base.

Each of the nucleic acid sequences comprising each attachment region in a barcode domain can comprise at least one adenine nucleotide, at least one thymine nucleotide, at least one cytosine nucleotide or any combination thereof and a 3' terminal guanosine nucleotide. Each of the nucleic acid sequences comprising each attachment region in a barcode domain can consist of at least one adenine nucleotide, at least on thymine nucleotide, at least one cytosine nucleotide or any combination thereof and a 3' terminal guanosine nucleotide. Each of the nucleic acid sequences comprising each attachment region in a barcode domain can consist essentially of at least one adenine nucleotide, at least one thymine nucleotide, at least one cytosine nucleotide or any combination thereof and a 3' terminal guanosine nucleotide.

Each of the nucleic acid sequences comprising each attachment region in a barcode domain can comprise at least one adenine nucleotide, at least one thymine nucleotide, at least one cytosine nucleotide or any combination thereof and a 5' terminal guanosine nucleotide. Each of the nucleic acid sequences comprising each attachment region in a barcode domain can consist of at least one adenine nucleotide, at least on thymine nucleotide, at least one cytosine nucleotide or any combination thereof and a 5' terminal guanosine nucleotide. Each of the nucleic acid sequences comprising each attachment region in a barcode domain can consist essentially of at least one adenine nucleotide, at least one thymine nucleotide, at least one cytosine nucleotide or any combination thereof and a 5' terminal guanosine nucleotide.

In some aspects, at least one attachment region in at least one attachment position of a barcode domain can comprise a 3' terminal guanosine nucleotide. In some aspects, at least one attachment region in at least two attachment positions of a barcode domain can comprise a 3' terminal guanosine nucleotide. In some aspects, at least one attachment region in at least three attachment positions of a barcode domain can comprise a 3' terminal guanosine nucleotide. A 3' terminal guanosine nucleotide can be L-DNA.

In some aspects, at least one attachment region in at least one attachment position of a barcode domain can comprise a 3' terminal guanosine nucleotide. In some aspects, at least one attachment region in at least two attachment positions of a barcode domain can comprise a 3' terminal guanosine nucleotide. In some aspects, at least one attachment region in at least three attachment positions of a barcode domain can comprise a 5' terminal guanosine nucleotide. A 3' terminal guanosine nucleotide can be L-DNA, for example L-deoxyguanosine (L-dG). The terminal L-dG nucleotide mitigates cross-junctional hybridization between attachment regions and/or attachment positions as well as maintain stability by providing base stacking interactions.

One or more attachment regions can be integral to a polynucleotide backbone; that is, the backbone is a single polynucleotide and the attachment regions are parts of the single polynucleotide's sequence. One or more attachment regions can be linked to a modified monomer (e.g., modified nucleotide) in the synthetic backbone such that the attachment region branches from the synthetic backbone. An attachment position can comprise more than one attachment region, in which some attachment regions branch from the synthetic backbone and some attachment regions are integral to the synthetic backbone. At least one attachment region in at least one attachment position can be integral to the synthetic backbone. Each attachment region in each of the at least three attachment positions can be integral to the synthetic backbone. At least one attachment region in at least one attachment position can branch from the synthetic backbone. Each attachment region in each of the at least three attachment positions can branch from the synthetic backbone.

Each attachment position within a barcode domain corresponds to one of sixteen dinucleotides i.e., either adenine-adenine, adenine-thymine/uracil, adenine-cytosine, adenine-guanine, thymine/uracil-adenine, thymine/uracil-thymine/uracil, thymine/uracil-cytosine, thymine/uracil-guanine, cytosine-adenine, cytosine-thymine/uracil, cytosine-cytosine, cytosine-guanine, guanine-adenine, guanine-thymine/uracil, guanine-cytosine or guanine-guanine. Thus, the one or more attachment regions located in a single attachment position of a barcode domain correspond to one of sixteen dinucleotides and comprise a nucleic acid sequence that is specific to the dinucleotide to which the attachment region corresponds. Attachment regions located in different attachment positions of a barcode domain contain unique nucleic acid sequences even if these positions within the barcode domain correspond to the same dinucleotide. For example, given a sequencing probe of the present disclosure that contains a target binding domain with a hexamer that encodes the sequence A-G-A-G-A-C, the barcode domain of this sequencing probe would contain three positions, with the first attachment position corresponding to an adenine-guanine dinucleotide, the second attachment position corresponding to an adenine-guanine dinucleotide and the third attachment position corresponding to an adenine-cytosine dinucleotide. The attachment regions located in position one of this example probe would comprise a nucleic acid sequence that is unique from the nucleic acid sequence of the attachment regions located in position two, even though both attachment position one and attachment position two correspond to the dinucleotide adenine-guanine. The sequences of specific attachment positions are designed and tested such that the complementary nucleic acid of a particular attachment position will not interact with a different attachment position. Additionally, the nucleotide sequence of a complementary nucleic acid is not limited; preferably it lacks substantial homology (e.g., 50% to 99.9%) with a known nucleotide sequence; this limits undesirable hybridization of a complementary nucleic acid and a target nucleic acid.

FIG. 1 shows an illustration of one exemplary sequencing probe of the present disclosure comprising an exemplary barcode domain. The exemplary barcode domain depicted in FIG. 1 comprises three attachment positions, $R_1$, $R_2$, and $R_3$. Each attachment position corresponds to a specific dinucleotide present within the 6-mer sequence ($b_1$ thru $b_6$) of the target binding domain. In this example, $R_1$ corresponds to positions $b_1$ and $b_2$, $R_2$ corresponds to positions $b_3$ and $b_4$, and $R_3$ corresponds to positions $b_5$ and $b_6$. Thus, each position decodes a particular dinucleotide present in the 6-mer sequence of the target binding domain, allowing for the identification of the particular two bases (A, C, G or T) present in each particular dinucleotide.

In the exemplary barcode domain depicted in FIG. 1, each attachment position comprises a single attachment region that is integral to the synthetic backbone. Each attachment region of the three attachment positions contains a specific nucleotide sequence that corresponds to the particular dinucleotide that is encoded by each attachment position. For example, attachment position $R_1$ comprises an attachment region that has a specific sequence that corresponds to the identity of the dinucleotide $b_1$-$b_2$.

The barcode domain can further comprise one or more binding regions. The barcode domain can comprise at least one single-stranded nucleic acid sequence adjacent or flanking at least one attachment position. The barcode domain can comprise at least two single-stranded nucleic acid sequences adjacent or flanking at least two attachment positions. The barcode domain can comprise at least three single-stranded nucleic acid sequences adjacent or flanking at least three attachment positions. These flanking portions are known as "Toe-Holds," which can be used to accelerate the rate of exchange of oligonucleotides hybridized adjacent to the Toe-Holds by providing additional binding sites for single-stranded oligonucleotides (e.g., "Toe-Hold" Probes; see, e.g., Seeling et al., "Catalyzed Relaxation of a Metastable DNA Fuel"; *J. Am. Chem. Soc.* 2006, 128(37), pp 12211-12220).

At least one attachment region within a barcode domain can be flanked on at least one side by a double-stranded nucleic acid sequence. At least two attachment regions within a barcode domain can be flanked on at least one side by a double-stranded nucleic acid sequence. At least three attachment regions within a barcode domain can be flanked on at least one side by a double-stranded nucleic acid sequence.

Figure 28:
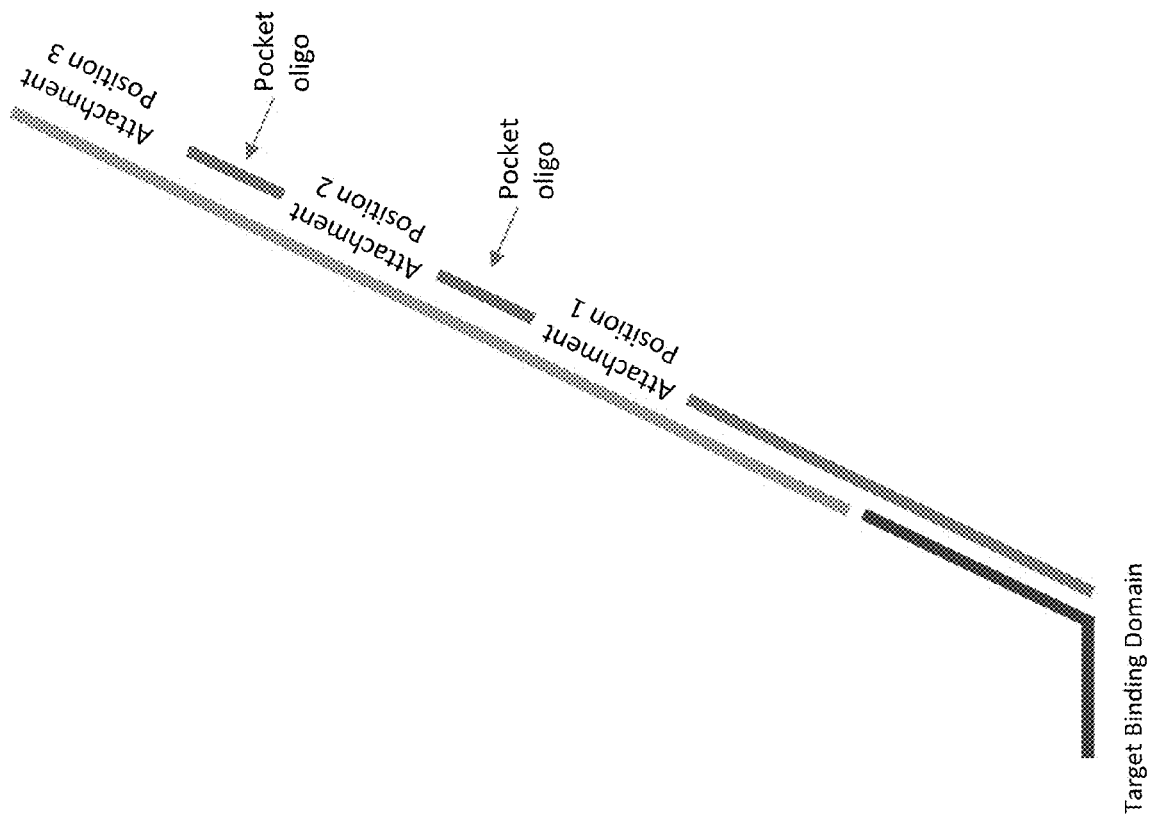
FIG. 28 is a schematic illustration of a sequencing probe of the present disclosure comprising pocket oligos.

Any attachment region within a barcode domain can be separated from any adjacent attachment position by a double-stranded nucleic acid sequence called a "pocket oligo". FIG. 28 shows an example of a sequencing probe with a barcode domain comprising three attachment positions. Attachment position one is separated from the adjacent attachment position two by a pocket oligo. Attachment position two is further separated from the adjacent attachment position three by another pocket oligo.

Each of the nucleic acids comprising a pocket oligo can be a canonical base or a modified nucleotide or nucleic acid analogue. Typical modified nucleotides or nucleic acid analogues useful in a pocket oligo are isoguanine and isocytosine. Alternatively still, each of the nucleic acids comprising a pocket oligo can independently be L-DNA. A pocket oligo can comprise at least one super T base (5-hydroxybutynl-2'-deoxyuridine). A pocket oligo can be about 25 nucleotides in length.

In some aspects, at least one, at least two or at least three attachment positions in a barcode domain can be adjacent to at least one flanking double-stranded polynucleotide. An at least one flanking double-stranded polynucleotide can comprise at least one modified nucleotide or nucleic acid analogue. An at least one flanking double-stranded polynucleotide can comprise L-DNA. An at least one flanking double-stranded polynucleotide can comprise at least one super T base (5-hydroxybutynl-2'-deoxyuridine). An at least one flanking double-stranded polynucleotide can be about 25 nucleotides in length.

At least one attachment region within a barcode domain can be flanked on at least one side by any polymer with similar mechanical properties as double-stranded DNA. Typical polymer-based spacers include polyethylene glycol (PEG) type polymers. At least two attachment regions within a barcode domain can be flanked on at least one side by any polymer with similar mechanical properties as double-stranded DNA. At least three attachment regions within a barcode domain can be flanked on at least one side by any polymer with similar mechanical properties as double-stranded DNA.

Figure 29:
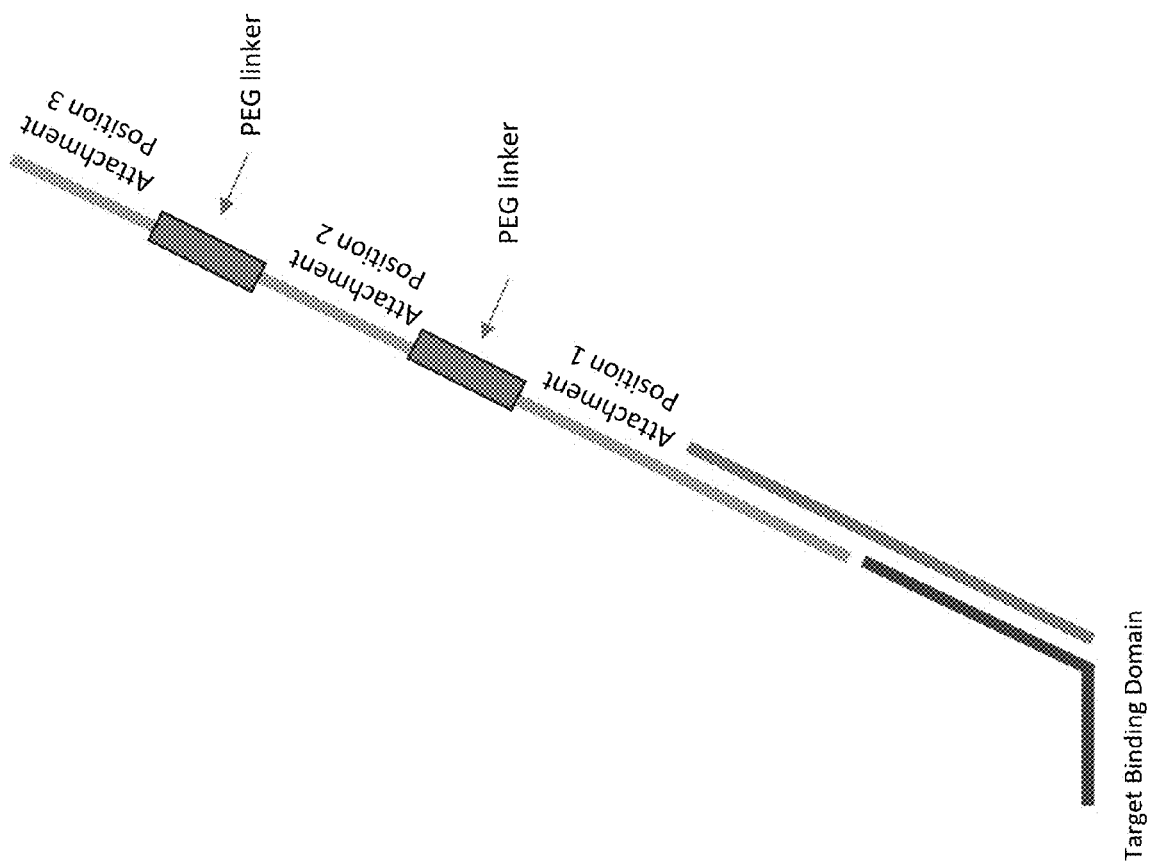
FIG. 29 is a schematic illustration of a sequencing probe of the present disclosure comprising PEG linker regions between each attachment position.

Any attachment region within a barcode domain can be separated from any adjacent attachment position by any polymer with similar mechanical properties as double-stranded DNA. Typical polymer-based spacers include polyethylene glycol (PEG) type polymers. FIG. 29 shows an example of a sequencing probe with a barcode domain comprising three attachment positions. Attachment position one is separated from the adjacent attachment position two by a PEG-linker. Attachment position two is further separated from the adjacent attachment position three by another PEG-linker.

At least one attachment region within a barcode domain can be flanked on at least one side by a single-stranded nucleic acid molecule that is abasic. An abasic nucleic acid molecule is a nucleic acid molecule that has neither a purine nor a pyrimidine base. At least two attachment regions within a barcode domain can be flanked on at least one side by a single-stranded nucleic acid molecule that is abasic. At least three attachment regions within a barcode domain can be flanked on at least one side by a single-stranded nucleic acid molecule that is abasic.

Figure 30:
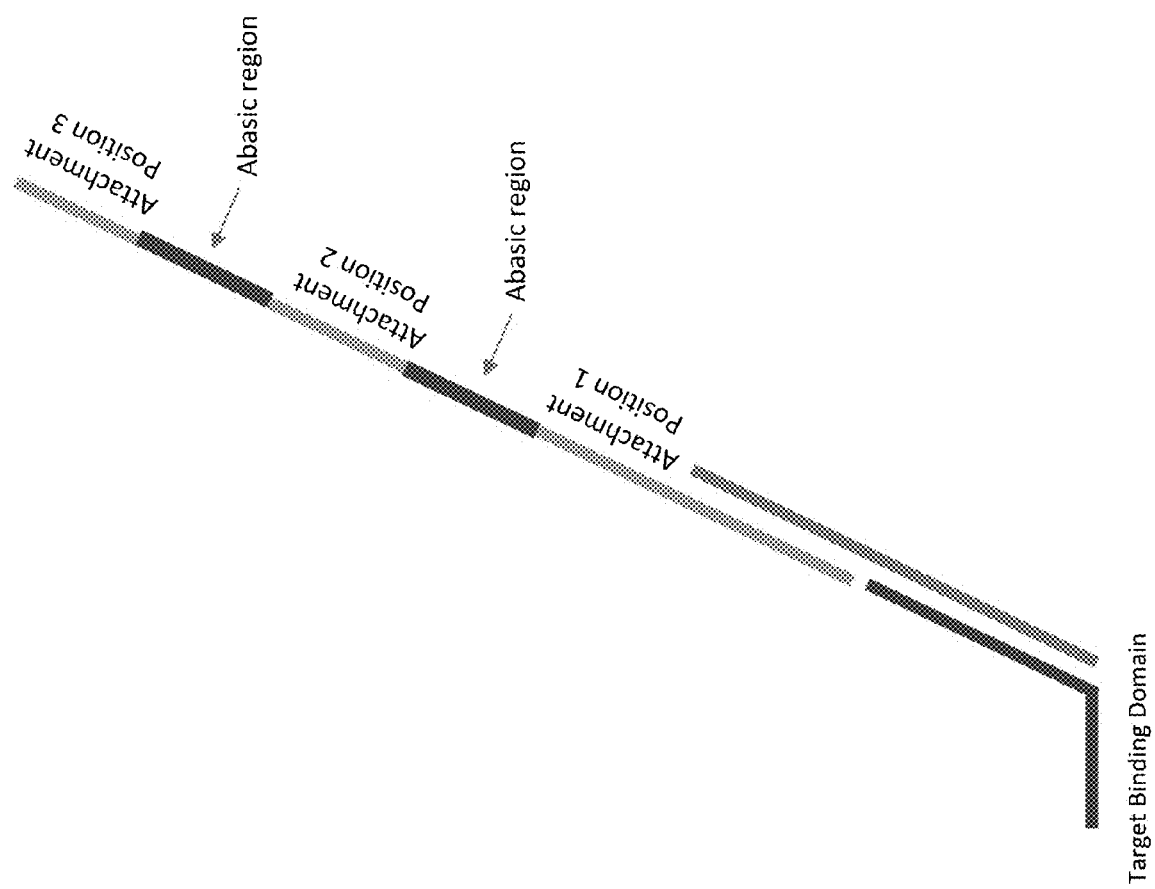
FIG. 30 is a schematic illustration of a sequencing probe of the present disclosure comprising abasic regions between each attachment position.

Any attachment region within a barcode domain can be separated from any adjacent attachment position a single-stranded nucleic acid molecule that is abasic. FIG. 30 shows an example of a sequencing probe with a barcode domain comprising three attachment positions. Attachment position one is separated from the adjacent attachment position two by a single-stranded nucleic acid molecule that is abasic. Attachment position two is further separated from the adjacent attachment position three by another single-stranded nucleic acid molecule that is abasic.

Figure 53:
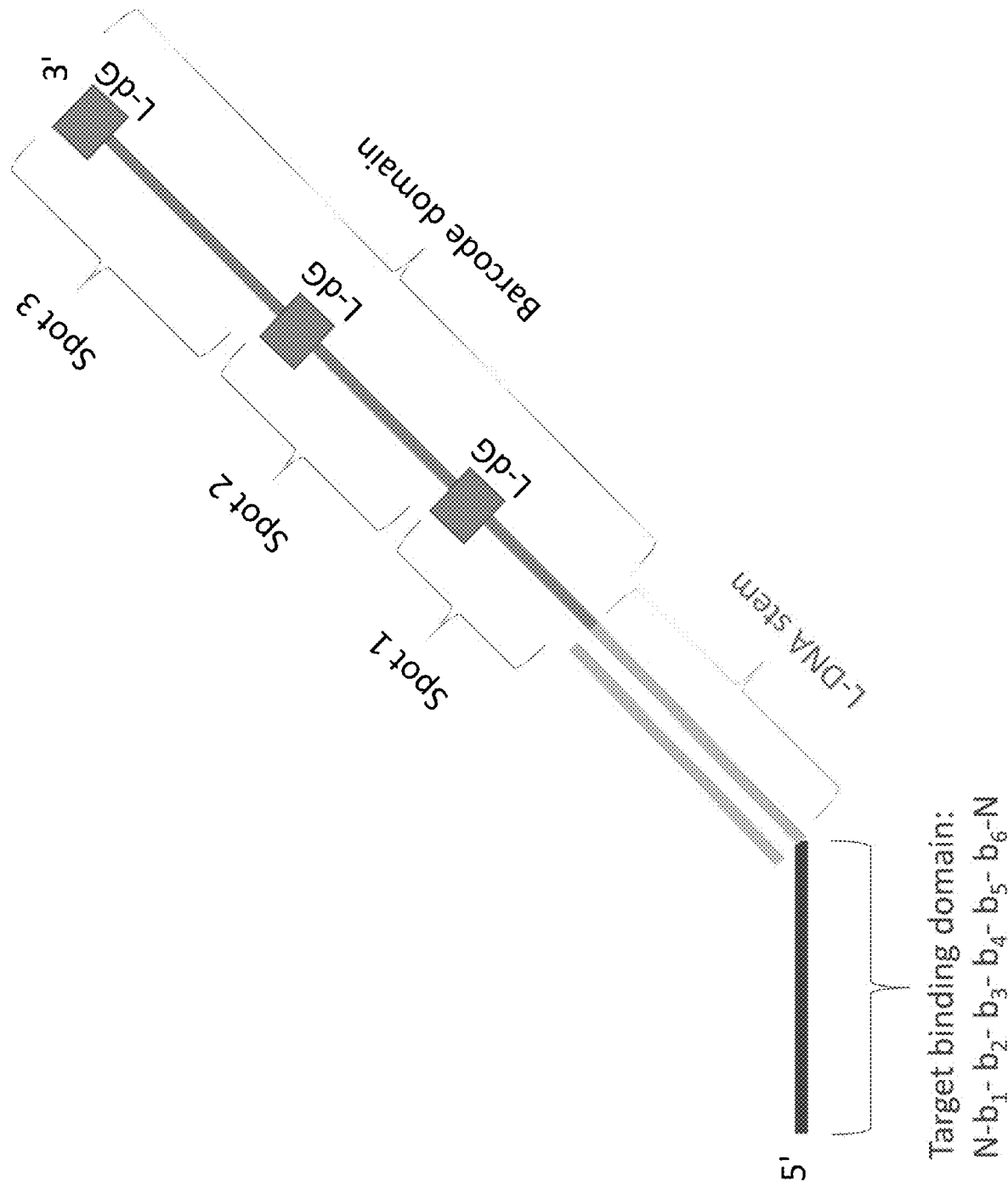
FIG. 53 is a schematic illustration of a sequencing probe of the present disclosure that consists entirely of L-DNA and that comprises attachment regions with 3' terminal L-dG nucleotides.

Any attachment region within a barcode domain can be separated from any adjacent attachment position by a 3' terminal guanosine nucleotide. In some aspects, at least one attachment region in at least two attachment positions of a barcode domain can comprise a 3' terminal guanosine nucleotide. FIG. 53 shows an example of a sequencing probe with a barcode domain comprising three attachment positions each one separated by a terminal L-G nucleotide. Attachment position one is separated from the adjacent attachment position two by a L-G nucleotide. Attachment position two is further separated from the adjacent attachment position three by another L-G nucleotide. Attachment position three is terminated on the 3' end with a L-G nucleotide.

Sequencing probes of the present disclosure can have overall lengths (including target binding domain, barcode domain, and any optional domains) of about 20 nanometers to about 50 nanometers. The sequencing probe's backbone can be a polynucleotide molecule comprising about 120 nucleotides, about 60 nucleotides, about 52 nucleotides or about 27 nucleotides.

Figure 7:
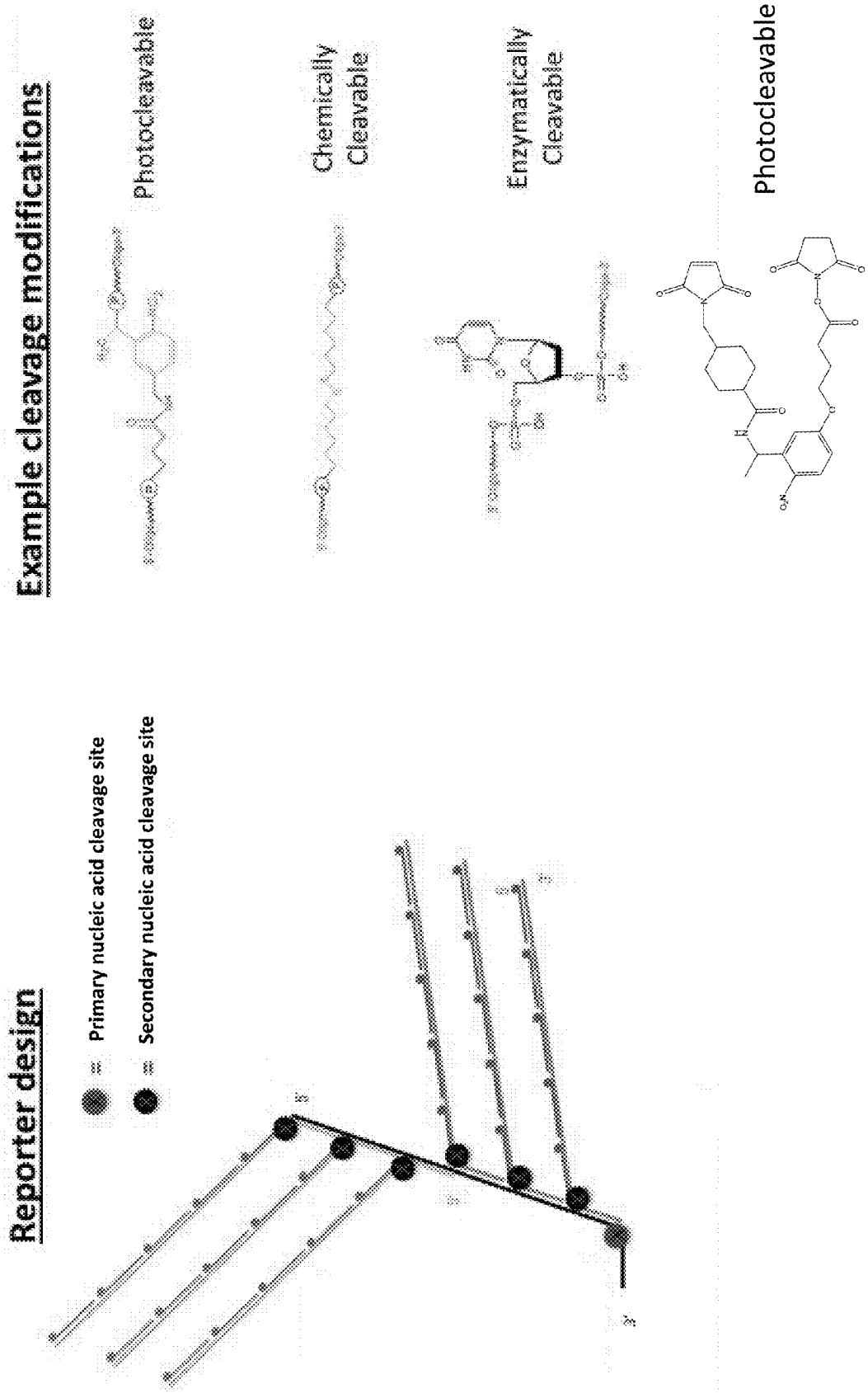
FIG. 7 shows possible positions for cleavable linker modifications within an exemplary reporter probe of the present disclosure.

A sequencing probe can comprise a cleavable linker modification. A cleavable linker modification can comprise at least one, at least two, at least three, at least four, at least five, at least six, at least seven, at least eight, at least nine, at least ten or any number of cleavable moieties. Any cleavable linker modification or cleavable moiety known to one of skill in the art can be utilized. Non-limiting examples of cleavable linker modifications and cleavable moieties include, but are not limited to, UV-light cleavable linkers, reducing agent cleavable linkers and enzymatically cleavable linkers. An example of an enzymatically cleavable linker is the insertion of deoxyuracil for cleavage by the USER™ enzyme. The cleavable linker modification can be located anywhere along the length of the sequencing probe, including, but not limited to, a region between the target binding domain and the barcode domain. The right panel of FIG. 7 depicts exemplary cleavable linker modifications that can be incorporated into the probes of the present disclosure.

Reporter Probes

A nucleic acid molecule that binds (e.g., hybridizes) to a complementary nucleic acid sequence within at least one attachment region within at least one attachment position of a barcode domain of a sequencing probe of the present disclosure and comprises (directly or indirectly) a detectable label is referred to herein as a "reporter probe" or "reporter probe complex," these terms are used interchangeably herein. The reporter probe can be DNA, RNA or PNA. Preferably, the reporter probe is DNA.

Figure 3:
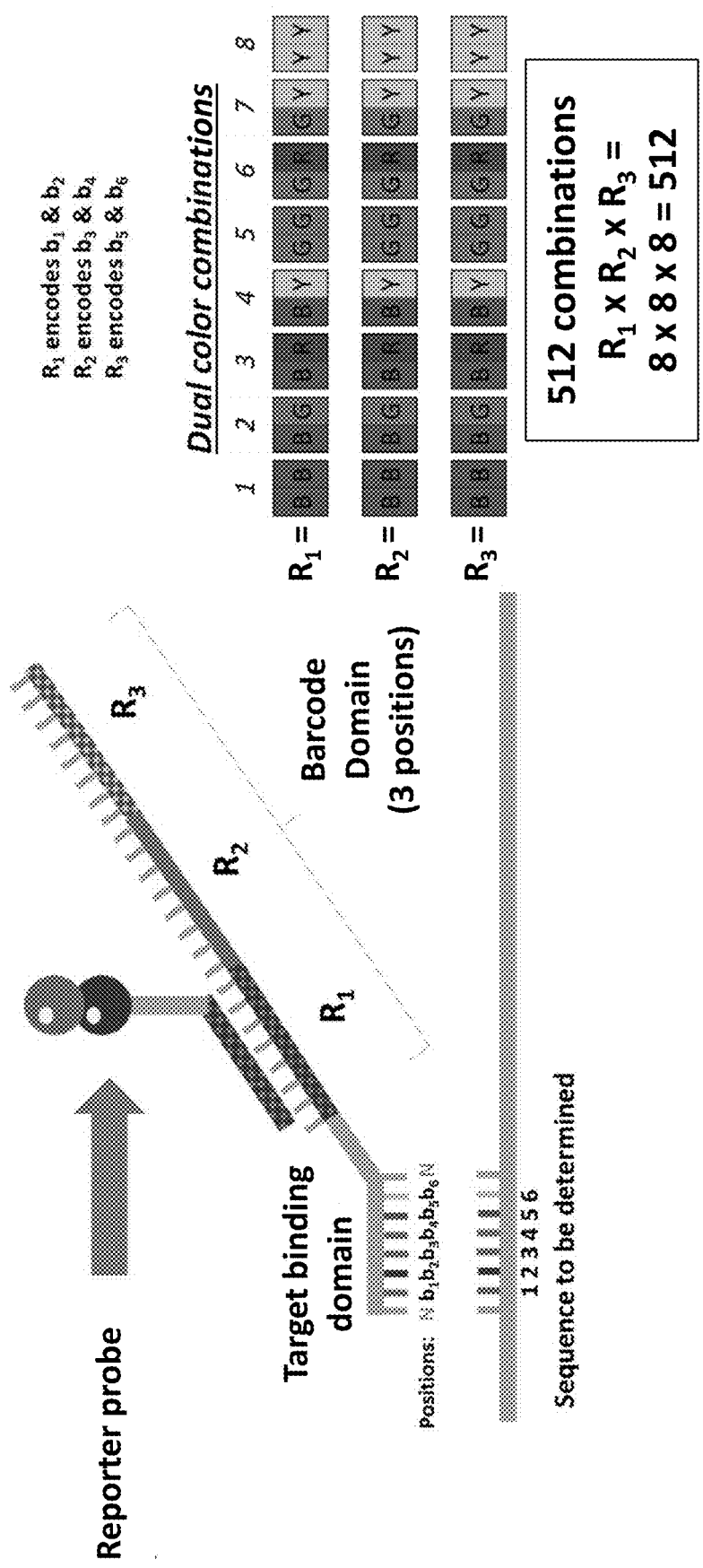
FIG. 3 is an illustration of an exemplary reporter complex of the present disclosure hybridized to an exemplary sequencing probe of the present disclosure.

A reporter probe can comprise at least two domains, a first domain capable of binding at least one first complementary nucleic acid molecule and a second domain capable of binding a first detectable label and at least a second detectable label. FIG. 3 shows a schematic of an exemplary reporter probe of the present disclosure bound to the first attachment position of a barcode domain of an exemplary sequencing probe. In FIG. 3, the first domain of the reporter probe (shown in hatched maroon) binds a complementary nucleic acid sequence within attachment position $R_1$ of the barcode domain and the second domain of the reporter probe (shown in gray) is bound to two detectable labels (one green label, one red label).

Alternatively, the reporter probe can comprise at least two domains, a first domain capable of binding at least one first complementary nucleic acid molecule and a second domain capable of binding at least one second complementary nucleic acid molecule. The at least one first and at least one second complementary nucleic acid molecules can be different (have different nucleic acid sequences).

A "primary nucleic acid molecule" is a reporter probe comprising at least two domains, a first domain capable of binding (e.g. hybridizing) to a complementary nucleic acid sequence within at least one attachment region within at least one attachment position of a barcode domain of a sequencing probe and a second domain capable of binding (e.g. hybridizing) to at least one additional complementary nucleic acid. A primary nucleic acid molecule can directly bind the complementary nucleic acid sequence within the at least one attachment region within the at least one attachment position of a barcode domain of a sequencing probe. A primary nucleic acid molecule can indirectly bind the complementary nucleic acid sequence within the at least one attachment region within the at least one attachment position of a barcode domain of a sequencing probe via a nucleic acid linker. This nucleic acid linker is called a "connector oligo".

Figure 31:
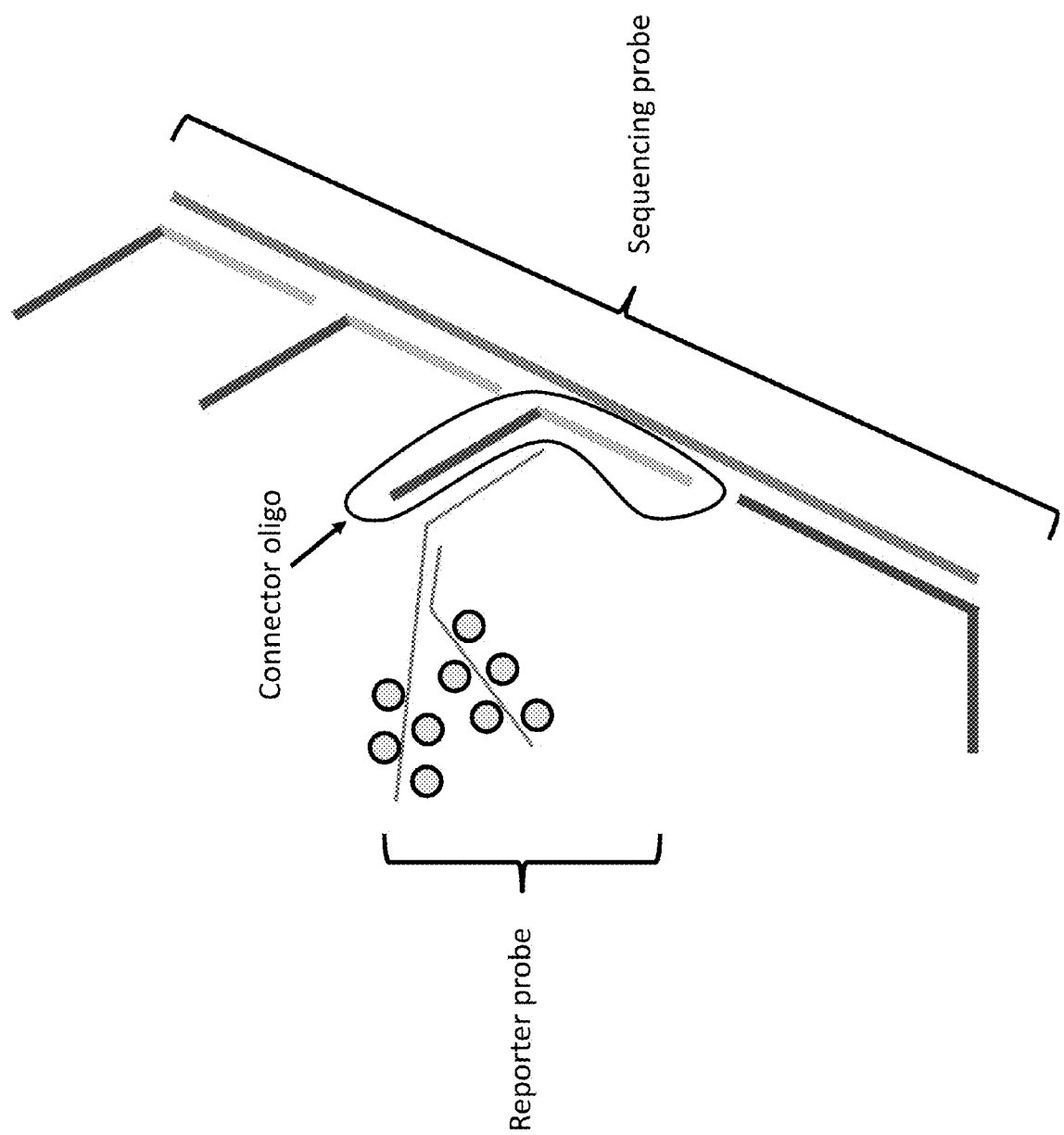
FIG. 31 is an illustration of an exemplary reporter complex of the present disclosure indirectly hybridized to an exemplary sequencing probe of the present disclosure via a connector oligo.

A connector oligo can comprise at least two domains, a first domain capable of binding (e.g. hybridizing) at least one first complementary nucleic acid sequence within at least one attachment region within at least one attachment position of a barcode domain and a second domain capable of binding (e.g. hybridizing) to the first domain of a primary nucleic acid molecule. FIG. 31 shows a sequencing probe bound to a reporter probe via a connector oligo.

Each of the nucleic acids comprising the first domain or the second domain of a connector oligo can be a canonical base or a modified nucleotide or nucleic acid analogue. Typical modified nucleotides or nucleic acid analogues useful in the first or second domain of a connector oligo are isoguanine and isocytosine. The use of modified nucleotides or nucleotide analogues such as isoguanine and isocytosine, for example, can improve binding efficiency and accuracy of the first domain of a connector oligo to the appropriate complementary nucleic acid sequence within at least one attachment region within at least one attachment position of a barcode domain of a sequencing probe while minimizing binding elsewhere, including to the target. The use of modified nucleotides or nucleotide analogues such as isoguanine and isocytosine, for example, can improve binding efficiency and accuracy of the second domain of a connector oligo to the appropriate first domain of a reporter probe while minimizing binding elsewhere, including to the target. Alternatively, each of the nucleic acids comprising the first or the second domain of a connector oligo can independently be L-DNA. In one example of a connector oligo, the first domain comprises D-DNA and the second domain comprises L-DNA. In another example of a connector oligo, the first domain comprises D-DNA and the second domain comprises isoguanine and/or isocytosine.

The first domain of a connector oligo can be about 8 to about 16 nucleotides in length. Preferably, the first domain of a connector oligo is 14 nucleotides in length. The second domain of a connector oligo can be about 4-12 nucleotides in length. Preferably, the second domain of a connector oligo can be about 8 nucleotides in length.

In aspects comprising a connector oligo, an attachment region can be referred to as being partially double-stranded. A partially double-stranded attachment region can comprise a double-stranded region and a single-stranded. The single-stranded region of a partially double-stranded attachment region can comprise at least one nucleic acid sequence that binds (e.g. hybridizes) to at least one complementary nucleic acid sequence. The at least one complementary nucleic acid sequence that binds (e.g. hybridizes) to the single-stranded region of a partially double-stranded attachment region can be a primary nucleic acid molecule.

Each of the nucleic acids comprising the double-stranded region of a partially double-stranded attachment region can independently be a canonical base or a modified nucleotide or nucleic acid analogue. At least one, two, at least three, at least four, at least five, least six, at least seven or at least eight nucleotides in the double-stranded region of a partially double-stranded attachment region can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the first domain of a primary nucleic acid molecule are isoguanine and isocytosine. Alternatively, each of the nucleic acids comprising the double-stranded region of a partially double-stranded attachment region can independently be L-DNA.

Each of the nucleic acids comprising the single-stranded region of a partially double-stranded attachment region can independently be a canonical base or a modified nucleotide or nucleic acid analogue. At least one, two, at least three, at least four, at least five, least six, at least seven or at least eight nucleotides in the single-stranded region of a partially double-stranded attachment region can be modified nucleotides or nucleic acid analogues. Typical ratios of modified nucleotides or nucleic acid analogues to canonical bases in a barcode domain are 1:2 to 1:8. Typical modified nucleotides or nucleic acid analogues useful in a single-stranded region of a partially double-stranded attachment region are isoguanine and isocytosine. The use of modified nucleotides or nucleic acid analogues such as isoguanine and isocytosine, for example, can improve binding efficiency and accuracy of a single-stranded region of a partially double-stranded attachment region to the appropriate complementary nucleic acid sequence of a primary nucleic acid molecule while minimizing binding elsewhere, including to the target. Alternatively, each of the nucleic acids comprising the first domain of a primary nucleic acid molecule can independently be L-DNA.

The primary nucleic acid molecule can comprise a cleavable linker. The cleavable linker can be located between the first domain and the second domain. Preferably, the cleavable linker is photo-cleavable. The cleavable linker can comprise at least one or at least two cleavable moieties. The at least one or at least two cleavable moieties can be photo-cleavable.

The first domain of a primary nucleic acid molecule can be about 6 to 16 nucleotides in length. Preferably, the first domain of a primary nucleic acid molecule is about 8 nucleotides in length.

Each of the nucleic acids comprising the first domain of a primary nucleic acid molecule can independently be a canonical base or a modified nucleotide or nucleic acid analogue. At least one, two, at least three, at least four, at least five, least six, at least seven or at least eight nucleotides in the first domain of a primary nucleic acid molecule can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the first domain of a primary nucleic acid molecule are isoguanine and isocytosine. The use of modified nucleotides or nucleotide analogues such as isoguanine and isocytosine, for example, can improve binding efficiency and accuracy of the first domain of a primary nucleic acid molecule to the appropriate complementary nucleic acid sequence within at least one attachment region within at least one attachment position of a barcode domain of a sequencing probe while minimizing binding elsewhere, including to the target. Alternatively, each of the nucleic acids comprising the first domain of a primary nucleic acid molecule can independently be L-DNA.

In some aspects, a first domain of a primary nucleic acid molecule can be composed entirely of L-DNA and the second domain of the primary nucleic acid molecule can be composed entirely of D-DNA.

In some aspects, a first domain of a primary nucleic acid molecule can comprise a 3' terminal cytosine nucleotide. In some aspects, a first domain of a primary nucleic acid molecule can comprise a 3' terminal cytosine nucleotide, wherein the 3' terminal cytosine nucleotide is L-DNA.

In some aspects, a first domain of a primary nucleic acid molecule can comprise a 5' terminal cytosine nucleotide. In some aspects, a first domain of a primary nucleic acid molecule can comprise a 5' terminal cytosine nucleotide, wherein the 5' terminal cytosine nucleotide is L-DNA.

In some aspects, a first domain of a primary nucleic acid molecule can comprise at least one adenine nucleotide, at least one thymine nucleotide, at least one guanine nucleotide or any combination thereof and a 3' terminal cytosine nucleotide. In some aspects, a first domain of a primary nucleic acid molecule can consist of at least one adenine nucleotide, at least one thymine nucleotide, at least one guanine nucleotide or any combination thereof and a 3' terminal cytosine nucleotide. In some aspects, a first domain of a primary nucleic acid molecule can consist essentially of at least one adenine nucleotide, at least one thymine nucleotide, at least one guanine nucleotide or any combination thereof and a 3' terminal cytosine nucleotide.

In some aspects, a first domain of a primary nucleic acid molecule can comprise at least one adenine nucleotide, at least one thymine nucleotide, at least one guanine nucleotide or any combination thereof and a 5' terminal cytosine nucleotide. In some aspects, a first domain of a primary nucleic acid molecule can consist of at least one adenine nucleotide, at least one thymine nucleotide, at least one guanine nucleotide or any combination thereof and a 5' terminal cytosine nucleotide. In some aspects, a first domain of a primary nucleic acid molecule can consist essentially of at least one adenine nucleotide, at least one thymine nucleotide, at least one guanine nucleotide or any combination thereof and a 5' terminal cytosine nucleotide.

The at least one additional complementary nucleic acid that binds the primary nucleic acid molecule is referred to herein as a "secondary nucleic molecule." The primary nucleic acid molecule can bind (e.g., hybridize) to at least one, at least two, at least three, at least four, at least five, or more secondary nucleic acid molecules. Preferably, the primary nucleic acid molecule binds (e.g., hybridizes) to four secondary nucleic acid molecules.

A secondary nucleic acid molecule can comprise at least two domains, a first domain capable of binding (e.g. hybridizing) to at least one complementary sequence in at least one primary nucleic acid molecule and a second domain capable of binding (e.g. hybridizing) to (a) a first detectable label and an at least second detectable label; (b) to at least one additional complementary nucleic acid; or (c) a combination thereof. In some aspects, a first domain of a secondary nucleic acid molecule can be composed entirely of L-DNA and the second domain of the secondary nucleic acid molecule can be composed entirely of D-DNA. In some aspects, both the first domain and second domain of a secondary nucleic acid molecule can be composed entirely of D-DNA.

The secondary nucleic acid molecule can comprise a cleavable linker. The cleavable linker can be located between the first domain and the second domain. Preferably, the cleavable linker is photo-cleavable.

Each of the nucleic acids comprising the first domain of a secondary nucleic acid molecule can independently be a canonical base or a modified nucleotide or nucleic acid analogue. At least one, two, at least three, at least four, at least five, or at least six nucleotides in the first domain of a secondary nucleic acid molecule can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the first domain of a secondary nucleic acid molecule are isoguanine and isocytosine. The use of modified nucleotides or nucleotide analogues such as isoguanine and isocytosine, for example, can improve binding efficiency and accuracy of the first domain of a secondary nucleic acid molecule to the appropriate complementary nucleic acid sequence within the second domain of a primary nucleic acid molecule while minimizing binding elsewhere.

The at least one additional complementary nucleic acid that binds the secondary nucleic acid molecule is referred to herein as a "tertiary nucleic molecule." The secondary nucleic acid molecule can bind (e.g., hybridize) to at least one, at least two, at least three, at least four, at least five, at least six, at least seven, or more tertiary nucleic acid molecules. Preferably, the at least one secondary nucleic acid molecule binds (e.g., hybridizes) to one tertiary nucleic acid molecule.

A tertiary nucleic acid molecule comprises at least two domains, a first domain capable of binding (e.g. hybridizing) to at least one complementary sequence in at least one secondary nucleic acid molecule and a second domain capable of binding (e.g. hybridizing) to a first detectable label and an at least second detectable label. Alternatively, the second domain can include the first detectable label and an at least second detectable label via direct or indirect attachment of the labels during oligonucleotide synthesis using, for example, phosphoroamidite or NHS chemistry. In some aspects, a first domain of a tertiary nucleic acid molecule can be composed entirely of L-DNA and the second domain of the tertiary nucleic acid molecule can be composed entirely of D-DNA. In some aspects, both the first domain and second domain of a tertiary nucleic acid molecule can be composed entirely of D-DNA. The tertiary nucleic acid molecule can comprise a cleavable linker. The cleavable linker can be located between the first domain and the second domain. Preferably, the cleavable linker is photo-cleavable.

Each of the nucleic acids comprising the first domain of a tertiary nucleic acid molecule can independently be a canonical base or a modified nucleotide or nucleic acid analogue. At least one, two, at least three, at least four, at least five, or at least six nucleotides in the first domain of a tertiary nucleic acid can be modified nucleotides or nucleotide analogues. Typical ratios of modified nucleotides or nucleotide analogues to canonical bases in a first domain of a tertiary nucleic acid molecule are 1:2 to 1:8. Typical modified nucleotides or nucleic acid analogues useful in the first domain of a tertiary nucleic acid molecule are isoguanine and isocytosine. The use of modified nucleotides or nucleotide analogues such as isoguanine and isocytosine, for example, can improve binding efficiency and accuracy of the first domain of a tertiary nucleic acid molecule to the appropriate complementary nucleic acid sequence within the second domain of a second nucleic acid molecule while minimizing binding elsewhere.

Reporter probes are bound to a first detectable label and an at least second detectable label to create a dual color combination. This dual combination of fluorescent dyes can include a duplicity of a single color, e.g. blue-blue. As used herein, the term "label" includes a single moiety capable to producing a detectable signal or multiple moieties capable of producing the same or substantially the same detectable signal. For example, a label includes a single yellow fluorescent dye such as ALEXA FLUOR™ 532 or multiple yellow fluorescent dyes such as ALEXA FLUOR™ 532.

The reporter probes can bind to a first detectable label and an at least second detectable label, in which each detectable label is one of four fluorescent dyes: blue (B); green (G); yellow (Y); and red (R). The use of these four dyes creates 10 possible dual color combinations BB; BG; BR; BY; GG; GR; GY; RR; RY; or YY. In some aspects, reporter probes of the present disclosure are labeled with one of 8 possible color combinations: BB; BG; BR; BY; GG; GR; GY; or YY as depicted in FIG. 3. The detectable label and an at least second detectable label can have the same emission spectrum or can have a different emission spectra.

In aspects comprising a sequencing probe and a primary nucleic acid molecule, the present disclosure provides a sequencing probe comprising a target binding domain and a barcode domain; wherein the target binding domain comprises any of the constructs recited in Table 1. An exemplary target binding domain comprises at least eight nucleotides and is capable of hybridizing to a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein any of the at least six nucleotides in the target binding domain can be modified nucleotides or nucleotide analogues and wherein the at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases. An exemplary barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule comprises a first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary primary nucleic acid molecule bound to each position of the at least three attachment positions determines the position and identity of the corresponding two nucleotides of the at least six nucleotides in the target nucleic acid that is bound by the target binding domain. The at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases.

In some aspects, at least one nucleotide in a target binding domain that does not identify a corresponding nucleotide in a target nucleic acid molecule can precede the nucleotides in the target binding domain that identify corresponding nucleotides in the target nucleic acid molecule. In some aspects, at least one nucleotide in a target binding domain that does not identify a corresponding nucleotide in a target nucleic acid can follow the nucleotides in the target binding domain that identify corresponding nucleotides in the target nucleic acid molecule.

In other aspects, an exemplary target binding domain can comprise at least six nucleotides capable of hybridizing to a target nucleic acid, wherein the at least six nucleotides in the target binding domain are capable of identifying a corresponding (complementary) nucleotide in the target nucleic acid molecule; wherein none of the at least six nucleotides or any of the at least six nucleotides in the target binding domain can be modified nucleotides or nucleotide analogues.

In aspects comprising a sequencing probe and a primary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule comprises at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary primary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule and a secondary nucleic acid molecule, the present disclosure provides a sequencing probe comprising a target binding domain and a barcode domain; wherein the target binding domain comprises any of the constructs recited in Table 1. An exemplary target binding domain comprises at least eight nucleotides and is capable of hybridizing to a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein any of the at least six nucleotides in the target binding domain can be modified nucleotides or nucleotide analogues and wherein the at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases. An exemplary barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary secondary nucleic acid molecule bound to each position of the at least three attachment positions determines the position and identity of the corresponding two nucleotides of the at least six nucleotides in the target nucleic acid that is bound by the target binding domain.

In other aspects, an exemplary target binding domain can comprise at least six nucleotides capable of hybridizing to a target nucleic acid, wherein the at least six nucleotides in the target binding domain are capable of identifying a corresponding (complementary) nucleotide in the target nucleic acid molecule; wherein none of the at least six nucleotides or any of the at least six nucleotides in the target binding domain can be modified nucleotides or nucleotide analogues.

In aspects comprising a sequencing probe, a primary nucleic acid molecule and a secondary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary secondary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule, a secondary nucleic acid molecule and a tertiary nucleic acid molecule, the present disclosure provides a sequencing probe comprising a target binding domain and a barcode domain; wherein the target binding domain comprises any of the constructs recited in Table 1. An exemplary target binding domain comprises at least eight nucleotides and is capable of hybridizing to a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein any of the at least six nucleotides in the target binding domain can be modified nucleotides or nucleotide analogues and wherein the at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases. An exemplary barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule, and wherein the at least one complementary secondary nucleic acid molecule is further bound by at least one complementary tertiary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary tertiary nucleic acid molecule bound to each position of the at least three attachment positions determines the position and identity of the corresponding two nucleotides of the at least six nucleotides in the target nucleic acid that is bound by the target binding domain.

In other aspects, an exemplary target binding domain can comprise at least six nucleotides capable of hybridizing to a target nucleic acid, wherein the at least six nucleotides in the target binding domain are capable of identifying a corresponding (complementary) nucleotide in the target nucleic acid molecule; wherein none of the at least six nucleotides or any of the at least six nucleotides in the target binding domain can be modified nucleotides or nucleotide analogues.

In aspects comprising a sequencing probe, a primary nucleic acid molecule, a secondary nucleic acid molecule and a tertiary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule, and wherein the at least one complementary secondary nucleic acid molecule is further bound by at least one complementary tertiary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary tertiary nucleic acid molecule bound to each position of the at least three attachment positions determines the position and identity of the corresponding two nucleotides of the at least six nucleotides in the target nucleic acid that is bound by the target binding domain.

The present disclosure also provides sequencing probes and reporter probes having detectable labels on both a secondary nucleic acid molecule and a tertiary nucleic acid molecule. For example, a secondary nucleic acid molecule can bind a primary nucleic acid molecule and the secondary nucleic acid molecule can comprise both a first detectable label and an at least second detectable label and also be bound to at least one tertiary molecule comprising a first detectable label and an at least second detectable label. The first and at least second detectable labels located on the secondary nucleic acid molecule can have the same emission spectra or can have different emission spectra. The first and at least second detectable labels located on the tertiary nucleic acid molecule can have the same emission spectra or can have different emission spectra. The emission spectra of the detectable labels on the secondary nucleic acid molecule can be the same or can be different than the emission spectra of the detectable labels on the tertiary nucleic acid molecule.

Figure 4:
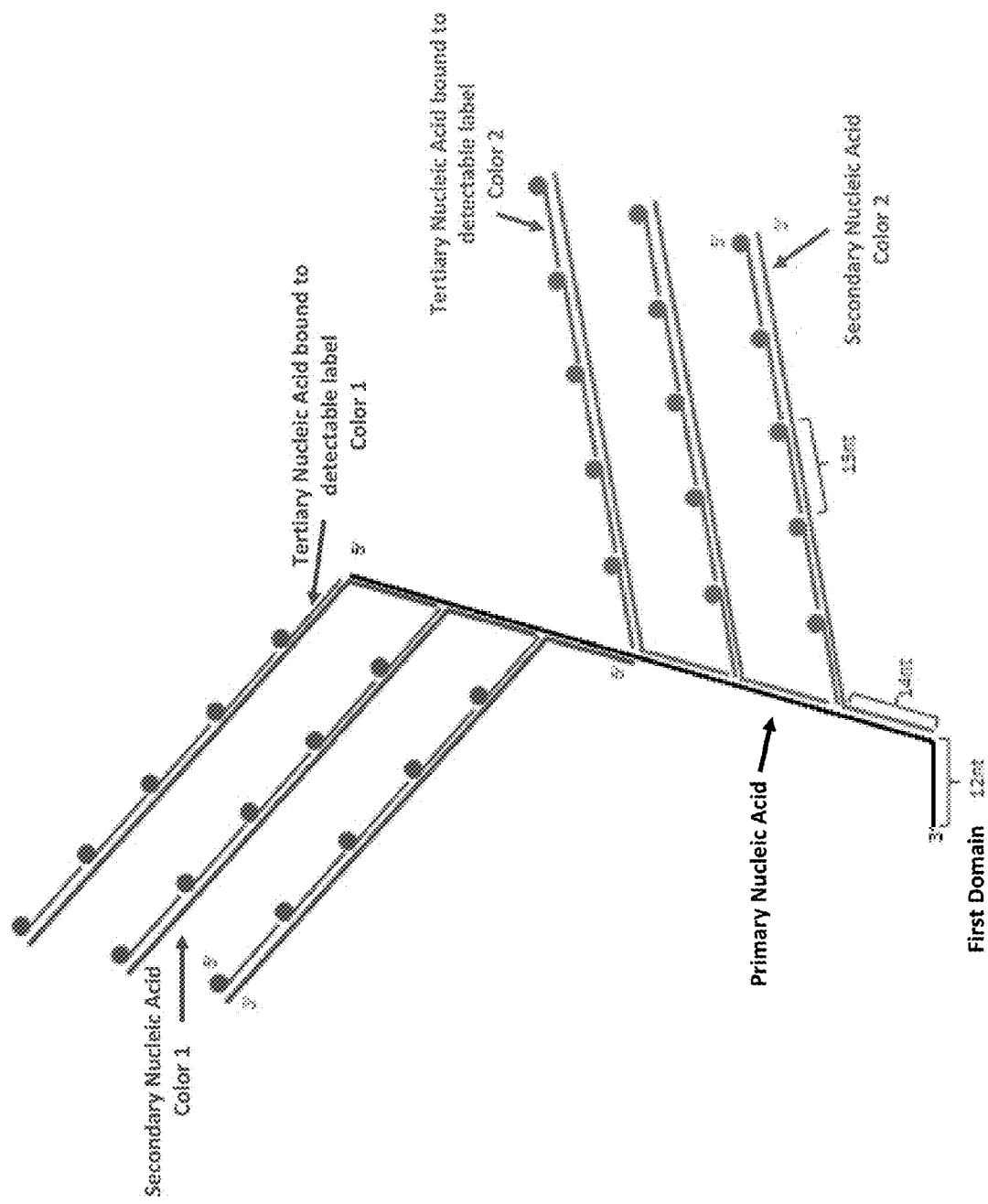
FIG. 4 shows a schematic illustration of an exemplary reporter probe of the present disclosure.

FIG. 4 is an illustrative schematic of an exemplary reporter probe of the present disclosure that comprises an exemplary primary nucleic acid molecule, secondary nucleic acid molecule and tertiary nucleic acid molecule. At the 3' end, the primary nucleic acid comprises a first domain, wherein the first domain comprises a twelve nucleotide sequence that hybridizes to a complementary attachment region within an attachment position of a sequencing probe barcode domain. At the 5' end is a second domain that is hybridized to six secondary nucleic acid molecules. The exemplary secondary nucleic acid molecules depicted in turn comprise a first domain in the 5' end that hybridizes to the primary nucleic acid molecule and a domain that in the 3' portion that hybridizes to five tertiary nucleic acid molecules.

A tertiary nucleic acid molecule comprises at least two domains. The first domain is capable of binding to a secondary nucleic acid molecule. The second domain of a tertiary nucleic acid is capable of binding to a first detectable label and at least second detectable label. The second domain of a tertiary nucleic acid can be bound to the first detectable label and at least second detectable label by the direct incorporation of one or more fluorescently-labeled nucleotide monomers into the sequence of the second domain of the tertiary nucleic acid. The second domain of the secondary nucleic acid molecule can be bound by the first detectable label and at least second detectable label by hybridizing short polynucleotides that are labeled to the second domain of the secondary nucleic acid. These short polynucleotides, called "labeled-oligos," can be labeled by direct incorporation of fluorescently-labeled nucleotide monomers or by other methods of labeling nucleic acids that are known to one of skill in that art. The exemplary tertiary nucleic acid molecules depicted in FIG. 4, which may be considered "labeled oligos" comprise a first domain that hybridizes to a secondary nucleic acid molecule and a second domain that is fluorescently labeled by indirect attachment of the labels during oligonucleotide synthesis using, for example, NHS chemistry or incorporation of one or more fluorescently-labeled nucleotide monomers during the synthesis of the tertiary nucleic acid molecule. The labeled-oligos can be DNA, RNA or PNA.

Labeled oligos can comprise a cleavable linker between the fluorescent moiety and the polynucleotide molecule. Preferably, the cleavable linker is photo-cleavable. The cleavable linker can also be chemically or enzymatically-cleavable.

In alternative aspects, the second domain of a secondary nucleic acid is capable of binding to a first detectable label and at least second detectable label. The second domain of the secondary nucleic acid can be bound to the first detectable label and at least second detectable label by the direct incorporation of one or more fluorescently-labeled nucleotide monomers into the sequence of the second domain of the secondary nucleic acid. The second domain of the secondary nucleic acid molecule can be bound by the first detectable label and at least second detectable label by hybridizing short polynucleotides that are labeled to the second domain of the secondary nucleic acid. These short polynucleotides, called labeled-oligos, can be labeled by direct incorporation of fluorescently-labeled nucleotide monomers or by other methods of labeling nucleic acids that are known to one of skill in that art.

A primary nucleic acid molecule can comprise about 100, about 95, about 90, about 85, about 80 or about 75 nucleotides. A primary nucleic acid molecule can comprise about 100 to about 80 nucleotides. A primary nucleic acid molecule can comprise about 90 nucleotides. A secondary nucleic acid molecule can comprise about 90, about 85, about 80, about 75 or about 70 nucleotides. A secondary nucleic acid molecule can comprise about 90 to about 80 nucleotides. A secondary nucleic acid molecule can comprise about 87 nucleotides. A secondary nucleic acid molecule can comprise about 25, about 20, about 15, or about 10 nucleotides. A tertiary nucleic acid molecule can comprise about 20 to about 10 nucleotides. A tertiary nucleic acid molecule can comprise about 15 nucleotides.

Reporter probes of the present disclosure can be of various designs. For example, a primary nucleic acid molecule can be hybridized to at least one (e.g., 1, 2, 3, 4, 5, 6, 7, 8, 9, 10, or more) secondary nucleic acid molecules. Each secondary nucleic acid molecule can be hybridized to at least one (e.g., 1, 2, 3, 4, 5, 6, 7, 8, 9, 10, or more) tertiary nucleic acid molecules. To create a reporter probe that is labeled with a particular dual color combination, the reporter probe is designed such that the probe comprises secondary nucleic acid molecules, tertiary nucleic acid molecules, labeled-oligos or any combination of secondary nucleic acid molecules, tertiary nucleic acid molecules and labeled-oligos that are labeled with each color of the particular dual color combination. For example, FIG. 4 depicts a reporter probe of the present disclosure that comprises 30 total dyes, with 15 dyes for color 1 and 15 dyes for color 2. To prevent color-swapping or cross hybridization between different fluorescent dyes, each tertiary nucleic acid or labeled-oligo that is bound to a specific label or fluorescent dye comprises a unique nucleotide sequence.

In some aspects, the present disclosure provides a 5×5 reporter probe. A 5×5 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 5 secondary nucleic acid molecules. Each secondary nucleic acid comprises a nucleotide sequence such that 5 tertiary nucleic acids that are bound by detectable labels can hybridize to each secondary nucleic acid.

In some aspects, the present disclosure provides a 4×3 reporter probe. A 4×3 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 4 secondary nucleic acid molecules. Each secondary nucleic acid comprises a nucleotide sequence such that 3 tertiary nucleic acids that are bound to detectable labels can hybridize to each secondary nucleic acid.

In some aspects, the present disclosure provides a 3×4 reporter probe. A 3×4 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 3 secondary nucleic acid molecules. Each secondary nucleic acid comprises a nucleotide sequence such that 4 tertiary nucleic acids that are bound to detectable labels can hybridize to each secondary nucleic acid.

In some aspects, the present disclosure provides a Spacer 3×4 reporter probe. A Spacer 3×4 reporter probe comprises a primary nucleic acid, wherein the primary nucleic acid comprises a first domain of 12 nucleotides. Located between the first domain and second domain of the primary nucleic acid is a spacer region consisting of 20 to 40 nucleotides. The spacer is identified as 20 to 40 nucleotides long; however, the length of a spacer is non-limiting and it can be shorter than 20 nucleotides or longer than 40 nucleotides. The second domain of the primary nucleic acid comprises a nucleotide sequence that can hybridize to 3 secondary nucleic acid molecules. Each secondary nucleic acid comprises a nucleotide sequence such that 4 tertiary nucleic acids that are bound to detectable labels can hybridize to each secondary nucleic acid.

In some aspects, a primary nucleic acid can comprise a first domain that is 12 nucleotides long. However, the length of the first domain of a primary nucleic acid is non-limited and can be less than 12 or more than 12 nucleotides. In one example, the first domain of a primary nucleic acid is 14 nucleotides. In another example, the first domain of a primary nucleic acid is 9 nucleotides. In a further example, the first domain of a primary nucleic acid is 8 nucleotides. Exemplary sequences for a 9 nucleotide first domain of a primary nucleic acid of a reporter probe include those in Table 15.

TABLE 15

| Reporter Position | 9-mer Sequence | Color |
| --- | --- | --- |
| 1 | CATTGGGTT | BB |
| 1 | CTGGTATGT | BG |
| 1 | CAGTGAGTG | BR |
| 1 | CAGGAAGGT | BY |
| 1 | CGATGGATG | GG |
| 1 | CGGTGGAAT | GR |
| 1 | CAAAAGAGG | GY |
| 1 | CAGGAGAAA | RR |
| 1 | CAAGGGTAG | YR |
| 1 | CGAGATGAG | YY |
| 2 | CTTGTGATG | BB |
| 2 | CGGGTTAGA | BG |
| 2 | CGTATGGTT | BR |
| 2 | CGATTGGTA | BY |
| 2 | CATGGTGTA | GG |
| 2 | CGGGGTTTA | GR |
| 2 | CAAATTGGT | GY |
| 2 | CGAAGTGGT | RR |
| 2 | CTGTTAGGG | YR |
| 2 | CGTGTTGTG | YY |
| 3 | CTTTGGTTT | BB |
| 3 | CGAGTGGGA | BG |
| 3 | CTAGTAGGG | BR |
| 3 | CTTTGTGTT | BY |

TABLE 15-continued

| Reporter Position | 9-mer Sequence | Color |
| --- | --- | --- |
| 3 | CATGGGGTG | GG |
| 3 | CGAAGTTGA | GR |
| 3 | CGGTGATTT | GY |
| 3 | CTATTGTGG | RR |
| 3 | CTTAGGGAG | YR |
| 3 | CGGTGGAGG | YY |

Any of the features of a specific reporter probe design of the present disclosure can be combined with any of the features of another reporter probe design of the present disclosure. For example, a 5×5 reporter probe can be modified to contain a spacer region of approximately 20 to 40 nucleotides between the complementary nucleic and the primary nucleic acid. In another example, a 4×3 reporter probe can be modified such that the 4 secondary nucleic acids comprise a nucleotide sequence that allows 5 tertiary nucleic acids that are bound to detectable labels to hybridize to each secondary nucleic acid, thereby creating a 4×5 reporter probe.

Without wishing to be bound by theory, a 5×5 reporter contains more fluorescent labels (25) than a 4×3 reporter (12) and therefore the fluorescent intensity of the 5×5 reporter will be greater. The fluorescence detected in any given field of view FOV is a function a variety of variable including the fluorescent intensity of the given reporter probes and the number of optionally bound target molecules within that FOV. The number of optionally bound target molecules per field of view (FOV) can be from 1 to 2.5 million targets per FOV. Typical numbers of bound target molecules per FOV are 20,000 to 40,000, 220,000 to 440,000 or 1 million to 2 million target molecules. Typical FOVs are 0.05 mm$^2$ to 1 mm$^2$. Further examples of typical FOVs are 0.05 mm$^2$ to 0.65 mm$^2$.

In some aspects, the present disclosure provides reporter probe designs in which the secondary nucleic acid molecules comprise "extra-handles" that are not hybridized to a tertiary nucleic acid molecule and are distal to the primary nucleic acid molecule. In some aspect, an "extra-handle" can be 12 nucleotides long ("12 mer"); however, their lengths are non-limited and can be less than 12 or more than 12 nucleotides. The "extra-handles" can each comprise the nucleotide sequence of the first domain of the primary nucleic acid molecule to which the secondary nucleic acid molecule is hybridized. Thus, when a reporter probe comprises "extra-handles", the reporter probe can hybridize to a sequencing probe either via the first domain of the primary nucleic acid molecule or via an "extra-handle." Accordingly, the likelihood that a reporter probe binds to a sequencing probe is increased. The "extra-handle" design can also improve hybridization kinetics. Without being bound by any theory, the "extra-handles" can increase the effective concentration of the reporter probe's complementary nucleic acid. A 5×4 "extra-handles" reporter probe is expected to yield approximately 4750 fluorescent counts per standard FOV. A 5×3 "extra-handles" reporter probe, a 4×4 "extra-handles" reporter probe, a 4×3 "extra-handles" reporter probe and a 3×4 "extra-handles" reporter probe are all expected to yield approximately 6000 fluorescent counts per standard FOV. Any reporter probe design of the present disclosure can be modified to include "extra-handles".

Individual secondary nucleic acid molecules of a reporter probe can hybridize to tertiary nucleic acid molecules that are all labeled with the same detectable label. For example, the left panel of FIG. 5 depicts a "5×6" reporter probe. A 5×6 reporter probe comprises one primary nucleic acid that comprises a second domain, wherein the second domain comprises a nucleotide sequence hybridized to 6 secondary nucleic acid molecules. Each secondary nucleic acid comprises a nucleotide sequence such that 5 tertiary nucleic acid molecules that are bound to detectable labels hybridized to each secondary nucleic acid. Each of the 5 tertiary nucleic acid molecules that bind to a particular secondary nucleic acid molecule are labeled with the same detectable label. Three of the secondary nucleic acid molecules bind to tertiary nucleic acid molecules labeled with a yellow fluorescent dye and the other three secondary nucleic acid bind to tertiary nucleic acid molecules labeled with a red fluorescent dye, for example.

Individual secondary nucleic acid molecules of a reporter probe can hybridize to tertiary nucleic acid molecules that are labeled with different detectable labels. For example, the middle panel of FIG. 5 depicts a "3×2×6" reporter probe design. A "3×2×6" reporter probe comprises one primary nucleic acid that comprises a second domain, wherein the second domain comprises a nucleotide sequence hybridized to 6 secondary nucleic acid molecules. Each secondary nucleic acid comprises a nucleotide sequence such that 5 tertiary nucleic acids that are bound to detectable labels hybridized to each secondary nucleic acid. Each secondary nucleic acid binds to both tertiary nucleic acid molecules labeled with a yellow fluorescent dye and to tertiary nucleic acid molecules labeled with a red fluorescent dye. In this specific example, three secondary nucleic acid molecules bind two red and three yellow tertiary nucleic acid molecules, while the other three secondary nucleic acid molecules bind two red and three yellow tertiary nucleic acid molecules. Each secondary nucleic acid molecule can bind to any number of tertiary nucleic acid molecules bound by different detectable labels. In the middle panel of FIG. 5, the tertiary nucleic acid molecules bound to an individual secondary nucleic acid molecule are arranged such that the colors of the label alternate (i.e. red-yellow-red-yellow-red or yellow-red-yellow-red-yellow).

In any of the described reporter probe designs, tertiary nucleic acids labeled with different detectable labels can be arranged in any order along the secondary nucleic acid. For example, the right panel of FIG. 5 depicts a "Fret resistant 3×2×6" reporter probe that is similar to the 3×2×6 reporter probe design except in the arrangement (e.g., linear order or grouping) of red and yellow tertiary nucleic acid molecules along each secondary nucleic acid molecule.

Figure 6:
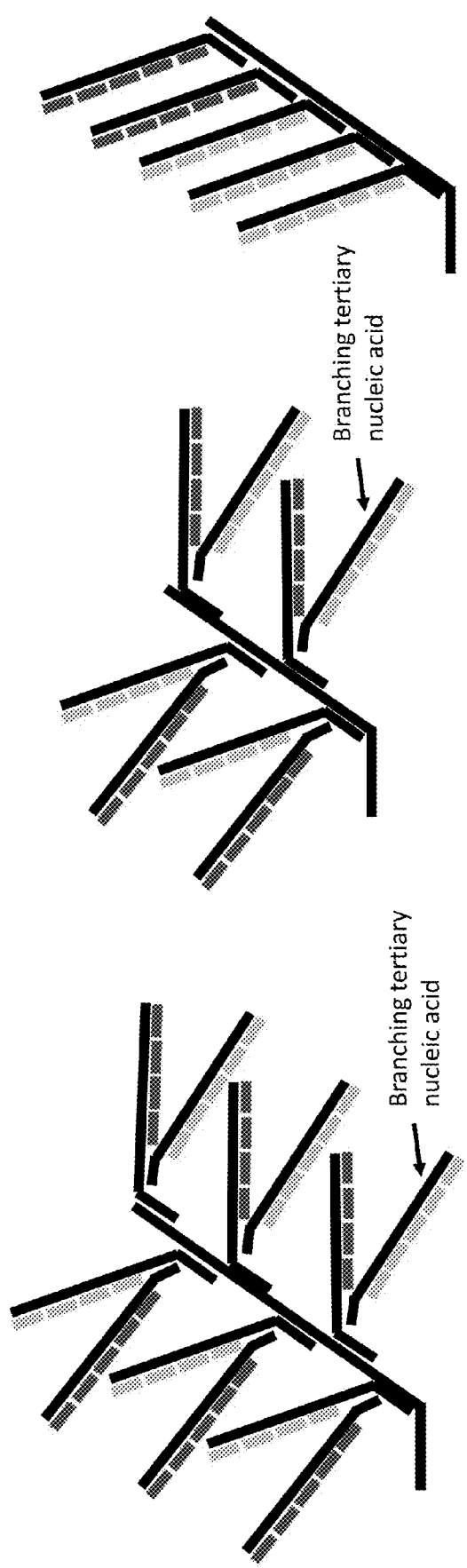
FIG. 6 is a schematic illustration of several exemplary reporter probes of the present disclosure comprising branching tertiary nucleic acids.

FIG. 6 depicts more exemplary reporter probe designs of the present disclosure that include individual secondary nucleic acid molecules that bind to varying tertiary nucleic acid molecules. The left panel depicts a "6×1×4.5" reporter probe that comprises one primary nucleic acid molecule, wherein the primary nucleic acid molecule comprises a second domain, wherein the second domain comprises a nucleotide sequence hybridized to six secondary nucleic acid molecules. Each secondary nucleic acid molecule is hybridized to five tertiary nucleic acid molecules. Four of the five tertiary nucleic acid molecules that hybridize to each secondary nucleic acid molecule are directly labeled with the same color detectable label. The fifth tertiary nucleic acid, denoted as the branching tertiary nucleic acid, is bound to 5 labeled-oligos of the other color of the dual color combination. Of the six secondary nucleic acids, three of them bind to a branching tertiary nucleic acid labeled with one color of the dual color combination (in this example red), while the other three secondary nucleic acids bind to a branching tertiary nucleic acid labeled with the other color of the dual color combination (in this example yellow). In total, the 6×1×4.5 reporter probe is labeled with 54 total dyes, 27 dyes for each color. The middle panel of FIG. 6 depicts a "4×1×4.5" reporter probe that shares the same overall architecture as the 6×1×4.5 reporter probe, except that the primary nucleic acid of the 4×1×4.5 reporter probe binds only 4 secondary nucleic acids, such that there are a total of 36 dyes, 18 for each color.

A reporter probe can comprise the same number of dyes for each color of the dual color combination. A reporter probe can comprise a different number of dyes for each color of the dual color combination. The selection as to which color has more dyes within a reporter probe can be made on the basis of the energy level of light that the two dyes absorb. For example, the right panel of FIG. 6 depicts a "5×5 energy optimized" reporter probe design. This reporter probe design comprises 15 yellow dyes (which are higher energy) and 10 red dyes (which are lower energy). In this example, the 15 yellow dyes can constitute a first label and the 10 red dyes can constitute a second label.

A detectable moiety, label or reporter can be bound to a secondary nucleic acid molecule, a tertiary nucleic acid molecule or to a labeled-oligo in a variety of ways, including the direct or indirect attachment of a detectable moiety such as a fluorescent moiety, colorimetric moiety and the like. One of skill in the art can consult references directed to labeling nucleic acids. Examples of fluorescent moieties include, but are not limited to, yellow fluorescent protein (YFP), green fluorescent protein (GFP), cyan fluorescent protein (CFP), red fluorescent protein (RFP), umbelliferone, fluorescein, fluorescein isothiocyanate, rhodamine, dichlorotriazinylamine fluorescein, cyanines, dansyl chloride, phycocyanin, phycoerythrin and the like.

Fluorescent labels and their attachment to nucleotides and/or oligonucleotides are described in many reviews, including Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). Particular methodologies applicable to the disclosure are disclosed in the following sample of references: U.S. Pat. Nos. 4,757,141; 5,151,507; and 5,091,519. One or more fluorescent dyes can be used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); Lee et al. U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. As used herein, the term "fluorescent label" comprises a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, NJ), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, OR) and the like. Alternatively, the above fluorophores and those mentioned herein can be added during oligonucleotide synthesis using for example phosphoroamidite or NHS chemistry. Protocols are known in the art for custom synthesis of nucleotides having other fluorophores (See, Henegariu et al. (2000) Nature Biotechnol. 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g., SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, OR), Cy2, Cy3, Cy3.5, Cy5, Cy5.5, Cy7 (Amersham Biosciences, Piscataway, NJ) and the like. FRET tandem fluorophores can also be used, including, but not limited to, PerCP-Cy5.5, PE-Cy5, PE-Cy5.5, PE-Cy7, PE-Texas Red, APC-Cy7, PE-Alexa dyes (610, 647, and 680), APC-Alexa dyes and the like.

Metallic silver or gold particles can be used to enhance signal from fluorescently labeled nucleotide and/or oligonucleotide sequences (Lakowicz et al. (2003) BioTechniques 34:62).

Other suitable labels for an oligonucleotide sequence can include fluorescein (FAM, FITC), digoxigenin, dinitrophenol (DNP), dansyl, biotin, bromodeoxyuridine (BrdU), hexahistidine (6xHis), phosphor-amino acids (e.g., P-tyr, P-ser, P-thr) and the like. The following hapten/antibody pairs can be used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

Detectable labels described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218; or the like, or in Wheeless et al., pgs. 21-76, in Flow Cytometry: Instrumentation and Data Analysis (Academic Press, New York, 1985). Spectrally resolvable organic dyes, such as fluorescein, rhodamine, and the like, means that wavelength emission maxima are spaced at least 20 nm apart, and in another aspect, at least 40 nm apart. For chelated lanthanide compounds, quantum dots, and the like, spectrally resolvable means that wavelength emission maxima are spaced at least 10 nm apart, or at least 15 nm apart.

Figure 32:
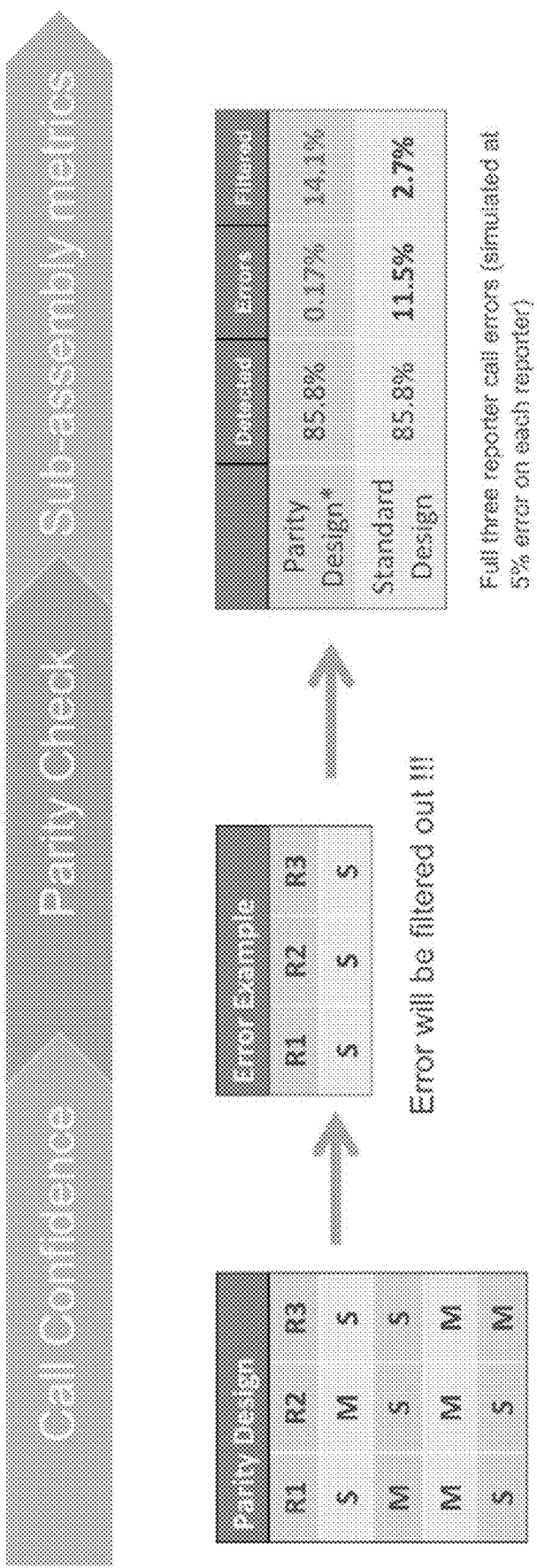
FIG. 32 is an illustration of a parity scheme used in the methods of the present disclosure.

The presence of 3 attachment positions in the barcode domain, each with up to 10 potential dual color combinations, allows for up to 1000 color combinations to exist. If the reporter probes are pooled in less than 1000 probes per pool then the ability to use parity checking to overcome errors can be utilized. There are many potential parity schemes that can exist that will allow parity checking, a single example scheme is shown in FIG. 32. In this example the actual colors present are not used as the parity check but rather the presence of single (S) color reporter probes (e.g. Red) and Multicolor (M) reporter probes (e.g. Red/Yellow) at each attachment position in the barcode domain are. As can be seen in the parity design the knowledge of the status (S or M) of any two reporter positions allows prediction of the third position. In the example shown an observation of S in any two positions requires the unobserved position to be M, observation of S and an M in any two positions means the other position must be S, while observation of two M reporter probes requires the other position to be M. This means that in order to get a code of three reporter probes with incorrectly detected reporter colors, two incorrect calls have to be made. FIG. 32 shows the results of a simulation at 5% reporter probe error that shows the increase in filtering of errors when parity checking is applied. There are multiple parity systems that can be applied this is just one example.

Another error correction routine is to swap color palette for each pool of reporter probes. A color palette is the set of reporter probes that are actually used for measuring a pool. Multiple reporter probes are not used in any pool, if 500 reporter probes are in a pool then only ½ the possible color combinations are needed. The simplest way to implement this is to have two palettes, palette A containing 500 reporter probes and palette B containing the other 500 reporter probes. Thus if sequencing pools 1,3,5,7 have palette A and pools 2,4,6,8 have palette B then running pools in the order 1,2,3,4,5,6,7,8 means each successive sequencing pool will have a separate palette. Thus, barcodes from pool 2 would not exist in the preceding and following pools (e.g. pools 1 and 3). This allows for simple automated troubleshooting and limiting of detections errors.

A reporter probe can comprise one or more cleavable linker modifications. The one or more cleavable linker modifications can be positioned anywhere in the reporter probe. A cleavable linker modification can be located between the first and second domains of a primary nucleic acid molecule of a reporter probe. A cleavable linker modification can be present between the first and second domains of the secondary nucleic acid molecules of a reporter probe. A cleavable linker modification can be present between the first and second domains of the primary nucleic acid molecule and secondary nucleic acid molecules of a reporter probe. The left panel of FIG. 7 depicts an exemplary reporter probe of the present disclosure comprising cleavable linker modification between the first and second domains of the primary nucleic acid and between the first and second domains of the secondary nucleic acids. In such instances as exemplified in the left panel of FIG. 7, the cleavable linker modifications may include one or more cleavable moieties such as those exemplified in the left panel of FIG. 7.

A cleavable linker modification can be a compound of the Formula (I):

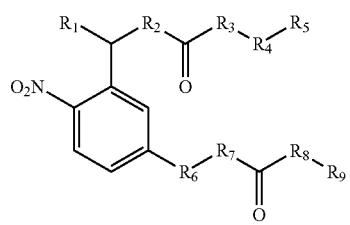

or a stereoisomer or salt thereof, wherein: $R_1$ is hydrogen, halogen, $C_{1-6}$alkyl, $C_{2-6}$alkenyl, $C_{2-6}$alkynyl, wherein said $C_{1-6}$alkyl, $C_{2-6}$alkenyl, $C_{2-6}$alkynl are each independently optionally substituted with at least one substituent $R_{10}$; $R_2$ is O, NH, or $N(C_{1-6}$alkyl); $R_3$ is cycloalkyl, heterocycloalkyl, aryl, or heteroaryl, each optionally substituted with at least one substituent $R_{10}$; each $R_4$ and $R_7$ are independently $C_{1-6}$alkyl, $C_{2-6}$alkenyl, $C_{2-6}$alkynyl, wherein said $C_{1-6}$alkyl, $C_{2-6}$alkenyl, $C_{2-6}$alkynl are each independently optionally substituted with at least one substituent $R_{10}$; $R_5$ and $R_9$ are each independently cycloalkyl, heterocycloalkyl, aryl, or heteroaryl, each optionally substituted with at least one substituent $R_{10}$; $R_6$ is O, NH or $N(C_{1-6}$alkyl); $R_8$ is O, NH, or $N(C_{1-6}$alkyl); each $R_{10}$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_{11}$, —$SO_2R_{11}$, —$SO_3^-$, —$COR_{11}$, —$CO_2R_{11}$, —$CONR_{11}R_{12}$, —$C(=NR_{11})NR_{12}R_{13}$, —$NR_{11}R_{12}$, —$NR_{12}COR_{12}$, —$NR_{11}CONR_{12}R_{13}$, —$NR_{11}CO_2R_{12}$, —$NR_{11}SONR_{12}R_{13}$, —$NR_{11}SO_2NR_{12}R_{13}$, or —$NR_{11}SO_2R_{12}$; and $R_{11}$, $R_{12}$, and $R_{13}$; which may be the same or different, are each independently hydrogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{1-6}$alkyloxy$C_{1-6}$alkyl-, cycloalkyl, heterocyclyl, aryl, or heteroaryl.

In one aspect, $R_1$ is $C_{1-6}$alkyl, preferably $C_{1-3}$alkyl such as methyl, ethyl, propyl or isopropyl; $R_2$ is NH or $N(C_{1-6}$alkyl); $R_3$ is a 5- to 6-membered cycloalkyl, preferably cyclohexyl; $R_4$ is $C_{1-6}$alkyl, preferably $C_{1-3}$alkylene such as methylene, ethylene, propylene, or isopropylene; $R_5$ is a 5- to 6-membered heterocyclyl comprising one nitrogen atom and 0 or 1 additional heteroatoms selected from N, O and S, wherein said heterocyclyl is optionally substituted with one or two $R_{10}$; $R_6$ is O; $R_7$ is $C_{1-6}$alkyl, preferably $C_{1-3}$alkylene such as methylene, ethylene, propylene, or isopropylene; $R_8$ is O; $R_9$ is a 5- to 6-membered heterocyclyl comprising one nitrogen atom and 0 or 1 additional heteroatoms selected from N, O and S, wherein said heterocyclyl is optionally substituted with one or two $R_{10}$; and each $R_{10}$ is independently halogen, $C_{1-6}$alkyl, halo$C_{1-6}$alkyl, oxo, —$SO_2H$, or —$SO_3^-$.

In one aspect, $R_3$ is cyclohexyl, $R_4$ is methylene, $R_5$ is 1H-pyrrole-2,5-dione, and $R_9$ is pyrrolidine-2,5-dione, optionally substituted with $SO_3^-$.

The linker compound can be

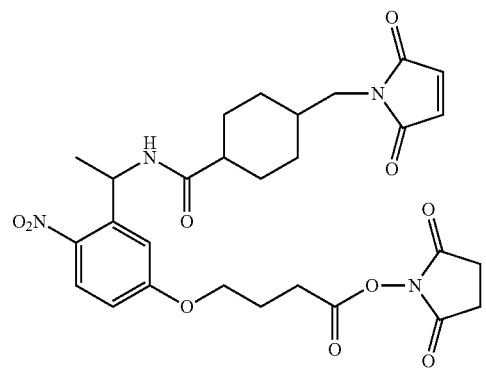 [SMILES: CC(NC(=O)C1CCC(CN2C(=O)C=CC2=O)CC1)c1cc(OCCCC(=O)ON2C(=O)CCC2=O)ccc1[N+](=O)[O-]]

or a stereoisomer or salt thereof

The linker compound can be

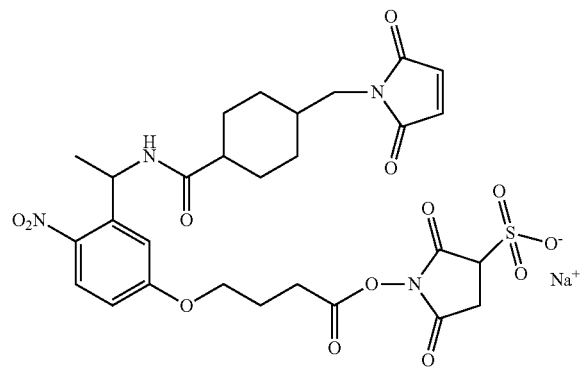 [SMILES: CC(NC(=O)C1CCC(CN2C(=O)C=CC2=O)CC1)c1cc(OCCCC(=O)ON2C(=O)CC(S(=O)(=O)[O-])C2=O)ccc1[N+](=O)[O-] ; [Na+]]

or a stereoisomer or salt thereof.

The linker compound or linker modification can be

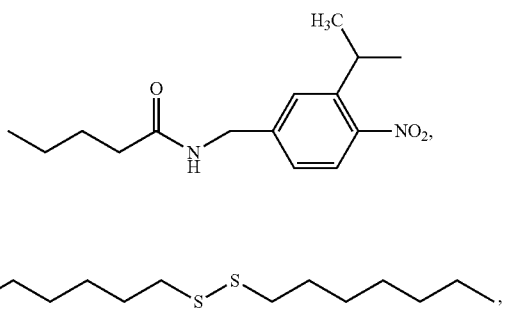

A cleavable linker modification or a cleavable moiety can be

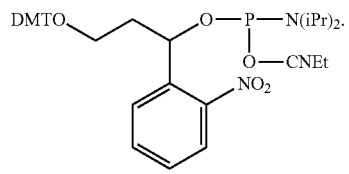

Reporter probes can be assembled by mixing together three stock solutions together with water. One stock solution contains primary nucleic acid molecules, one stock solution contains secondary nucleic acid molecules and the final stock solution contains the tertiary nucleic acid molecules. Table 2 depicts exemplary amounts of each stock solution that can be mixed to assemble particular reporter probe designs.

TABLE 2

| Reporter probe Design | Volume (µl) of primary nucleic acid molecules (10 µM stock) | Volume (µl) of secondary nucleic acid molecules (10 µM stock) | Volume (µl) of tertiary nucleic acid molecules (10 µM stock) | Volume (µl) of Water |
|---|---|---|---|---|
| 5 × 4 | 1 | 4.5 | 2.25 | 92.25 |
| 5 × 3 | 1 | 4.5 | 1.8 | 92.7 |
| 4 × 4 | 1.28 | 4.5 | 2.25 | 91.97 |
| 4 × 3 | 1.28 | 4.5 | 1.8 | 92.42 |
| 3 × 4 | 1.8 | 4.5 | 2.25 | 91.45 |

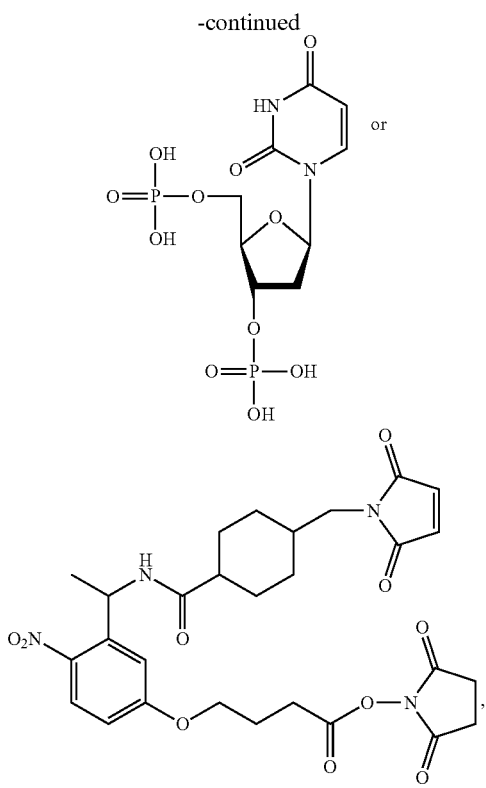

The linker compound or linker modification can be

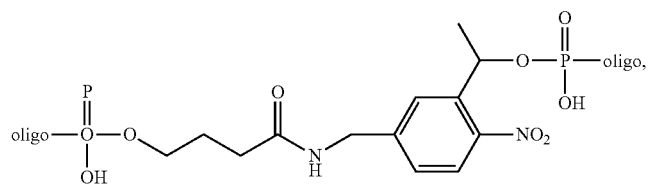

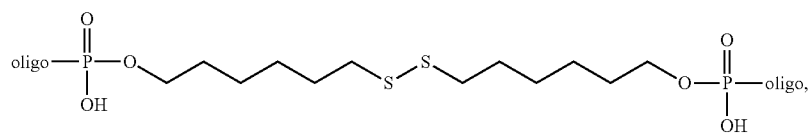

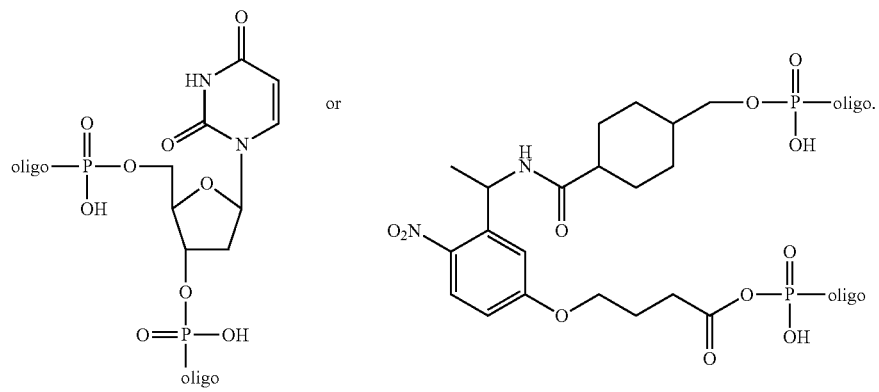

Target Nucleic Acid

The present disclosure provides methods for sequencing a nucleic acid using the sequencing probes disclosed herein. The nucleic acid that is to be sequenced using the method of the present disclosure is herein referred to as a "target nucleic acid". The term "target nucleic acid" shall mean a nucleic acid molecule (DNA, RNA, or PNA) whose sequence is to be determined by the probes, methods, and apparatuses of the disclosure. In general, the terms "target nucleic acid", "target nucleic acid molecule,", "target nucleic acid sequence," "target nucleic acid fragment," "target oligonucleotide" and "target polynucleotide" are used interchangeably and are intended to include, but not limited to, a polymeric form of nucleotides that can have various lengths, either deoxyribonucleotides or ribonucleotides, or analogs thereof. Non-limiting examples of nucleic acids include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), non-coding RNA (ncRNA), cDNA, recombinant polynucleotides, branched polynucleotides, plasmids, vectors, isolated DNA of a sequence, isolated RNA of a sequence, nucleic acid probes, and primers. Prior to sequencing using the methods of the present disclosure, the identity and/or sequence of the target nucleic is known. Alternatively, the identity and/or sequence is unknown. It is also possible that a portion of the sequence of a target nucleic acid is known prior to sequencing using the methods of the present disclosure. For example, the method can be directed at determining a point mutation in a known target nucleic acid molecule.

The present methods directly sequence a nucleic acid molecule obtained from a sample, e.g., a sample from an organism, and, preferably, without a conversion (or amplification) step. As an example, for direct RNA-based sequencing, the present methods do not require conversion of an RNA molecule to a DNA molecule (i.e., via synthesis of cDNA) before a sequence can be obtained. Since no amplification or conversion is required, a nucleic acid sequenced in the present disclosure will retain any unique base and/or epigenetic marker present in the nucleic acid when the nucleic acid is in the sample or when it was obtained from the sample. Such unique bases and/or epigenetic markers are lost in sequencing methods known in the art.

The present methods can be used to sequence at single molecule resolution. In other words, the present methods allow the user to generate a final sequence based on data collected from a single target nucleic acid molecule, rather than having to combine data from different target nucleic acid molecules, preserving any unique features of that particular target.

The target nucleic acid can be obtained from any sample or source of nucleic acid, e.g., any cell, tissue, or organism, in vitro, chemical synthesizer, and so forth. The target nucleic acid can be obtained by any art-recognized method. The nucleic acid can be obtained from a blood sample of a clinical subject. The nucleic acid can be extracted, isolated, or purified from the source or samples using methods and kits well known in the art.

A target nucleic acid can be fragmented by any means known in the art. Preferably, the fragmenting is performed by an enzymatic or a mechanical means. The mechanical means can be sonication or physical shearing. The enzymatic means can be performed by digestion with nucleases (e.g., Deoxyribonuclease I (DNase I)) or one or more restriction endonucleases.

When a nucleic acid molecule comprising the target nucleic acid is an intact chromosome, steps should be taken to avoid fragmenting the chromosome.

The target nucleic acid can include natural or non-natural nucleotides, comprising modified nucleotides or nucleic acid analogues, as well-known in the art.

The target nucleic acid molecule can include DNA, RNA, and PNA molecules up to hundreds of kilobases in length (e.g. 1, 2, 3, 4, 5, 10, 20, 30, 40, 50, 100, 200, 500, or more kilobases). A target nucleic acid molecule can comprise about 50 to about 400 nucleotides, or about 90 to about 350 nucleotides.

Capture Probes

The target nucleic acid can be immobilized (e.g., at one, two, three, four, five, six, seven, eight, nine, ten, or more positions) to a substrate.

Exemplary useful substrates include those that comprise a binding moiety selected from the group consisting of ligands, antigens, carbohydrates, nucleic acids, receptors, lectins, and antibodies. The capture probe comprises a substrate binding moiety capable of binding with the binding moiety of the substrate. Exemplary useful substrates comprising reactive moieties include, but are not limited to, surfaces comprising epoxy, aldehyde, gold, hydrazide, sulfhydryl, NETS-ester, amine, alkyne, azide, thiol, carboxylate, maleimide, hydroxymethyl phosphine, imidoester, isocyanate, hydroxyl, pentafluorophenyl-ester, psoralen, pyridyl disulfide or vinyl sulfone, polyethylene glycol (PEG), hydrogel, or mixtures thereof. Such surfaces can be obtained from commercial sources or prepared according to standard techniques. Exemplary useful substrates comprising reactive moieties include, but are not limited to, OptArray-DNA NETS group (Accler8), Nexterion Slide AL (Schott) and Nexterion Slide E (Schott).

The substrate can be any solid support known in the art, e.g., a coated slide and a microfluidic device, which is capable of immobilizing a target nucleic acid. The substrate can be a surface, membrane, bead, porous material, electrode or array. The substrate can be a polymeric material, a metal, silicon, glass or quartz for example. The target nucleic acid can be immobilized onto any substrate apparent to those of skill in the art.

When the substrate is an array, the substrate can comprise wells, the size and spacing of which is varied depending on the target nucleic acid molecule to be attached. In one example, the substrate is constructed so that an ultra-dense ordered array of target nucleic acids is attached. Examples of the density of the array of target nucleic acids on a substrate include from 500,000 to 10,000,000 target nucleic acid molecules per $mm^2$, from 1,000,000 to 4,000,000 target nucleic acid molecules per $mm^2$ or from 850,000 to 3,500,000 target nucleic acid molecules per $mm^2$.

The wells in the substrate are locations for attachment of a target nucleic acid molecule. The surface of the wells can be functionalized with reactive moieties described above to attract and bind specific chemical groups existing on the on the target nucleic acid molecules or capture probes bound to the target nucleic acid molecules to attract, immobilize and bind the target nucleic acid molecule. These functional groups are well known to be able to specifically attract and bind biomolecules through various conjugation chemistries.

For single nucleic acid molecule sequencing on a substrate such as an array, a universal capture probe or universal sequence complementary to the substrate binding moiety of a capture probe is attached to each well. A single target nucleic acid molecule is then bound to the universal capture probe or universal sequence complementary to the substrate binding moiety of a capture probe bound to the capture probe and sequencing can commence.

For single nucleic acid molecule sequencing on a substrate such as an array, a single target nucleic acid molecule can be bound to a capture probe. The substrate binding moiety of the capture probe can then be bound to an adapter oligonucleotide. The adapter nucleotide is then bound to a lawn oligonucleotide that is attached to each well and sequencing can commence. Exemplary sequences for lawn oligonucleotides are shown in Table 8.

TABLE 8

| Exemplary Lawn Oligo Sequence | SEQ ID NO. |
|---|---|
| 5AmMC6/TGGTGAGGTTGTTGGTAGTAGTGAGTTTGTAGGGT | 100 |
| 5AmMC6/TGGTGAGGTTGTTGGTAGTAGTGAG | 101 |
| 5AmMC6/TTTTTTTTTTTTTTTTTTTTTTTTTTTTTT | 102 |
| 5AmMC6/CATCTCAAACACCTTCTACAATATGACCTAACACAC | 103 |
| 5AmMC6/GTGATGGTTATAAGAGGTGTTGATATATTTATAGTA | 104 |
| 5AmMC6/TATTGATATTGAGAAAGCGTTTGATGATGTATTGAT | 105 |
| 5AmMC6/TAGTTATGTAGTAGTTTGCGAAAGAGTTATAGTTAT | 106 |
| /5AmMC6/ACTACCCTACTCTACCCTTCTAAGATATACATATAC | 107 |
| 5AmMC6/TG/isodG/TGA/isodG/GTT/isodG/TTG/isodG/TA/isodG/TA/isodG/TGA/isodG/TTT/isodG/TAG/isodG/GT | 108 |
| 5[BiotinTEG]/L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//L-dT//3AmMO/ | 114 |

5amMC6 = 5' amine with a 6 carbon linker; isodG = isoguanine; 3AmMO = 3'

5[BiotinTEG] = 5' Biotin-TEG

5[BiotinTEG]=5' Biotin-TEG

Each of the nucleic acids comprising a lawn oligonucleotide or an adapter oligonucleotide can independently be a canonical base or a modified nucleotide or nucleic acid analogue. Typical modified nucleotides or nucleic acid analogues useful in a lawn oligonucleotide or an adapter oligonucleotide are isoguanine and isocytosine. Alternatively still, each of the nucleic acids comprising the lawn oligonucleotides can independently be L-DNA. In some aspects, a lawn oligonucleotide can comprise L-DNA. A lawn oligonucleotide can consist of L-DNA. A lawn oligonucleotide can consist essentially of L-DNA. The use of modified nucleotides or nucleotide analogues such as isoguanine and isocytosine or L-DNA, for example, can improve binding efficiency and accuracy of an adapter oligonucleotide to an appropriate complementary nucleic acid sequence within a lawn oligonucleotide while minimizing binding elsewhere.

A lawn oligonucleotide can further comprise a 5' amine with a 6 carbon linker, herein referred to as 5AmMC6. 5AmMC6 can be used to attach a lawn oligonucleotide to a substrate.

Figure 33:
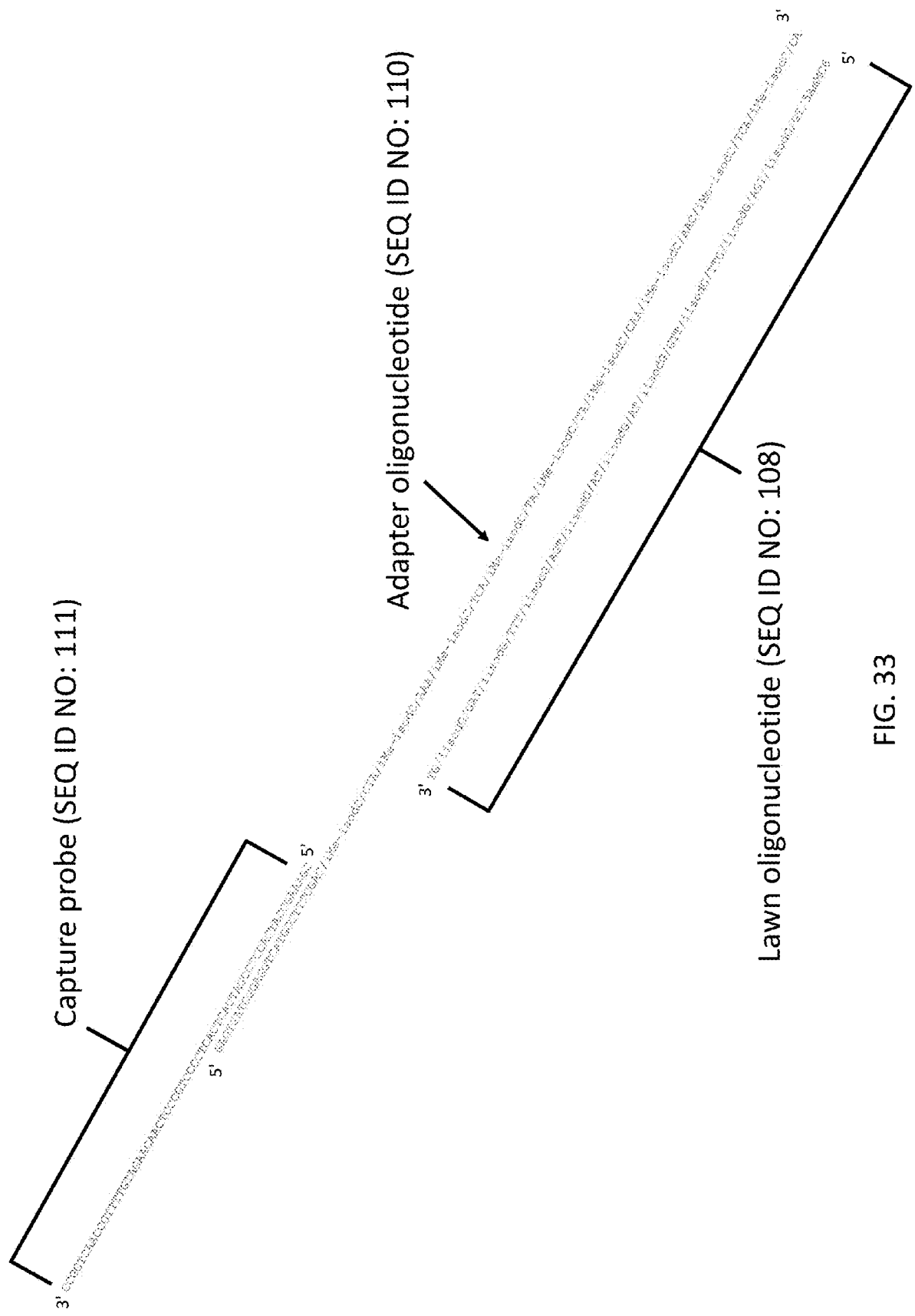
FIG. 33 is a schematic illustration of a capture probe, adaptor oligonucleotide and lawn oligonucleotide complex of the present invention.

An example of a capture probe, adaptor oligonucleotide and lawn oligo complex is shown in FIG. 33. In this Figure, an exemplary adapter sequence and an exemplary capture probe sequence that hybridize are in green, the sequence that is the reverse complement of an exemplary lawn oligo is in blue and the exemplary sequence in red on the capture probe hybridizes with a target gene, which in this example is the gene TP53.1. The sequence of the exemplary capture probe is 3'-CCGGTCAACCGTTTTGTAGAACAACTCCCGTCCCCTCACTCACTAGCCTCCAGTACC GAAAGC-5' (SEQ ID No: 111). The sequence of the exemplary adapter sequence is 5'-GAGTGATCGGAGGTCATGGCTTTCGAC/iMe-isodC/CTA/iMe-isodC/AAA/iMe-isodC/TCA/iMe-isodC/TA/iMe-isodC/TA/iMe-isodC/CAA/iMe-isodC/AAC/iMe-isodC/TCA/iMe-isodC/CA-3' (SEQ ID No: 110). The sequence of the sequence of the exemplary lawn oligonucleotide is TG/iisodG/GAT/iisodG/TTT/iisodG/AGT/iisodG/AT/iisodG/AT/iisodG/GTT/iisodG/TTG/iisod G/AGT/iisodG/GT/5AmMC6 (SEQ ID NO: 108).

In some aspects, a lawn oligonucleotide can comprise at least one affinity moiety, at least two affinity moieties, at least three affinity moieties, at least four affinity moieties, at least five affinity moieties, at least six affinity moieties, at least seven affinity moieties, at least eight affinity moieties, at least nine affinity moieties or at least ten affinity moieties. The affinity moiety can be biotin. Thus, a lawn oligonucleotide can comprise at least one biotin moiety, at least two biotin moieties, at least three biotin moieties, at least four biotin moieties, at least five biotin moieties, at least six biotin moieties, at least seven biotin moieties, at least eight biotin moieties at least nine biotin moieties or at least ten biotin moieties.

Figure 67:
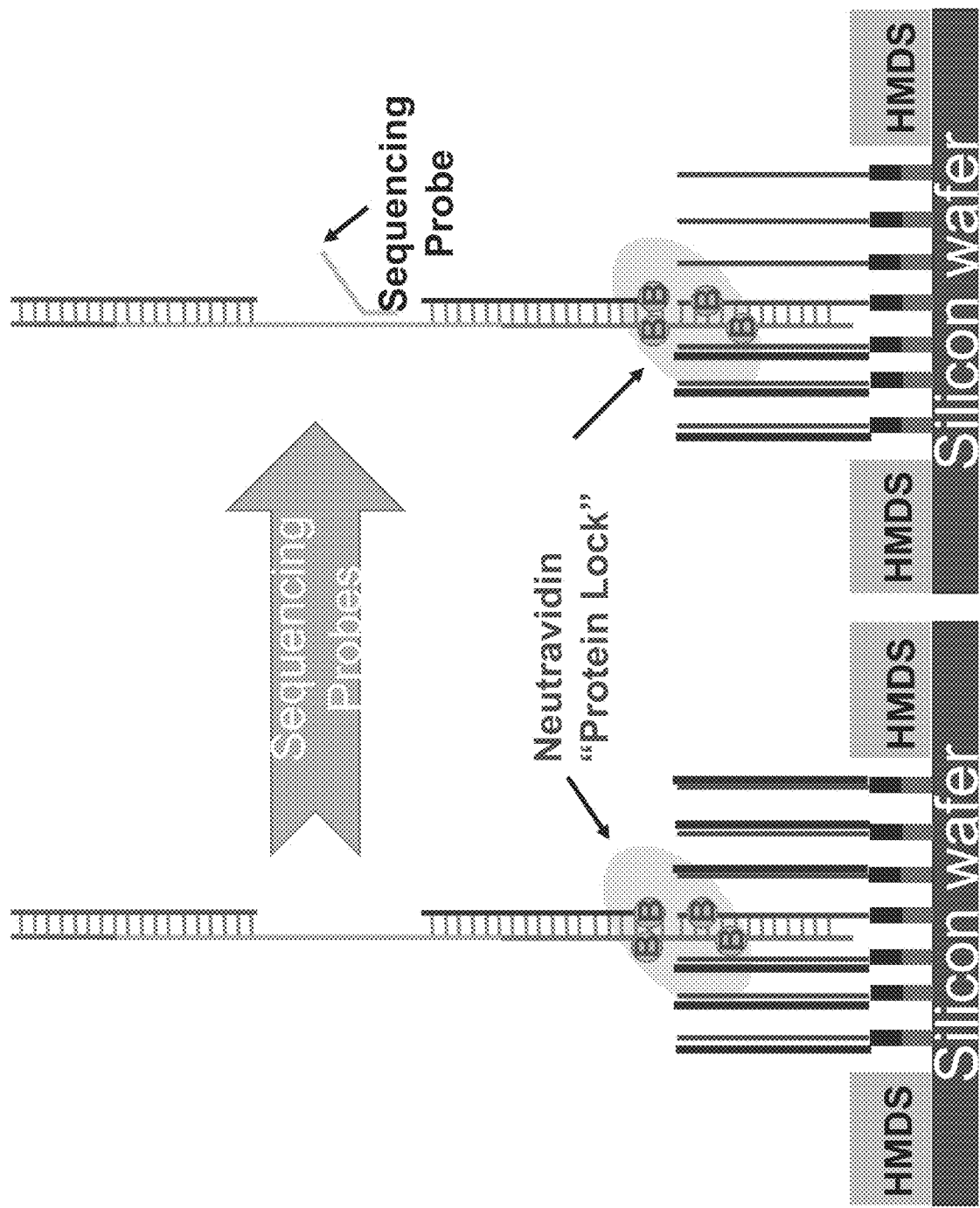
FIG. 67 is a schematic illustration of a target nucleic acid immobilized to a solid substrate using the methods and compositions of the present disclosure. The target nucleic acid is immobilized using a protein lock between biotin moieties located on the capture probes and lawn oligonucleotides and a neutravidin moiety.

In some aspects, a capture probe of the present disclosure that is hybridized to a target nucleic acid can comprise at least one first affinity moiety, such as, but not limited to, a biotin moiety. The capture probe hybridized to the target nucleic acid can then hybridize, either directly or indirectly, with at least one lawn oligonucleotide on a substrate, wherein the at least one lawn oligonucleotide comprises at least one first affinity moiety, such as, but not limited to, a biotin moiety. After hybridization of the capture probe to the lawn oligonucleotide, the resultant capture probe-target nucleic acid-lawn oligonucleotide complex can be incubated with a second affinity moiety, wherein the second affinity moiety is able to bind to the first affinity moiety located on the capture probe and the first affinity moiety located on the lawn oligonucleotide. In a non-limiting example, if the first affinity moiety located on the capture probe and the first affinity moiety located on the lawn oligonucleotide are both biotin, neutravidin can be used as a second affinity moiety. The second affinity moiety will bind to the first affinity moiety located on the capture probe and the first affinity moiety located on the lawn oligonucleotide, creating a protein bridge that is herein referred to as a "protein lock". A protein lock can be used to more stably immobilize a target nucleic acid onto a substrate. FIG. 67 shows a schematic illustration of a protein lock using biotinylated capture probes and lawn oligonucleotides and neutravidin.

The target nucleic acid can be bound by one or more capture probes (i.e. two, three, four, five, six, seven, eight, nine, ten or more capture probes). A capture probe comprises a domain that is complementary to a portion of the target nucleic acid and a domain that comprises a substrate binding moiety. The portion of the target nucleic acid to which a capture probe is complementary can be an end of the target nucleic acid or not towards an end. A capture probe can comprise a cleavable moiety between a domain that is complementary to a portion of the target nucleic acid and a domain that comprises a substrate binding moiety.

Alternatively, a capture probe can comprise a first domain that is complementary to a portion of the target nucleic acid, a second domain that comprises a substrate binding moiety, and a third domain that comprises a different substrate binding moiety. A capture probe can comprise a cleavable moiety between any domains.

A capture probe can be phosphorylated at the 5' end. Alternatively, a capture probe can comprise at least one phosphorothioate bond. A capture probe can comprise at least two phosphorothioate bonds. Preferably, the at least one or the at least two phosphorothioate bonds are located at the 5' end of the capture probe.

The substrate binding moiety of the capture probe can be biotin and the substrate can be avidin (e.g., streptavidin). Useful substrates comprising avidin are commercially available including TB0200 (Accelr8), SAD6, SAD20, SAD100, SAD500, SAD2000 (Xantec), SuperAvidin (Array-It), streptavidin slide (catalog #MPC 000, Xenopore) and STREPTAVIDINnslide (catalog #439003, Greiner Bio-one). The substrate binding moiety of the capture probe can be avidin (e.g., streptavidin) and the substrate can be biotin. Useful substrates comprising biotin that are commercially available include, but are not limited to, Optiarray-biotin (Accler8), BD6, BD20, BD100, BD500 and BD2000 (Xantec).

The substrate binding moiety of the capture probe can be a reactive moiety that is capable of being bound to the substrate by photoactivation. The substrate can comprise the photoreactive moiety, or the first portion of the nanoreporter can comprise the photoreactive moiety. Some examples of photoreactive moieties include aryl azides, such as N((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

The substrate binding moiety of a capture probe can be a nucleic acid that can hybridize to a binding moiety of a substrate that is complementary. Each of the nucleic acids comprising a substrate binding moiety of a capture probe can independently be a canonical base or a modified nucleotide or nucleic acid analogue. At least one, at least two, at least three, at least four, at least five, or at least six nucleotides in the substrate binding moiety of a capture probe can be modified nucleotides or nucleotide analogues. Typical ratios of modified nucleotides or nucleotide analogues to canonical bases in a substrate binding moiety of a capture probe are 1:2 to 1:8. Typical modified nucleotides or nucleic acid analogues useful in a substrate binding moiety of a capture probe are isoguanine and isocytosine.

The substrate binding moiety of the capture probe can be immobilized to the substrate via other binding pairs apparent to those of skill in the art. After binding to the substrate, the target nucleic acid can be elongated by applying a force (e.g., gravity, hydrodynamic force, electromagnetic force "electrostretching", flow-stretching, a receding meniscus technique, and combinations thereof) sufficient to extend the target nucleic acid. A capture probe can comprise or be associated with a detectable label, i.e., a fiducial spot.

The target nucleic acid can be bound by a second capture probe which comprises a domain that is complementary to a second portion of the target nucleic acid. The second portion of the target nucleic acid bound by the second capture probe is different than the first portion of the target nucleic acid bound by the first capture probe. The portion can be an end of the target nucleic acid or not towards an end. Binding of a second capture probe can occur after or during elongation of the target nucleic acid or to a target nucleic acid that has not been elongated. The second capture probe can have a binding as described above.

The target nucleic acid can be bound by a third, fourth, fifth, sixth, seventh, eighth, ninth or tenth capture probe which comprises a domain that is complementary to a third, fourth, fifth, sixth, seventh, eighth, ninth or tenth portion of the target nucleic acid. The portion can be an end of the target nucleic acid or not towards an end. Binding of a third, fourth, fifth, sixth, seventh, eighth, ninth or tenth capture probe can occur after or during elongation of the target nucleic acid or to a target nucleic acid that has not been elongated. The third, fourth, fifth, sixth, seventh, eighth, ninth or tenth capture probe can have a binding as described above.

The capture probe is capable of isolating a target nucleic acid from a sample. Here, a capture probe is added to a sample comprising the target nucleic acid. The capture probe binds the target nucleic acid via the region of the capture probe that his complementary to a region of the target nucleic acid. When the target nucleic acid contacts a substrate comprising a moiety that binds the capture probe's substrate binding moiety, the nucleic acid becomes immobilized onto the substrate.

Figure 8:
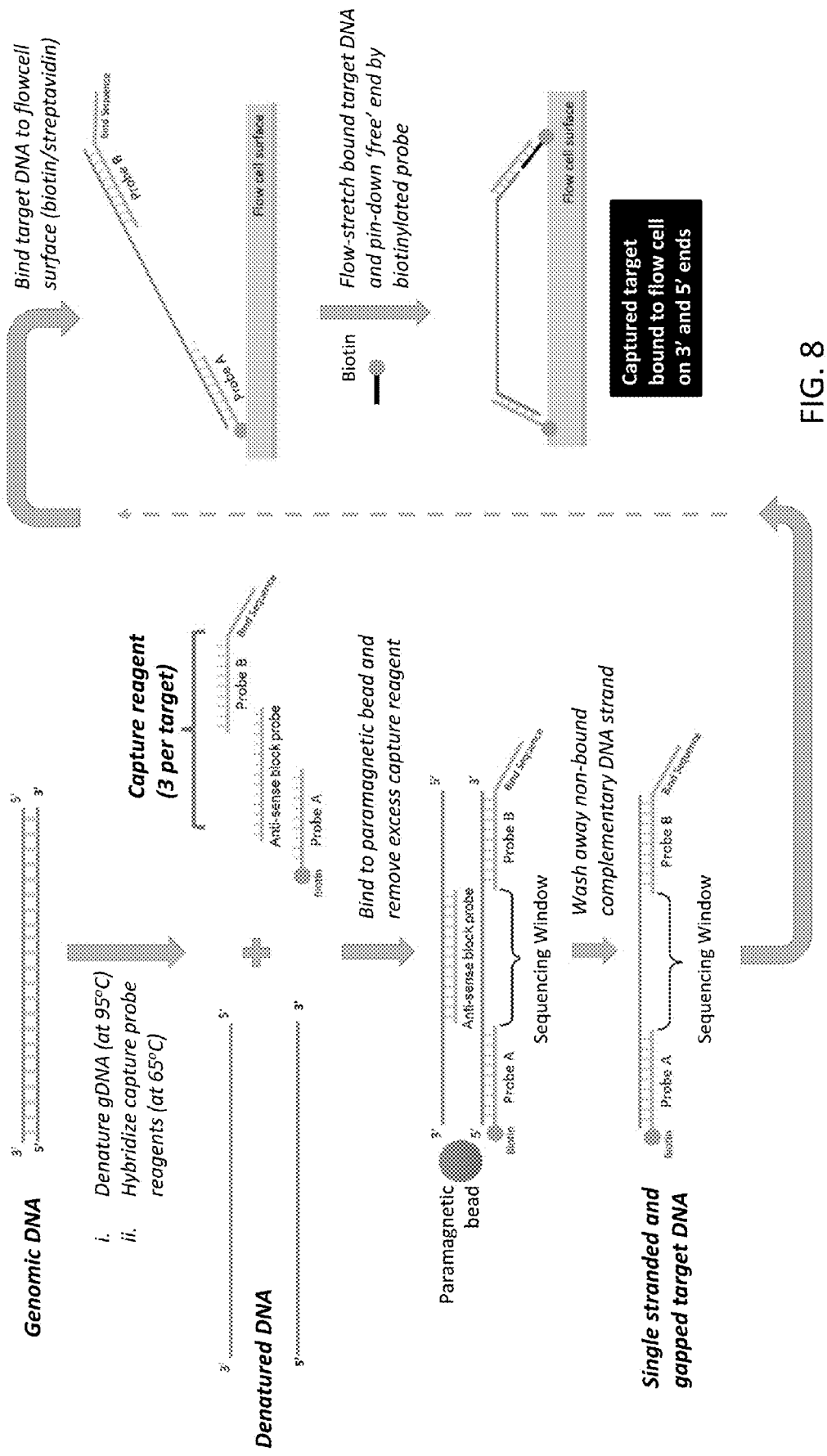
FIG. 8 is a schematic illustration of the capture of a target nucleic acid using the two capture probe system of the present disclosure.

FIG. 8 shows the capture of a target nucleic acid using a two capture probe system of the present disclosure. Genomic DNA is denatured at 95° C. and hybridized to a pool of capture reagents. This pool of capture reagents comprise the oligonucleotides Probe A, Probe B, and antisense block probes. Probe A comprises a biotin moiety at the 3' end of the probe and a sequence that is complementary to the 5' end of the target nucleic acid. Probe B comprises a purification binding sequence that can be bound by paramagnetic beads at the 5' end of the probe and a nucleotide sequence that is complementary to the 3' end of the target nucleic acid. The anti-sense block probe comprises a nucleotide sequence that is complementary to the anti-sense strand of the portion of the target nucleic acid that is to be sequenced. After hybridization with the capture reagents, a sequencing window is created on the target nucleic acid between the hybridized Probe A and Probe B. The target nucleic acid is purified using paramagnetic beads that bind to the 5' sequence of Probe B. Any excess capture reagents or complementary anti-sense DNA strands are washed away, resulting in the purification of the intended target nucleic acid. The purified target nucleic acid is then flowed through a flow chamber that includes a surface that can bind to the biotin moiety on the hybridized Probe A, such as streptavidin. This results in the tethering of one end of the target nucleic acid to the surface of the flow cell. To capture the other end, the target nucleic acid is flow-stretched and a biotinylated probe complementary to the purification binding sequence of Probe B is added. Upon hybridizing to the purification binding sequence of Probe B, the biotinylated probe can bind to the surface of the flow cell, resulting in a captured target nucleic acid molecule that is elongated and bound to the flow cell surface at both ends.

To ensure that a user "captures" as many target nucleic acid molecules as possible from high fragmented samples, it is helpful to include a plurality of capture probes, each complementary to a different region of the target nucleic acid. For example, there can be three pools of capture probes, with a first pool complementary to regions of the target nucleic acid near its 5' end, a second pool complementary to regions in the middle of the target nucleic acid, and a third pool near its 3' end. This can be generalized to "n-regions-of-interest" per target nucleic acid. In this example, each individual pool of fragmented target nucleic acid bound to a capture probe comprising or bound to a biotin tag. 1/nth of input sample (where n=the number of distinct regions in target nucleic acid) is isolated for each pool chamber. The capture probe binds the target nucleic acid of interest. Then the target nucleic acid is immobilized, via the capture probe's biotin, to an avidin molecule adhered to the substrate. Optionally, the target nucleic acid is stretched, e.g., via flow or electrostatic force. All n-pools can be stretched-and-bound simultaneously, or, in order to maximize the number of fully stretched molecules, pool 1 (which captures most 5' region) can be stretched and bound first; then pool 2, (which captures the middle-of-target region) is then can be stretched and bound; finally, pool 3 is can be stretched and bound.

A target nucleic acid can be captured using a "two bead-based step purification" system of the present disclosure. There are four capture probes, Probe A, Probe B, Probe C and Probe D. Probe A comprises an OA-sequence, a nucleic acid sequence that is complementary to the 5' end of the target nucleic acid, and a nucleic acid sequence attached to a biotin moiety. An OA-sequence can comprise the nucleotide sequence CGAAAGCCATGACCTCCGAT-CACTC (SEQ ID NO: 109) and can bind to a lawn oligonucleotide. The nucleic acid sequence attached to the biotin moiety is connected to the nucleic acid sequence that is complementary to the 5' end of the target nucleic acid via a cleavable linker. Probe B and Probe C comprise a nucleic acid sequence that is complementary to the target nucleic acid and a nucleic acid sequence attached to a biotin moiety. The nucleic acid sequence that is attached to the biotin moiety is connected to the nucleic acid sequence that is complementary to the target nucleic acid via a cleavable linker. Probe D comprises a nucleic acid sequence complementary to the 3' end of the target nucleic acid, a purification binding sequence called a G-sequence, and a biotin moiety. The biotin moiety is connected to the G-sequence via a cleavable linker. The four capture probes are first hybridized to the target nucleic acid. All of the probes hybridize at non-overlapping positions along the target nucleic acid, with Probe B and Probe C hybridizing between Probe A and Probe D. The target nucleic acid is then purified using streptavidin paramagnetic beads that bind to the biotin moieties on the capture probes. Excess, non-target genomic DNA is washed away from the beads. The target nucleic acid-capture probe complexes are then released from the streptavidin magnetic beads by cleavage of the cleavable linkers within each capture probe. The target nucleic acid-capture probe complexes are further purified using paramagnetic beads that bind to the purification G-sequence on probe D. Excess capture probes are washed away and the target nucleic acid-capture probe complexes are eluted from the paramagnetic beads.

A target nucleic acid can be captured using a "one bead-based step purification with lambda exonuclease" system of the present disclosure. There are four capture probes, Probe A, Probe B, Probe C and Probe D. Probe A comprises a sequence that is complementary to the 5' end of the target nucleic acid sequence. The 5' end of Probe A comprises two phosphorothioate bonds. Probe B, Probe C and Probe D comprise a nucleic acid sequence attached to a biotin moiety at the 3' end of the probes and a nucleic acid sequence that is complementary to the target nucleic acid at the 5' end of the probes. The 5' ends of Probe B, Probe C and Probe D are phosphorylated. Probe A, Probe B, Probe C and Probe D hybridize at non-overlapping positions along the target nucleic acid. After hybridization of the probes to the target nucleic acid, the target nucleic acid is purified using streptavidin paramagnetic beads. Excess gDNA and capture probes are washed away. The target nucleic acid-capture probe complex is eluted from the beads. Then Probe B, Probe C and Probe D are digested using lambda exonuclease, which preferentially degrades double-stranded DNA that is phosphorylated at the 5' end.

A target nucleic acid can be captured using a "one bead-based step purification with FEN1" system of the present disclosure. There are four capture probes, Probe A, Probe B, Probe C and Probe D. Probe A comprises a 3' nucleic acid sequence that does not hybridize to the target nucleic acid, a nucleic acid sequence that is complementary to the 5' end of the nucleic acid, and a 5' nucleic acid sequence that does not hybridize to the target nucleic acid and that comprises a biotin moiety. Probe B and Probe C comprise a 3' nucleic acid sequence that does not hybridize to the target nucleic acid, a nucleic acid sequence that is complementary to the target nucleic acid, and a 5' nucleic acid sequence that does not hybridize to the target nucleic acid and that comprises a biotin moiety. Probe D comprises a 3' sequence that does not hybridize to the target nucleic acid and a 5' sequence that is complementary to the target nucleic acid. Probe A, Probe B, Probe C and Probe D hybridize to the target nucleic acid such that Probe A is adjacent to Probe B such that the 5' nucleic acid sequence that does not hybridize to the target nucleic acid sequence and that comprises a biotin moiety on Probe A and the 3' nucleic acid sequence that does not hybridize to the target nucleic acid on Probe B form a branched double stranded DNA substrate with a 5' DNA flap, and Probe B is adjacent to Probe C such that the 5' nucleic acid sequence that does not hybridize to the target nucleic acid sequence and that comprises a biotin moiety on Probe B and the 3' nucleic acid sequence that does not hybridize to the target nucleic acid on Probe C form a branched double stranded DNA substrate with a 5' DNA flap, and Probe C is adjacent to Probe D such that the 5' nucleic acid sequence that does not hybridize to the target nucleic acid sequence and that comprises a biotin moiety on Probe C and the 3' nucleic acid sequence that does not hybridize to the target nucleic acid on Probe D form a branched double stranded DNA substrate with a 5' DNA flap. After hybridization of the probes to the target nucleic acid sequence, the target nucleic acid is purified using streptavidin paramagnetic beads. Excess genomic DNA and excess probes are washed away from the beads. The target nucleic acid is eluted from the beads by incubating with Thermostable Flap Endonuclease 1 (FEN1). FEN1 cleaves the 5' DNA flaps, thereby separating the biotin moieties from the hybridized capture probes, releasing the target nucleic acid-capture probe complex.

Figure 9:
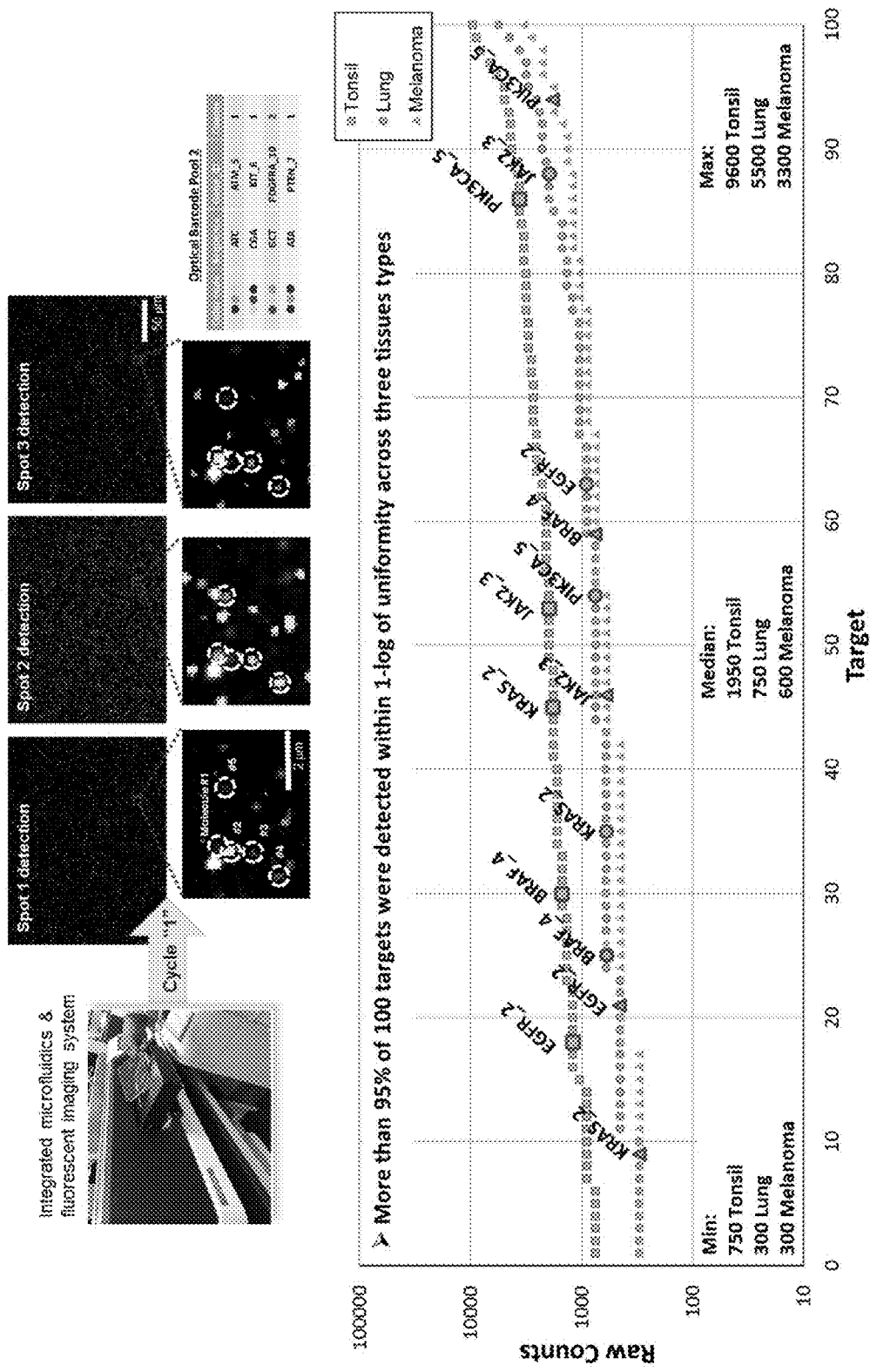
FIG. 9 shows the results from an experiment using the present methods to capture and detect a multiplex cancer panel, composed of 100 targets, using a FFPE sample.

The present disclosure also allows a user to capture and concurrently sequence a plurality of target nucleic acids, a plurality of capture probes can be hybridized to a mixed sample of target nucleic acids. A plurality of target nucleic acids can include a group of more than one nucleic acid, in which each nucleic acid contains the same sequence, or a group of more than one nucleic acid, in which each nucleic acid does not necessarily contain the same sequence. Likewise, the plurality of capture probes can include either a group of more than one capture probe that are identical in sequence, or a group of more than one capture probe that are not necessarily identical in sequence. For example, using a plurality of capture probes that all contain the same sequence can allow the user to capture a plurality of target nucleic acids that all contain the same sequence. By sequencing this plurality of target nucleic acids containing the same sequence, a higher level of sequencing accuracy can be achieved due to data redundancy. In another example, two or more specific genes of interest can be captured and sequenced concurrently using a group of capture probes that includes capture probes complementary to each gene of interest. This allows the user to perform multiplexed sequencing of specific genes. FIG. 9 shows the results from an experiment using the present methods to capture and detect a multiplex cancer panel, composed of 100 targets, using a FFPE sample.

A capture probe can also comprise a domain that binds (e.g. hybridizes) to a "multiplexing oligo". A multiplexing oligo can comprise at least three domains. The first domain can comprise a nucleic acid sequence that hybridizes to a capture probe. The second domain can comprise a unique nucleic acid sequence that identifies a sample. The third domain can comprise a substrate binding moiety. A plurality of multiplexing oligos can be used in combination with capture probes of the present disclosure to concurrently sequence a plurality of target nucleic acids from at least two samples. Multiplexing oligos can be used to concurrently sequence a plurality of target nucleic acids from at least three, at least four, at least five, at least six, at least seven, at least eight, at least nine, at least ten, at least 100 or at least 1000 samples.

An example of the use of multiplexing oligos to concurrently sequence three target nucleic acid molecules from three samples is as follows: a target nucleic acid from each of the three samples (Sample 1, Sample 2 and Sample 3) is hybridized to two capture probes, Probe A and Probe B. Probe A comprises two domains. The first domain comprises a substrate binding moiety. The second domain comprises a sequence complementary to the 5' end of the target nucleic acid. Probe B comprises two domains. The first domain comprises a sequence complementary to the 3' end of the target nucleic acid. The second domain comprises a sequence complementary to a multiplex oligo. After the two capture probes are hybridized to the target nucleic acid, the second domain of Probe B is hybridized to a multiplex oligo. The multiplex oligo comprises three domains. The first domain comprises a sequence complementary to the second domain of Probe B. The second domain comprises a unique nucleic acid sequence that identifies the sample. The third domain comprises a substrate binding moiety. After hybridization of the multiplexing oligo, an endonuclease cleavage step is performed to remove any overhanging DNA on the target nucleic acid such that Probe A is hybridized to the 5' end of the target nucleic acid and Probe B is hybridized to the 3' end of the target nucleic acid. After endonuclease treatment, the multiplexing oligo is ligated to the 3' end of the target nucleic acid and Probe B is then removed. The target nucleic acid-Probe A complex is further purified and subsequently sequenced. Since each target nucleic acid from each sample is ligated to a multiplexing oligo, the sample from which the target nucleic acid was derived can be identified by sequencing the multiplexing oligo.

When complete sequencing coverage is desired, the number of distinct capture probes required is inversely related to the size of target nucleic acid fragment. In other word, more capture probes will be required for a highly-fragmented target nucleic acid. For sample types with highly fragmented and degraded target nucleic acids (e.g., Formalin-Fixed Paraffin Embedded Tissue) it can be useful to include multiple pools of capture probes. On the other hand, for samples with long target nucleic acid fragments, e.g., in vitro obtained isolated nucleic acids, a single capture probe at a 5' end can be sufficient.

The region of the target nucleic acid between two capture probes or after one capture probe and before a terminus of the target nucleic acid is referred herein as a "sequencing window". The sequencing window created when two capture probes are used to capture a target nucleic acid is labeled in FIG. 8. The sequencing window is a portion of the target nucleic acid that is available to be bound by a sequencing probe. The minimum sequencing window is a target binding domain length (e.g., 4 to 10 nucleotides) and a maximum sequencing window is the majority of a whole chromosome.

When large target nucleic acid molecules are sequenced using the present methods, a "blocker oligo" or a plurality of blocker oligos can be hybridized along the length of the target nucleic acid to control the size of the sequencing window. Blocker oligos hybridize to the target nucleic acid at specific locations, thereby preventing the binding of sequencing probes at those locations, creating smaller sequencing windows of interest. By creating smaller sequencing windows, the sequencing reactions is confined to specific regions of interest on the target DNA molecule, increasing the speed and accuracy of sequencing. The use of blocker oligos is particularly useful when sequencing particular mutations at known locations within a target nucleic acid, as the entire target nucleic acid does not need to be sequenced. In a non-limiting example, the methods of the present disclosure can be used for the targeted sequencing of two heterozygous sites to distinguish between two different haplotypes.

A capture probe can comprise a nucleic acid molecule complex. A nucleic acid molecule complex can comprise a partially double-stranded nucleic acid molecule. In some aspects, a partially double-stranded nucleic acid molecule can comprise a target specific domain, a duplex domain, a single-stranded purification sequence, a cleavable moiety, a single-stranded overhang domain, a sample specific domain, a substrate specific domain or any combination thereof.

In some aspects, any one strand of a partially double-stranded nucleic acid molecule can comprise about 40 to about 150 nucleotides, or about 60 to about 135 nucleotides, or about 10 to about 90 nucleotides, or about 25 to about 75 nucleotides, or about 60 nucleotides, or about 50 to about 100 nucleotides.

In some aspects, any one strand of a partially double-stranded nucleic acid molecule can comprise at least one, or at least two, or at least three, or at least four, or at least five, or at least six, or at least seven, or at least eight, or at least nine, or at least ten affinity moieties.

In some aspects, any one strand of a partially double-stranded nucleic acid molecule can comprise at least one cross-linking moiety. A cross-linking moiety can be a chemical cross-linking moiety or a photoreactive cross-linking moiety.

A capture probe can comprise a single-stranded nucleic acid molecule. In aspects, a single-stranded nucleic acid molecule can comprise a target specific domain, a duplex domain, a single-stranded purification sequence, a cleavable moiety, a single-stranded overhang domain, a sample specific domain, a substrate specific domain or any combination thereof.

A target specific domain, a duplex domain, a single-stranded purification sequence, a cleavable moiety, a single-stranded overhang domain, a sample specific domain or a substrate specific domain can comprise at least one natural base or comprise no natural bases. In some aspects, a target specific domain, a duplex domain, a single-stranded purification sequence, a cleavable moiety, a single-stranded overhang domain, a sample specific domain or a substrate specific domain can comprise at least one modified nucleotide or nucleic acid analog or comprise no modified nucleotides A target specific domain, a duplex domain, a single-stranded purification sequence, a cleavable moiety, a single-stranded overhang domain, a sample specific domain or a substrate specific domain can comprise any combination of natural bases (e.g. 0, 1, 2, 3, 4, 5, 6, 7, 8, 9, 10, or more natural bases) and modified nucleotides or nucleic acid analogs (e.g. 0, 1, 2, 3, 4, 5, 6, 7, 8, 9, 10 or more modified When present in a combination, the natural bases and modified nucleotides or nucleic acid analogs can be arranged in any order.

A target specific domain can comprise a nucleic acid sequence that is complementary to a portion of a target nucleic acid molecule and that hybridizes to a target nucleic acid molecule. In some aspects, a target specific domain can comprise about 10 to about 150 nucleotides, or about 25 to about 100 nucleotides, or about 35 to about 100 nucleotides, or about 25 to about 125 nucleotides, or about 15 to about 100 nucleotides.

In some aspects, a target specific domain can hybridize within at least about 100 base pairs of the 3' end of a target nucleic acid molecule. In some aspects, a target specific domain can hybridize within at least about 100 of the 5' end of a target nucleic acid molecule.

A duplex domain can comprise a nucleic acid sequence that is capable of annealing to another nucleic acid strand to form a partially or fully double-stranded nucleic acid molecule. In some aspects, a duplex domain can comprise about 14 to about 45 nucleotides, or about 25 to about 35 nucleotide, or about 30 nucleotides, or about 10 to about 60 nucleotides, or about 30 to about 50 nucleotides A single-stranded purification sequence can comprise a nucleic acid sequence suitable for use in purification. A single-stranded purification sequence can comprise an F tag. A single-stranded purification can comprise an F-like tag. A single stranded purification sequence can comprise the nucleotide sequence AACATCACACAGACC (SEQ ID NO: 112). A single stranded purification sequence can comprise the nucleotide sequence GTCTATCATCACAGC (SEQ ID NO: 113).

A single-stranded purification sequence can comprise at least one affinity moiety, or at least two affinity moieties, or at least three affinity moieties, or at least four affinities, or at least five affinity moieties, or at least six affinity moieties, or at least seven affinity moieties, or at least eight affinity moieties, or at least nine affinity moieties or at least ten affinity moieties. The affinity moiety can be biotin. Thus, in some aspects, a single-stranded purification sequence can comprise at least one, at least two, at least three, at least four, at least five, at least six, at least seven, at least eight, at least nine or at least ten biotin moieties.

A single stranded purification sequence can comprise at least 50 nucleotides, or about 15 to about 50 nucleotides.

A cleavable moiety can comprise an enzymatically cleavable moiety. An enzymatically cleavable can comprise a USER sequence for cleavage by the USER enzyme. Alternatively, a cleavable moiety can comprise a photo-cleavable moiety.

A single-stranded overhang domain can comprise a single-stranded nucleic acid sequence that is capable of forming together with a target nucleic acid molecule a 5'-overhanging flap structure.

A sample specific domain can comprise a nucleic acid sequence that identifies the biological sample from which the target nucleic acid molecule was obtained. A sample specific domain can comprise L-DNA. A sample specific domain can comprise D-DNA. A sample specific domain can comprise a combination of L-DNA and D-DNA. A sample specific domain can hybridize to any probe of the present disclosure. A sample specific domain can comprises about 28 nucleotides.

In some aspects, a sample specific domain can comprise at least one attachment position or at least two attachment positions. In the aspects wherein a sample specific domain comprises at least one attachment position or at least two attachment positions, an attachment position can comprise about 14 nucleotides, or about 10 nucleotides, or about 8 nucleotides.

A substrate specific domain can comprise a nucleic acid sequence that hybridizes to a complementary nucleic acid molecule attached to a substrate. The substrate can be an array. A substrate specific domain can comprise a nucleic acid sequence that hybridizes to a lawn oligonucleotide.

A substrate specific domain can comprise a poly-A sequence. A substrate specific domain can comprise a poly-T sequence. A substrate specific domain can comprise an L-poly-A sequence, wherein the nucleotides of the poly A sequence are L-DNA. A substrate specific domain can comprise an L-poly-T sequence, wherein the nucleotides of the poly T sequence are L-DNA. A substrate specific domain can comprise L-DNA. A substrate specific domain can comprise about 30 nucleotides.

Figure 34:
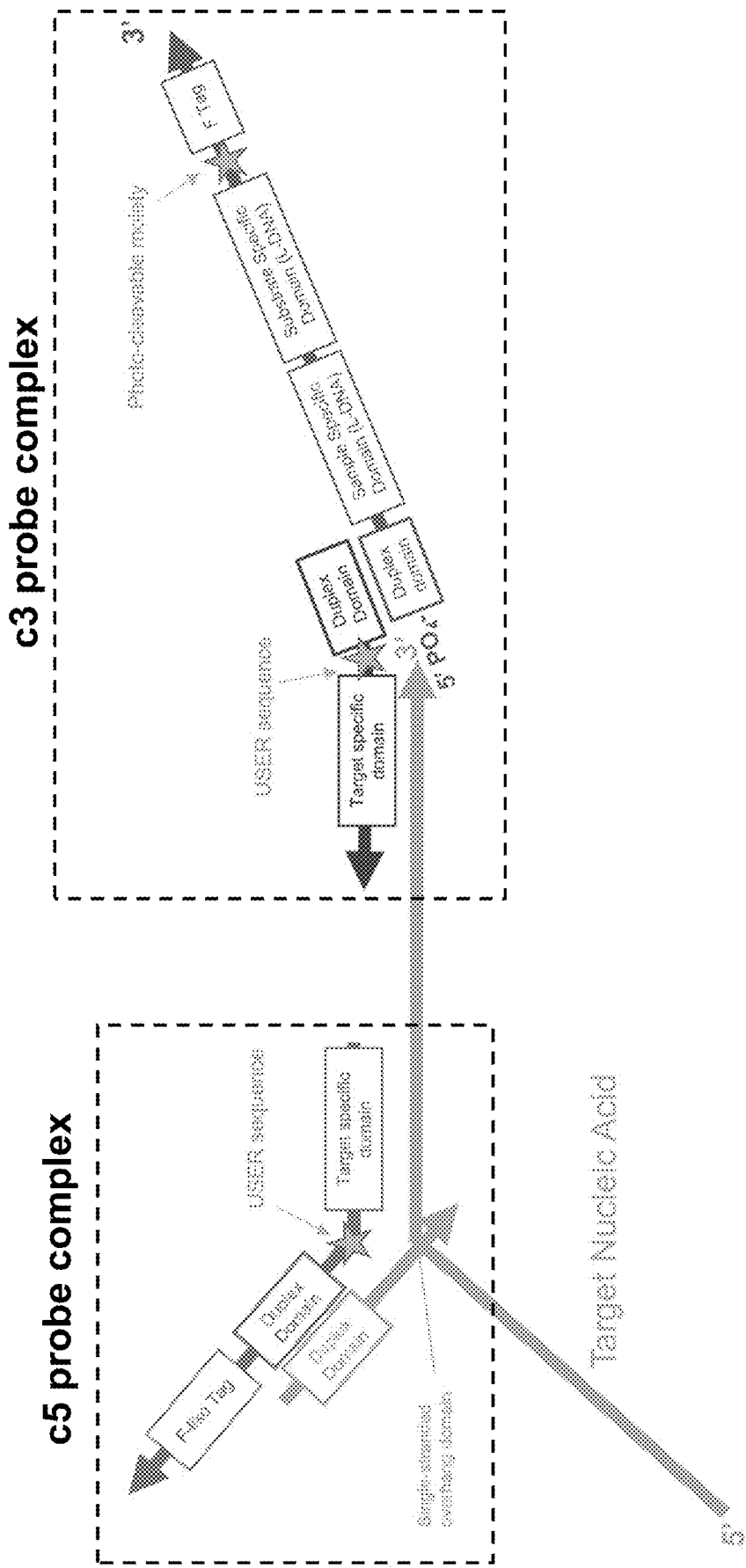
FIG. 34 is a schematic illustration of a c5 probe complex and c3 probe complex of the present disclosure hybridized to a target nucleic acid.

FIG. 34 shows a schematic illustration of an exemplary capture probe comprising a nucleic acid molecule complex called a "c5 probe complex" bound to a target nucleic acid. The c5 probe complex comprises a partially double-stranded nucleic acid molecule. One strand of the partially double-stranded nucleic acid molecule comprises a target specific domain hybridized to the target nucleic acid, a duplex domain that is annealed to the other strand of the partially double-stranded nucleic acid molecule, a first single-stranded purification sequence and a cleavable moiety located between the target specific domain and the duplex domain. In this non-limiting example, the single-stranded purification sequence comprises an F-like tag and the cleavable moiety comprises an enzymatically cleavable USER sequence. The other strand of the partially double-stranded nucleic acid molecule comprises a duplex domain that is annealed to the other strand of the partially double-stranded nucleic acid molecule and a single-stranded overhang domain. In this non-limiting example, the single-stranded overhang domain and the target nucleic acid molecule form a 5'-overhanging flap structure.

FIG. 34 also shows a schematic illustration of an exemplary capture probe comprising a nucleic acid molecule complex called a "c3 probe complex" bound to a target nucleic acid. The c3 probe complex comprises a partially double-stranded nucleic acid molecule. One strand of the partially double-stranded nucleic acid molecule comprises a target specific domain hybridized to the target nucleic acid, a duplex domain that is annealed to the other strand of the partially double-stranded nucleic acid molecule and a cleavable moiety located between the target specific domain and the duplex domain. In this non-limiting example, the cleavable moiety comprises an enzymatically cleavable USER sequence. The other strand of the partially double-stranded nucleic acid molecule comprises a duplex domain that is annealed to the other strand of the partially double-stranded nucleic acid molecule, a sample specific domain, a substrate specific domain, a single-stranded purification sequence and a cleavable moiety located between the single-stranded purification sequence and the substrate specific domain. In this non-limiting example, the sample specific domain comprises L-DNA, the substrate specific domain comprises L-DNA, the single-stranded purification sequence comprises an F tag and the cleavable moiety is a photo-cleavable moiety.

Figure 41:
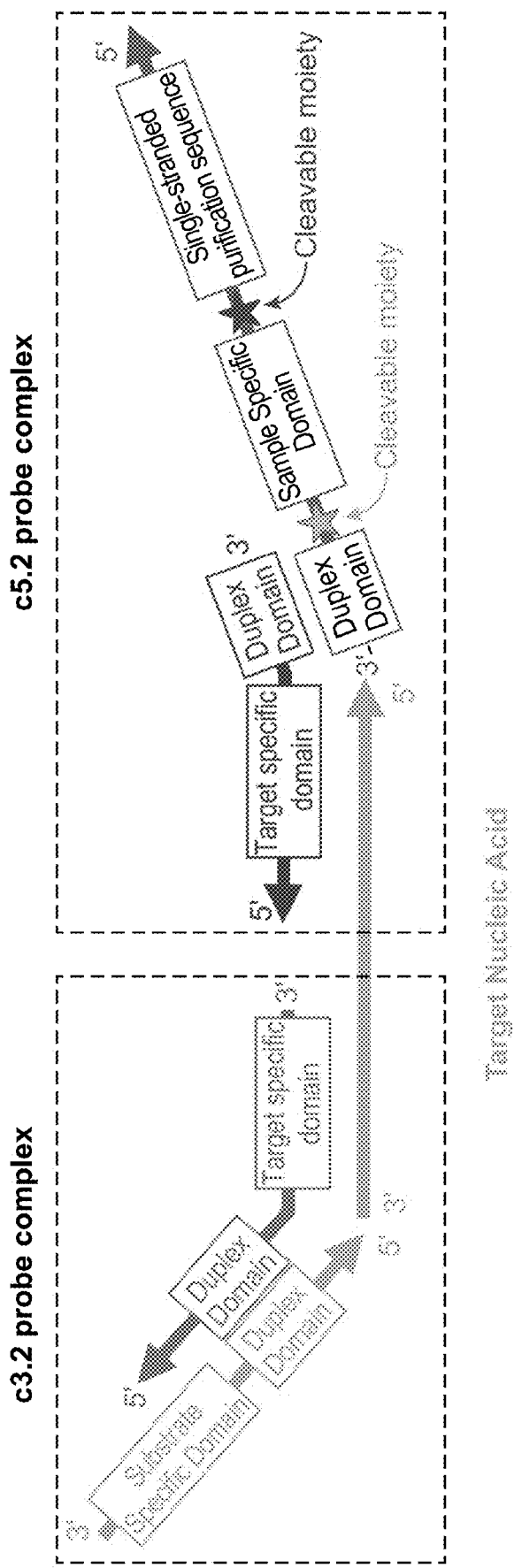
FIG. 41 is a schematic illustration of a c3.2 probe complex and a c5.2 probe complex of the present disclosure hybridized to a target nucleic acid.

FIG. 41 shows a schematic illustration of an exemplary capture probe comprising a nucleic acid molecule complex called a "c3.2 probe complex" bound to a target nucleic acid molecule. The c3.2 probe complex comprises a partially double-stranded nucleic acid molecule.

One strand of the partially double-stranded nucleic acid molecule comprises a target specific domain hybridized to the target nucleic acid and a duplex domain that is annealed to the other strand of the partially double-stranded nucleic acid molecule. In some aspects, this strand can optionally comprise at least one first affinity moiety. In some aspects, this strand can optionally comprise a cleavable moiety located between the target specific domain and the duplex domain. The other strand of the partially double-stranded nucleic acid molecule comprises a duplex domain that is annealed to the other strand of the partially double-stranded nucleic acid molecule and a substrate specific domain. In some aspects, this strand can optionally comprise at least one, or at least two, or at least three second affinity moieties.

FIG. 41 also shows a schematic illustration of an exemplary capture probe comprising a nucleic acid molecule complex call the "c5.2 probe complex" bound to a target nucleic acid molecule. The c5.2 probe complex comprises a partially double-stranded nucleic acid molecule. One strand of the partially double-stranded nucleic acid molecule comprises a target specific domain hybridized to the target nucleic acid, a duplex domain that is annealed to the other strand of the partially double-stranded nucleic acid molecule. In some aspects, this strand can optionally comprise cleavable moiety located between the target specific domain and the duplex domain. The other strand of the partially double-stranded nucleic acid molecule comprises a duplex domain that is annealed to the other strand of the partially double-stranded nucleic acid molecule, a sample specific domain and a first single-stranded purification sequence, a first cleavable moiety located between the duplex domain and the sample specific domain and a second cleavable moiety located between the sample specific domain and the first single-stranded purification sequence. In some aspects, the first single-stranded purification sequence can comprise at least one affinity moiety, for example, at least one biotin moiety. In some aspects, the first single-stranded purification sequence can be replaced with at least one biotin moiety, such that the other strand of the partially double-stranded nucleic acid molecule comprises a duplex domain that is annealed to the other strand of the partially double-stranded nucleic acid molecule, a sample specific domain, at least one biotin moiety, a first cleavable moiety located between the duplex domain and the sample specific domain and a second cleavable moiety located between the sample specific domain and the at least one biotin moiety.

Sample Preparation Methods of the Present Disclosure

The present disclosure provides methods of sample preparation comprising immobilizing a target nucleic acid molecule to a substrate.

Sample preparation methods of the present invention can comprise a CRISPR-based fragmentation step (see, e.g., Baker and Mueller, "CRISPR-mediated isolation of specific megabase segments of genomic DNA", *Nucleic Acids Research* 2017, 45(19), e165; Tsai et al., "Amplification-free, CRISPR-Cas9 targeted enrichment and SMRT sequencing of repeat-expansion disease causative genomic regions", bioRxiv 203919; doi: https://doi.org/10.1101/203919; Nachmanson et al., "Targeted genome fragmentation with CRISPR/Cas9 improves hybridization capture, reduces PCR bias, and enables efficient high-accuracy sequencing of small targets", bioRxiv 207027; doi: https://doi.org/10.1101/207027). CRISPR fragmentation can comprise in vitro fragmenting genomic DNA (gDNA) obtained from a biological sample by cleaving proximal to protospacer adjacent motif (PAM) sites located within gDNA. A PAM site can comprise the nucleotide sequence NGG, wherein N is any nucleobase. Alternatively, a PAM site can comprise the nucleotide sequence NGA, wherein N is any nucleobase. The fragments produced by CRISPR-based fragmentation can be purified using biotinylated CRISPR-complexes or with an anti-CAS9 antibody A method for capturing a target nucleic acid can comprise (1) fragmenting gDNA using a CRISPR-based fragmentation step; (2) contacting the fragmented gDNA with at least two capture probes, wherein at least one of the at least two capture probes is a c5 probe complex as described above, and at least one of the at least two capture probes is a c3 probe complex as described above, such that a c3 probe complex and a c5 probe complex hybridize to a target nucleic acid to form the complex shown in FIG. 34; (3) removing the 5'-overhanging flap structure by contacting the composition with FEN1; (4) ligating the 3' end of the target nucleic acid to the 5' end of the strand of the c3 probe complex that comprises the substrate specific domain; (5) binding the single-stranded purification sequence of the c5 probe complex to a first substrate; (6) cleaving the cleavable moieties located between the duplex domain and the target specific domain of each of the c3 and c5 probe complexes; (7) binding the single-stranded purification sequence of the c3 probe complex to a second substrate; (8) cleaving the cleavable moiety located between the single-stranded purification sequence and the substrate specific domain of the ligated c3 probe complex; and (9) hybridizing the substrate specific domain to a complementary nucleic acid molecule attached to a third substrate.

In some aspects of the preceding method, step (9) can be performed before step (8).

In some aspects of the preceding method, steps (3) and (4) can be performed concurrently. In some aspects of the preceding method, steps (3) and (4) can be performed simultaneously.

In some aspects, the preceding method can optionally include a step in between steps (6) and (7), wherein target nucleic acid-capture probe complexes derived from different biological samples are pooled together. In this aspect, the target nucleic acid-capture probe complexes derived from different samples will comprise c3 probe complexes comprising unique sample specific domains, such that the target specific domain identifies the biological sample from which each target nucleic acid was obtained.

Figure 35:
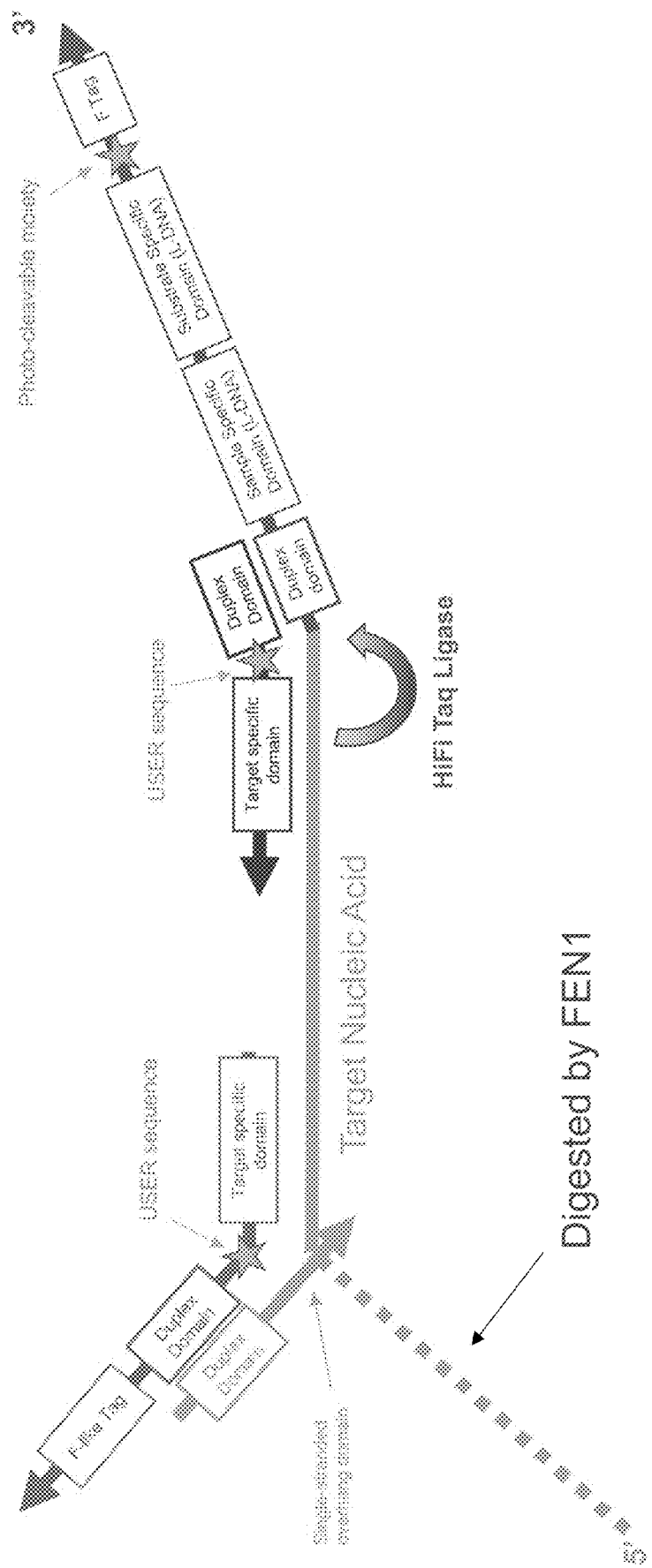
FIG. 35 is a schematic illustration of a target nucleic acid-c3 probe-c5 probe complex of the present disclosure after digestion with FEN1.
Figure 36:
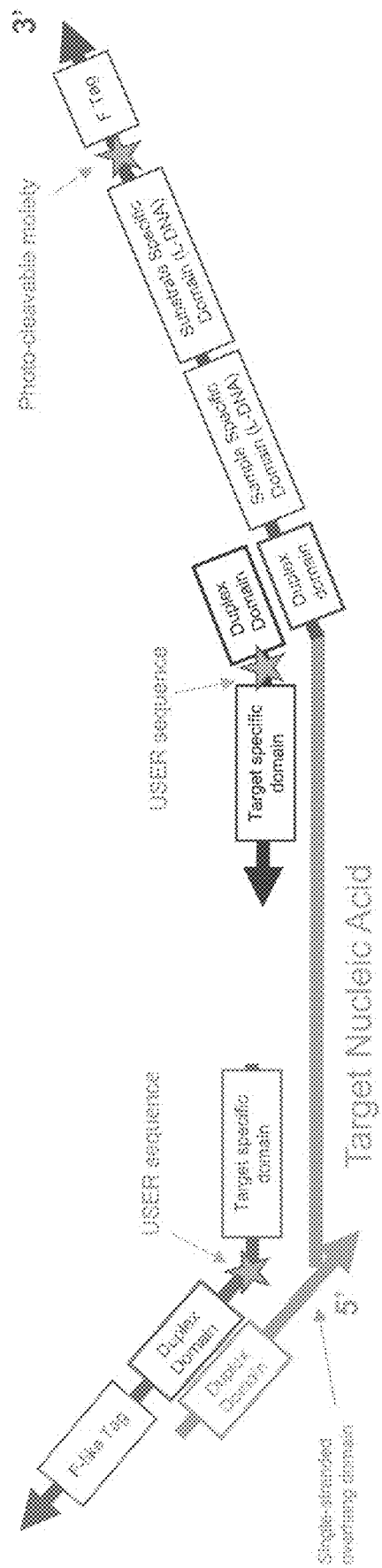
FIG. 36 is a schematic illustration of a target nucleic acid-c3 probe-c5 probe complex of the present disclosure after ligation.
Figure 37:
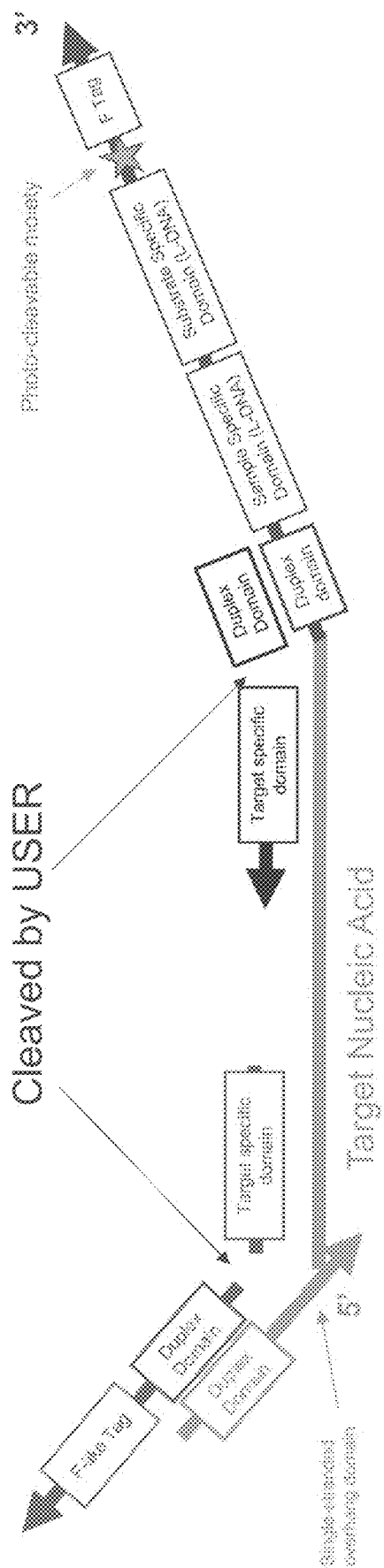
FIG. 37 is a schematic illustration of USER-mediated cleavage of a target nucleic acid-c3 probe-c5 probe complex of the present disclosure
Figure 38:
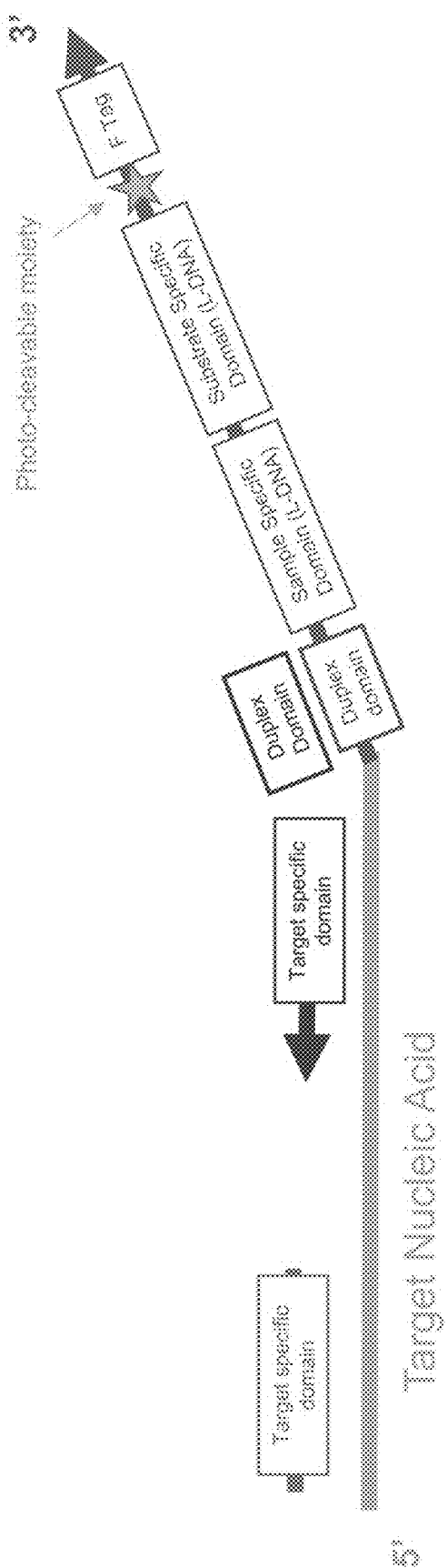
FIG. 38 is a schematic illustration a target nucleic acid-c3 probe-c5 probe complex of the present disclosure after USER-mediated cleavage.
Figure 39:
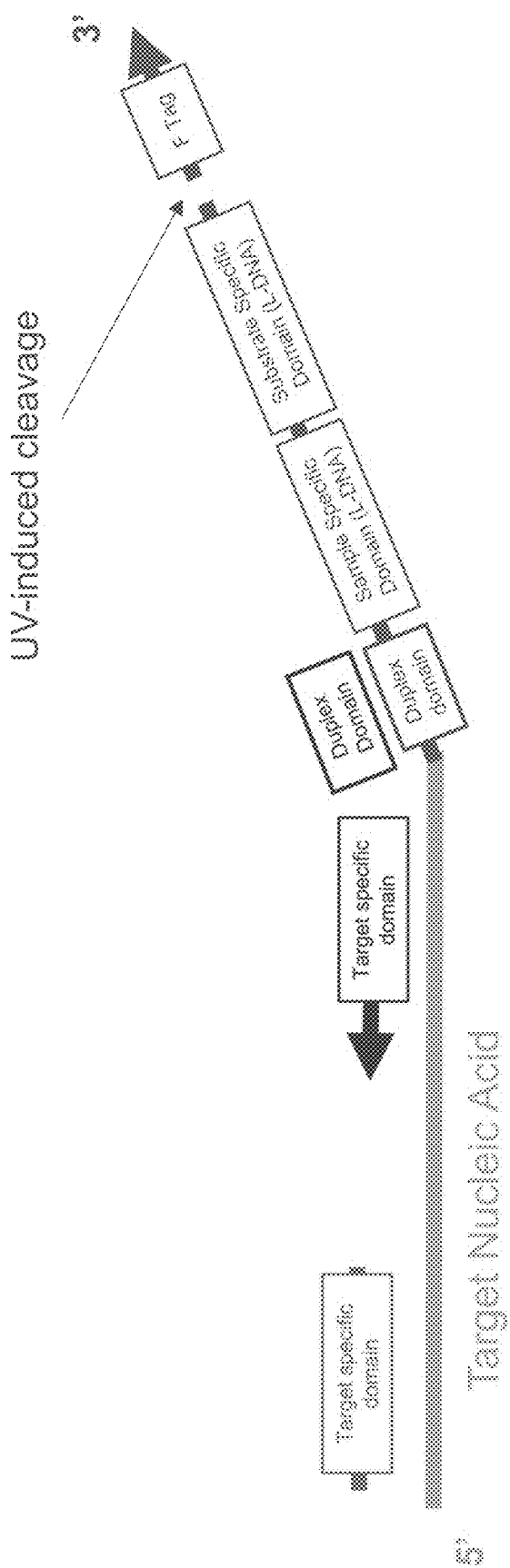
FIG. 39 is a schematic illustration of UV-mediated cleavage of a target nucleic acid-c3 probe-c5 probe complex of the present disclosure.
Figure 40:
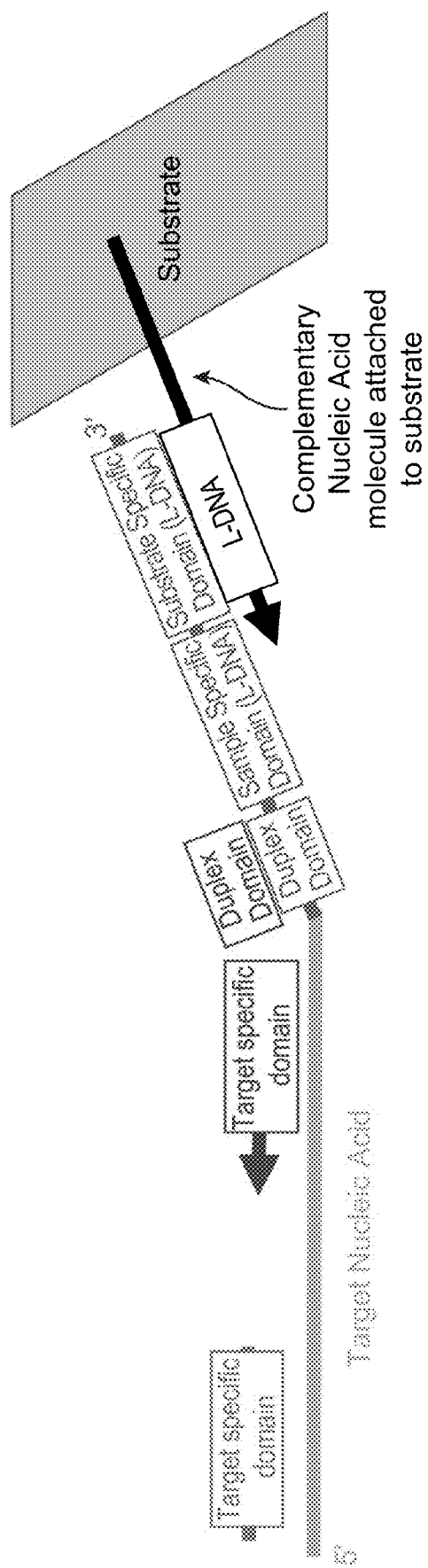
FIG. 40 is a schematic illustration a target nucleic acid-c3 probe-c5 probe complex of the present disclosure after UV-mediated cleavage attached via a complementary nucleic acid to a substrate.

An example of a sample preparation method of the present disclosure is shown in FIGS. 34-40. In this non-limiting example, gDNA obtained from a biological sample is first fragmented using CRISPR-based fragmentation. After fragmentation, a target nucleic acid is hybridized to two capture probes as shown in FIG. 34. In this non-limiting example, the two capture probes are a c3 probe complex and a c5 probe complex, as described above. The c3 probe complex and the c5 probe complex hybridize to the target nucleic acid at non-overlapping locations along the target nucleic acid. The c3 probe complex hybridizes to the target nucleic acid via the target specific domain within no more than 8 nucleotides of the 3' end of the target nucleic acid such and the c5 probe complex hybridizes to the target nucleic acid via the target specific domain such that the c5 probe complex hybridized 5' to the c3 probe complex. The single-stranded overhang domain of the c5 probe complex and the target nucleic acid molecule form a 5'-overhanging flap structure. After hybridization of the two capture probes, the target nucleic acid-capture probe complex is incubated with FEN1 and ligase. The FEN1 removes the 5'-overhanging flap structure and the 3' end of the target nucleic acid is ligated to the strand of the c3 probe complex that comprises the substrate specific domain by the ligase, as shown in FIG. 35. The resultant complex, shown in FIG. 36 is bound to the F-like beads that hybridize to the F-like tag present in the c5 probe complex. The beads are washed and USER enzyme is added. The USER enzyme cleaves the cleavable moieties located between the target specific domains and the duplex domains of both the c3 probe complex and the c5 probe complex, thereby releasing the target nucleic acid from the F-like beads, as shown in FIG. 37. The eluted complex, as shown in FIG. 38 is further purified using SPRI beads to. The purified complex is then bound to F-beads that hybridize to the F tag present in the c3 probe complex. After washing, the target nucleic acid is eluted from the F-beads by exposing the beads to UV light, thereby cleaving the photocleavable moiety in the c3 probe complex located between the substrate specific domain and the F tag, as shown in FIG. 39. The resultant complex is then bound to a substrate by hybridizing the substrate specific domain of ligated c3 probe complex to a complementary nucleic acid attached to the substrate, as shown in FIG. 40.

Figure 42:
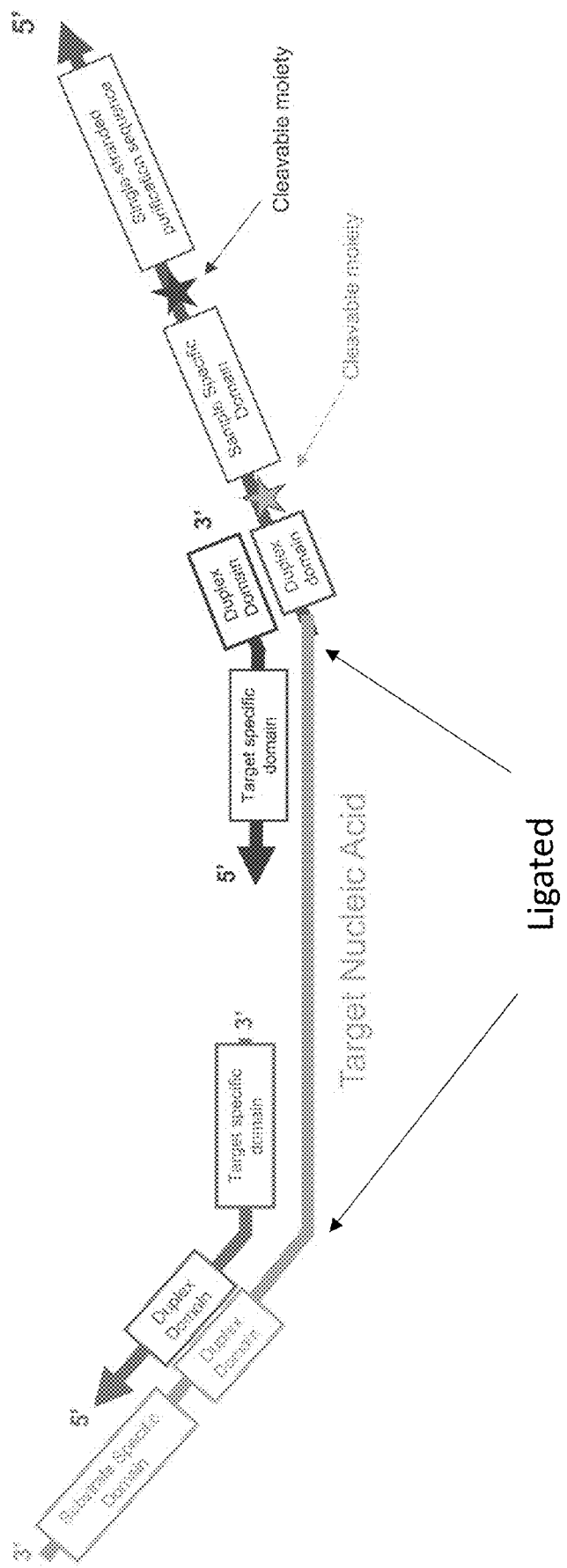
FIG. 42 is a schematic illustration of a target nucleic acid complex of the present disclosure after ligation of the c3.2 and c5.2 probe complexes.
Figure 43:
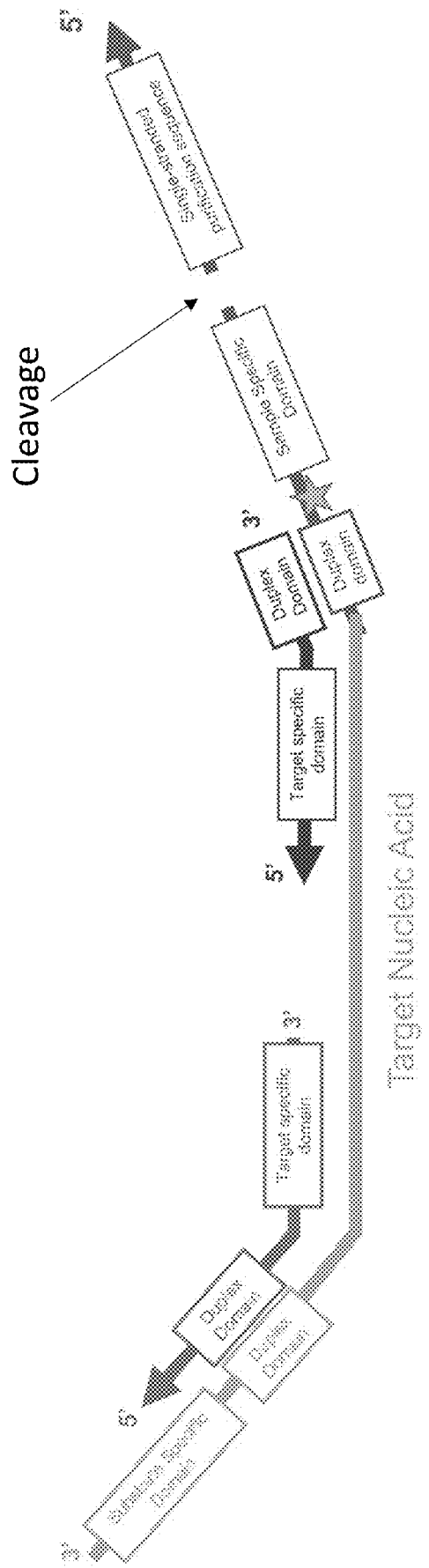
FIG. 43 is a schematic illustration of the cleavage and release of the single-stranded purification sequence in a target nucleic acid complex of the present disclosure.
Figure 44:
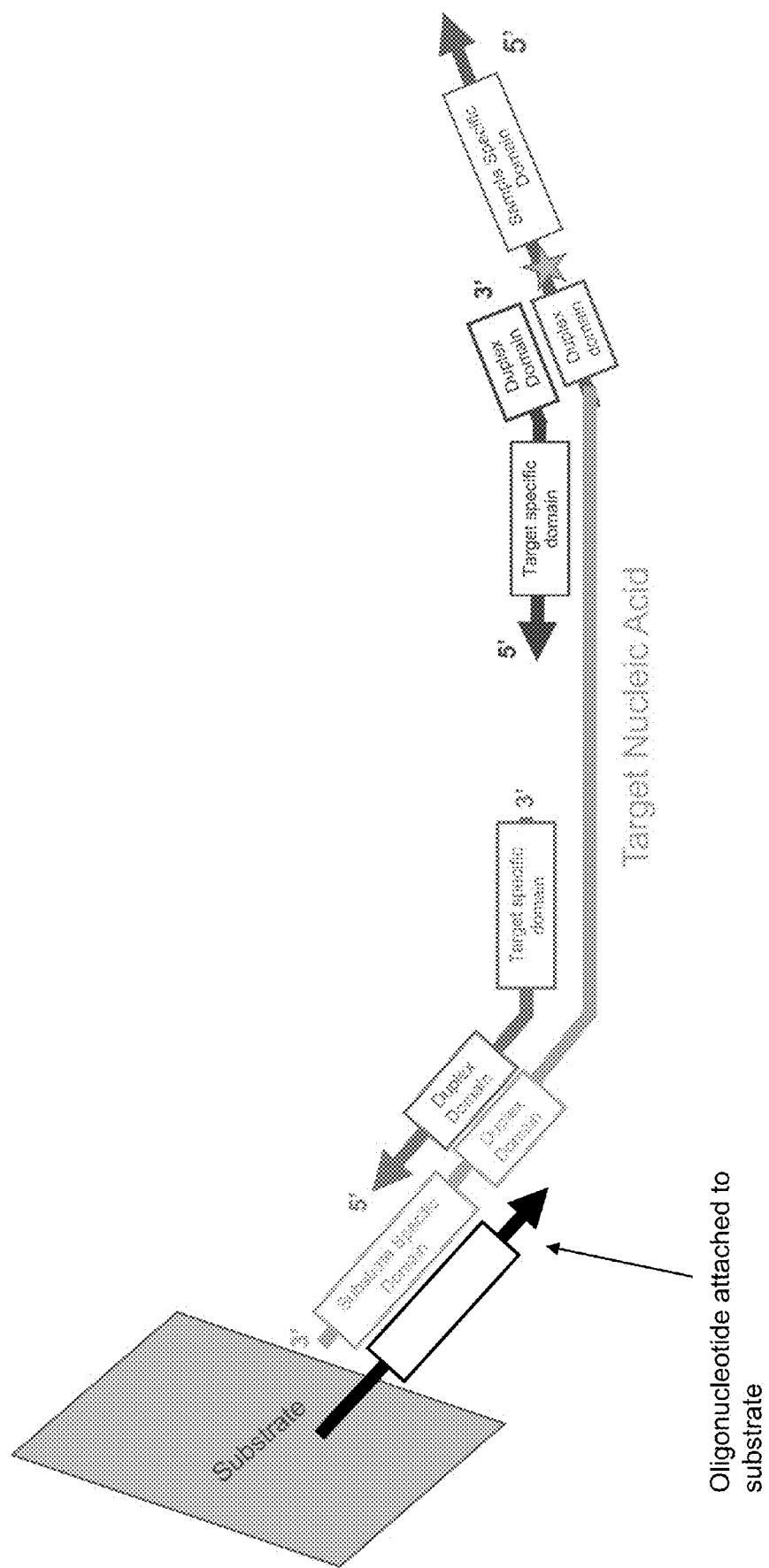
FIG. 44 is a schematic illustration of a target nucleic acid complex of the present disclosure immobilized on a substrate of the present disclosure.

An example of another sample preparation method of the present disclosure is shown in FIGS. 41-46. In this non-limiting example, gDNA obtained from a biological sample is first fragmented, for example, by CRISPR-based fragmentation. After fragmentation, a target nucleic acid is hybridized to two capture probes as shown in FIG. 41. In this non-limiting example, the two capture probes are a c3.2 probe complex and a c5.2 probe complex, as described above. The c3 probe complex and the c5 probe complex hybridize to the target nucleic acid at non-overlapping locations along the target nucleic acid. The c5.2 probe complex hybridizes to the target nucleic acid via the target specific domain such that the c5.2 probe complex hybridizes 5' to the c3.2 probe complex. After hybridization of the two capture probes, the target nucleic acid is ligated to the one strand of the c3.2 probe complex and one strand of the c5.2 complex, as shown in FIG. 42. The ligation can comprise enzymatic ligation, autoligation, chemical ligation or any combination thereof. In aspects comprising enzymatic ligation, the enzymatic ligation can be performed using a high fidelity, template-directed nick ligase. The resultant complex, shown in FIG. 42, can then be bound to beads comprising at least one oligonucleotide that hybridizes to the single-stranded purification sequence. The beads can be washed and the cleavable moiety located between the sample specific domain and the single-stranded purification sequence can be cleaved, thereby releasing the target nucleic acid from the beads, as shown in FIG. 43. The resultant complex can then be immobilized onto a substrate by hybridizing the substrate specific domain to an oligonucleotide attached to the substrate as shown in FIG. 44. The substrate/oligonucleotide complex can be any array of the present disclosure.

The preceding method can further comprise hybridizing at least one reporter probe to the sample specific domain, wherein the reporter probe comprises a first detectable label and a second detectable label. The first and the second detectable label can then be identified, thereby identifying the sample from which the target nucleic acid originated based on the identity of the first detectable label and the second detectable label.

Alternatively, the preceding method can further comprising hybridizing a first reporter probe to the sample specific domain, wherein the reporter probe comprises a first detectable label and a second detectable label. The first and the second detectable label can then be identified. The first detectable label and the second detectable label can then be removed, and a second reporter probe comprising a third detectable label and a fourth detectable label can be hybridized to the sample specific domain. The third detectable label and the fourth detectable label can then be identified, thereby identifying the sample from which the target nucleic acid originated based on the identity of the first detectable label, the second detectable label, the third detectable label and the fourth detectable label.

Figure 45:
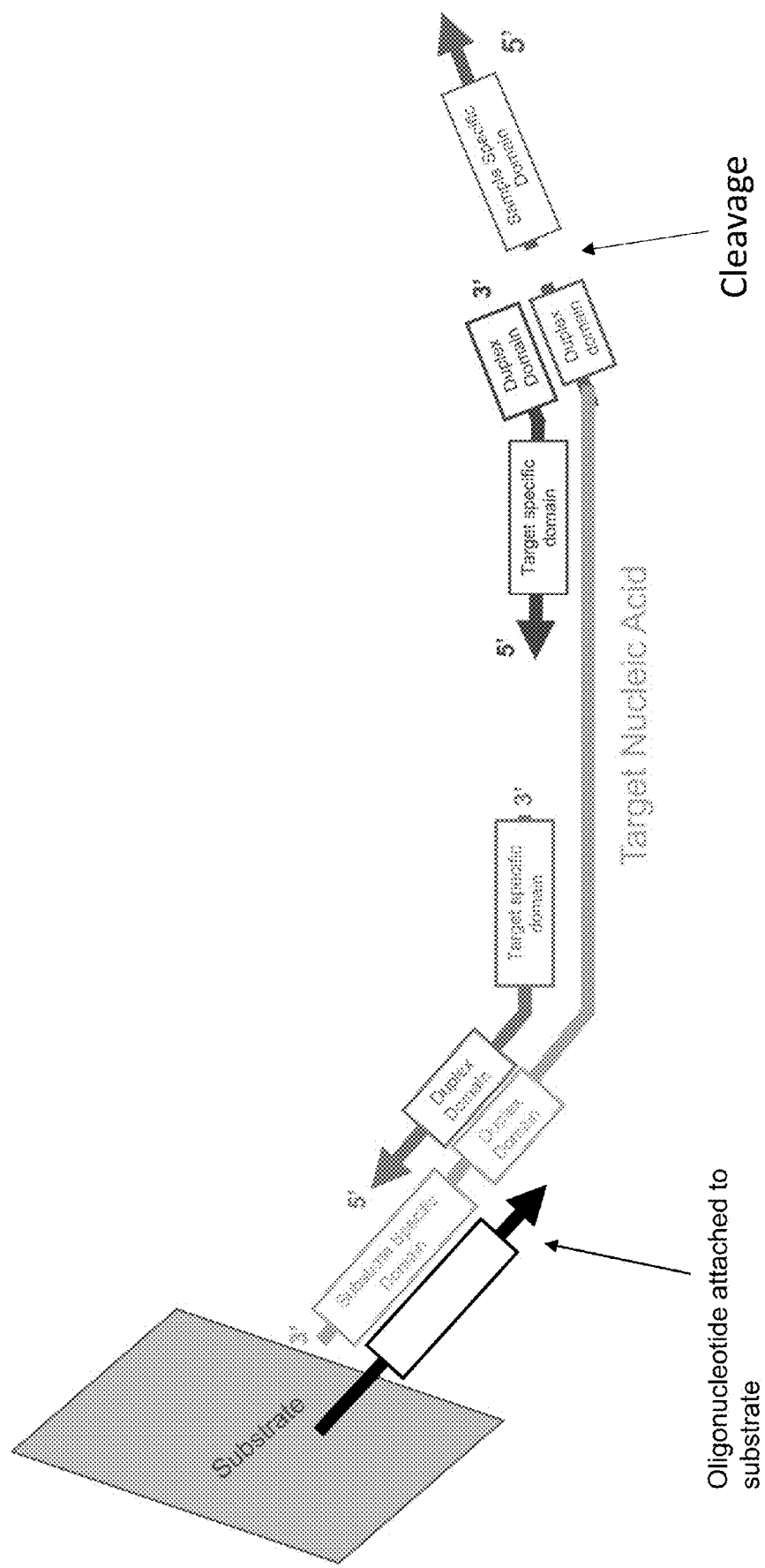
FIG. 45 is a schematic illustration of the cleavage and release of the substrate specific domain after immobilization of a target nucleic acid complex of the present disclosure to a substrate of the present disclosure.
Figure 46:
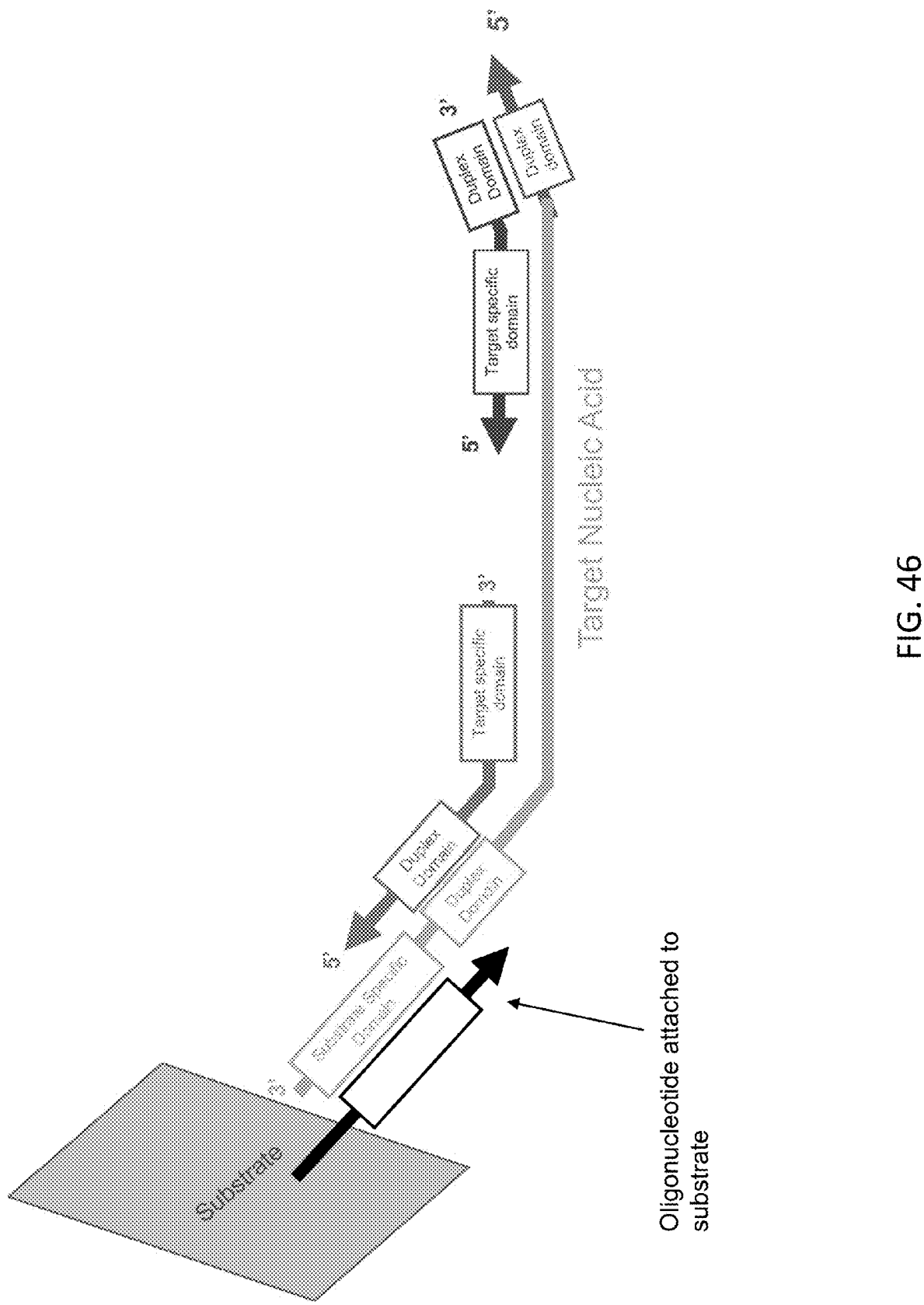
FIG. 46 is a schematic illustration of a target nucleic acid complex of the present disclosure after release of the substrate specific domain immobilized on a substrate of the present disclosure.

After identifying the sample from which the target nucleic acid originated, the cleavable moiety located between the sample specific domain and the duplex domain can be cleaved, as shown in FIG. 45, thereby releasing the sample specific domain.

Methods of the Present Disclosure

The sequencing method of the present disclosure comprises reversibly hybridizing at least one sequencing probe disclosed herein to a target nucleic acid.

A method for sequencing a nucleic acid can comprise (1) hybridizing a sequencing probe described herein to a target nucleic acid. The target nucleic acid can optionally be immobilized to a substrate at one or more positions. An exemplary sequencing probe can comprise a target binding domain and a barcode domain; wherein the target binding domain comprises any of the constructs recited in Table 1. An exemplary target binding domain comprises at least eight nucleotides hybridized to the target nucleic acid, wherein at least six nucleotides in the target binding domain can identify a corresponding nucleotide in the target nucleic acid molecule (for example, those six nucleotides identify the complementary six nucleotides with the target molecule to which it is hybridized) and wherein at least two nucleotides in the target binding domain do not identify a corresponding nucleotide in the target nucleic acid molecule (for example, those at least two nucleotides do not identify the complementary two nucleotides with the target molecule to which it is hybridized); wherein any of the at least six nucleotides in the target binding domain can be modified nucleotides or nucleotide analogues; and wherein the at least two nucleotides in the target binding domain that do not identify a corresponding nucleotide in the target nucleic acid molecule can be any of the four canonical bases that is not specific to the target dictated by the at least six nucleotides in the target binding domain or universal bases or degenerate bases. An exemplary barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

In other aspects, an exemplary target binding domain can comprise at least six nucleotides hybridized to the target nucleic acid, wherein the at least six nucleotides in the target binding domain can identify a corresponding nucleotide in the target nucleic acid molecule (for example, when the target binding domain sequence is exactly six nucleotides, those six nucleotides identify the complementary six nucleotides with the target molecule to which it is hybridized); wherein none of the at least six nucleotides or any of the at least six nucleotides in the target binding domain can be modified nucleotides or nucleotide analogues.

Following hybridizing of a sequencing probe to the target nucleic acid, the method comprises (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the immobilized target nucleic acid. For example, when the first complementary nucleic acid molecule comprises two detectable labels, the two detectable labels identify the at least two nucleotides in the immobilized target nucleic acid.

Following detection of the at least two detectable labels, removing the at least two detectable labels from the first complementary nucleic acid molecule. Thus, the method further comprises (5) binding to the first attachment position a first hybridizing nucleic acid molecule lacking a detectable label, thereby unbinding the first complementary nucleic acid molecule comprising the detectable labels, or contacting the first complementary nucleic acid molecule compris-ing the detectable labels with a force sufficient to release the first detectable label and at least second detectable label. Thus, following step (5) no detectable labels are bound to the first attachment positions. The method further comprises (6) binding a second complementary nucleic acid molecule comprising a third detectable label and an at least fourth detectable to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule have been detected, thereby identifying the linear order of at least six nucleotides for at least a first region of the immobilized target nucleic acid that was hybridized by the target binding domain of the sequencing probe; and (10) removing the sequencing probe from the optionally immobilized target nucleic acid.

The method can further comprise (11) hybridizing a second sequencing probe to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule have been detected, thereby identifying the linear order of at least six nucleotides for at least a second region of the immobilized target nucleic acid that was hybridized by the target binding domain of the second sequencing probe; and (20) removing the second sequencing probe from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. For example, the first hybridizing nucleic acid molecule lacking a detectable label can comprise the same nucleic acid sequence as that portion of the first complementary nucleic acid molecule that binds to a first attachment position of the at least three attachment positions of the barcode domain. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The present disclosure also provides a method for sequencing a nucleic acid comprising (1) hybridizing a sequencing probe described herein to a target nucleic acid. The target nucleic acid can optionally be immobilized to a substrate at one or more positions. An exemplary sequencing probe can comprise a target binding domain and a barcode domain; wherein the target binding domain comprises any of the constructs recited in Table 1. An exemplary target binding domain comprises at least eight nucleotides hybridized to the target nucleic acid, wherein at least six nucleotides in the target binding domain can identify a corresponding nucleotide in the target nucleic acid molecule (for example those six nucleotides identify the complementary six nucleotides with the target molecule to which it is hybridized) and wherein at least two nucleotides in the target binding domain do not identify a corresponding nucleotide in the target nucleic acid molecule (for example, those at least two nucleotides do not identify the complementary two nucleotides with the target molecule to which it is hybridized); wherein any of the at least six nucleotides in the target binding domain can be modified nucleotides or nucleotide analogues; and wherein the at least two nucleotides in the target binding domain that do not identify a corresponding nucleotide in the target nucleic acid molecule can be any of the four canonical bases that is not specific to the target dictated by the at least six nucleotides in the target binding domain or universal bases or degenerate bases. An exemplary barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

In other aspects, an exemplary target binding domain can comprise at least six nucleotides hybridized to the target nucleic acid, wherein the at least six nucleotides in the target binding domain can identify a corresponding nucleotide in the target nucleic acid molecule (for example, when the target binding domain sequence is exactly six nucleotides, those six nucleotides identify the complementary six nucleotides with the target molecule to which it is hybridized); wherein none of the at least six nucleotides or any of the at least six nucleotides in the target binding domain can be modified nucleotides or nucleotide analogues.

Following hybridizing of a sequencing probe to the target nucleic acid, the method comprises (2) binding a first complementary nucleic acid molecule comprising a first detectable label and an at least second detectable label to a first attachment position of the at least three attachment positions of the barcode domain; (3) detecting and recording the first and at least second detectable label of the bound first complementary nucleic acid molecule.

Following detection and recording of the at least two detectable labels, removing the at least two detectable labels from the first complementary nucleic acid molecule. Thus, the method further comprises (4) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label. Thus, following step (4) no detectable labels are bound to the first attachment positions. The method further comprises (5) binding a second complementary nucleic acid molecule comprising a third detectable label and an at least fourth detectable to a second attachment position of the at least three attachment positions of the barcode domain; (6) detecting and recording the third and at least fourth detectable label of the bound second complementary nucleic acid molecule; (7) repeating steps (4) to (6) until each attachment position of the at least three attachment positions in the barcode domain have been bound by a complementary nucleic acid molecule comprising two detectable labels, and the two detectable labels of the bound complementary nucleic acid molecule have been detected and recorded; (8) identifying the position and identity of the at least six nucleotides for at least a first region of the immobilized target nucleic acid that was hybridized to the target binding domain of the sequencing probe using the detectable labels recorded in step (3), step (6) and step (7); and (9) removing the sequencing probe from the optionally immobilized target nucleic acid.

The method can further comprise (10) hybridizing a second sequencing probe to a target nucleic acid that is optionally immobilized to a substrate at one or more positions, and wherein the target binding domain of the first sequencing probe and the second sequencing probe are different; (11) binding a first complementary nucleic acid molecule comprising a first detectable label and an at least second detectable label to a first attachment position of the at least three attachment positions of the barcode domain; (12) detecting and recording the first and at least second detectable label of the bound first complementary nucleic acid molecule; (13) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (14) binding a second complementary nucleic acid molecule comprising a third detectable label and an at least fourth detectable label to a second attachment position of the at least three attachment positions of the barcode domain; (15) detecting and recording the third and at least fourth detectable label of the bound second complementary nucleic acid molecule; (16) repeating steps (13) to (15) until each attachment position of the at least three attachment positions in the barcode domain have been bound by a complementary nucleic acid molecule comprising two detectable labels, and the two detectable labels of the bound complementary nucleic acid molecule have been detected and recorded; (17) identifying the position and identity of the at least six nucleotides for at least a second region of the immobilized target nucleic acid that was hybridized by the target binding domain of the second sequencing probe using the detectable labels recorded in step (12), step (15) and step (16); and (18) removing the second sequencing probe from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (4) and (5) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. For example, the first hybridizing nucleic acid molecule lacking a detectable label can comprise the same nucleic acid sequence as that portion of the first complementary nucleic acid molecule that binds to a first attachment position of the at least three attachment positions of the barcode domain. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The preceding method can further comprise a medium suitable for recording of the detectable labels. This medium can be a suitable computer readable medium.

The present disclosure further provides methods of sequencing a nucleic acid utilizing a plurality of sequencing probes disclosed herein. For example, the target nucleic acid is hybridized to more than one sequencing probe and each probe can sequence the portion of the target nucleic acid to which it is hybridized.

The present disclosure also provides a method for sequencing a nucleic acid comprising (1) hybridizing at least one first population of first sequencing probes comprising a plurality of the sequencing probes described herein to a target nucleic acid that is optionally immobilized to a substrate at one or more positions; (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the immobilized target nucleic acid; (5) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label; (6) binding a second complementary nucleic acid molecule comprising a third detectable label and an at least fourth detectable to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a first region of the immobilized target nucleic acid that was hybridized by the target binding domain of the sequencing probe; and (10) removing the at least one first population of first sequencing probes from the optionally immobilized target nucleic acid.

The method can further comprise (11) hybridizing at least one second population of second sequencing probes comprising a plurality of the sequencing probes disclosed herein to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a second region of the immobilized target nucleic acid that was hybridized by the target binding domain of the sequencing probe; and (20) removing the at least one second population of second sequencing probes from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The present disclosure also provides a method for sequencing a nucleic acid comprising (1) hybridizing at least one first population of first sequencing probes comprising a plurality of the sequencing probes described herein to a target nucleic acid that is optionally immobilized to a substrate at one or more positions; (2) binding a first complementary nucleic acid molecule comprising a first detectable label and an at least second detectable label to a first attachment position of the at least three attachment positions of the barcode domain; (3) detecting and recording the first and at least second detectable label of the bound first complementary nucleic acid molecule; (4) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label; (5) binding a second complementary nucleic acid molecule comprising a third detectable label and an at least fourth detectable to a second attachment position of the at least three attachment positions of the barcode domain; (6) detecting and recording the third and at least fourth detectable label of the bound second complementary nucleic acid molecule; (7) repeating steps (4) to (6) until each attachment position of the at least three attachment positions in the barcode domain have been bound by a complementary nucleic acid molecule comprising two detectable labels, and the two detectable labels of the bound complementary nucleic acid molecule have been detected and recorded; (8) identifying the position and identity of the at least six nucleotides for at least a first region of the immobilized target nucleic acid that was hybridized by the target binding domain of the sequencing probe using the detectable labels recorded in step (3), step (6) and step (7); and (9) removing the at least one first population of first sequencing probes from the optionally immobilized target nucleic acid.

The method can further comprise (10) hybridizing at least one second population of second sequencing probes comprising a plurality of the sequencing probes disclosed herein to a target nucleic acid that is optionally immobilized to a substrate at one or more positions, and wherein the target binding domain of the first sequencing probe and the second sequencing probe are different; (11) binding a first complementary nucleic acid molecule comprising a first detectable label and an at least second detectable label to a first attachment position of the at least three attachment positions of the barcode domain; (12) detecting and recording the first and at least second detectable label of the bound first complementary nucleic acid molecule; (13) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (14) binding a second complementary nucleic acid molecule comprising a third detectable label and an at least fourth detectable label to a second attachment position of the at least three attachment positions of the barcode domain; (15) detecting and recording the third and at least fourth detectable label of the bound second complementary nucleic acid molecule; (16) repeating steps (13) to (15) until each attachment position of the at least three attachment positions in the barcode domain have been bound by a complementary nucleic acid molecule comprising two detectable labels, and the two detectable labels of the bound complementary nucleic acid molecule have been detected and recorded; (17) identifying the position and identity of the least six nucleotides for at least a second region of the immobilized target nucleic acid that was hybridized by the target binding domain of the second sequencing probe using the detectable labels recorded in step (12), step (15) and step (16); and (18) removing the at least one second population of second sequencing probes from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (4) and (5) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The preceding method can further comprise a medium suitable for recording of the detectable labels. This medium can be a suitable computer readable medium.

The sequencing methods are further described herein.

Figure 10:
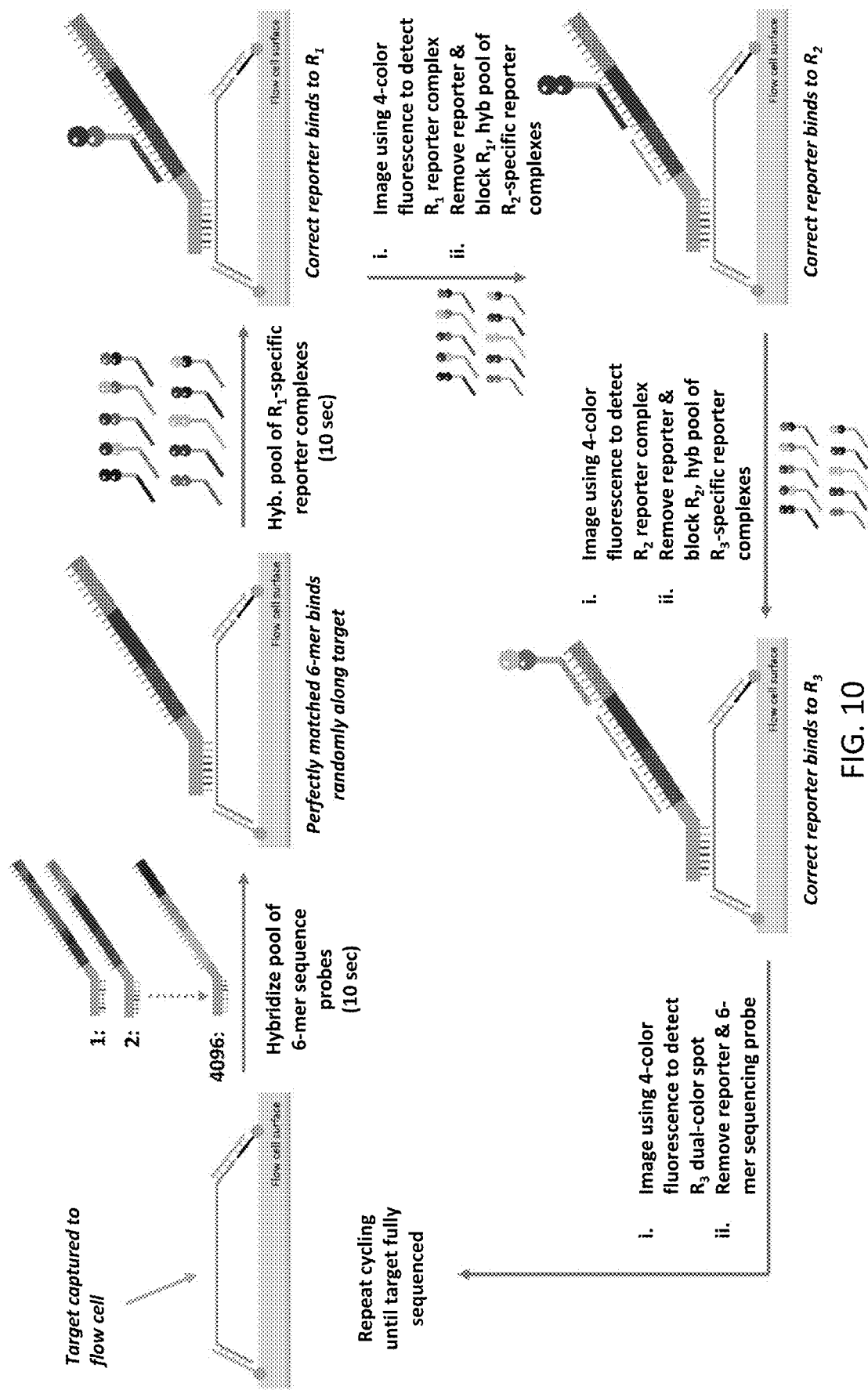
FIG. 10 is a schematic illustration of a single cycle of the sequencing method of the present disclosure.

FIG. 10 shows a schematic overview of a single exemplary sequencing cycle of the present disclosure. Although immobilizing a target nucleic acid prior to sequencing is not required for the instant methods, in this example, the method begins with a target nucleic acid that has been captured using capture probes and bound to a flow cell surface as shown in the left upper-most panel. A pool of sequencing probes is then flowed into the flow cell to allow sequencing probes to hybridize to the target nucleic acid. In this example, the sequencing probes are those depicted in FIG. 1. These sequencing probes comprise a 6-mer sequence within the target binding domain that hybridizes to the target nucleic acid. The 6-mer is flanked on either side by (N) bases which can be a universal/degenerate base or composed of any of the four canonical bases that is not specific to the target dictated by bases $b_1$-$b_2$-$b_3$-$b_4$-$b_5$-$b_6$. Using 6-mer sequences, a set of 4096 (4^6) sequencing probes enables the sequencing of any target nucleic acid. For this example, the set of 4096 sequencing probes are hybridized to the target nucleic acid in 8 pools of 512 sequencing probes each. The 6-mer sequences in the target binding domain of the sequencing probes will hybridize along the length of the target nucleic acid at positions where there is a perfect complementary match between the 6-mer and the target nucleic acid, as shown in upper middle panel of FIG. 10. In this example, a single sequencing probe hybridizes to the target nucleic acid. Any unbound sequencing probes are washed out of the flow cell.

These sequencing probes also comprise a barcode domain with three attachment positions $R_1$, $R_2$ and $R_3$, as described above. The attachment regions within attachment position $R_1$ comprise one or more nucleotide sequences that correspond to the first dinucleotide of the 6-mer of the sequencing probe. Thus, only reporter probes comprising complementary nucleic acids that correspond to the identity of the first dinucleotide present in the target binding domain of the sequencing probe will hybridize to attachment position $R_1$. Likewise, the attachment regions within attachment position $R_2$ of the sequencing probe correspond to the second dinucleotide present in the target binding domain and the attachment regions within attachment position $R_3$ of the sequencing probe correspond to the second dinucleotide present in the target binding domain The method continues in the right upper-most panel of FIG. 10. A pool of reporter probes is flowed into the flow cell. Each reporter probe in the reporter probe pool comprises a detectable label, in the form of a dual color combination, and a complementary nucleic acid that can hybridize to a corresponding attachment region within the attachment position $R_1$ of a sequencing probe. The dual color combination and the complementary nucleic acid of a particular reporter probe correspond to one of 16 possible dinucleotides, as described above. Each pool of reporter probes is designed such that the dual color combination that corresponds to a specific dinucleotide is established before sequencing. For example, in the sequencing experiment depicted in FIG. 10, for the first pool of reporter probes that is hybridized to attachment position $R_1$, the dual color combination Yellow-Red can correspond to the dinucleotide Adenine-Thymine. After hybridization of the reporter probe to attachment position $R_1$ as shown in the upper right panel of FIG. 10, any unbound reporter probes are then washed out of the flow cell and the detectable label of the bound reporter probe is recorded to determine the identity of the first dinucleotide of the 6-mer.

The detectable label attributed to the reporter probe hybridized to attachment position $R_1$ is removed. To remove the detectable label, the reporter probe can include a cleavable linker and the addition of the appropriate cleaving agent can be added. Alternatively, a complementary nucleic acid lacking a detectable label is hybridized to attachment position $R_1$ of the sequencing probe and displaces the reporter probe with the detectable label. Irrespective of the method of removing the detectable label, the attachment position $R_1$ no longer emits a detectable signal. The process by which an attachment position of a barcode domain that was previously emitting a detectable signal is rendered no longer able to emit a detectable signal is referred to herein as "darkening".

A second pool of reporter probes is flowed into the flow cell. Each reporter probe in the reporter probe pool comprises a detectable label, in the form of a dual color combination, and a complementary nucleic acid that can hybridize to a corresponding attachment region within attachment position $R_2$ of a sequencing probe. The dual color combination and the complementary nucleic acid of a particular reporter probe correspond to one of 16 possible dinucleotides. It is possible that a particular dual color combination corresponds to one dinucleotide in the context of the first pool of reporter probes, and a different dinucleotide in the context of the second pool of reporter probes. After hybridization of the reporter probes to attachment position $R_2$, as shown in the bottom right panel of FIG. 10, any unbound reporter probes are then washed out of the flow cell and the detectable label is recorded to determine the identity of the second dinucleotide of the 6-mer present in the sequencing probe.

To remove the detectable label at position $R_2$, the reporter probe can include a cleavable linker and the addition of the appropriate cleaving agent can be added. Alternatively, a complementary nucleic acid lacking a detectable label is hybridized to attachment position $R_2$ of the sequencing probe and displaces the reporter probe with the detectable label. Irrespective of the method of removing the detectable label, the attachment position $R_2$ no longer emits a detectable signal.

A third pool of reporter probes is then flowed into the flow cell. Each reporter probe in the third reporter probe pool comprises a detectable label, in the form of a dual color combination, and a complementary nucleic acid that can hybridize to a corresponding attachment region within attachment position $R_3$ of a reporter probe. The dual color combination and the complementary nucleic acid of a particular reporter probe correspond to one of 16 possible dinucleotides. After hybridization of the reporter probes to position $R_3$, as shown in the bottom middle panel of FIG. 10, any unbound reporter probes are then washed out of the flow cell and the detectable label is recorded to determine the identity of the third dinucleotide of the 6-mer present in the sequencing probe. In this way, all three dinucleotides of the target binding domain are identified and can be assembled together to reveal the sequence of the target binding domain and therefore the sequence of the target nucleic acid.

To continue to sequence the target nucleic acid, any bound sequencing probes can be removed from the target nucleic acid. The sequencing probe can be removed from the target nucleic acid even if a reporter probe is still hybridized to position $R_3$ of the barcode domain. Alternatively, the reporter probe hybridized to position $R_3$ can be removed from the barcode domain prior to the removal of the sequencing probe from the target binding domain, for example, by using the darkening procedures as described above for reporters at positions $R_1$ and $R_2$.

The sequencing cycle depicted in FIG. 10 can be repeated any number of times, beginning each sequencing cycle either with the hybridization of the same pool of sequencing probes to the target nucleic acid molecule or with the hybridization of a different pool of sequencing probes to the target nucleic acid. It is possible that the second pool of sequencing probes bind to the target nucleic acid at a position that overlaps the position at which the first sequencing probe or pool of sequencing probes were bound during the first sequencing cycle. Thereby certain nucleotides within the target nucleic acid can be sequenced more than once and using more than one sequencing probe.

Figure 11B:
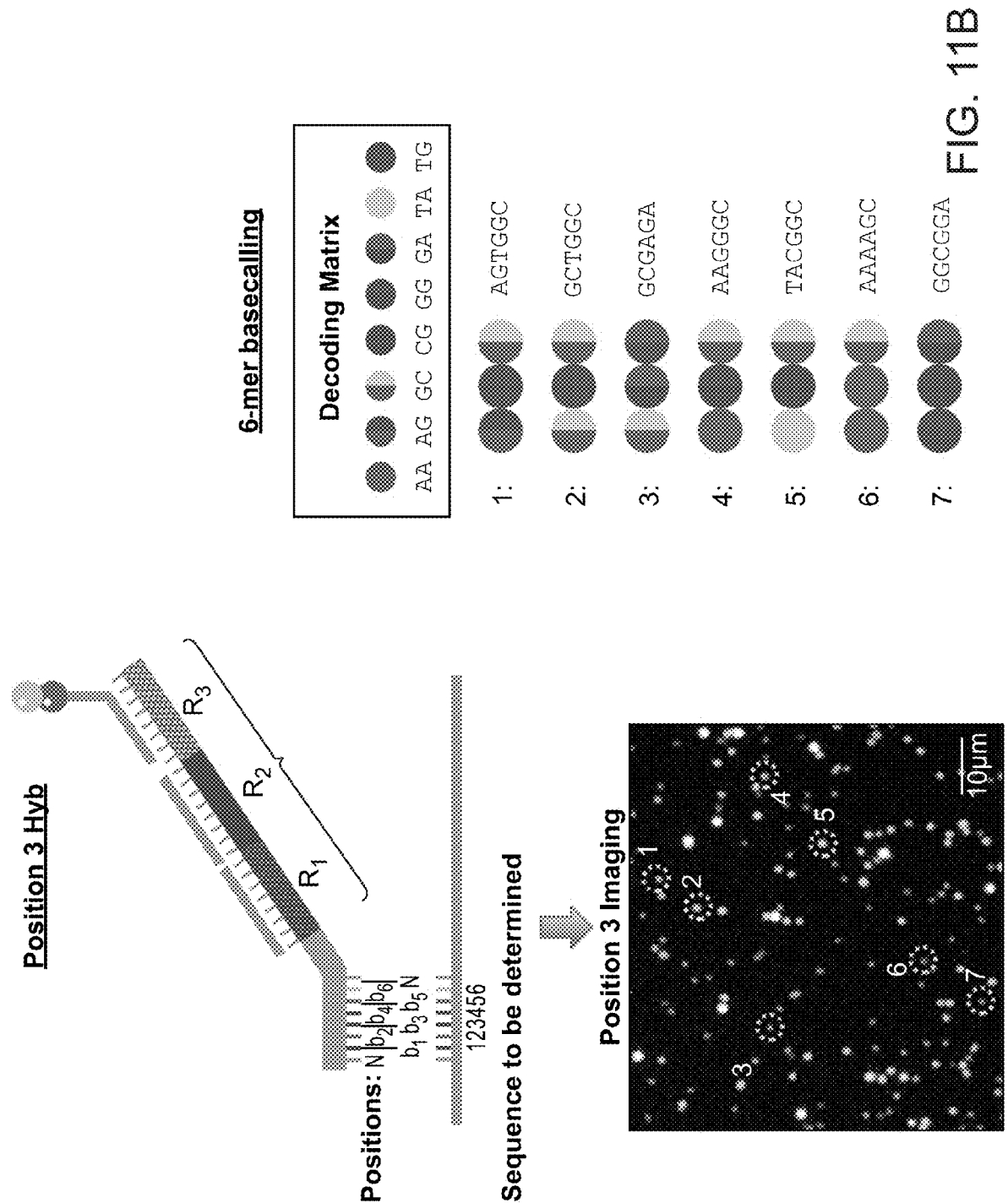

FIGS. 11A-11B depict a schematic of one full cycle of the sequencing method of the present disclosure and the corresponding imaging data collected during this cycle. In this example, the sequencing probe used are those depicted in FIG. 1 and the sequencing steps are the same as those depicted in FIG. 10 and described above. After the sequencing domain of the sequencing probe is hybridized to the target nucleic acid, a reporter probe is hybridized to the first attachment position ($R_1$) of the sequencing probe. The first reporter probe is then imaged to record color dots. In FIGS. 11A-11B, the color dots are labeled with dotted circles. The color dots correspond to a single sequencing probe that is being recorded during the full cycle. In this example, 7 sequencing probes are recorded (1 to 7). The first attachment position of the barcode domain is then darkened and a dual fluorescence reporter probe is hybridized to the second attachment position ($R_2$) of the sequencing probe. The second reporter probe is then imaged to record color dots. The second attachment position of the barcode domain is then darkened and a dual fluorescence reporter is hybridized to the third attachment position ($R_3$) of the sequencing probe. The third reporter probe is then imaged to record color dots. The three color dots from each sequencing probe 1 to 7 are then arranged in order. Each color spot is then mapped to a specific dinucleotide using the decoding matrix to reveal the sequence of the target binding domain of sequencing probes 1 to 7.

During a single sequencing cycle, the number of reporter probe pools needed to determine the sequence of the target binding domain of any sequencing probes bound to a target nucleic acid is identical to the number of attachment positions in the barcode domain. Thus, for a barcode domain having three positions, three reporter probe pools will be cycled over the sequencing probes.

A pool of sequencing probes can comprise a plurality of sequencing probes that are all identical in sequence or a plurality of sequencing probes that are not all identical in sequence. When a pool of sequencing probes include a plurality of sequencing probes that are not all identical in sequence, each different sequencing probe can be present in the same number, or different sequencing probes can be present in different numbers.

Figure 12:
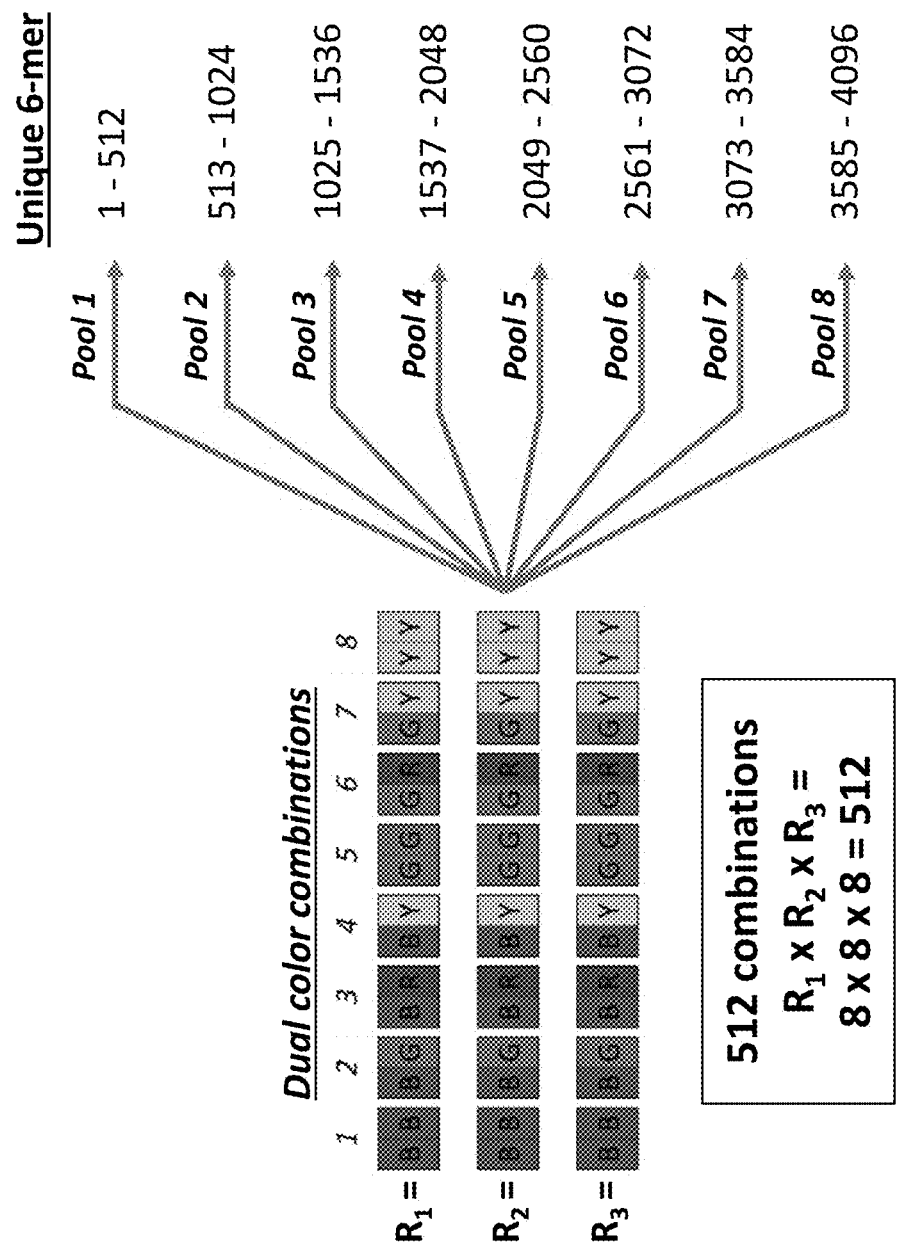
FIG. 12 illustrates an exemplary sequencing probe pool configuration of the present disclosure in which the eight color combinations are used to design eight different pools of sequencing probes.

FIG. 12 shows an exemplary sequencing probe pool configuration of the present disclosure in which the eight color combinations specified above are used to design eight different pools of sequencing probes when the sequencing probe contains: (a) a target binding domain that has 6 nucleotides (6-mer) that specifically binds to the target nucleic acid and (b) three attachment positions ($R_1$, $R_2$ and $R_3$) in the barcode domain. There are a possible 4096 unique 6-mer sequences (4×4×4×4×4×4=4096). Given that each of the three attachment positions in the barcode domain can be hybridized to a complementary nucleic acid bound by one of eight different color combinations, there are 512 unique sets of 3 color combinations possible (8*8*8=512). For example, a probe where $R_1$ hybridizes to a complementary nucleic acid bound to the color combination GG, $R_2$ hybridizes to a complementary nucleic acid bound to the color combination BG, and $R_3$ hybridizes to a complementary nucleic acid bound to the color combination YR, the set of 3 color combinations is accordingly GG-BG-YR. Within a pool of sequencing probes, each unique set of three color combinations will correspond to a unique 6mer within the target binding domain. Given each pool contains 512 unique 6mers, and there are a total of 4096 possible 6mers, eight pools are needed to sequence all possible 6mers (4096/512=8). The specific sequencing probes that are placed in each of the 8 pools is determined to ensure optimal hybridization of each sequencing probe to the target nucleic acid. To ensure optimal hybridization several precautions are taken including: (a) separating perfect timer complements into different pools; (b) separating 6mers with a high Tm and a low Tm into different pools; and (c) separating 6mers into different pools based on empirically-learned hybridization patterns.

Figure 13:
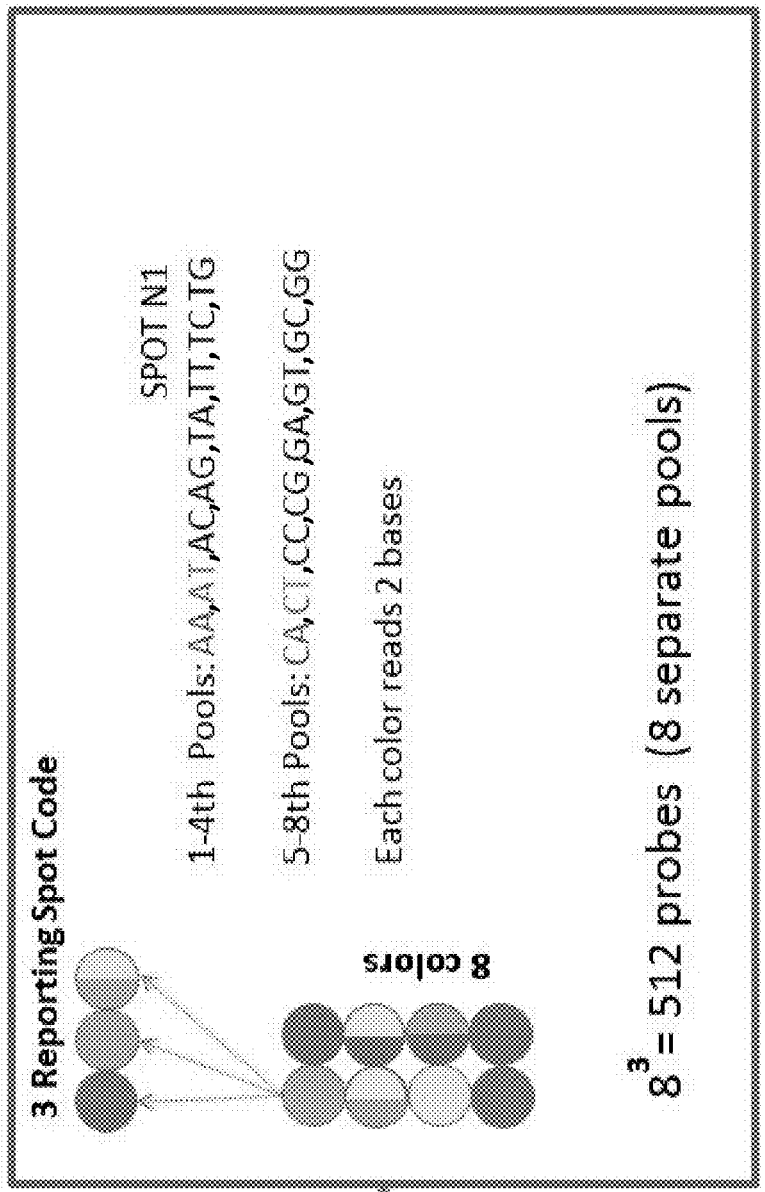
FIG. 13 compares the barcode domain design disclosed in U.S. 2016/019470 with the barcode domain design of the present disclosure.

FIG. 13 shows the difference between the sequencing probes described in US Patent Publication No. 20160194701 and the sequencing probes of the present disclosure. As depicted on the left panel of FIG. 13, US Patent Publication No. 20160194701 describes a sequencing probe with a barcode domain that comprises six attachment positions that are hybridized to complementary nucleic acids. Each complementary nucleic acids is bound to one of four different fluorescent dyes. In this configuration, each color (red, blue, green, yellow) corresponds to one nucleotide (A, T, C, or G) in the target binding domain. This probe design creates 4096 unique probes (4^6). As depicted in the right panel of FIG. 13, in one example of the present disclosure, the barcode domain of each sequencing probe comprises 3 attachment positions that are hybridized to complementary nucleic acids, as depicted in the right panel of FIG. 13. Unlike US Patent Publication No. 20160194701, these complementary nucleic acids are bound by 1 of 8 different color combinations (GG, RR, GY, RY, YY, RG, BB, and RB). Each color combination corresponds to a specific dinucleotide in the target binding domain. This configuration creates 512 unique probes (8^3). To cover all possible hexamer combinations within a target binding domain (4096), 8 separate pools of these 512 unique probes are needed to sequence an entire target nucleic acid. Since 8 color combinations are used to label the complementary nucleic acid, but there are 16 possible dinucleotides, certain color combinations will correspond to different dinucleotides depending on which pool of sequencing probes is being used. For example, in FIG. 13, in the $1^{st}$, $3^{rd}$, and $4^{th}$ pools of sequencing probes, the color combination BB corresponds to the dinucleotide AA and the color combination GG corresponds to the dinucleotide AT. In the $5^{th}$, $6^{th}$, $7^{th}$, and $8^{th}$ pools of sequencing probes, the color combination BB corresponds to the dinucleotide CA and the color combination CT corresponds to the dinucleotide AT.

A plurality of sequencing probes (i.e. more than one sequencing probe) can be hybridized within the sequencing window. During sequencing, the identity and spatial position of the detectable labels bound to each sequencing probe in the plurality of hybridized sequencing probes is recorded. This allows for subsequent identification of both the position and identity of a plurality of dinucleotides. In other words, by hybridizing a plurality of sequencing probes simultaneously to a single target nucleic acid molecule, multiple positions along the target nucleic acid can be sequenced concurrently, increasing the speed of sequencing.

In some aspects, a single sequencing probe can be hybridized to a captured target nucleic acid molecule. In some aspects, a plurality of sequencing probes can be hybridized to a captured target nucleic acid molecule. A sequencing window between two hybridized 5' and 3' capture probes can allow for the hybridization of a single sequencing probe or a plurality of sequencing probes along the length of the target nucleic acid molecule. By hybridizing a plurality of sequencing probes along the length of the target nucleic acid molecule, more than one location on the target nucleic acid molecule can be sequence concurrently, increasing the speed of sequencing. The fluorescence signal from individual probes of a plurality of probes bound along the length of a target nucleic acid can be spatially resolved.

In some aspects, sequencing probes can bind at even intervals along the length of target nucleic acid. In some aspects, sequencing probes need not bind at even intervals along the length of a target nucleic acid. The signals from a plurality of sequencing probes bound along the length of a target nucleic acid can be spatially resolved to obtain sequencing information at multiple locations of a target nucleic acid concurrently.

The distribution of probes along a length of target nucleic acid is critical for resolution of detectable signal. There are occasions when too many probes in a region can cause overlap of their detectable label, thereby preventing resolution of two nearby probes. This is explained as follows. Given that one nucleotide is 0.34 nm in length and given that the lateral (x-y) spatial resolution of a sequencing apparatus is about 200 nm, a sequencing apparatus's resolution limit is about 588 base pair (i.e., a 1 nucleotide/0.34 nm×200 nm). That is to say, the sequencing apparatus mentioned above would be unable to resolve signals from two probes hybridized to a target nucleic acid when the two probes are within about 588 base pair of each other. Thus, two probes, depending on the resolution of the sequencing apparatus, will need be spaced approximately 600 bp's apart before their detectable label can be resolved as distinct "spots". So, at optimal spacing, there should be a single probe per 600 bp of target nucleic-acid. Preferably, each sequencing probe in a population of probes will bind no closer than 600 nucleotides from each other. A variety of software approaches (e.g., utilize fluorescence intensity values and wavelength dependent ratios) can be used to monitor, limit, and potentially deconvolve the number of probes hybridizing inside a resolvable region of a target nucleic acid and to design probe populations accordingly. Moreover, detectable labels (e.g., fluorescent labels) can be selected that provide more discrete signals. Furthermore, methods in the literature (e.g., Small and Parthasarthy: "Superresolution localization methods." *Annu. Rev. Phys Chem.*, 2014; 65:107-25) describe structured-illumination and a variety of super-resolution approaches which decrease the resolution limit of a sequencing microscope up to 10's-of-nanometers. Use of higher resolution sequencing apparatuses allow for use of probes with shorter target binding domains.

As mentioned above, designing the Tm of probes can affect the number of probes hybridized to a target nucleic acid. Alternately or additionally, the concentration of sequencing probes in a population can be increased to increase coverage of probes in a specific region of a target nucleic acid. The concentration of sequencing probes can be reduced to decrease coverage of probes in a specific region of a target nucleic acid, e.g., to above the resolution limit of the sequencing apparatus.

While the resolution limit for two detectable labels is about 600 nucleotides, this does not hinder the powerful sequencing methods of the present disclosure. In certain aspects, a plurality of the sequencing probes in any population will not be separated by 600 nucleotides on a target nucleic acid. However, statistically (following a Poisson distribution), there will be target nucleic acids that only have one sequencing probe bound to it, and that sequencing probe is the one optically resolvable. For target nucleic acids that have multiple probes bound within 600 nucleotides (and thus are not optically resolvable), the data for these unresolvable sequencing probes may be discarded. Importantly, the methods of the present disclosure provide multiple rounds of binding and detecting pluralities of sequencing probes. Thus, it is possible in some rounds the signal from all the sequencing probes are detected, in some rounds the signal from only a portion of the sequencing probes are detected and in some rounds the signal from none of the sequencing probes is detected. In some aspects, the distribution of the sequencing probes bound to the target nucleic acid can be manipulated (e.g., by controlling concentration or dilution) such that only one sequencing probe binds per target nucleic acid.

Randomly, but in part depending on the length of the target binding domain, the Tm of the probes, and concentration of probes applied, it is possible for two distinct sequencing probes in a population to bind within 600 nucleotides of each other.

Alternately or additionally, the concentration of sequencing probes in a population can be reduced to decrease coverage of probes in a specific region of a target nucleic acid, e.g., to above the resolution limit of the sequencing apparatus, thereby producing a single read from a resolution-limited spot.

If the sequence, or part of the sequence, of a target nucleic acid is known prior to sequencing the target nucleic acid using the methods of the present disclosure, the sequencing probes can be designed and chosen such that no two sequencing probes will bind to the target nucleic acid within 600 nucleotides of each other.

Prior to hybridizing sequencing probes to a target nucleic acid, one or more complementary nucleic acid molecules can be bound by a first detectable label and an at least second detectable label can be hybridized to one or more of the attachment positions within the barcode domain of the sequencing probes. For example, prior to hybridization to a target nucleic acid, one or more complementary nucleic acid molecules bound by a first detectable label and an at least second detectable label can be hybridized to the first attachment position of each sequencing probe. Thus, when contacted with its target nucleic acid, the sequencing probes are capable of emitting a detectable signal from the first attachment position and it is unnecessary to provide a first pool of complementary nucleic acids or reporter probes that are directed to the first position on the barcode domain. In another example, one or more complementary nucleic acid molecules bound by a first detectable label and an at least second detectable label can be hybridized to all of the attachment positions within the barcode domain of the sequencing probes. Thus, in this example, a six nucleotide sequence can be read without needing to sequentially replace complementary nucleic acids. Use of this pre-hybridized sequencing probe-reporter probe complex would reduce the time to obtain sequence information since many steps of the described method are omitted. However, this probe would benefit from detectable labels that are non-overlapping, e.g., fluorophores are excited by non-overlapping wavelengths of light or the fluorophores emit non-overlapping wavelengths of light In some aspects of the methods of the present disclosure, the signal intensity from a recorded color dot can be used to more accurately sequence a target nucleic acid. In some aspects, the spot intensity of a particular color within a color dot can be used to determine the probability that a specific color dot corresponds to color combinations that are the duplicity of one color (i.e. BB, GG, YY, or RR).

Figure 14:
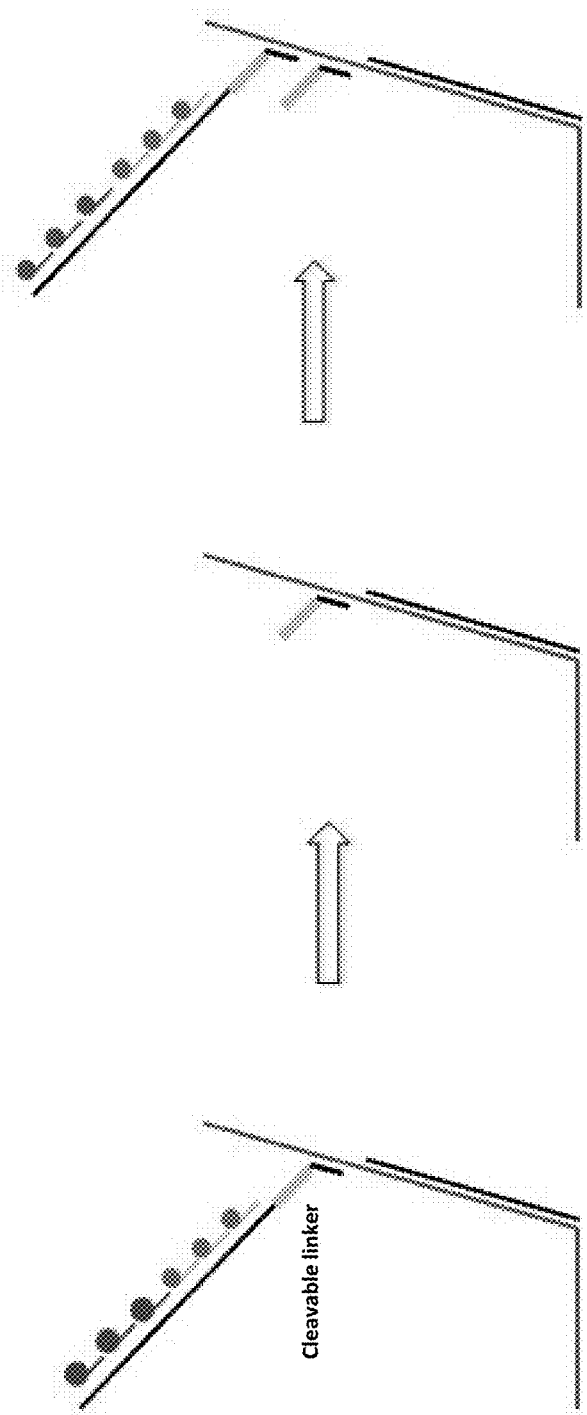
FIG. 14 is a schematic illustration of a sequencing cycle of the present disclosure in which a cleavable linker modification is used to darken a barcode position.

The darkening of a position within a barcode domain can be accomplished by strand cleavage at a cleavable linker modification present within the reporter probes that are hybridized to that position. FIG. 14 depicts the use of a cleavable linker modification to darken a barcode position during a sequencing cycle. The first step, depicted on the furthest left panel of FIG. 14, comprises hybridizing a primary nucleic acid of a reporter probe to the first attachment position of a sequencing probe. The primary nucleic acid hybridizes to a specific, complementary sequence within an attachment region of the first position of the barcode domain. The first and second domains of the primary nucleic acid are covalently linked by a cleavable linker modification. In the second step, the detectable labels are then recorded to determine the identity and position of a specific dinucleotide in the target binding domain of the sequencing probe. In the third step, the first position of the barcode domain is darkened by cleaving the reporter probe at the cleavable linker modification. This releases the second domain of the primary nucleic acid, thereby releasing the detectable labels. The first domain of the primary nucleic acid molecule, now lacking any detectable label, is left hybridized to the first attachment position of the barcode domain, thereby the first position of the barcode domain no longer emits a detectable signal and will not be able to hybridize to any other reporter probe in subsequent sequencing steps. In the final step, depicted in the furthest right panel of FIG. 14, a reporter probe is hybridized to the second position of the barcode domain to continue sequencing.

An attachment position of a barcode domain can be darkened by displacing any secondary or tertiary nucleic acid in the reporter probe that is bound by a detectable label while still allowing the primary nucleic acid molecule of the reporter probe to remain hybridized to the sequencing probe. This displacement can be accomplished by hybridizing to the primary nucleic acid secondary or tertiary nucleic acids that are not bound by a detectable label. FIG. 15 is an illustrative example of an exemplary sequencing cycle of the present disclosure in which a position within a barcode domain is darkened by displacement of labeled secondary nucleic acids. The far left panel of FIG. 15 depicts the start of a sequencing cycle in which a primary nucleic acid molecule of a reporter probe is hybridized to the first attachment position of a barcode domain of a sequencing probe. Secondary nucleic acid molecules bound to a detectable label are then hybridized to the primary nucleic acid molecule and the detectable label is recorded. To darken the first position of the barcode domain, the secondary nucleic acid molecules bound to a detectable label are displaced by secondary nucleic acid molecules that lack a detectable label. In the next step of the sequencing cycle, a reporter probe comprising detectable labels is hybridized to the second position of the barcode domain.

An attachment position of a barcode domain can be darkened by displacing any primary nucleic acid molecule of the reporter probe by hybridizing to the sequencing probe at the corresponding barcode domain attachment position nucleic acids that are not bound by a detectable label. In those instances where a barcode domain comprises at least one single-stranded nucleic acid sequence adjacent or flanking at least one attachment position, the nucleic acid not bound by a detectable label can displace a primary nucleic acid molecule by hybridizing to the flanking sequence and a portion of the barcode domain occupied by the primary nucleic acid molecule. If needed, the rate of detectable label exchange can be accelerated by incorporating small single-stranded oligonucleotides that accelerate the rate of exchange of detectable labels (e.g., "Toe-Hold" Probes; see, e.g., Seeling et al., "Catalyzed Relaxation of a Metastable DNA Fuel"; *J. Am. Chem. Soc.* 2006, 128(37), pp 12211-12220).

The complementary nucleic acids comprising a detectable label or reporter probes can be removed from the attachment region but not replaced with a hybridizing nucleic acid lacking a detectable label. This can occur, for example, by adding a chaotropic agent, increasing the temperature, changing salt concentration, adjusting pH, and/or applying a hydrodynamic force. In these examples, fewer reagents (i.e., hybridizing nucleic acids lacking detectable labels) are needed.

The methods of the present disclosure can be used to concurrently capture and sequence RNA and DNA molecules, including mRNA and gDNA, from the same sample. The capture and sequencing of both RNA and DNA molecules from the same sample can be performed in the same flow cell. In some aspects, the methods of the present disclosure can be used to concurrently capture, detect, and sequence both gDNA and mRNA from a FFPE sample.

The sequencing method of the present disclosure further comprise steps of assembling each identified linear order of nucleotides for each region of an immobilized target nucleic acid, thereby identifying a sequence for the immobilized target nucleic acid. The steps of assembling uses a non-transitory computer-readable storage medium with an executable program stored thereon. The program instructs a microprocessor to arrange each identified linear order of nucleotides for each region of the target nucleic acid, thereby obtaining the sequence of the nucleic acid. Assembling can occur in "real time", i.e., while data is being collected from sequencing probes rather than after all data has been collected or post complete data acquisition.

Figure 16:
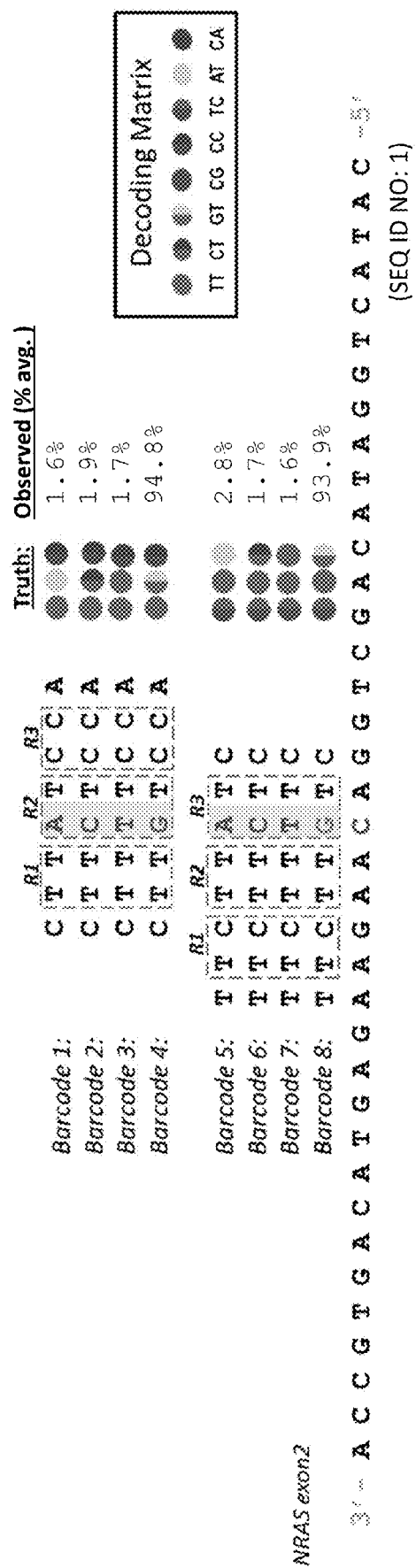
FIG. 16 is schematic illustration of how the sequencing method of the present disclosure allows for the sequencing of the same base of a target nucleic acid with different sequencing probes.

The raw specificity of the sequencing method of the present disclosure is approximately 94%. The accuracy of the sequencing method of the present disclosure can be increased to approximately 99% by sequencing the same base in a target nucleic acid with more than one sequencing probe. FIG. 16 depicts how the sequencing method of the present disclosure allows for the sequencing of the same base of a target nucleic acid with different sequencing probes. The target nucleic acid in this example is a fragment of NRAS exon2 (SEQ ID NO: 1). The particular base of interest is a cytosine (C) that is highlighted in the target nucleic acid. The base of interest will be hybridized to two different sequencing probes, each with a distinct footprint of hybridization to the target nucleic acid. In this example, sequencing probes 1 to 4 (barcode 1 to 4) bind three nucleotides to the left of the base of interest, while sequencing probes 5 to 8 (barcodes 5 to 8) bind 5 nucleotides to the left of the base of interest. Thereby, the base of interest will be sequenced by two different probes, thereby increasing the amount of base calls for that specific position, and thereby increasing overall accuracy at that specific position. FIG. 17 shows how multiple different base calls for a specific nucleotide position on the target nucleotide, recorded from one or more sequencing probes, can be combined to create a consensus sequence (SEQ ID NO: 2), thereby increasing the accuracy of the final base call.

The terms "Hyb & Seq chemistry," "Hyb & Seq sequencing," and "Hyb & Seq" refer to the methods of the present disclosure described above.

Arrays of the Present Disclosure and Methods Using Said Arrays

The present disclosure provides compositions and methods for immobilizing nucleic acid molecules, including arrays and methods of using arrays, as described in detailed herein.

The present disclosure provides a composition comprising a planar solid support substrate; a first layer on the planar solid support substrate; a second layer on the first layer; wherein the second layer comprises a plurality of nanowells, wherein each nanowell provides access to an exposed portion of the first layer, wherein each nanowell comprises a plurality of first oligonucleotides covalently attached to the exposed portion of the first layer.

The present disclosure provides a composition comprising: a planar solid support substrate; a first layer on the planar solid support substrate in contact with a first surface of the planar solid support substrate; a second layer on the first layer in contact with a second surface of the first layer, wherein the second surface of the first layer is not in contact with a surface of the planar solid support substrate; wherein the second layer comprises a plurality of nanowells, wherein each nanowell provides access to an exposed portion of the first layer, wherein each nanowell comprises a plurality of first oligonucleotides covalently attached to the exposed portion of the first layer.

A first layer can comprise a first surface in contact with a surface of a planar solid support substrate and a second surface in contact with a second layer but not in contact with a surface of the planar solid support substrate.

A second layer can comprise a first surface in contact with a surface of a first layer and a second surface exposed to the environment.

Figure 47:
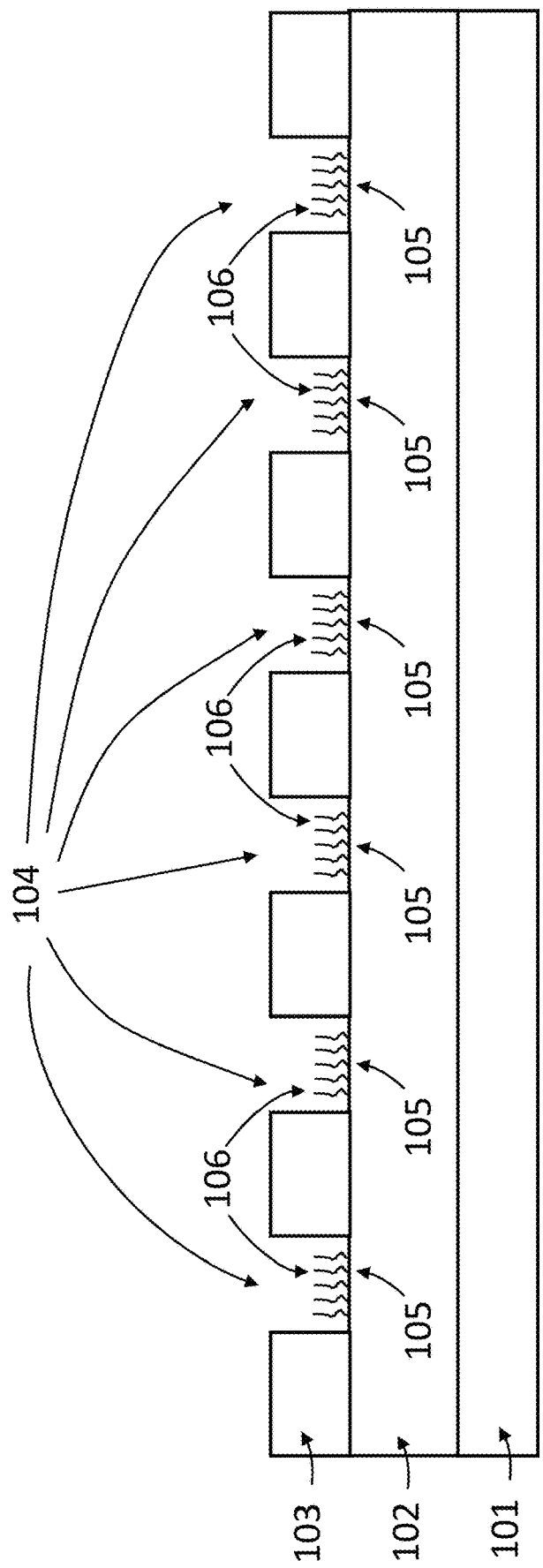
FIG. 47 is a schematic cross section of an exemplary array of the present invention

FIG. 47 is a schematic cross section of an exemplary array of the present invention. The array comprises a planar solid support substrate 101, a first layer 102 on the planar solid support substrate 101, and a second layer 103 on the first layer 102. The second layer 103 comprises a plurality of nanowells 104. Each nanowell 104 is open on two sides thereby exposing a portion of the first layer in each nanowell 105. A plurality of first oligonucleotides 106 is covalently attached to the exposed first layer 105 in each nanowell.

In some aspects, a planar solid support substrate can be a surface, membrane, bead, porous material or electrode. A planar solid support substrate can comprise, but is not limited to, a polymeric material, a metal, silicon, glass or quartz for example.

In some aspects, a first layer 102 can comprise an oxide film, such as, but not limited to, silicon dioxide.

In some aspects, a first layer 102 can have a thickness of about 50 to about 150 nm. A first layer 102 can have a thickness of about 90 nm.

In some aspects, a second layer 103 can comprise, but is not limited to, bis(trimethylsilyl)amine, also known as hexamethyldisilazane (HMDS or HDMS).

In some aspects, a second layer 103 can comprises a material that is not chemically reactive, such that the second layer does not bind biological macromolecules.

In some aspects, a second layer 103 can have a thickness of about 1 nm to about 10 nm. A second layer 103 can have a thickness of about 3 nm to about 4 nm.

In some aspects, the planar solid support substrate comprises silicon, the first layer comprises silicon dioxide and the second layer comprises HMDS.

In some aspects, the planar solid support substrate comprises glass, the first layer comprises silicon dioxide and the second layer comprises HMDS.

In some aspects, a second layer can comprise about $0.1 \times 10^5$ and about $100 \times 10^7$ nanowells per square millimeter. A second layer can comprise about $0.1 \times 10^6$ and about $100 \times 10^6$ nanowells per square millimeter. A second layer can comprise about $1 \times 10^6$ and about $10 \times 10^6$ nanowells per square millimeter. A second layer can comprise about $2 \times 10^6$ and about $5 \times 10^6$ nanowells per square millimeter. A second layer can comprise about $3 \times 10^6$ nanowells per square millimeter.

As used herein, "density of nanowells" refers to the number of nanowells present within a specified surface area. For example, a second layer that has a surface area of 1.0 $mm^2$ and that comprises $1.0 \times 10^6$ nanowells is said to have a density of nanowells that is $1.0 \times 10^6$ nanowells/$mm^2$.

In some aspects, the density of nanowells can be between about $0.1\times10^5$ and about $100\times10^7$ nanowells/mm². The density of nanowells can be between about $0.1\times10^6$ and about $100\times10^6$ nanowells/mm². The density of nanowells can be between about $1\times10^6$ and about $10\times10^6$ nanowells/mm². The density of nanowells can be between about $2\times10^6$ and about $5\times10^6$ nanowells/mm². The density of nanowells can be about $3\times10^6$ nanowells/mm².

In some aspects, the surface area of an exposed portion of the first layer in a nanowell can be about 200 to about 50,000 nm². The surface area of the exposed portion of the first layer in each nanowell is can be about 300 to about 40,000 nm². The surface area of the exposed portion of the first layer in each nanowell can be about 700 to about 8,000 nm². The surface area of the exposed portion of the first layer in each nanowell can be about 2,000 to about 3,000 nm².

In some aspects, the exposed portion of the first layer in each nanowell is circular. In some aspects, the exposed portion of the first layer in each nanowell is elliptical. In some aspects, the exposed portion of the first layer in each nanowell is rectangular. In some aspects, the exposed portion of the first layer in each nanowell is square. In some aspects, the exposed portion of the first layer in each nanowell is hexagonal or octagonal. In some aspects, the exposed portion of the first layer in each nanowell has a shape of a regular polygon. In some aspects, the exposed portion of the first layer in each nanowell has a shape of an irregular polygon.

In some aspects in which an exposed portion of the first layer in a nanowell is circular, the exposed portion of the first layer can have a diameter of about 10 nm to about 200 nm. The exposed portion of the first layer can have a diameter of about 20 nm to about 200 nm. The exposed portion of the first layer can have a diameter of about 30 nm to about 100 nm. The exposed portion of the first layer can have diameter of about 50 nm to about 60 nm. The exposed portion of the first layer can have a diameter of about 60 nm.

In some aspects of the, a nanowell can be cylindrical. A nanowell can be rectangular. A nanowell can be cuboid. A nanowell can be polyhedral. A nanowell can have a shape of a right circular cylinder. A nanowell can have the shape of an elliptical cylinder. A nanowell can have the shape of a rectangular prism. A nanowell can have the shape of a cube. A nanowell can have the shape of a triangular prism. A nanowell can have the shape of a cone. A nanowell can have the shape of a pyramid. A nanowell can have the shape of a square pyramid.

Figure 48:
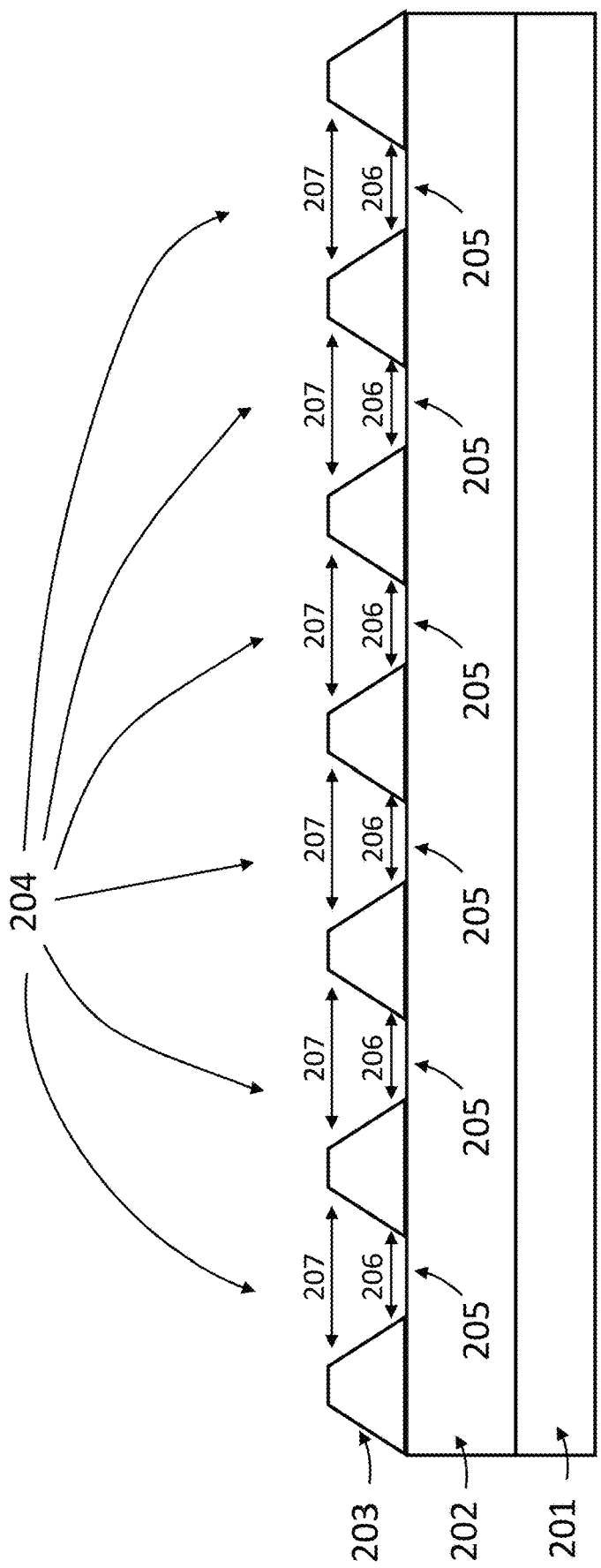
FIG. 48 is a schematic cross section of an exemplary array of the present invention comprising nanowells that have the shape of a pyramid.

In some aspects, one portion of a nanowell may have different dimensions than another portion of the same nanowell. In a non-limiting example shown in FIG. 48, an array of the present disclosure comprising a planar solid support substrate 201, a first layer 202 on the planar solid support substrate 201, and a second layer 203 on the first layer 202. The second layer 203 comprises a plurality of nanowells 204. Each nanowell 204 is open on two sides thereby exposing a portion of the first layer in each nanowell 205. The portion of the nanowells closest to the first layer 202 have a diameter 206 that is smaller than the diameter 207 of the portion of the nanowells furthest from the first layer.

Figure 49:
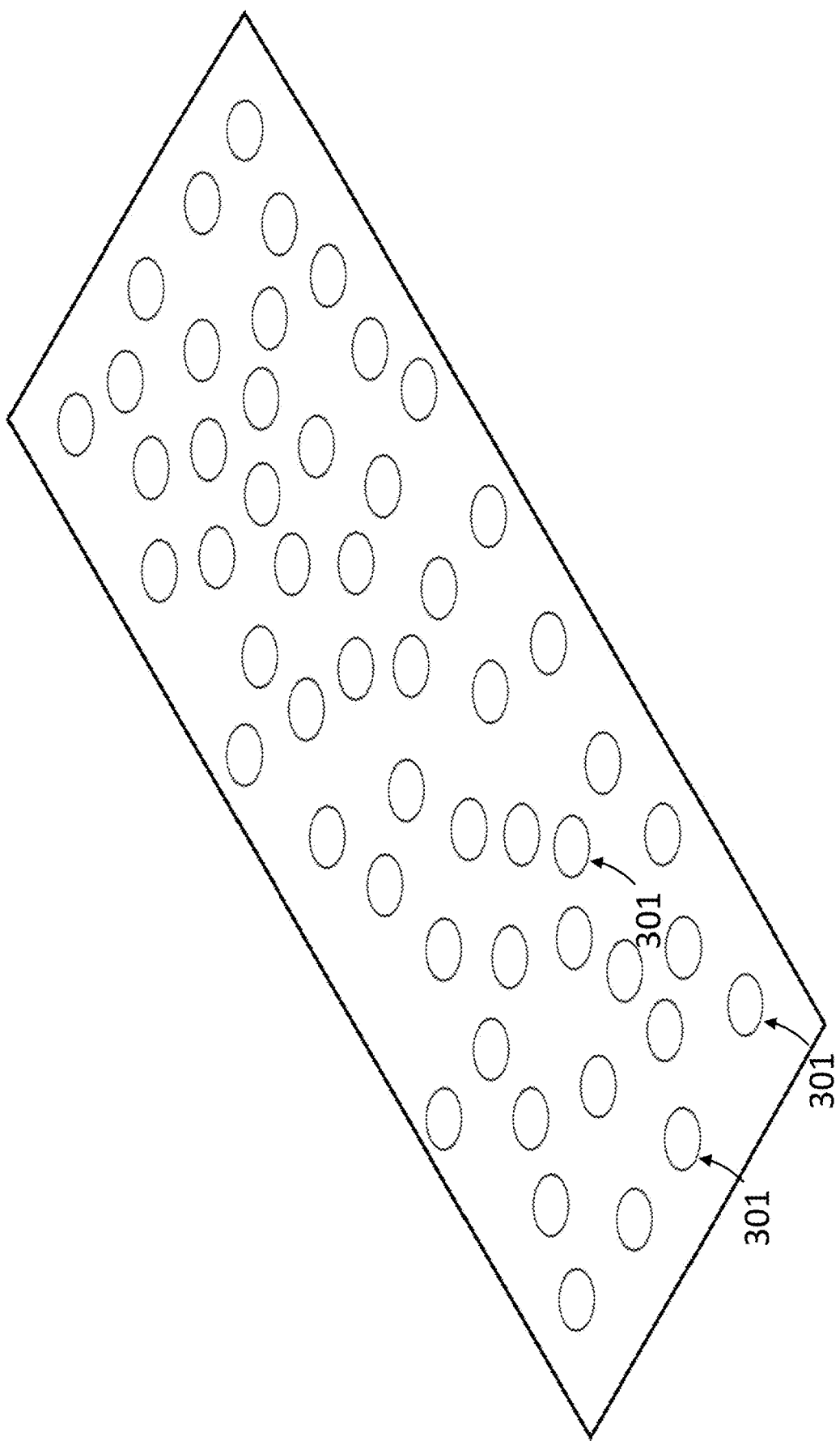
FIG. 49 is a schematic diagram of an exemplary array of the present disclosure comprising a plurality of cylindrical nanowells arranged in a random pattern.

In some aspects, a plurality of nanowells can be arranged in a random pattern. As used herein, the terms "arranged in a random pattern", "randomly-patterned" or "random" refer to a non-ordered, non-Cartesian distribution (in other words, not arranged at pre-determined points along the x- and y-axes of a grid or at defined "clock positions", degrees or radii from the center of a radial pattern) of features, such as nanowells or pads that are not achieved through an intentional design (or program by which such a design may be achieved) or by specific placement of features. A "randomly-patterned" set of features may be achieved by dropping, spraying, plating or spreading a solution, emulsion, aerosol, vapor or dry preparation onto a support without any manner to direct any features to specific sites thereon. FIG. 49 shows a schematic diagram of an exemplary array of the present disclosure comprising a plurality of cylindrical nanowells 301 arranged in a random pattern.

Figure 50:
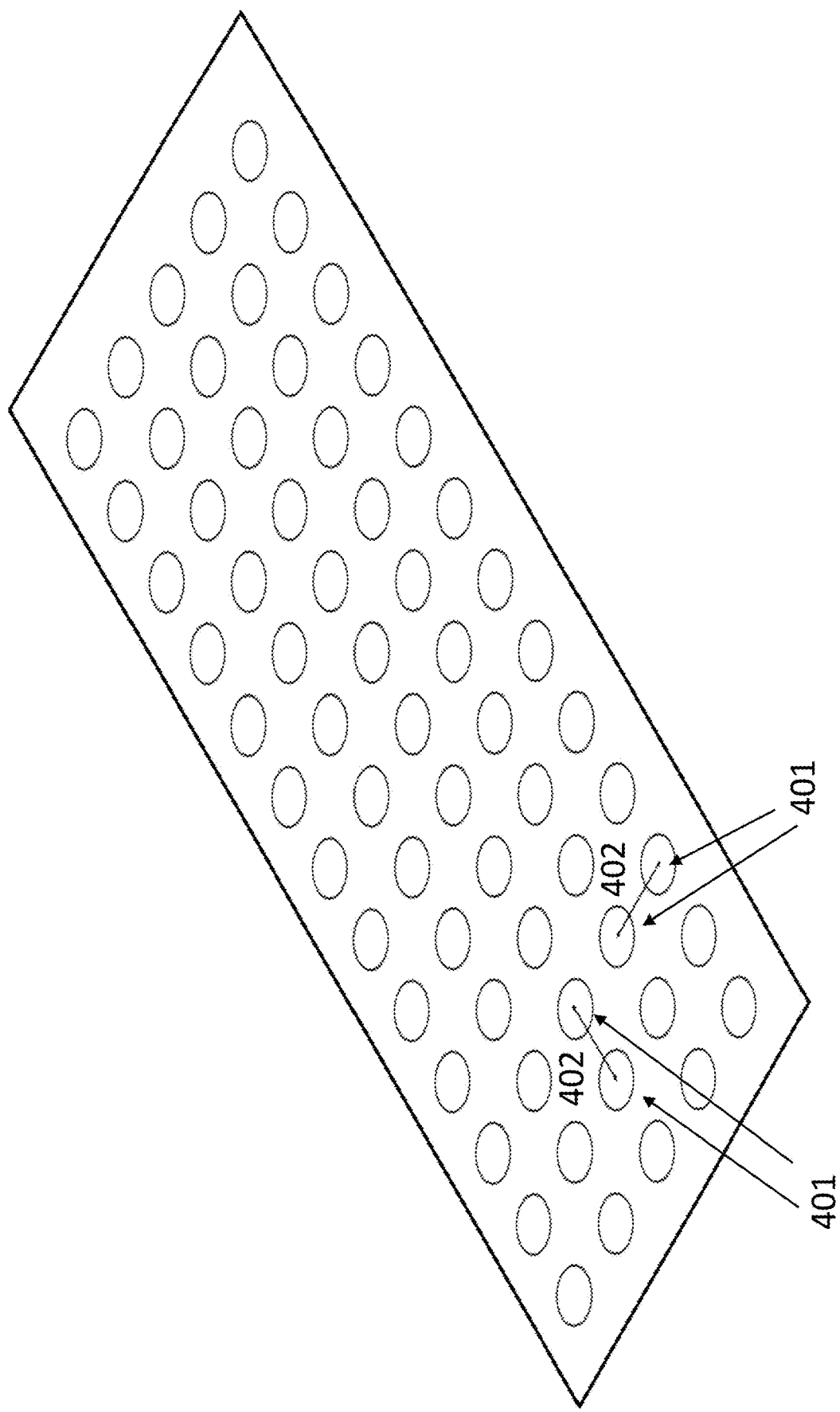
FIG. 50 is a schematic diagram of an exemplary array of the present disclosure comprising cylindrical nanowells arranged in an ordered grid with a constant pitch.

In some aspects, a plurality of nanowells can be arranged in an ordered pattern. As used herein, the terms "arranged in an ordered pattern" or "ordered pattern" refer to a distribution of features that is arranged along regular, pre-determined points along an x- and y-axes of a grid or at defined "clock positions", degrees or radii from the center of a radial pattern. In some aspects, a plurality of nanowells can be arranged in an ordered grid. The ordered grid can have a pitch of about 50 nm to about 3500 nm. The ordered grid can have a pitch of about 100 nm to about 3200 nm. The ordered grid can have a pitch of about 300 nm to 1000 nm. The ordered grid can have a pitch of about 440 nm to about 710 nm. The ordered grid has a pitch of about 575 nm. The ordered grid has a pitch of about 577 nm. As used herein, the term "pitch" refers to the distance between the center of two adjacent features that are arranged on an ordered grid. FIG. 50 shows a schematic diagram of an exemplary array of the present disclosure comprising nanowells 401 that are arranged in an ordered grid with a constant pitch 402.

The oligonucleotides attached to an array and/or substrate can also be referred to herein as lawn oligonucleotides.

In some aspects, the nucleic acid length of a first oligonucleotide can be about 10 to about 100 nucleotides. The nucleic acid length of a first oligonucleotide can be about 20 to about 40 nucleotides.

In some aspects, a first oligonucleotide can comprise at least one natural base. A first oligonucleotide can comprise no natural bases. A first oligonucleotide can comprise at least one modified nucleotide or nucleic acid analog. A first oligonucleotide can comprise no modified nucleotides or nucleic acid analogs. A first oligonucleotide can comprise at least one universal base. A first oligonucleotide can comprise no universal bases. A first oligonucleotide can comprise at least one degenerate base. A first oligonucleotide can comprise no degenerate bases.

In some aspects, a first oligonucleotide can comprise RNA, D-DNA, L-DNA, LNA, isoguanine, isocytosine, abasic nucleotides or any combination thereof.

In some aspects, each first oligonucleotide in a plurality of first oligonucleotides can comprise the same sequence. Each first oligonucleotide in a plurality of first oligonucleotides can comprise different sequences.

In some aspects, each nanowell in a plurality of nanowells comprises the same plurality of first oligonucleotides. In other aspects, each nanowell in a plurality of nanowells comprises a different plurality of first oligonucleotides.

A plurality of first oligonucleotides can comprise 2, 3, 4, 5, 6, 7, 8, 9, 10, 50, 100, 200, 300, 400, 500, 600, 700, 800, 900, 1,000, 10,000, 100,000, or 1,000,000 first oligonucleotides.

The arrays of the present disclosure can be fabricated using methods known in the art, including, but not limited to photolithography, etc. Methods for fabricating arrays are described in U.S. Pat. No. 7,250,371 and US 2006/0134917, the contents of which are incorporated by reference in their entirety.

In some aspects, the exposed portion of the first layer in each nanowell can be functionalized with reactive moieties to attract and bind specific chemical groups existing on a biological macromolecule, such as a first oligonucleotide or a target nucleic acid complex. These functional groups are well known to be able to specifically attract and bind biological macromolecules through various conjugation chemistries. Exemplary reactive moieties include, but are not limited to, surfaces comprising epoxy, aldehyde, gold, hydrazide, sulfhydryl, NHS-ester, amine, alkyne, azide, thiol, carboxylate, maleimide, hydroxymethyl phosphine, (3-aminopropyl)trimethyoxysilane, imidoester, isocyanate, hydroxyl, pentafluorophenyl-ester, psoralen, pyridyl disulfide or vinyl sulfone, polyethylene glycol (PEG), hydrogel, or mixtures thereof.

In some aspects, a biological macromolecule, including but not limited to, a nucleic acid molecule, can be attached to the exposed portion of the first layer in each nanowell using a photoreactive moiety. Some examples of photoreactive moieties include aryl azides, such as N((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

The present disclosure provides a method of immobilizing at least one target nucleic acid from a sample comprising: a) providing a composition of the present disclosure; and b) contacting the composition with at least one target nucleic acid, wherein the at least one target nucleic acid hybridizes to a first oligonucleotide, thereby immobilizing at least one target nucleic acid such that no more than one target nucleic acid is immobilized within a single nanowell.

Figure 51:
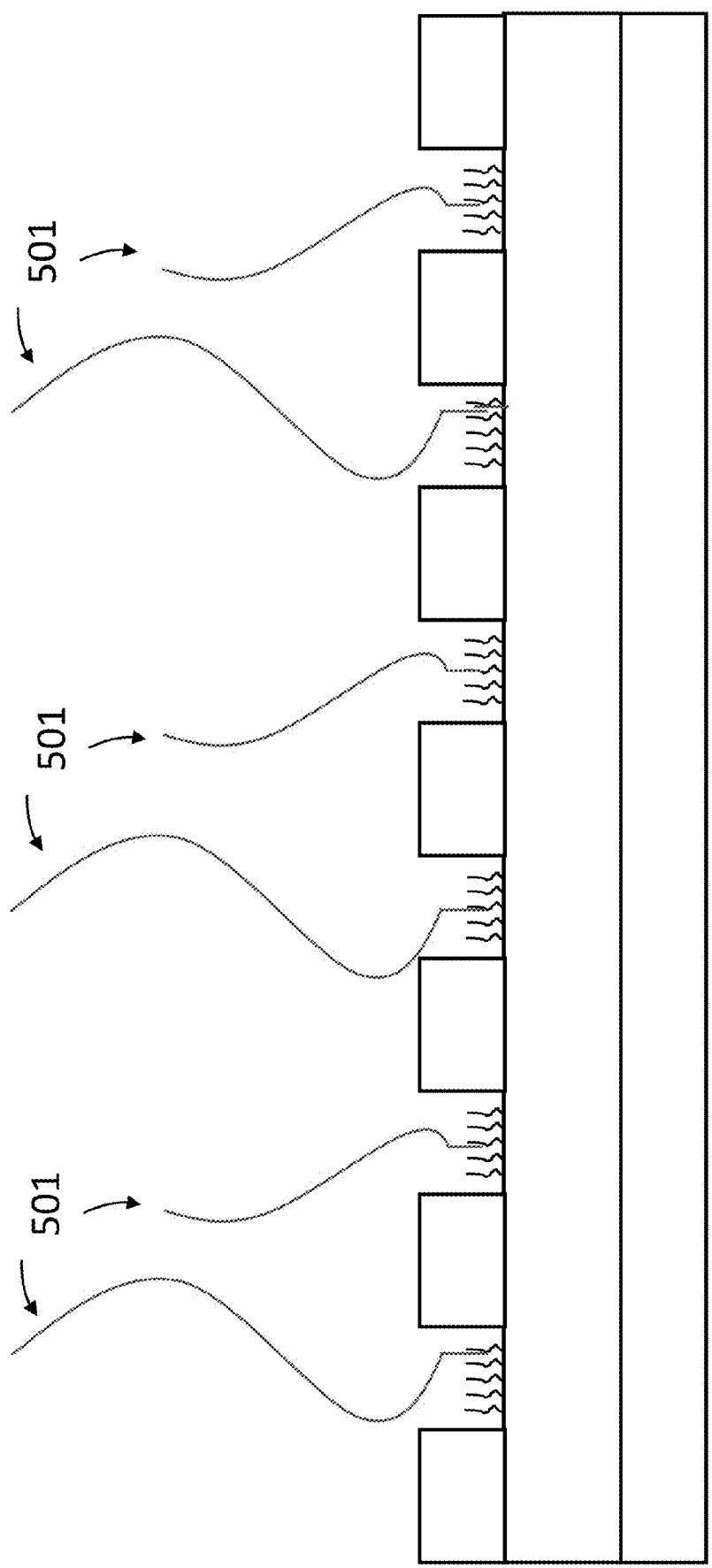
FIG. 51 is a schematic cross section of an exemplary array of the present invention wherein a single target nucleic acid complex is immobilized in each nanowell.

FIG. 51 shows a schematic diagram of the exemplary array shown in FIG. 47 with one target nucleic acid complex 501 immobilized in each nanowell.

The immobilization methods of the present disclosure have the advantage that the size (e.g. volume) of the nanowells on the array prevent more than one target nucleic acid complex from hybridizing within a single nanowell. Thus, after immobilization, each nanowell on an array contains one or zero target nucleic acid complexes. This is advantageous to applications such as single molecule sequencing. By immobilizing only one target nucleic acid complex within a single nanowell, individual target nucleic acid complexes can be individually interrogated, for example, using fluorescent probes known in the art (e.g. see U.S. Pat. Nos. 8,148,512, 7,473,767, 7,919,237, 7,941,279, 8,415, 102, 8,492,094, 8,519,115, U.S. 2009/0220978, U.S. 2009/0299640, U.S. 2010/0015607, U.S. 2010/0261026, U.S. 2011/0086774, U.S. 2011/0145176, U.S. 2011/0201515, U.S. 2011/0229888, U.S. 2013/0004482, U.S. 2013/0017971, U.S. 2013/0178372, U.S. 2013/0230851, U.S. 2013/0337444, U.S. 2013/0345161, U.S. 2014/0005067, U.S. 2014/0017688, U.S. 2014/0037620, U.S. 2014/0087959, U.S. 2014/0154681, U.S. 2014/0162251, and U.S. 2016/0194701 each of which is incorporated herein by reference in their entireties).

Figure 52:
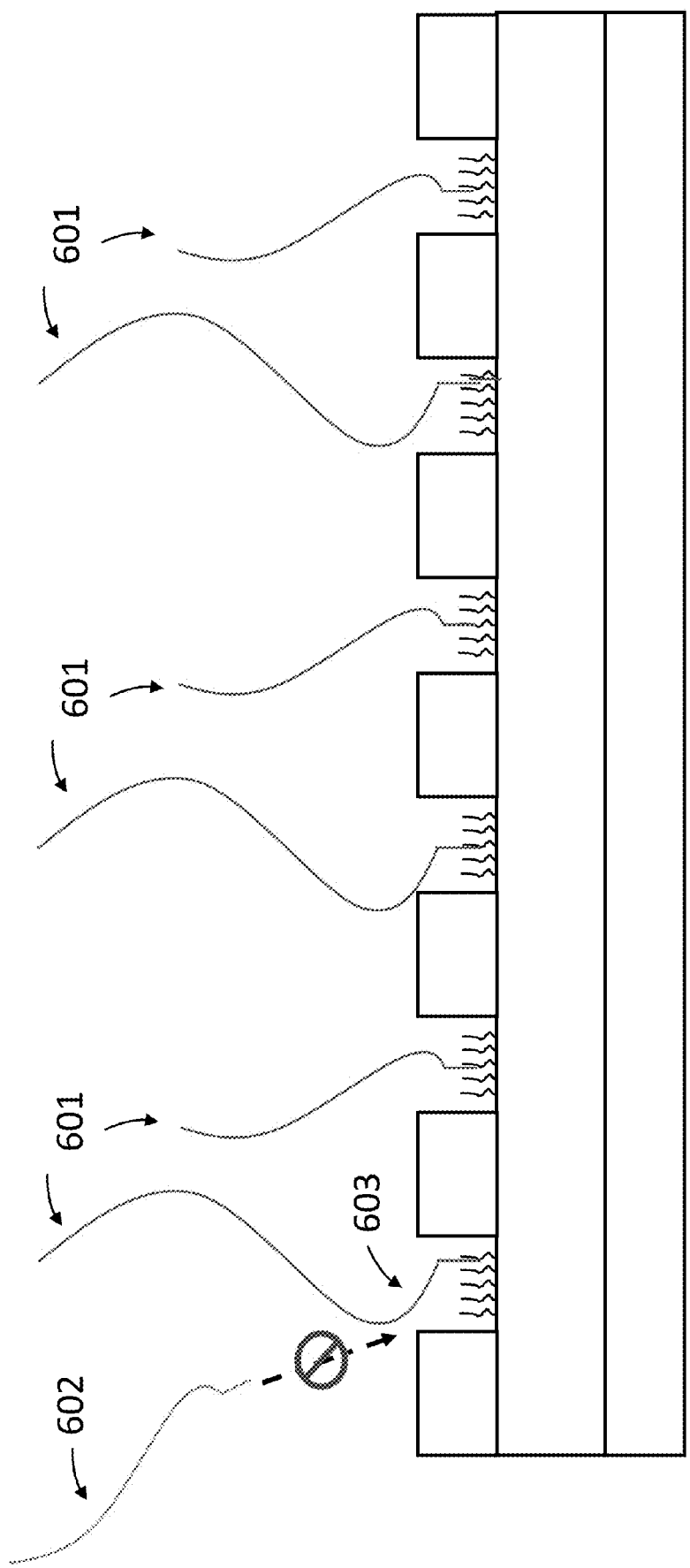
FIG. 52 is a schematic cross section of an exemplary array of the present invention wherein a single target nucleic acid complex is immobilized in each nanowell thereby preventing the immobilization of other target nucleic acid complexes.

FIG. 52 shows a schematic diagram of the exemplary array shown in FIG. 47 with one target nucleic complex 601 immobilized in each nanowell. The target nucleic acid complex 602 is unable to bind in the leftmost nanowell 603, as nanowell 603 is already occupied by a target nucleic acid complex 601.

In some aspects, a nanowell can have a volume that is approximately equal to, equal to, or less than the excluded volume of a target nucleic acid, such that only one target nucleic acid complex can physically fit into a single nanowell at a given time.

In some aspects, nanowells are spaced such that the signal from a fluorescent probe hybridized/bound to a biological macromolecule immobilized within a nanowell is optically resolvable from the signal of fluorescent probe hybridized/bound to a biological macromolecule immobilized in an adjacent nanowell.

In some aspects, a target nucleic acid comprise at about 10 nucleotides to about 100,000 nucleotides. In some aspects, a target nucleic acid can comprise about 100, or about 250, or about 500, or about 750, or about 1,000, or about 5,000 nucleotides, or about 10,000 nucleotides, or about 100,000 nucleotides, or about 1,000,000 nucleotides, or about 10,000,000 nucleotides.

In some aspects, a target nucleic acid can comprise, but is not limited to, polymeric forms of nucleotides that can have various lengths, either deoxyribonucleotides or ribonucleotides, or analogs thereof. Non-limiting examples of target nucleic acids include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), non-coding RNA (ncRNA), cDNA, recombinant polynucleotides, branched polynucleotides, plasmids, vectors, isolated DNA of a sequence, isolated RNA of a sequence, nucleic acid probes, and primers. The identity and/or sequence of target nucleic can be known. Alternatively, the identity and/or sequence of a target nucleic acid can be unknown. It is also possible that a portion of the sequence of a target nucleic acid is known.

A target nucleic acid can be obtained from any sample or source of nucleic acid, e.g., any cell, tissue, or organism, in vitro, chemical synthesizer, and so forth. The target nucleic acid can be obtained by any art-recognized method. A target nucleic acid can be obtained from a blood sample of a clinical subject. A target nucleic acid can be isolated from a biological sample. A target nucleic acid can be extracted, isolated, or purified from the source or samples using methods and kits well known in the art. In some aspects, a tissue sample is a biopsied tumor or a portion thereof, i.e., a clinically-relevant tissue sample. For example, the tumor may be from a breast cancer. The sample may be an excised lymph node.

A target nucleic acid can be fragmented by any means known in the art prior to immobilization. Preferably, the fragmenting is performed by an enzymatic or a mechanical means. The mechanical means can be sonication or physical shearing. The enzymatic means can be performed by digestion with nucleases (e.g., Deoxyribonuclease I (DNase I)) or one or more restriction endonucleases. A target nucleic acid can be fragmented using a CRISPR-based fragmentation step. A CRISPR-based fragmentation step allows for target fragmentation and the creation of target nucleic acids of a desired size. In a non-limiting example, CRISPR-based fragmentation can create target nucleic acids that are of a size that prevents more than one target nucleic acid complex from being immobilized in a single nanowell.

In some aspects of the methods of the present disclosure, a target nucleic acid can indirectly hybridize to a first oligonucleotide via a second oligonucleotide, wherein the second oligonucleotide comprises a first region that hybridizes to the first oligonucleotide and a second region that hybridizes to the at least one target nucleic acid.

A second oligonucleotide can comprise at least one natural base. A second oligonucleotide can comprise no natural bases. A second oligonucleotide can comprise at least one modified nucleotide or nucleic acid analog. A second oligonucleotide can comprise no modified nucleotides or nucleic acid analogs. A second oligonucleotide can comprise at least one universal base. A second oligonucleotide can comprise at least one universal base. A second oligonucleotide can comprise no universal bases. A second oligonucleotide can comprise at least one degenerate base. A second oligonucleotide can comprise no degenerate bases.

A second oligonucleotide can comprises D-DNA, L-DNA, LNA, isoguanine, isocytosine, abasic nucleotides or combinations thereof. A second oligonucleotide can comprise L-DNA. A second oligonucleotide can comprise a sequence that identifies the sample.

In some aspects of the methods of the present disclosure, a target nucleic acid can indirectly hybridize to a first oligonucleotide via a second oligonucleotide and a third oligonucleotide, wherein the second oligonucleotide comprises a first region that hybridizes to the first oligonucleotide and a second region that hybridizes to a first region on the third oligonucleotide and wherein the third oligonucleotide comprises a first region that hybridizes to the second region of the second oligonucleotide and a second region that hybridizes to a target nucleic acid.

A third oligonucleotide can comprise at least one natural base. A third oligonucleotide can comprise no natural bases. A third oligonucleotide can comprise at least one modified nucleotide or nucleic acid analog. A third oligonucleotide can comprise no modified nucleotides or nucleic acid analogs. A third oligonucleotide can comprise at least one universal base. A third oligonucleotide can comprise at least one universal base. A third oligonucleotide can comprise no universal bases. A third oligonucleotide can comprise at least one degenerate base. A third oligonucleotide can comprise no degenerate bases.

A third oligonucleotide can comprises D-DNA, L-DNA, LNA, isoguanine, isocytosine, abasic nucleotides or combinations thereof. A third oligonucleotide can comprise L-DNA. A third oligonucleotide can comprise a sequence that identifies the sample.

In some aspects of the methods of the present disclosure, a target nucleic acid can directly hybridize to a first oligonucleotide. A target nucleic acid can directly hybridize to a first oligonucleotide via a nucleic acid probe ligated to the 3' end of the target nucleic acid A nucleic acid probe can comprise at least one natural base. A nucleic acid probe can comprise no natural bases. A nucleic acid probe can comprise at least one modified nucleotide or nucleic acid analog. A nucleic acid probe can comprise no modified nucleotides or nucleic acid analogs. A nucleic acid probe can comprise at least one universal base. A nucleic acid probe can comprise at least one universal base. A nucleic acid probe can comprise no universal bases. A nucleic acid probe can comprise at least one degenerate base. A nucleic acid probe can comprise no degenerate bases.

A nucleic acid probe of a target nucleic acid complex can comprise RNA, D-DNA, L-DNA, LNA, isoguanine, isocytosine, abasic nucleotides or any combination thereof.

A nucleic acid probe can comprise a cleavable linker. A cleavable linker can be a photocleavable linker or an enzymatically cleavable linker.

In some aspects of the methods of the present disclosure, after a target nucleic acid is immobilized, the target nucleic acid can be sequenced. The target nucleic acid can be sequenced using any method known in the art. Preferably, the target nucleic acid is sequenced by direct detection methods (e.g. see WO 2016/081740, WO 2018/094385 each of which is incorporated herein by reference in their entireties).

As used herein, the term "array" is used in its broadest sense to refer to a substrate comprising a plurality of features, wherein a feature comprises one or more immobilized biological macromolecules and/or wherein a feature is capable of capturing and immobilizing one or more biological macromolecules. Thus, in some aspects, the compositions of the present invention can be considered arrays.

The terms "feature", "pad", "spot" and "nanowell" are herein used interchangeably to refer to a structure and/or area that comprises one or more immobilized biological macromolecules and/or is capable of capturing and immobilizing one or more biological macromolecules.

As used herein, the term "biological macromolecule" is used in its broadest sense to refer to organic molecules such as, but not limited to, carbohydrates, lipids, proteins, peptides, or nucleic acid molecules.

As used herein, the term "immobilized" refers to a linkage between a nucleic acid molecule and a surface. A linkage can be non-covalent. For example, a target nucleic acid can be immobilized to a solid support substrate by hybridizing to an oligonucleotide that is covalently linked to surface.

As used herein, "excluded volume" refers to the volume of space occupied by a particular molecule to the exclusion of other such molecules.

Any of the above aspects can be combined with any other aspect as disclosed herein.

Definitions

The terms "annealing" and "hybridization," as used herein, are used interchangeably to mean the formation of a stable duplex. In one aspect, stable duplex means that a duplex structure is not destroyed by a stringent wash under conditions such as a temperature of either about 5° C. below or about 5° C. above the Tm of a strand of the duplex and low monovalent salt concentration, e.g., less than 0.2 M, or less than 0.1 M or salt concentrations known to those of skill in the art. The term "perfectly matched," when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" comprises, but is not limited to, the pairing of nucleoside analogs, such as deoxyinosine, nucleosides with 2-aminopurine bases, PNAs, and the like, that can be employed. A "mismatch" in a duplex between two oligonucleotides means that a pair of nucleotides in the duplex fails to undergo Watson-Crick bonding.

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target subsequence. Stringent conditions are sequence-dependent and are different in different circumstances. Longer fragments can require higher hybridization temperatures for specific hybridization. As other factors can affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, "Molecular Cloning A Laboratory Manual, 2nd Ed." Cold Spring Harbor Press (1989) and Anderson Nucleic Acid Hybridization, 1st Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

Detectable labels associated with a particular position of a probe can be "readout" (e.g., its fluorescence detected) once or multiple times; a "readout" can be synonymous with the term "basecall". Multiple reads improve accuracy. A target nucleic acid sequence is "read" when a contiguous stretch of sequence information derived from a single original target molecule is detected; typically, this is generated via multi-pass consensus (as defined below). As used herein, the term "coverage" or "depth of coverage" refers to the number of times a region of target has been sequenced (via discrete reads) and aligned to a reference sequence. Read coverage is the total number of reads that map to a specific reference target sequence; base coverage is the total number of basecalls made at a specific genomic position.

A "read" is a unit of sequencer output. A contiguous stretch of sequence information derived from a single original target molecule. Each read has a quality metric that associates the confidence level of the base calls within the read. A unit of sequencer output. A contiguous stretch of sequence information derived from a single original target molecule. In Hyb & Seq, all reads are generated via multi-pass consensus.

The "readlength" is a metric describing length of sequence (in bp) from each read. This metric is determined by the sequencing technology.

As used in herein, a "Hyb & Seq cycle" refers to all steps required to detect each attachment region on a particular probe or population of probes. For example, for a probe capable of detecting six positions on a target nucleic acid, one "Hyb & Seq cycle" will include, at least, hybridizing the probe to the target nucleic acid, hybridizing complementary nucleic acids/reporter probes to attachment region at each of the six positions on the probe's barcode domain, and detecting the detectable labels associated with each of the six positions.

The term "k-mer probe" is synonymous with a sequencing probe of the present disclosure. The k-mer readout is the fundamental unit of Hyb & Seq's data. A single k-mer readout is obtained from a single target molecule per single Hyb & Seq cycle. Multiple Hyb & Seq cycles are performed to generate enough discrete k-mer readouts from a single target molecule to enable an unambiguous alignment of discrete k-mers into a contiguous stretch of sequence When two or more sequences from discrete reads are aligned, the overlapping portions can be combined to create a single consensus sequence. In positions where overlapping portions have the same base (a single column of the alignment), those bases become the consensus. Various rules can be used to generate the consensus for positions where there are disagreements among overlapping sequences. A simple majority rule uses the most common base in the column as the consensus. A "multi-pass consensus" is an alignment of all discrete probe readouts from a single target molecule. Depending on the total number of cycles of probe populations/polls applied, each base position within a single target molecules can be queried with different levels of redundancy or overlap; generally, redundancy increases the confidence level of a basecall.

A "consensus" is when two or more DNA sequences from discrete reads are aligned, the overlapping portions can be combined to create a single consensus sequence. In positions where overlapping portions have the same base (a single column of the alignment), those bases become the consensus. Various rules can be used to generate the consensus for positions where there are disagreements among overlapping sequences. A simple majority rule uses the most common base in the column as the consensus.

The "Raw Accuracy" is a measure of system's inherent ability to correctly identify a base. Raw accuracy is dependent on sequencing technology. "Consensus Accuracy" is a measure of system's ability to correctly identify a base with the use of additional reads and statistical power. "Specificity" refers to the percentage of reads that map to the intended targets out of total reads per run. "Uniformity" refers to the variability in sequence coverage across target regions; high uniformity correlates with low variability. This feature is commonly reported as the fraction of targeted regions covered by ≥20% of the average coverage depth across all targeted regions. Stochastic errors (i.e., intrinsic sequencing chemistry errors) can be readily corrected with 'multi-pass' sequencing of same target nucleic acid; given a sufficient number of passes, substantially 'perfect consensus' or 'error-free' sequencing can be achieved.

The methods described herein can be implemented and/or the results recorded using any device capable of implementing the methods and/or recording the results. Examples of devices that can be used include but are not limited to electronic computational devices, including computers of all types. When the methods described herein are implemented and/or recorded in a computer, the computer program that can be used to configure the computer to carry out the steps of the methods can be contained in any computer readable medium capable of containing the computer program. Examples of computer readable medium that can be used include but are not limited to diskettes, CD-ROMs, DVDs, ROM, RAM, non-transitory computer-readable media, and other memory and computer storage devices. The computer program that can be used to configure the computer to carry out the steps of the methods, assemble sequence information, and/or record the results can also be provided over an electronic network, for example, over the internet, an intranet, or other network.

A "Consumable Sequencing Card" can be incorporated into a fluorescence imaging device known in the art. Any fluorescence microscope with a number of varying features is capable of performing this sequencing readout. For instance: wide-field lamp, laser, LED, multi-photon, confocal or total-internal reflection illumination can be used for excitation and/or detection. Camera (single or multiple) and/or Photomultiplier tube (single or multiple) with either filter-based or grating-based spectral resolution (one or more spectrally resolved emission wavelengths) are possible on the emission-detection channel of the fluorescence microscope. Standard computers can control both the Consumable Sequencing Card, the reagents flowing through the Card, and detection by the fluorescence microscope.

The sequencing data can be analyzed by any number of standard next-generation-sequencing assemblers (see, e.g., Wajid and Serpedin, "Review of general algorithmic features for genome assemblers for next generation sequencers" *Genomics, proteomics & bioinformatics*, 10 (2), 58-73, 2012). The sequencing data obtained within a single diffraction limited region of the microscope is "locally-assembled" to generate a consensus sequence from the multiple reads within a diffraction spot. The multiple diffraction spot assembled reads are then mapped together to generate contiguous sequences representing the entire targeted gene set, or a de-novo assembly of entire genome(s).

Additional teachings relevant to the present disclosure are described in one or more of the following: U.S. Pat. Nos. 8,148,512, 7,473,767, 7,919,237, 7,941,279, 8,415,102, 8,492,094, 8,519,115, U.S. 2009/0220978, U.S. 2009/0299640, U.S. 2010/0015607, U.S. 2010/0261026, U.S. 2011/0086774, U.S. 2011/0145176, U.S. 2011/0201515, U.S. 2011/0229888, U.S. 2013/0004482, U.S. 2013/0017971, U.S. 2013/0178372, U.S. 2013/0230851, U.S. 2013/0337444, U.S. 2013/0345161, U.S. 2014/0005067, U.S. 2014/0017688, U.S. 2014/0037620, U.S. 2014/0087959, U.S. 2014/0154681, U.S. 2014/0162251, and U.S. 2016/0194701 each of which is incorporated herein by reference in their entireties.

EXAMPLES

Example 1—Single-Molecule Long Reads Using Hyb & Seq Chemistry

The presently disclosed sequencing probes and methods of utilizing the sequencing probes is conveniently termed, Hyb & Seq. This term is utilized throughout the specification to describe the disclosed sequencing probes and methods. Hyb & Seq is a library-free, amplification-free, single-molecule sequencing technique that uses nucleic acid hybridization cycles of fluorescent molecular barcodes onto native targets.

Long reads using Hyb & Seq are demonstrated on a single molecule DNA target 33 kilobases (kb) long with the following key steps: (1) long DNA molecules are captured and hydro-dynamically stretched onto the sequencing flow-cell; (2) multiple perfectly matched sequencing probes hybridize across the long single molecule target; (3) fluorescent reporters hybridize to the barcode region in the sequencing probes to identify all the bound sequences; and/or (4) relative positions of sequences within a single molecule target are determined using spatially-resolved fluorescence data.

Key advantages of long reads using Hyb & Seq, include but are not limited to: read lengths determined by molecule length, not limited by chemistry; simple, limited sample preparation results in less fragmentation; positional information associated with sequencing probes aids assembly; and/or capability to phase variants into long-range haplotypes.

Hyb & Seq Chemistry Design—Sequencing Probes comprise a target binding domain that base-pairs with a single molecule target and a barcode domain having at least three positions ($R_1$, $R_2$, and R3) that correspond to the hexamer sequence present in the target binding domain. A set of 4096 sequencing probes enables sequencing of any target sequence. Reporter Probes: Three reporter probes bind sequentially to the positions of the barcode domain. Each reporter complex corresponds to a specific dinucleotide. Hybridization drives the functionality.

Long read and short read sequencing methods of the present disclosure can use the same simple probe hybridization workflow for targeted capture of nucleic acids. A plurality of sequencing probes can hybridize to a target nucleic acid concurrently, and optical resolution allows several spots per long target to be individually distinguished. By hybridizing and recording a plurality of sequencing probes concurrently, the information content of a single read is increased. Long-range haplotypes are inherent in single-molecule analysis and can be assembled by actual physical location rather than computational reconstruction. Long sequencing reads up to hundreds of kilobases are feasible using the sequencing methods of the present disclosure.

Sequencing probes can hybridize to stretched targets (preferably hydro-dynamically stretched targets) at expected sequence-specific positions and relative physical distances. The sequencing methods of the present disclosure have increased information content compared to short-read technologies, allowing more bases to be read out each cycle. The sequencing methods of the present disclosure also record the relative position of sequencing readouts, which aids in assembly of long reads. Using the sequencing methods of the present disclosure, read length=consensus sequence length=length of captured target molecule.

In one experiment using the methods of the present disclosure, 33 kilobase DNA fragments were captured, stretched, hybridized to sequencing probes and reporter probes, and detected. The sequencing methods of the present disclosure are compatible with DNA fragments up to 33 kilobases and beyond. Read length is limited only by initial length of the target nucleic acid fragment, not enzymes or sequencing chemistry.

The methods of the present disclosure possess additional capabilities with respect to targeted phased long reads. Long-range phased haplotypes are inherent in data and easily identified for phasing of variants. Sequencing of the entire long target molecule is not necessary as "blocker oligos" can be used to limit sequence cycling to sequencing windows of interest.

The results of Example 1 show that the sequencing method of the present disclosure is capable of single molecule sequencing with long read lengths. In particular, the results show: successful capture and hydro-dynamic stretching of a 15 kilobase and 33 kilobase single-stranded DNA molecule; spatially-resolved fluorescence data accurately corresponds to the actual relative positions across the long single molecule; and simultaneous readout of 10+ base sequences per sequencing cycle.

Example 2—Assembly Algorithm: Accurate, Reference-Guided Assembly of Hyb & Seq Reads for Targeted Sequencing to Resolve Short Nucleotide Variants and InDels The Assembly Algorithm is an open source algorithm designed to perform assembly of Hyb & Seq's unique hexamer readouts (hexamer spectra). The Assembly Algorithm may also be known as the ShortStack or HexSembler™ analysis software. The algorithm is a statistical approach to target identification utilizing hexamer reads from each imaged feature and to perform assembly of hexamer readouts into a consensus sequence on a single molecule basis with error-correction.

Single molecule sequencing using Hyb & Seq chemistry and the Assembly Algorithm was performed as follows: hexamer readout of the single molecule target was generated after each cycle of hybridization using Hyb & Seq chemistry; after many cycles of hybridization, hexamer spectra that cover each single molecule target regions were produced; and hexamer spectra are used with a reference sequence of each of the target nucleic acid molecules to derive the consensus sequence of each single-molecule target.

Figure 18A:
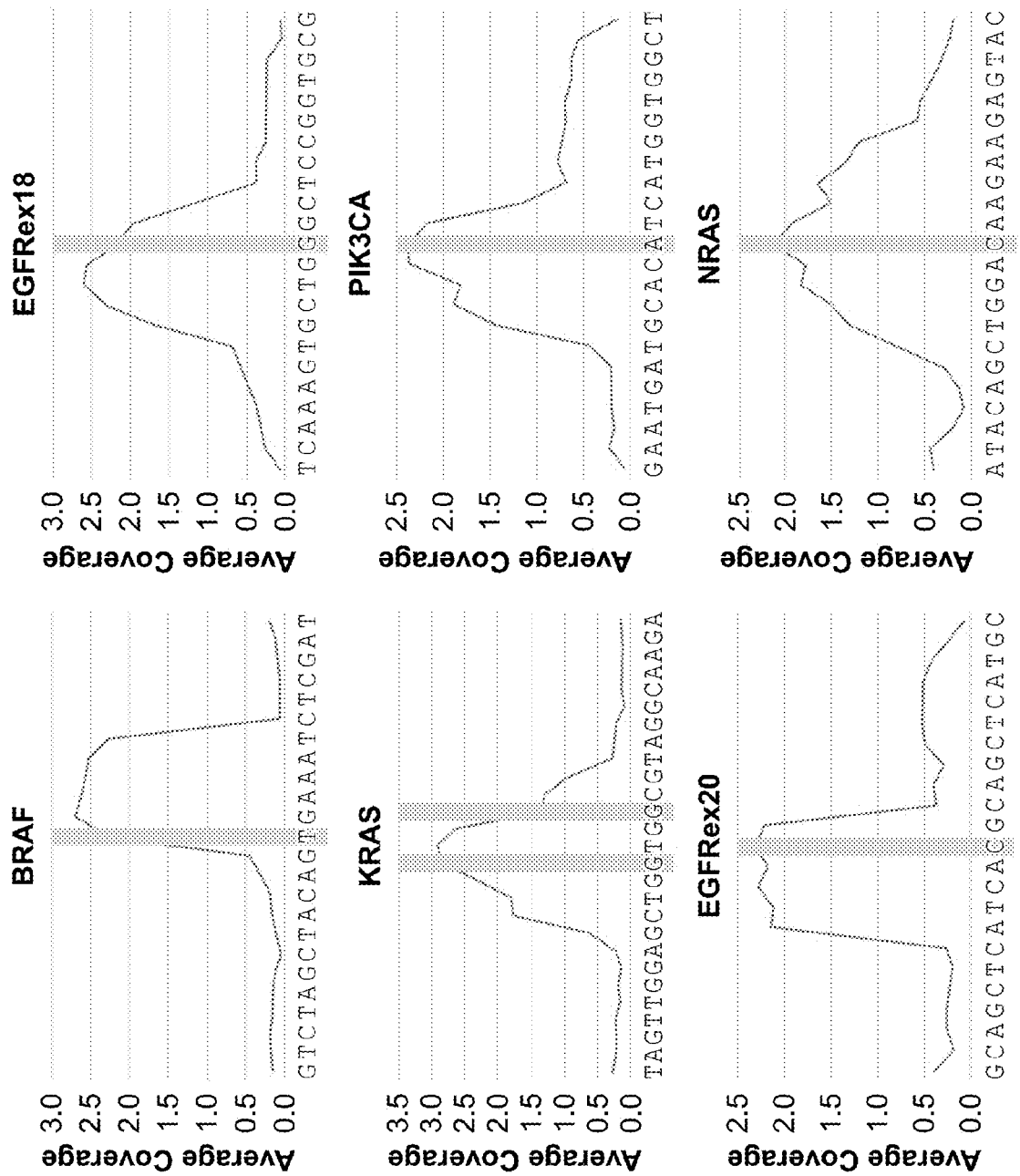
FIGS. 18A and 18B show the results from a sequencing experiment obtained using the sequencing method of the present disclosure and analyzed using the Assembly Algorithm. For plots in FIG. 18A, starting at the top left plot proceeding clockwise, sequences shown correspond to SEQ ID NOs: 3, 4, 6, 8, 7 and 5. For the table on the right, starting at the top moving down, sequences correspond to SEQ ID NOs: 3, 4, 7, 8, 6 and 5.
Figure 18B:
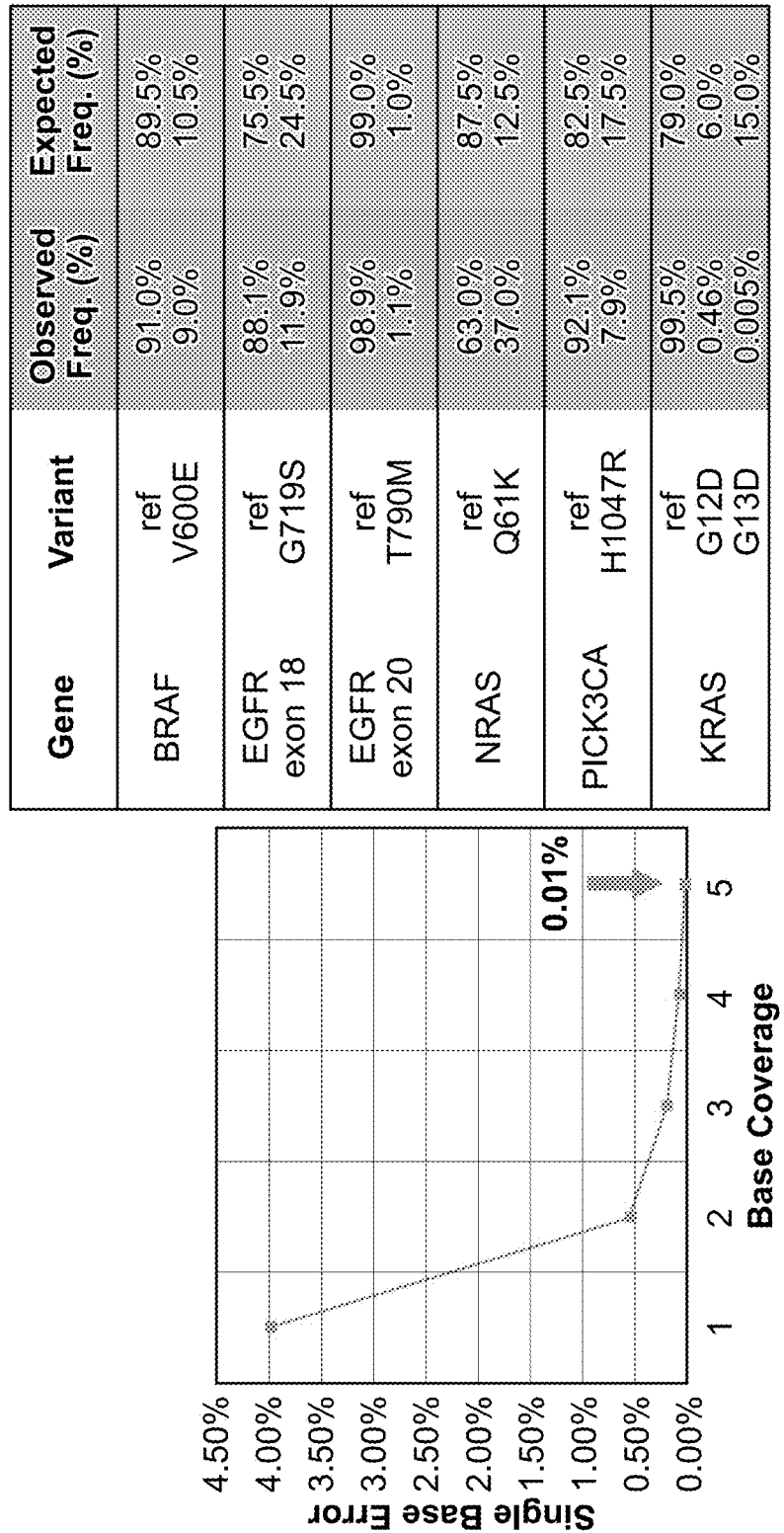

The results of target sequencing using Hyb & Seq technology with the Assembly Algorithm show: single molecule target identification algorithm using the hexamer spectra had 100% success rate; reference guided assembly algorithm produced single molecule consensus accuracy of >99% (~QV 32) at 5× coverage; concordant somatic variant detection ($R^2$ ~90%) was demonstrated using a pre-characterized reference gDNA sample; and/or in silico experiments using all hexamers and the Assembly Algorithm confirmed average QV>90 across larger target panels The Assembly Algorithm can accurately assemble Hyb & Seq data. FIGS. 18A and 18B show the results from a sequencing experiment obtained using the sequencing method of the present disclosure and analyzed using the Assembly Algorithm. In this experiment, the target nucleic acids that were sequenced included fragments of the genes BRAF (SEQ ID NO: 3), EGFRex18 (SEQ ID NO: 4), KRAS (SEQ ID NO: 5), PIK3CA (SEQ ID NO: 6), EGFRex20 (SEQ ID NO: 7) and NRAS (SEQ ID NO: 8). FIGS. 18A and 18B show both the base coverage and variant calling. The coverage plots show coverage of bases in FFPE (formalin-fixed paraffin-embedded) gDNA. The results show that most bases across a variety of targets are covered by available sequencing probes. The error plots show error rate vs coverage at queried position in FFPE gDNA samples across a variety of targets. The results show that at 8× coverage, error rates are <1%. The frequency plot shows the correlation between expected and known frequency of variants in sequenced Horizon gDNA samples. The table provides sequenced Horizon Genomic Reference gDNA and shows that the fraction of variant molecules is consistent with known frequency of reference sample.

The results in Example 2 show that the Assembly Algorithm is an accurate algorithm for sub-assembly of hexamer spectra obtained using the sequencing method of the present disclosure. In particular the results show: 100% accuracy in target identification and average per-base quality values >30 using simulated data; at 5× coverage, >99% accuracy in base calling in experimental Hyb & Seq data; detection of variants from genomic DNA at frequencies consistent with known values ($R^2$ ~90%); and computational performance is efficient and scales linearly with the number of hexamers assembled, capable of assembling 69 k molecules in ~15 min on a personal computer.

Example 3—Library-Free, Targeted Sequencing of Native gDNA from FFPE Samples Using Hyb & Seq™ Technology—the Hybridization Based Single Molecule Sequencing System A targeted cancer panel sequencing of native gDNA from FFPE samples using the sequencing method of the present disclosure (Hyb & Seq) was performed to demonstrate: targeted single-molecule sequencing of oncogene targets with accurate base-calling; accurate detection of known oncogenic Single Nucleotide Variants (SNVs) and Insertions/Deletions (InDels); multiplexed capture of oncogene targets from FFPE-extracted gDNA (median DNA fragment size 200 bases); and/or end-to-end automated sequencing performed on an advanced prototype instrument.

Hyb & Seq chemistry and workflow were demonstrated as follows: genomic targets of interest are directly captured onto the sequencing flow cell; a pool containing hundreds of hexamer sequencing probes is flowed into the sequencing chamber; fluorescent reporter probes sequentially hybridize to the barcode region of the sequencing probe to identify the hexamer bases over 3 reporter exchange cycles; once the bases are identified, the sequencing probe is washed away; and the cycle is repeated with a new pool of sequencing probes until the target regions have been read to sufficient depth Key Advantages of Hyb & Seq: simple and rapid FFPE workflow—Clinical specimen to start of sequencing within 60 minutes; no enzymes or amplification/No library construction; 15 minutes of total hands-on-time; high accuracy—Low chemistry error rate+intrinsic error correction; and/or both long & short reads—Read length defined by input sample, not limited by chemistry.

Hyb & Seq Chemistry Design is as described in Example 1. Hyb & Seq sample preparation for processing FFPE tissues consists of three simple steps: (1) Single-tube deparaffinization and lysis; (2) Removal of particulates using a syringe filter; and (3) Optional DNA fragmentation and target capture. The process requires one to three 10 micron FFPE curls used per sample. The entire process is completed within 60 minutes and it needs only common lab equipment: heat block, pipette, filter and reagents.

Figure 19:
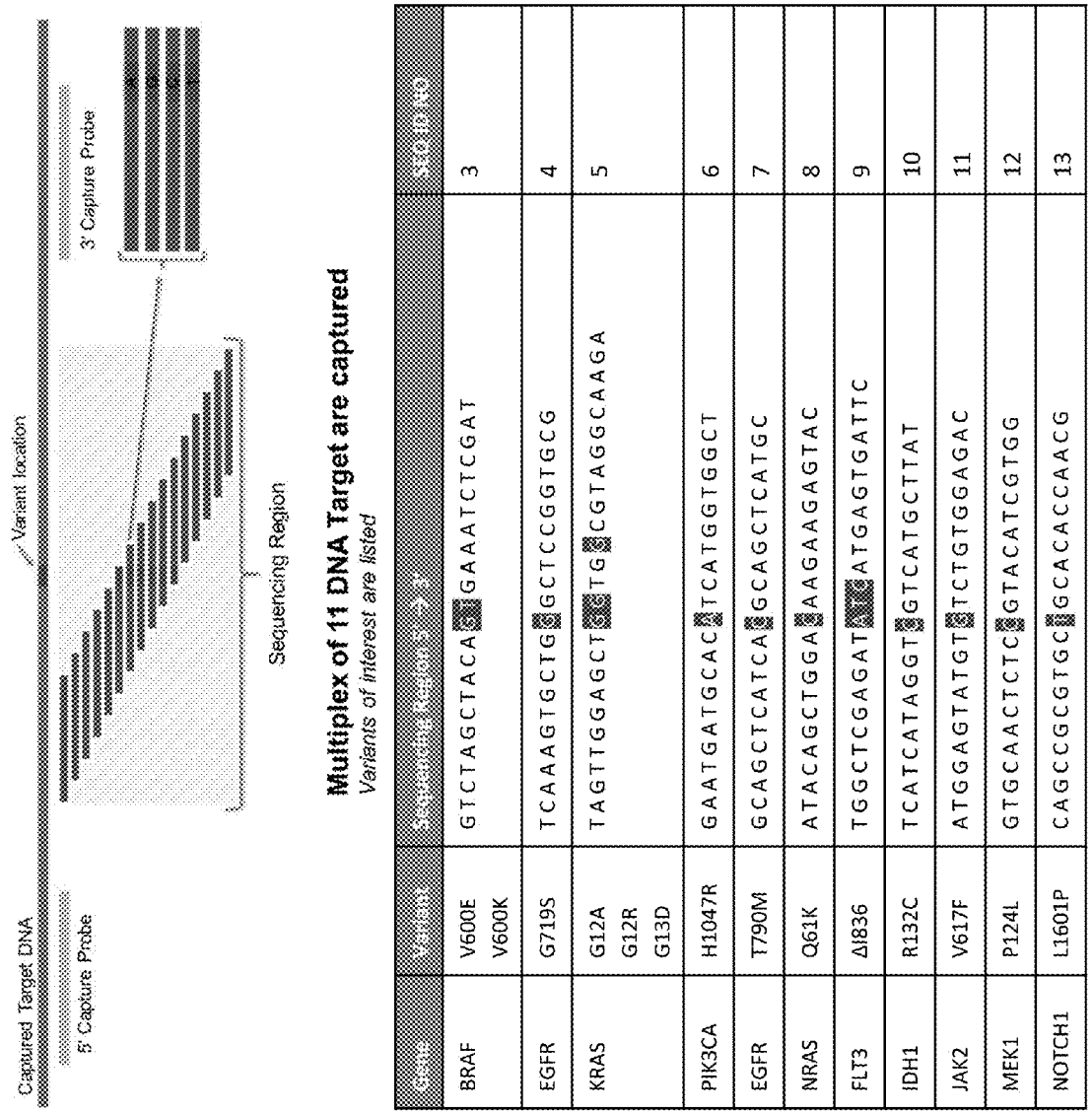
FIG. 19 shows a schematic illustration of the experimental design for the multiplexed capture and sequencing of oncogene targets from a FFPE sample.

FIG. 19 shows a schematic illustration of the experimental design for the multiplexed capture and sequencing of oncogene targets from a FFPE sample. A total of 425 sequencing probes were designed and constructed to sequence portions of 11 oncogenic gene targets (SEQ ID NOs: 3-13). The loci of known variant for each gene target was covered with many sequencing probes (perfect match+ single mismatch). Base coverage and base by base accuracy was measured across these regions. Using a pre-characterized reference sample, accuracy of variant detection was obtained. The top panel of FIG. 19 shows that sequencing Probes (blue) align to a target sequence (grey) surrounding a known variant location (red). For each variant location (red), 4 probe sequences were included with each (A, G, C, T) base variant. During Sequencing, single target DNA molecules were tracked for 800 barcode exchange cycles, providing multiple hexamer reads which are reassembled by the Assembly Algorithm, as described in Example 2.

FIG. 18 shows the sequencing results including the average coverage of each target, the single base error rate, and the observed vs. expected variant frequencies. The results in Example 3 show that Hyb & Seq sequencing can be used to perform multiplexed sequencing of 11 target regions in FFPE and reference gDNA samples with Single nucleotide variations detected with low error.

Example 4—Direct Single-Molecule RNA Sequencing without cDNA Conversion Using Hyb & Seq™ Chemistry Direct single-molecule RNA sequencing using Hyb & Seq chemistry was demonstrated as follows: native RNA molecules were captured directly without cDNA conversion and immobilized onto sequencing flow cell; a pool containing hundreds of hexamer sequencing probes was flowed into the sequencing flow cell; a perfectly matched sequencing probe was hybridized randomly on a single molecule RNA target; fluorescent reporter probes were sequentially hybridized to barcode region of sequencing probe to identify hexamer bases; and bases were identified and then sequencing probes washed away; cycle was repeated until target had been read to sufficient depth.

Key results: targeted single-molecule RNA was sequenced showing similar coverage profiles to DNA; RNA molecules were stably maintained on the flow cell throughout more than 200 Hyb & Seq cycles; mRNA and genomic DNA were simultaneously captured and quantitated from a single FFPE slice; and/or eight transcripts were multiplex captured and quantitated using as little as 10 ng of total RNA.

Figure 20:
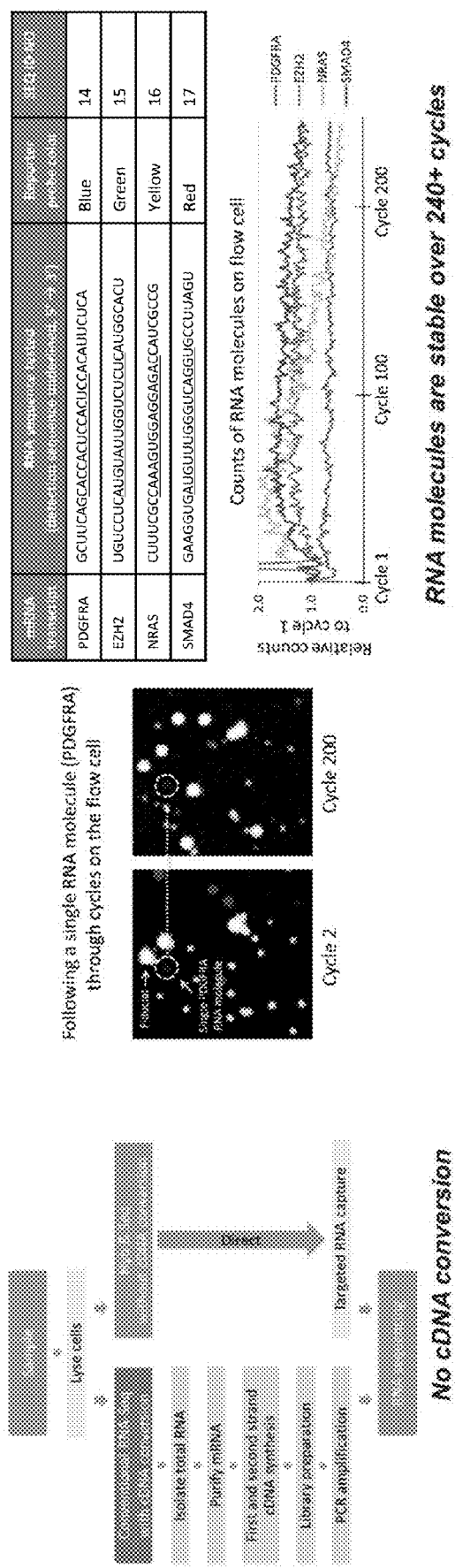
FIG. 20 shows an illustrative schematic of direct RNA sequencing and the results from experiments to test the compatibility of RNA molecules with the sequencing method of the present disclosure.

Hyb & Seq Chemistry Design is as described in Example 1. The left panel of FIG. 20 shows an illustrative schematic of the experimental steps associated with direct RNA sequencing compared to the steps associated with conventional RNA sequencing performed using cDNA conversion. The middle and left panels of FIG. 20 show results from experiments to test the compatibility of RNA molecules with the sequencing method of the present disclosure. In the experiment, 4 target RNA molecules were sequenced (SEQ ID NOs: 14-17). The results show that RNA molecules can be captured and detected for at least 200 sequencing cycles, demonstrating the compatibility of the sequencing methods of the present disclosure and RNA molecules.

Figure 21:
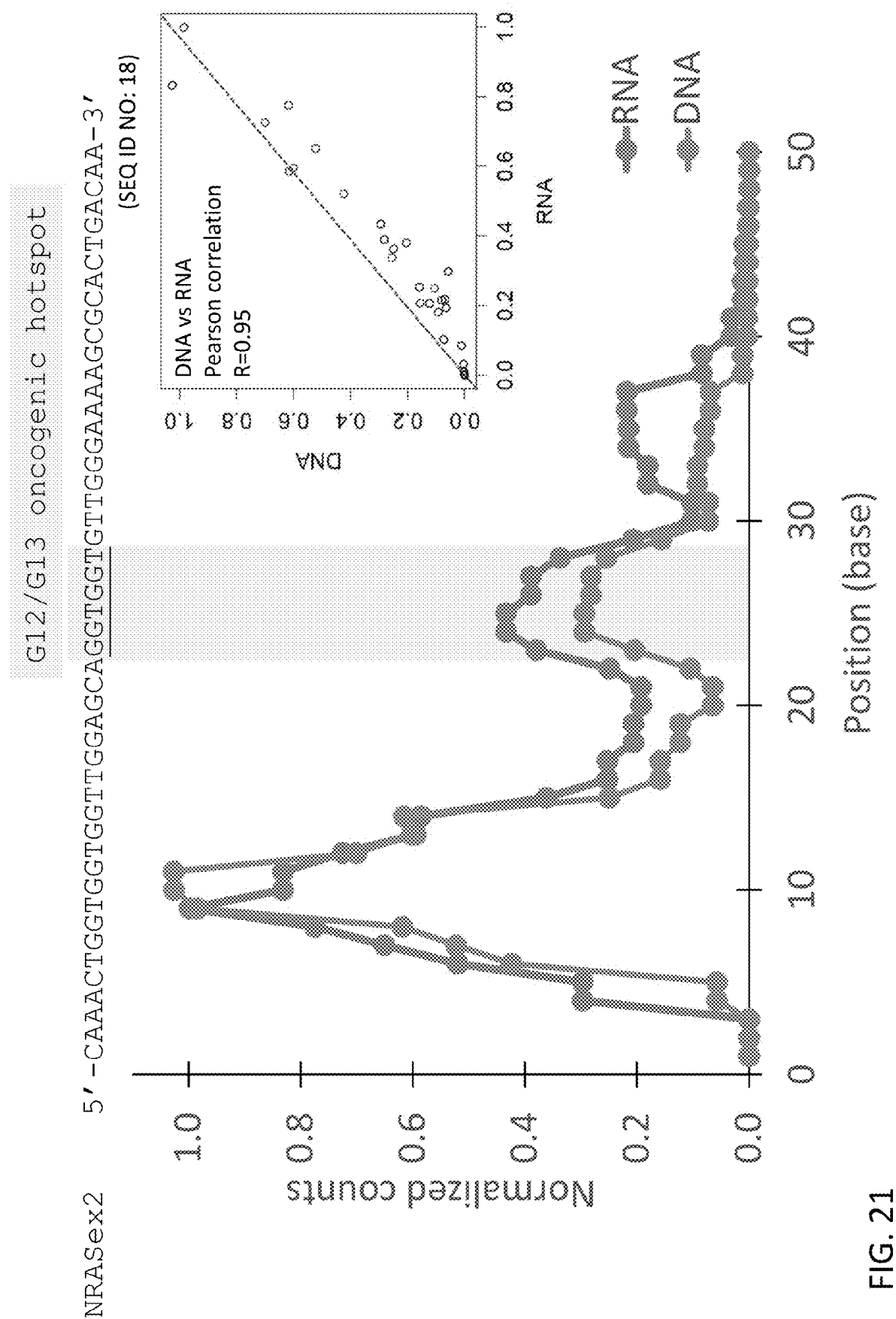
FIG. 21 shows the sequencing of a RNA molecule and a DNA molecule that have the same nucleotide sequence using the sequencing method of the present disclosure.

FIG. 21 shows the results from an experiment to validate direct single-molecule RNA sequencing using the sequencing method of the present disclosure. Native RNA molecules encoding a fragment of NRASex2 (SEQ ID NO: 18) were captured directly without cDNA conversion and immobilized onto a sequencing flow cell and sequenced using the present methods. The experiment was also repeated using captured DNA molecules instead of RNA. FIG. 21 shows that sequencing coverage for DNA and RNA was comparable, demonstrating that RNA can be directly sequenced without conversion to cDNA using the sequencing method of the present disclosure.

In some aspects, the present disclosure provides integrated capture of RNA and DNA from a FFPE sample. Samples are prepared using the same FFPE workflow described in Example 3. The same capture protocol is used, but with RNA- and DNA-specific capture probes. The DNA and RNA molecules are concurrently sequenced in the same flow cell with the same sequencing probes. In some aspects, specific RNA and DNA capture probes are required to concurrently capture RNA and DNA.

Multiplex capture of 8 mid-to-high expressing transcripts on Human Universal Reference RNA with various input amounts of total RNA (0 ng, 1 ng, 10 ng, 100 ng, 1000 ng) was also performed. Multiplexed captured RNA molecules were immobilized onto a flow cell and specific sequencing probes and reporter probes were hybridized to the immobilized RNA molecules for quantitation. Quantitation of counts for each specific RNA target showed an increase with as the total amount of input RNA was increased.

The results in Example 4 show that single-molecule RNA sequencing is achieved with Hyb & Seq chemistry. In particular, the results demonstrate: (1) direct RNA sequencing without cDNA conversion; (2) RNA molecules are stable throughout the Hyb & Seq cycling process; (3) both RNA and DNA molecules can be captured and sequenced in one Hyb & Seq workflow; and (4) target capture of mRNA panel can be performed with as little as 10 ng of total RNA input.

Example 5—Integrative Bioinformatics Algorithm for High Throughput Molecule-Level Short-Reads Generated from Hyb & Seq Sequencing Platform The Assembly Algorithm software is designed to perform standard sequencing-based bioinformatics analysis tasks such as alignment, error-correction, mutation-calling, and read assembly. The steps of the Assembly Algorithm software pipeline can include: alignment of hexamers and coverage estimation; mutated sequence identification; graph data structure construction; and/or molecule level sequence reconstruction and error correction.

All algorithms were performed strictly within the information obtained from a single molecule, ensuring that the final mutation call results were not biased by the mutation frequency of the sample. Hexamers were grouped into different molecules according to the panel binding position. To assign molecules to targets, the hexamers were aligned per molecule to all different target regions and the top matched gene target was selected.

A statistical metric was measured to assess the quality of the molecule identification. The alignment against N different target regions produces a distribution of N summed coverage values for each target. The top summed coverage score match was selected as the correct match. Z-score statistics of the selected top match score against the score distribution of all N different targets were measured. Low confidence molecule identifications (under z-score of 2.5 sigma) were filtered out.

Key Advantages of the Assembly Algorithm include: accurately handles possible sequence ambiguities by implementing a hierarchical hash index design; and/or advanced algorithm design structure assures the mapping quality by prioritization and prevents the overestimation of mutations.

In addition, the mutation graph data structure enables computational modeling of various types of mutations (substitution, insertion, and deletion) and produces output for sequence reconstruction and variant calling: substitution variants are represented as additional nodes in the graph of same length with the original sequence; insertions can be modeled by adding any length of connected nodes; deletions are modeled as adding an artificial node in the graph with empty base pair string; in a blind mutation search (i.e. a search for mutation tolerant sequence alignments), hamming distances are measured from every reference sequence position and new nodes are added to the graph representing searched mutations; and/or coverage estimation for mutated hexamers is performed using the hierarchical hash table.

The constructed graph data structure enables molecule level sequence reconstruction and instrument error correction. In the constructed graph, the dynamic programming algorithm was applied to find the best scoring path where the score was defined as the normalized base coverages. The best scoring path of the graph represented the molecule level sequence reconstruction. The correct mutated sequences were included, while the instrument errors in hexamers were discarded.

Simulated data sets confirmed that the software was able deliver highly accurate molecule level sequence assembly and mutation calling results. These results show the mutation calling accuracy for 10 random mutations. In medium instrument error datasets, the accuracy showed 99.39% (targeted search) and 98.02% (blind search) on average. Under the elevated instrument error simulations, the performance showed 97.19% (targeted search) and 93.53% (blind search) on average. When the molecule level base coverage threshold was increased to 2×, results improved to 99.5% (2× coverage) and 99.9% (3× coverage).

The Assembly Algorithm software can process a broad scope of various mutations, including insertions and deletions selected between 1 bp and 15 bp with a mutation calling accuracy of 94.4% (1× coverage), 97.7% (2× coverage), to 98.5% (3× coverage).

Example 6—Sample Preparation for Processing FFPE Tissue for Hyb & Seq

Formalin-fixed paraffin embedded (FFPE) tissue is a challenging sample input type for traditional sequencing platforms. Hyb & Seq's sample preparation methods successfully process FFPE tissue inputs for downstream sequencing. First, the nucleic acid(s) to be sequenced is extracted from formalin-fixed, paraffin embedded (FFPE) tissue in a single-step process. One or more 10 μm thick FFPE curl is heated in an aqueous-based nucleic acid extraction buffer to simultaneously melt the paraffin wax, decompose the tissue, and release nucleic acid from the cells. Suitable extraction buffers are known in the art and typically include proteinases, detergents such as Triton-100, chelating agents such as EDTA, and ammonium ions. The FFPE curl and extraction buffer are incubated at 56° C. for 30 minutes to separate the paraffin from the tissue and allow the Proteinase K to digest the tissue structure and expose the embedded cells to the detergent to enable cell lysis. The solution is inverted three times at 8 minute intervals to assist in mixing of the reagents during the tissue deparaffinization and digestion process. Following this step, the solution is heated to 98° C. to facilitate the reversal of the formaldehyde cross-links to further assist in the extraction of nucleic acids.

Once the nucleic acids have been extracted from the FFPE tissue, the solution is filtered using a glass fiber filter with 2.7 μm pore size (Whatman) to remove tissue debris and congealed paraffin. The resulting solution is a homogenous, semi-opaque solution containing nucleic acids which are highly fragmented due to the formalin-fixation process and storage conditions. If further fragmentation is required, the DNA can be mechanically sheered using a Covaris focused-ultrasonicator. Due to buffer conditions, extended sonication is required to shear the nucleic acids. Sonicating using the standard settings of 50 W peak incident power, 20% duty factor, 200 cycles/burst were used for 600 seconds to achieve the maximal increase in targets captured. To achieve shorter fragment length, emulsified paraffin can be precipitated out of the filtered solution by centrifuging at 21,000 g and 4° C. for 15 minutes. This allows the DNA to be sheared down to about 225 bp, Next, target capture is performed by binding pairs of capture probes to target nucleic acid molecules during a rapid hybridization step. The 5' capture probe contains a 3' biotin moiety, which allows the target to bind to a streptavidin-coated flow cell surface during the target deposition process. The 3' capture probe contains a 5' tag sequence (G-sequence) that enables binding to beads during the purification process. The reaction rate is driven by the capture probe concentration which are added in the low nanomolar range to maximize the reaction rate. The capture probes hybridize to the target in a manner that flanks to region of interest in order to generate a sequencing window. For each DNA target, the capture probe set also includes an oligo composed of the same sequence as the sequencing window to hybridize to targets' antisense strand and prevent reannealing. The solution containing the capture probes is heated to 98° C. for 3 minutes to denature the genomic DNA, followed by a 15-minute incubation at 65° C. The concentration of NaCl in the range of 400 mM to 600 mM is used for this hybridization reaction. A panel of over 100 targets that have been experimentally validated is listed in the Table 3, detailing the gene and exon of the targeted DNA region.

TABLE 3

| Gene and Exon of targeted DNA regions | |
|---|---|
| Gene | Target |
| ABL1 | ABL1_ex4 |
|  | ABL1_ex6 |
|  | ABL1_ex7 |
| AKT1 | AKT1_ex6 |
| ALK | ALK_ex26 |
| APC | APC_ex5 |
|  | APC_ex16 |
|  | APC_ex17 |
|  | APC_ex17 |
|  | APC_ex17 |
|  | APC_ex17 |
|  | APC_ex17 |
| ATM | ATM_ex8 |
|  | ATM_ex9 |
|  | ATM_ex11 |
|  | ATM_ex26 |
|  | ATM_ex34 |
|  | ATM_ex39 |
|  | ATM_ex49 |
|  | ATM_ex49 |
|  | ATM_ex55 |
|  | ATM_ex59 |
| BRAF | BRAF_ex8 |
|  | BRAF_ex11 |
|  | BRAF_ex13 |
|  | BRAF_ex15 |
| CDH1 | CDH1_ex9 |
| CSF1R | CSF1R_ex3 |
|  | CSF1R_ex22 |
| CTNNB1 | CTNNB1_ex3 |
|  | CTNNB1_ex6 |
|  | CTNNB1_ex16 |
| EGFR | EGFR_ex3 |
|  | EGFR_ex10 |
|  | EGFR_ex15 |
|  | EGFR_ex18 |
|  | EGFR_ex20 |
|  | EGFR_ex21 |
| ERBB2 | ERBB2_ex7 |
| ERBB4 | ERBB4_ex4 |
|  | ERBB4_ex5 |
|  | ERBB4_ex7 |
|  | ERBB4_ex8 |
|  | ERBB4_ex23 |
|  | ERBB4_ex25 |
| EZH2 | EZH2_ex8 |
|  | EZH2_ex11 |
|  | EZH2_ex15 |
| FBXW7 | FBXW7_ex2 |
|  | FBXW7_ex5 |
|  | FBXW7_ex7 |
|  | FBXW7_ex8 |
|  | FBXW7_ex9 |
|  | FBXW7_ex10 |
| FGFR1 | FGFR1_ex6 |
| FGFR2 | FGFR2_ex7 |
| FLT3 | FLT3_ex11 |
|  | FLT3_ex12 |
|  | FLT3_ex21 |
| GNAQ | GNAQ_ex5 |
| IDH1 | IDH1_ex4 |
|  | IDH1_ex10 |
| IDH2 | IDH2_ex4 |
| JAK2 | JAK2_ex3 |
|  | JAK2_ex7 |
|  | JAK2_ex14 |
|  | JAK2_ex20 |
| KDR | KDR_ex7 |
|  | KDR_ex7 |
|  | KDR_ex9 |
|  | KDR_ex11 |

TABLE 3-continued

Gene and Exon of targeted DNA regions

| Gene | Target |
| --- | --- |
| | KDR_ex27 |
| | KDR_ex30 |
| KIT | KIT_ex5 |
| | KIT_ex9 |
| | KIT_ex14 |
| | KIT_ex14 |
| | KIT_ex17 |
| | KIT_ex18 |
| KRAS | KRAS_ex2 |
| | KRAS_ex3 |
| | KRAS_ex4 |
| MEK | MEK_ex3 |
| MET | MET_ex2 |
| | MET_ex3 |
| | MET_ex11 |
| | MET_ex14 |
| | MET_ex16 |
| | MET_ex19 |
| MLH1 | MLH1_ex12 |
| | MLH1_ex16 |
| NOTCH1 | NOTCH1_ex26 |
| NRAS | NRAS_ex2 |
| | NRAS_ex3 |
| | NRAS_ex3 |
| | NRAS_ex4 |
| PDGFRA | PDGFRA_ex1 |
| | PDGFRA_ex4 |
| | PDGFRA_ex7 |
| | PDGFRA_ex10 |
| | PDGFRA_ex11 |
| | PDGFRA_ex14 |
| | PDGFRA_ex15 |
| | PDGFRA_ex16 |
| | PDGFRA_ex18 |
| | PDGFRA_ex23 |
| PIK3CA | PIK3CA_ex2 |
| | PIK3CA_ex3 |
| | PIK3CA_ex7 |
| | PIK3CA_ex10 |
| | PIK3CA_ex14 |
| | PIK3CA_ex21 |
| | PIK3CA_ex21 |
| PTEN | PTEN_ex5 |
| | PTEN_ex7 |
| | PTEN_ex8 |
| PTENP1 | PTENP1_ex1 |
| RB1 | RB1_ex10 |
| | RB1_ex17 |
| | RB1_ex17 |
| | RB1_ex20 |
| | RB1_ex22 |
| RET | RET_ex12 |
| | RET_ex15 |
| SMAD4 | SMAD4_ex3 |
| | SMAD4_ex8 |
| | SMAD4_ex9 |
| | SMAD4_ex10 |
| | SMAD4_ex11 |
| SMARCB1 | SMARCB1_ex5 |
| TP53 | TP53_ex4 |
| | TP53_ex6 |

After the targeted DNA regions are bound with capture probes, they are purified from the rest of the genomic DNA to create an enriched solution of the targets. Beads coated with the anti-sense oligo (anti G-sequence) to the 3' capture probes' binding sequence are incubated with the capture reaction mix for 15 minutes at room temperature. After the binding step, the beads are washed three times with 0.1× SSPE to remove non-target DNA and the biotin-containing 5' capture probes. Following the washes, the beads are re-suspended in 14 µL of 0.1×SSPE then heated at 45° C. for 10 minutes to elute the purified DNA targets from the beads. After elution, 1 µL of 5 M NaCl is added to ensure the capture probes remain bound to the DNA targets.

The final step of the sample preparation process is the deposition of the DNA targets onto the flow cell surface, where they can be analyzed using the probes of the present disclosure as disclosed herein. A syringe pump is utilized to control the rate at which the targets are loaded into the flow cell fluidic channel, such that all targets have time to diffuse across the height of the channel and bind to the streptavidin surface. This method of loading generates a density gradient of targets, where the highest number of molecules per unit area is greatest at the fluidic channel inlet and decreases along the channel length in the direction of the fluidic flow towards the outlet. A flow rate of 0.35 µL/second achieves a quantitative capture within a channel length of about 10 mm for a channel width of 1.6 mm and height of 40 µm. Once the targets are bound to the surface by the biotinylated 5' capture probe, a solution of biotinylated oligo (G-hooks) that are the reverse complement of the 3' capture probes' bind sequence are injected to pin down the free end of the targets to create a bridged structure, where the ssDNA region in the middle is the sequencing window of interest. Next, a solution of G-sequence oligos are added to hybridize to the excess G-hooks on the surface to reduce the amount of ssDNA on the surface. FIG. 8 shows the capture of a target nucleic acid using a two capture probe system of the present disclosure.

Example 7—Multi-Color Reporter Image Processing for Hyb & Seq

The image processing pipeline includes the following steps background subtraction, registration, feature detection, and classification. In background subtraction, the mean background of any given channel is a function of shot noise and exposure. In our system, the blue channel has the highest background levels coupled with greater variance. A simple tophat filter with a circular structuring element of radius 7 pixels is applied to perform localized background subtraction. For registration, it is imperative that the features of interest as perfectly aligned for multi-color and multi-cycle feature analysis. This system requires two forms of registration. For the first form, a local affine transformation is applied to all image channels within a single acquisition stack. This transformation is a function of the optical system and hence is consistent for a given instrument. This function is computed in advance for every run and is applied to every image acquired. For the second form, a global transformation in the form of a rigid shift is computed using normalized cross-correlation to capture drift of the mechanical gantry during the run. The next step is feature detection.

Once all the images are registered, features are detected using a matched filter via a LoG (Laplace of Gaussian) filter. The filter is applied with a fixed kernel size (matched to the diffraction limit of the features) and a varying standard deviation (matched to the wavelength of the corresponding channel) to match to enhance spot response. Local maxima are used to identify potential reporter locations. The associated intensity values for each identified feature are retrieved for classification. The final step is classification. The multi-color reporter intensities are classified using the Gaussian naïve-Bayes model. The model assumes that the reporter intensities are independent and follow a normal distribution. The model then calculates the probability that a specific feature $\hat{y}$ (specified by intensities in all channels $\hat{x}_i$) belongs to a certain class ($C_k$) using a maximum a posteriori or MAP rule:

$$\hat{y} = \text{argmax}_{\{k \in \{1,...K\}\}} p(C_k) \prod_{i=1}^{n} p(x_i \mid C_k)$$

In an example of a coding scheme using 2 dyes: blue and red, there are six classes (including background) possible in a 2-color coding scenario. In the implemented system, the choice of four colors results in 14 potential classes. Note that there is some overlap between the single half dye vs full dye distributions. Consequently, classification between these classes presents a higher error rate, with a maximum miss-classification rate of 11.8% between 'xG' and 'GG'. The miss-classification rates for the 10 Class model is less than 0.2%. Since each reporter requires a maximum of eight classes, it is simple to choose the ones with least classification error. The detected color code is translated into an identified base pair based on a look up table. Using the probes of the present disclosure as disclosed herein, a feature is tracked across multi-cycles.

Example 8—Target Nucleic Acid Purification and Deposition Using Capture Probes To capture target nucleic acid molecules, a two capture probe system is used for highly specific enrichment. Capture probes are designed to bind to the target nucleic acid at positions flanking the targeted region of interest, creating a "sequencing window". The 5' capture probe, referred to as CapB, contains a 3' biotin moiety. The 3' capture probe, referred to as CapA, contains a 5' affinity tag sequence, referred to as the G-sequence. On average, capture probes are approximately 40 nucleotides in length and designed based on Tm and sequence context. Sequencing windows are around 70 nucleotides in length and are easily adjusted. FIG. 8 shows a schematic of the two capture probe system.

The biotin moiety on CapB tethers the target nucleic acid to a streptavidin-coated flow cell surface for sequencing. The affinity tag on CapA allows for the reversible binding of target nucleic acid molecules to magnetic beads during purification. The use of CapA and CapB allows for highly stringent target enrichment since both probes remain bound to a single target nucleic acid molecule in order for that target to survive both the magnetic bead purification and the surface deposition process. Multiplexed capture has been demonstrated with up to 100 targets at once. In order to achieve an efficient capture within a short period of time, capture probes are added at the concentration range of 1 nM to 10 nM.

In experimental tests, a panel of ~10 target nucleic acid molecules were purified using G-beads and the two probe capture system. CapA and CapB probes were first hybridized to target nucleic acids. The G-sequence portion of the bound CapA probes were then hybridized to the G-hooks on the G-beads, thereby linking the target nucleic acid molecule to the G-beads. A series of stringent washes using 0.1×SSPE was performed to remove non-targeted DNA and unbound CapB. To release the target nucleic acid molecules from the G-beads, a low-salt, 45° C. elution was performed to denature the G-sequence while still permitting CapA and CapB to remain hybridized to the target nucleic acid.

Tests show that when purifying a panel of ~100 target nucleic acid molecules, the non-specific/background signal increases significantly. This increase in background could be due to several factors including: (1) increased interactions between CapA and CapB probe species, which leads to increased amounts of free CapB probe carried through purification; and (2) increased interaction between CapB probes and the G-hooks or the G-beads, which leads to the purification of unwanted target nucleic acids. Furthermore, as the size of the panel increases, the possible interactions between CapB species, CapA species, and sequencing probes increase exponentially. These interactions can interfere with the ability to densely deposit targets and lead to wasted sequencing reads.

To reduce non-specific and background signal due to the purification of free probe species and unwanted target nucleic acid molecules, several modifications to the purification procedure can be made. First, the inclusion of formamide at a concentration of 30% v/v in the buffer used during the binding of target nucleic acid molecules to G-beads decreases background counts by two-fold (as measured by counts in controls lacking target molecules), likely through interfering with imperfect hybridizations of free capture probe with G-hooks, allowing excess probes to be washed away. Secondly, the inclusion of four iso-dG bases in the G-hook on the G-beads (iso-G-hooks) and the complementary iso-dC bases in the CapA G-sequence decreases background counts by three-fold (as measured by counts in controls lacking target molecules). Iso-dC and iso-dG are isomer variants of the natural dC and dG bases. Since, iso bases will base-pair with other iso bases but not natural bases, imperfect hybridization between capture probes and iso-G-hooks can only exist between the non-iso bases of the G-sequence and iso-G-hooks. These imperfect interactions are more easily disrupted during stringent washes. Finally, subsequent purification of the iso-G-bead eluates with Ampure® XP (Agencourt Biosciences Company) beads further decreases background counts by at least 20-fold (as measured by counts in controls lacking target molecules). During, Ampure® XP bead purification, a DNA sample is mixed with a suspension of carboxylated magnetic beads in a solution of polyethylene glycol (PEG) and NaCl. The concentration of PEG and NaCl can be titrated such that only molecules above a molecular weight threshold precipitate and bind to the beads. Hyb & Seq targets hybridized to capture probes are on the order of 81 kDa, while free probes are on the order of 17 kDa or less. By mixing the Ampure® XP bead suspension with iso-G-bead eluate at a volume ratio of 1.8:1, hybridized targets are bound to the beads and a significant portion of free probes can be washed away before the final elution.

Thus, a model purification workflow consists of the following steps: (1) Hybridization of capture probe-target nucleic acid assemblies to iso-G-beads in 5×SSPE/30% formamide; (2) Washing of the iso-G-beads with 0.1×SSPE; (3) Elution of capture probe-target nucleic acid assemblies at 45° C. in 0.1×SSPE; (4) Binding of iso-G bead eluates to a 1.8× volume of Ampure® XP beads; (5) Washing of Ampure® XP beads with 75% ethanol; and (6) Elution of capture probe-target nucleic acid assemblies in 0.1×SSPE, such that the targets are eluted in 7.5 followed by the addition of 0.5 µL of 5 M NaCl.

After purification, capture probe-target nucleic acid assemblies are deposited onto the sequencing surface using an infusion syringe pump to slowly inject the purified targets through the flow cell. To determine the deposition gradient, the flow cell is imaged at various positions along the channel length. For a channel height of 20 µm, loading the sample at a flow rate of 0.167 µL/min will concentrate the targets such that 80% of all targets bind within 5.1 mm along the channel length, which represents ~240 FOVs for the Gen2 imager with a FOV of 0.0357 mm² and flow cell channel width of 1.7 mm. The gradient can be modulated by adjusting the flow rate during deposition.

The procedures described above were used to test the purification and deposition of a 100plex target nucleic acid panel with genomic DNA sheared to a size of ~300 base pairs. A series of experiments was performed in triplicate with a range of DNA input between 25 ng and 500 ng. The total number of targets on the flow cell was extrapolated by imaging the deposition gradient to obtain the number of average counts. The capture efficiency was 6.6% and was consistent over the range of DNA mass inputs.

Example 9—Design and Features of Sequencing Probes

Sequencing probes hybridize to a target nucleic acid molecule via a target binding domain. In the present example, the target binding domain is 8 nucleotides long and contains a locked nucleic acid (LNA) hexamer that is flanked by (N) bases that can be a universal/degenerate base or a canonical base ($N_1$-$B_1$-$B_2$-$B_3$-$B_4$-$B_5$-$B_6$-$N_2$, where $B_1$ to $B_6$ are LNAs and $N_1$ and $N_2$ are universal/degenerate bases or a canonical base that is independent of the nucleic acid sequence of the (6-mer) sequence $B_1$-$B_2$-$B_3$-$B_4$-$B_5$-$B_6$). A complete set of 4,096 sequencing probes encodes all possible hexamers and enables sequencing of any target nucleic acid. Each sequencing probe also includes a barcode domain that encodes for the hexamer sequence present in the target binding domain. Each barcode domain contains three positions (R1, R2, and R3). Each position in the barcode domain corresponds to a specific dinucleotide in the hexamer of the target binding domain and contains a unique sequence that can bind to a specific labeled reporter complex. A schematic overview of sequencing probes are shown in FIG. 1. Each position in the barcode domain encodes eight "color combinations", created using four fluorescent dyes: blue (B); green (G); yellow (Y); and red (R). During each cycle of sequencing, a reporter complex is bound to one of the three positions in the barcode domain, indicating the identity of the corresponding dinucleotide in the hexamer of the target binding domain. During three sequential sequencing cycles, three "color combinations" are recorded, one for each position in the barcode domain, allowing for the identification of the entire hexamer of the target binding domain. The 4,096 sequencing probes are split into 8 pools and each is associated with one of 512 possible barcodes.

Example 10—Reporter Complex Design, Purification, and Binding Conditions

In this example, each reporter complex is a 37 DNA oligomer branched structure designed to hold a total of 30 fluorescent dyes, with 15 dyes for each color of the color combination. The 37 DNA oligomers that make up the reporter complex can be classified by their size. The largest oligomer, called the primary nucleic acid, is covalently attached to a complementary nucleic acid that is either 12 or 14 nucleotides in length. The primary nucleic acid is 96 nucleotides long. The primary complementary nucleic acid binds to positions R1, R2, or R3 on the barcode domain of the sequencing probe. The next largest DNA oligomers are 89 nucleotides long and are called secondary nucleic acids. There are six secondary nucleic acids per reporter complex, with three secondary nucleic acids per for each color of the color combination. Each secondary nucleic acid comprises a 14 nucleotide long sequences that allows the secondary nucleic acids to hybridize to the primary nucleic acid. The smallest DNA oligomers are 15 nucleotides long and are called the tertiary nucleic acids. There are 30 tertiary nucleic acids per two color probe, with 15 tertiary nucleic acids per color. Five tertiary nucleic acids bind to each secondary nucleic acid. A schematic of the 37 DNA oligomer branched structure is shown in FIG. 4.

The tertiary nucleic acids include a detectable label in the form of a fluorescent dye. There are four fluorescent dyes: blue (B); green (G); yellow (Y); and red (R). Combining dyes together in a reporter complex results in ten possible two-color combinations (BB, BG, BR, BY, GG, GR, GY, RR, YR, YY). To prevent color-swapping or cross hybridization between different fluorescent dyes, each secondary and tertiary nucleic acid that correspond to a specific fluorescent dye contains a unique sequence. For example, each tertiary nucleic acid labeled with the Alexa 488 fluorophore, or blue color, comprises a complementary sequences only to the blue secondary nucleic acid. The blue secondary nucleic acid further has a distinct sequence that is complementary only to the primary nucleic acid molecules that correspond to a color combination that includes blue.

Each complementary nucleic acid contains a sequence that is distinct between positions R1, R2, and R3 of the barcode domain of the sequencing probe. Thus, even if positions R1 and R2 of the same barcode domain encode for the same dinucleotide, the binding of the complementary nucleic acid molecule that identifies that dinucleotide at position R1 will not bind to position R2. Likewise, the complementary nucleic acid molecule that identifies that dinucleotide at position R2 will not bind to position R1. Complementary nucleic acids are designed such that they can be unbound from the sequencing probe efficiently using competitive toe-hold exchange (for complementary nucleic acids 12 nucleotides in length) or UV cleavage (for complementary nucleic acids 14 nucleotides in length).

Preparation of the reporter complex occurs in two sequential hybridization steps: (1) tertiary nucleic acids to secondary nucleic acids and then (2) tertiary nucleic acids+secondary nucleic acids to the primary nucleic acid. Four separate tertiary nucleic acid-to-secondary nucleic acid reactions are prepared by combining 100 µM of secondary nucleic acids and 600 uM of tertiary nucleic acids in 4.2×SSPE buffer at room temperature for 30 minutes. Twenty-four reporter probes are then prepared separately using 2 uM of primary nucleic acid, 7.2 uM of secondary nucleic acid+Dye #1 tertiary nucleic acid, and 7.2 uM secondary nucleic acid+Dye #2 tertiary nucleic acid in 4.8×SSPE. These reactions are heated at 45° C. for 5 minutes and then cooled at room temperature for 30 minutes. The 24 reactions are then pooled into three different pools corresponding to the barcode domain (i.e. $R_1$, $R_2$, and R3). For example, eight different reporter probes (2 uM each) binding to the $R_1$ barcode domain are pooled together, diluting ten-fold to a final working concentration of 200 nM each reporter complex. The reporter complex can be purified using high pressure liquid chromatography (HPLC). HPLC purification can remove free oligomers and malformed probes to yield reporter probes.

Following reporter complex preparation is standard testing for quality assurance. Each of the three pools of reporter probes are tested for binding to its corresponding barcode region ($R_1$, $R_2$, or $R_3$) in three separate flow cells. Testing is performed on a modified sequencing probe construct, with only the barcode domain present and immobilized on the flow cell. All eight 12-mers representing each color is multiplexed and all eight reporter probes are expected to be identified with high color counts.

To improve the efficiency and accuracy of hybridization of the reporter probes and the barcode domains of the sequencing probes, various buffer additives were tested. Results from experiments indicate that buffers containing 5% Dextran Sulfate (500K) and either 15% Formamide or 15% Ethylene Carbonate allow for the most efficient and accurate hybridization of reporter probes and sequencing probes at short hybridization times. However, results from other experiments indicate that Ethylene Carbonate has a negative impact on the surface of the sequencing slide, resulting in high loss of target nucleic acids over time. Thus, buffers containing 5% Dextran Sulfate (500K) and 15% Formamide are superior for efficient and accurate hybridization of the reporter probes and sequencing probes.

Example 11—Design and Validation of Complementary Nucleic Acid Sequences

Reporter probes contain a complementary nucleic acid that binds to a specific position (R1, R2, or R3) on the barcode domain of a sequencing probe. Complementary nucleic acids containing either 12 nucleotides (12mer) or 14 nucleotides (14mer) were designed and tested to determine optimal sequences for hybridization. For screening, the following criteria was used to determine optimal sequences: sequences had to display high binding efficiency as defined by reporter and sequencing probe binding at >80% efficiency in 10 sequencing cycles; sequences had to display fast hybridization kinetics occurring within 15 second to 30 seconds; and sequences had to display high specificity with <5% cross-hybridization error in the reporter pool.

Table 4 shows the twenty-four 12mer sequences (SEQ ID NOs: 19-42) that were identified. Since each barcode domain contains three positions, the twenty-four 12mer sequences can be divided into three groups to create an 8×8×8 12mer reporter set.

TABLE 4

| Reporter Position | 12-mer Sequence | Reporter Name | Color | SEQ ID NO |
|---|---|---|---|---|
| 1 | AGGACAGATGAC | R1BB-07 | BB | 19 |
| 1 | GTATCGGATGAC | R1BG-07d (R1RR-06) | BG | 20 |
| 1 | AGGAGTGATGAC | R1BR-07 | BR | 21 |
| 1 | AGGGGTGAGGAG | R1GG-07c (R1YR-07) | GG | 22 |
| 1 | AGAGGGGATGAC | R1GR-07 | GR | 23 |
| 1 | AGTGGGGAGGAG | R1GY-07c (R1BY-07) | GY | 24 |
| 1 | AGCCGAGATGAC | R1RR-07 | RR | 25 |
| 1 | AGGGTGGATGAC | R1YY-07 | YY | 26 |
| 2 | TGGATGGAAAAG | R2 BB (forGRv5) | BB | 27 |
| 2 | GAAGGAGAAAAG | R2 BG (forGYv5) | BG | 28 |
| 2 | GGGGATGAAAAG | R2 BR (forGRv4) | BR | 29 |
| 2 | GTGAGGGAAAAG | R2 BY (forYYv5) | BY | 30 |

TABLE 4-continued

| Reporter Position | 12-mer Sequence | Reporter Name | Color | SEQ ID NO |
|---|---|---|---|---|
| 2 | AGCCGAGAAAAG | R2 GG | GG | 31 |
| 2 | CGAGAGGAAAAG | R2 GY (forGGv5) | GY | 32 |
| 2 | GAGGGCGAAAAG | R2 RR (forGGv4) | RR | 33 |
| 2 | AGCGTGGAAAAG | R2 YY | YY | 34 |
| 3 | TGAGAAGGGTAG | RPTR12-BG_Screen3_D2 | BG | 35 |
| 3 | GTTGTTATTGTG | RPTR12-BR_RC_D4 | BR | 36 |
| 3 | TTTGGGTTTAGG | RPTR12-BY_RC_D3 | BY | 37 |
| 3 | GTTAGTGGGAAA | RPTR12-GR_RC_D7 | GR | 38 |
| 3 | ATGGGAAAAGT | RPTR12-GY_RC_D6 | GY | 39 |
| 3 | GAGTTGGATGAG | RPTR12-RR_RC_D10 | RR | 40 |
| 3 | ATGTTGTGGGTA | RPTR12-YR_RC_D9 | YR | 41 |
| 3 | GAGGGTTTTAAG | RPTR12-YY_RC_D8 | YY | 42 |

The 14mer sequences were designed in a similar manner but differ from the 12mer sequences in three ways. First, 14mer sequences contain a longer hybridization sequence given that 14mer sequences contain 14 single stranded nucleotides that bind to a specific position on a barcode domain rather than the 12 single stranded nucleotides present in a 12mer. Second, 14mer sequences contain more sequence diversity because they were not designed to accommodate toe-holding-mediated removal. Since 14mer sequences hybridize more strongly to sequencing probes, the efficiency of toe-holding-mediated removal is decreased. Thus, sequence independent removal strategies were explored for the 14mer sequences, alleviating sequence constraints during screening. Sequences for screening were designed using an algorithm that includes the following set of rules: Nucleotide composition lacking either "G" or "C" (i.e. low complexity sequences); GC content between 40% to 60%; Melting temperature (Tm) between 35° C. and 37° C.; Hairpin folding energy (dG)>2; and Compatibility with other sequencing probes (hamming distance >=7). To minimize the hybridization of 14mer sequences to genomic sequences that can be present in target nucleic acids, potential sequences were filtered using the External RNA Controls Consortium sequences as a guide. Third, 14mer sequences were designed to be removed from the barcode domains of sequencing probes by strand cleavage using cleavable linker modifications at the point where the 14mer complementary nucleic acid is attached to the primary nucleic acid of the reporter complex. The removal of the 14mer sequences results in the "darkening" of the reporter complex signal, allowing for the next cycle of sequencing and signal detection to occur. Various cleavable linker modifications were tested including UV-light cleavable linkers, reducing agent (such as TCEP) cleavable linkers and enzymatically cleavable linkers (such as uracil cleaved by the USER™ enzyme). All of these cleavable linker modifications were found to promote efficient reporter complex darkening. Darkening was further enhanced by the introduction of cleavable linker modifications into the secondary nucleic acids. These cleavable linker modifications were placed between the sequence that hybridizes to the primary nucleic acid and the sequence that hybridizes to the tertiary nucleic acids. FIG. 7 shows the possible positions for cleavable linker modifications within a reporter probe.

Screening of potential 14mer sequences resulted in the identification of two groups of acceptable sequences. Table 5 shows the first group, which contained 24 sequences (SEQ ID NOs: 43-66). These 24 sequences could be split into three groups to create an 8×8×8 14mer reporter set.

Table 6 shows the other group, which contained 30 sequences (SEQ ID NOs: 67-96). These 30 sequences could be split into three groups to create a 10×10×10 14mer reporter set.

TABLE 5

| Reporter | 14-mer Sequence | Reporter Name | Color | SEQ ID |
|---|---|---|---|---|
| A | ATCTTTTCCCCACT | R14-BG_RC-Sc3_B2 | BG | 43 |
| A | CCCCACTATTTCTT | RPTR14-BY_Screen4_I2 | BY | 44 |
| A | CTACCCACAACATA | RPTR14-YR_Screen3_D9 | YR | 45 |
| A | CCATATAAACCCCA | R14-GG_RC-Sc3_B5 | GG | 46 |
| A | AAACTCCAATCTCC | R14-GR_RC-Sc3_B7 | GR | 47 |
| A | CTATTCTCAACCTA | RPTR14-YY_RS0255_H8 | YY | 48 |
| A | CCCCCTCTTTTAAA | R14-BB_RC-Sc3_B1 | BB | 49 |
| A | CCAATCTTACCTCA | RPTR14-RR_Screen3_B10 | RR | 50 |
| B | CCCTCACATAACTT | RPTR14-BG_Screen4_I1 | BG | 51 |
| B | CTCCTCTACTTTCC | RPTR14- | BB | 52 |
| B | CCCTAAACCCAAAA | RPTR14-BY_Screen3_D3 | BY | 53 |
| B | CACTTTTTCCCATC | RPTR14-GY_Screen3_D6 | GY | 54 |
| B | CATCTGATTCCTCC | R14- | RR | 55 |
| B | CTAAACCCCTACT | R14-BR_RC-Sc3_B4 | BR | 56 |
| B | CCTTTACAAACACA | RPTR14-GR_RS0247_H7 | GR | 57 |
| B | ATACCACCCTCTTT | RPTR14-YY_Screen3_B8 | YY | 58 |
| C | TATTCTTCTACCCC | RPTR14-YR_Screen4_I5 | YR | 59 |
| C | TCTACCCTTCTCAT | R14-BG_RC-Sc3_D2 | BG | 60 |
| C | CCACAATAACAACC | RPTR14-BR_Screen3_D4 | BR | 61 |
| C | ACCTTAACATTCCC | R14-GG_RC-Sc3_D5 | GG | 62 |
| C | ATTTCCCACTAACC | RPTR14-GR_Screen3_D7 | GR | 63 |
| C | ACTTAAAACCCTCC | RPTR14-YY_Screen3_D8 | YY | 64 |
| C | TACCTATTCCTCCA | RPTR14-BB_Screen3_D1 | BB | 65 |
| C | CCCCTTTCTCTAAG | RPTR14- | RR | 66 |

TABLE 6

| Reporter | 14-mer Sequence | Reporter Name | Color | SEQ ID |
|---|---|---|---|---|
| A | GATGATGGTAGGTG | R14_PC_J2_BB_v2 | BB | 67 |
| A | ATGAGAAGGGTAGA | R14_PC_D2_BG_v2 | BG | 68 |
| A | GTTTTGTTGGTGAG | R14_PC_K2_BY_v2 | BY | 69 |
| A | TTAGTGTGTTGGAG | R14_PC_K5_BR_v2 | BR | 70 |
| A | ATGTAGGAGAGAGA | R14_PC_L1_GG_v2 | GG | 71 |
| A | GGGAATGTTAAGGT | R14_PC_D5_GY_v2 | GY | 72 |
| A | GGTTAGTGGGAAAT | R14_PC_rcD7_GR_v2 | GR | 73 |
| A | GGAGGGTTTTAAGT | R14_PC_rcD8_YY_v2 | YY | 74 |
| A | GTAGTGTGGATGTT | R14_PC_J5_YR_v2 | YR | 75 |
| A | CTTAGAGAAAGGGG | R14_PC_ERCC51_RR_v2 | RR | 76 |
| B | GGAAGAGGATGAAA | R14_PC_K1_BB_v2 | BB | 77 |
| B | AAGTTATGTGAGGG | R14_PC_spB_BG_v1 | BG | 78 |
| B | GGAAAGTAGAGGAG | R14_PC_spB_BY_v1 | BY | 79 |
| B | TTTTGGGTTTAGGG | R14_PC_spB_BR_v1 | BR | 80 |
| B | AGATGTATGGGTGA | R14_PC_L2_GG_v2 | GG | 81 |
| B | GATGGGAAAAAGTG | R14_PC_spB_GY_v1 | GY | 82 |
| B | GGAGGAATCAGATG | R14_PC_spB_GR_v1 | GR | 83 |
| B | AGAGGGATTGATGA | R14_PC_J4_YY_v2 | YY | 84 |
| B | TGTGTTTGTAAAGG | R14_PC_spB_YR_v1 | YR | 85 |
| B | AAGGAGTGATAGGA | R14_PC_J1_RR_v2 | RR | 86 |
| C | TGGTGATTTAGAGG | R14_J3_BB_v2 | BB | 87 |
| C | GGGGTAGAAGAATA | R14_rcI5_BG_v2 | BG | 88 |
| C | AAGAAATAGTGGGG | R14_PC_spA_BY_v1 | BY | 89 |
| C | TATGTTGTGGGTAG | R14_PC_spA_BR_v1 | BR | 90 |
| C | GTTAAAGGGAGGTT | R14_K3_GG_v2 | GG | 91 |
| C | TGGGGTTTATATGG | R14_PC_spA_GY_v1 | GY | 92 |
| C | AGGGAATATGGAGA | R14_K6_GR_v2 | GR | 93 |
| C | TAGGTTGAGAATAG | R14_PC_spA_YY_v1 | YY | 94 |
| C | TTTAAAAGAGGGGG | R14_PC_spA_YR_v1 | YR | 95 |
| C | TGAGGTAAGATTGG | R14_PC_spA_RR_v1 | RR | 96 |

After screening, the 8×8×8 12mer, 8×8×8 14mer, and 10×10×10 14mer reporter sets were validated experimentally. For the 8×8×8 12mer binding scheme, validation was performed using a Hyb & Seq prototype to record 10 sequencing cycles. Three pools of reporter probes were used in both long and short workflow methods. All 512 possible sequencing probe barcode domains were tested. Table 7 shows the experimental steps of the long and short workflow methods.

TABLE 7

| Steps in One Cycle | Long workflow: Reporter hyb without toehold | Short workflow: Reporter hyb with toehold |
|---|---|---|
| 1 | Reporter 1 for 15 s, 30 s, or 60 s | Reporter 1 for 30 s |
| 2 | Image | Image |
| 3 | Toehold 1 for 60 s to dark | Reporter 2 + Toehold 1 for 15 s |
| 4 | Image | Image |
| 5 | Reporter 2 for 15 s, 30 s, or 60 s | Reporter 3 + Toehold 2 for 15 s |
| 6 | Image | Image |
| 7 | Toehold 2 for 60 s to dark | Wash |
| 8 | Image | Image |
| 9 | Reporter 3 for 15 s, 30 s, or 60 s | |
| 10 | Image | |
| 11 | Wash | |
| 12 | Image | |

Long workflow experiments resulted in >97% darkening efficiency. For short workflow experiments, it was assumed that darkening was about as efficient, however it was expected that a small frequency of non-darkened reporters would carry over in each image and be miscalled as a new reporter. Indeed, the highest barcode count in the short workflow experiment was YYYYYY, which was likely an artifact of non-darkening and background. The performance of the 8×8×8 12mer reporter set was generally lower in the short workflow compared to the long workflow. Reporter complex one (which binds to position R1 of the barcode domain) and reporter complex three (which binds to position R3 of the barcode domain) had lower efficiencies in the short workflow compared to long workflow. This is expected for reporter complex three since it includes eight additional toe-hold oligonucleotides, at a high concentrations of 2.5 uM each, which can interfere with reporter hybridizations. Reporter complex one should behave similarly between the two workflows, as no toe-holds were used to remove the first reporter complex in either the short or long workflows. Total error was also higher (1.3- to 2-fold) in the short workflow compared to long workflow for all three reporter probes.

The 8×8×8 14mer reporter set was validated by testing the efficiency, specificity, and speed of hybridization to all 512 possible sequencing probe barcode domains. The sequencing probe barcode domains were immobilized directly onto the glass of a Hyb & Seq sequencing cartridge. 8×8×8 14mer reporter probes hybridized with an average efficiency of 88% in only 15 seconds with an average error rate of 5.1%. The majority of this error is due to incorrect identification of the reporter not due to incorrect hybridization. Misclassification error of reporters remains the largest component of reporter error.

The 10×10×10 14mer reporter set was validated by testing for efficiency, specificity, and speed of hybridization to 30 complementary, truncated sequencing probe barcode domains. Each barcode domain contained only one reporter binding site. These barcode domains were immobilized directly onto the glass of a Hyb & Seq sequencing cartridge. The 10×10×10 14mer reporter set hybridized with an average efficiency of 90% in only 15 seconds with an average error rate of 5.0%. Again, the vast majority of error was due to incorrect identification of the reporter not due to incorrect hybridization.

Example 12—Design and Testing of Standard and Three-Part Sequencing Probes

The target binding and barcode domains of a sequencing probe are separated by a double-stranded "stem". FIG. 2 shows two sequencing probe architectures that were experimentally tested. On a standard sequencing probe, the target binding and barcode domains are present on the same oligonucleotide, which binds to a stem oligonucleotide to create a 36 nucleotide long double-stranded region. Using this architecture, each sequencing probes in a pool of probes use the same stem sequence. On a three-part probe, the target binding and barcode domains are separate DNA oligonucleotides that are bound together by a 36 nucleotide stem oligonucleotide. To prevent possible exchange of barcode domains, each barcode has a unique stem sequence and are hybridized separately before pooling sequencing probes.

Figure 22:
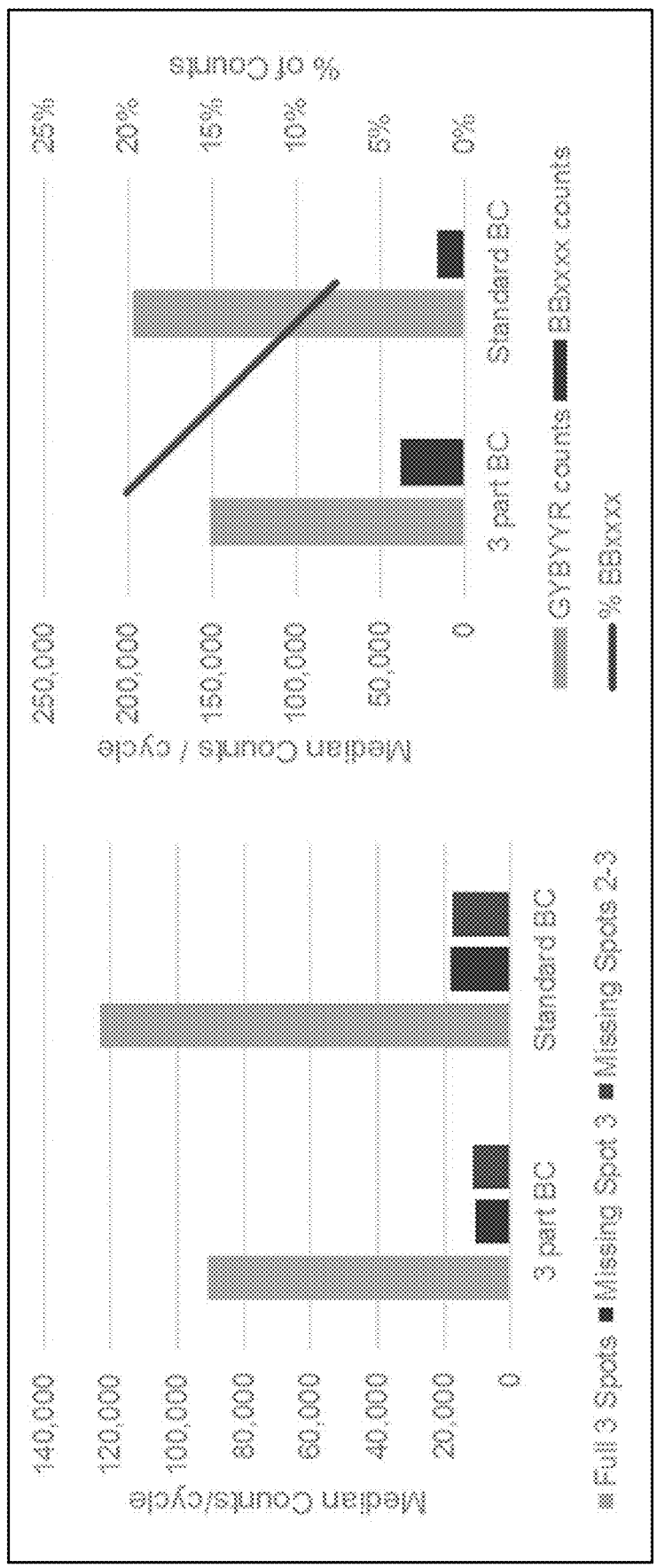
FIG. 22 shows a comparison of the performance of standard and three-part sequencing probes of the present disclosure.

FIG. 22 shows the results of a series of experiment performed to compare three-part sequencing probes to standard sequencing probes. These experiments confirmed that three-part sequencing probes survive an entire sequencing cycle with ~80% of all reads for both configurations including the detection of the third reporter probe. When compared to standard sequencing probes, three-part probes show ~12% fewer counts. To study the propensity for exchange of the barcode domain oligo, a high concentration of a short alternative oligonucleotide containing the same stem sequence was added to the reaction. The results indicated that ~13% of detected three-part sequencing probes had exchanged barcode oligoes. Oligonucleotide exchange will need to be mitigated with the incorporation of unique stem sequences. Despite the slight reduction in performance, three-part probes provide the benefits of design flexibility, speedy oligo synthesis, and reduced cost.

Example 13—Effect of Locked Nucleic Acid Substitutions in the Target Binding Domain The effect of the substitution of locked nucleic acids (LNAs) into the target binding domain of sequencing probes was tested as follows. Sequencing probes were hybridized to reporter probes in solution and properly formed sequencing probe-reporter probes were purified. The sequencing probe-reporter probes were then hybridized to synthetic target nucleic acids in solution and loaded onto a prototype sequencing cartridge. The synthetic target nucleic acid consisted of 50 nucleotides and was biotinylated. Sequencing probes were tested either individually or in a pool of nine. For the pool of nine sequencing probes, the probes were designed to bind along the length of the target nucleic acid. For analysis, the entire reaction was deposited by a breadboard instrument onto a streptavidin-coated cover slide and then flow stretched. The reporter probes were then imaged and counted using the appropriate instrument and software, for example with the NanoString nCounter® instrument and software.

Figure 23:
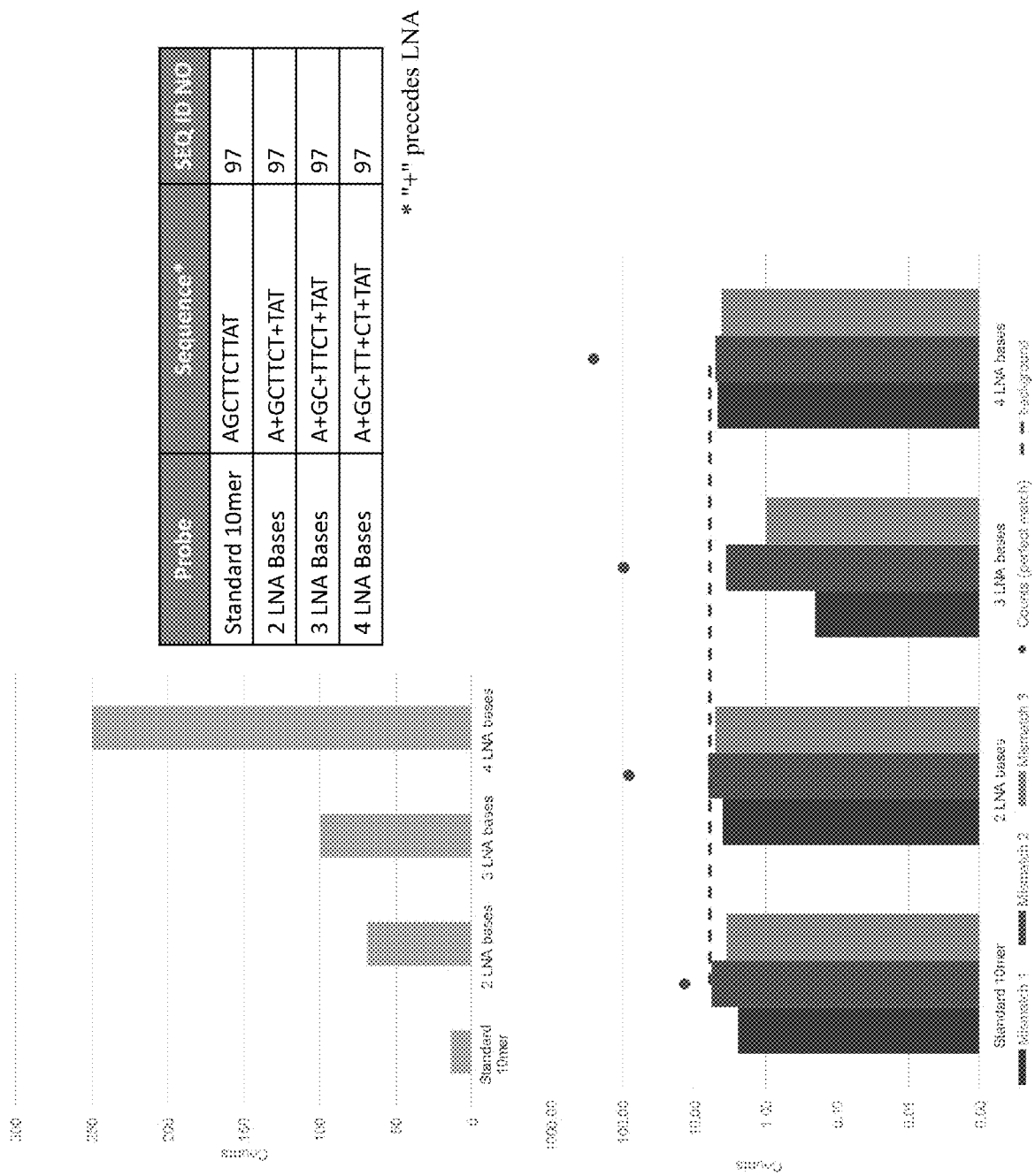
FIG. 23 shows the effect of LNA substitutions within exemplary target binding domains of the present disclosure using individual probes.
Figure 24:
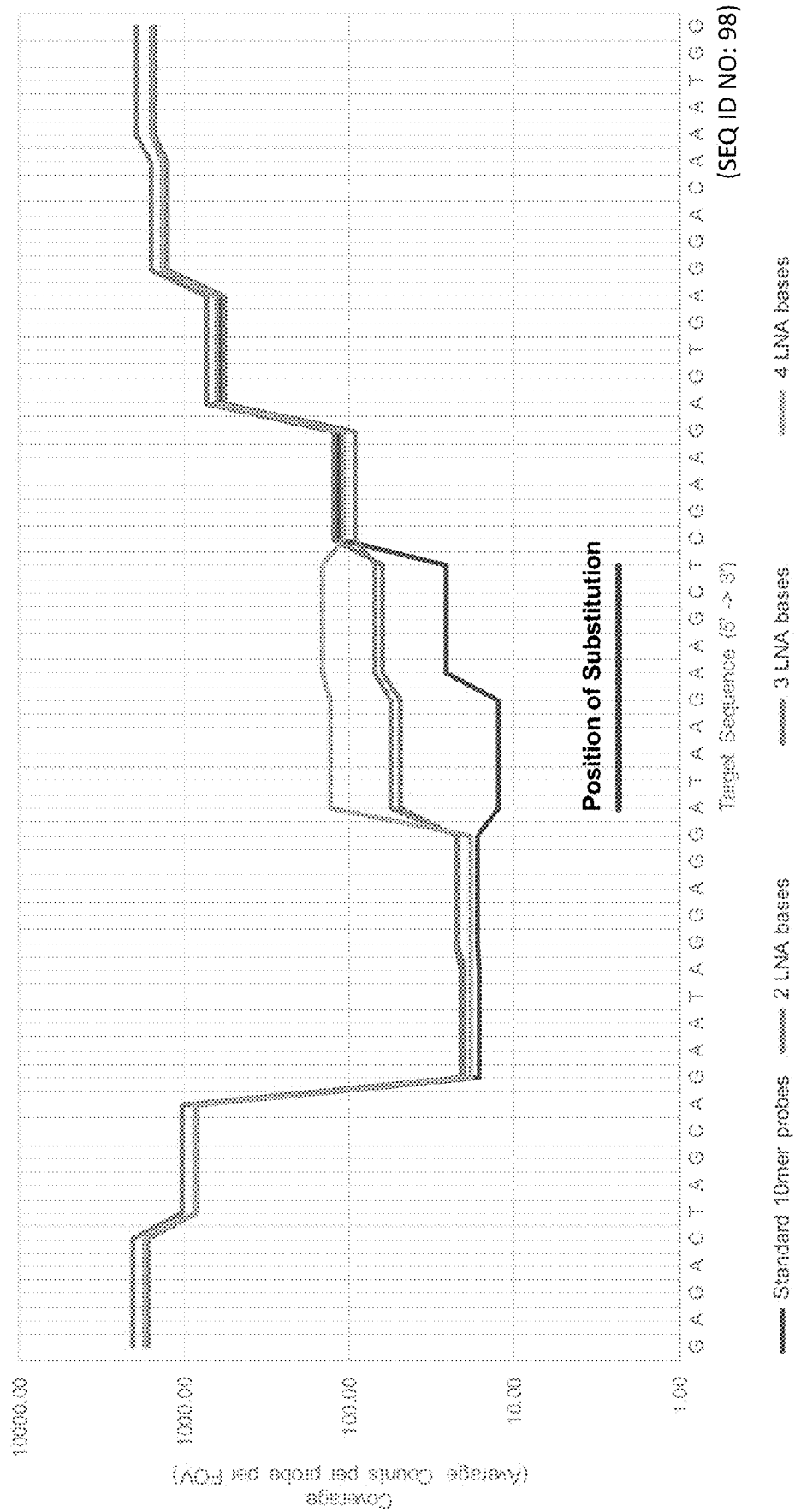
FIG. 24 shows the effect of LNA substitutions within exemplary target binding domains of the present disclosure using a pool of nine probes.

Each sequencing probe contained a target binding domain of 10 nucleotides (SEQ ID NO: 97). LNA substitutions within the target binding domains were made to include 2, 3, or 4 LNA bases at the positions shown in FIG. 23. FIG. 23 shows that the binding affinity of the individual sequencing probes for the target nucleic acid increased as the number of LNA bases increased. Importantly, FIG. 23 shows that the incorporation of LNA bases did not decrease the specificity of sequence probe binding. The pool of nine sequencing probes was tested to determine base coverage when probes could compete for target binding. FIG. 24 shows that when a single LNA probe was introduced into the pool, the coverage of the affected bases was increased with little effect on the binding of surrounding probes. These results indicated that LNA base substitutions can improve base sensitivity without reducing specificity.

Figure 25:
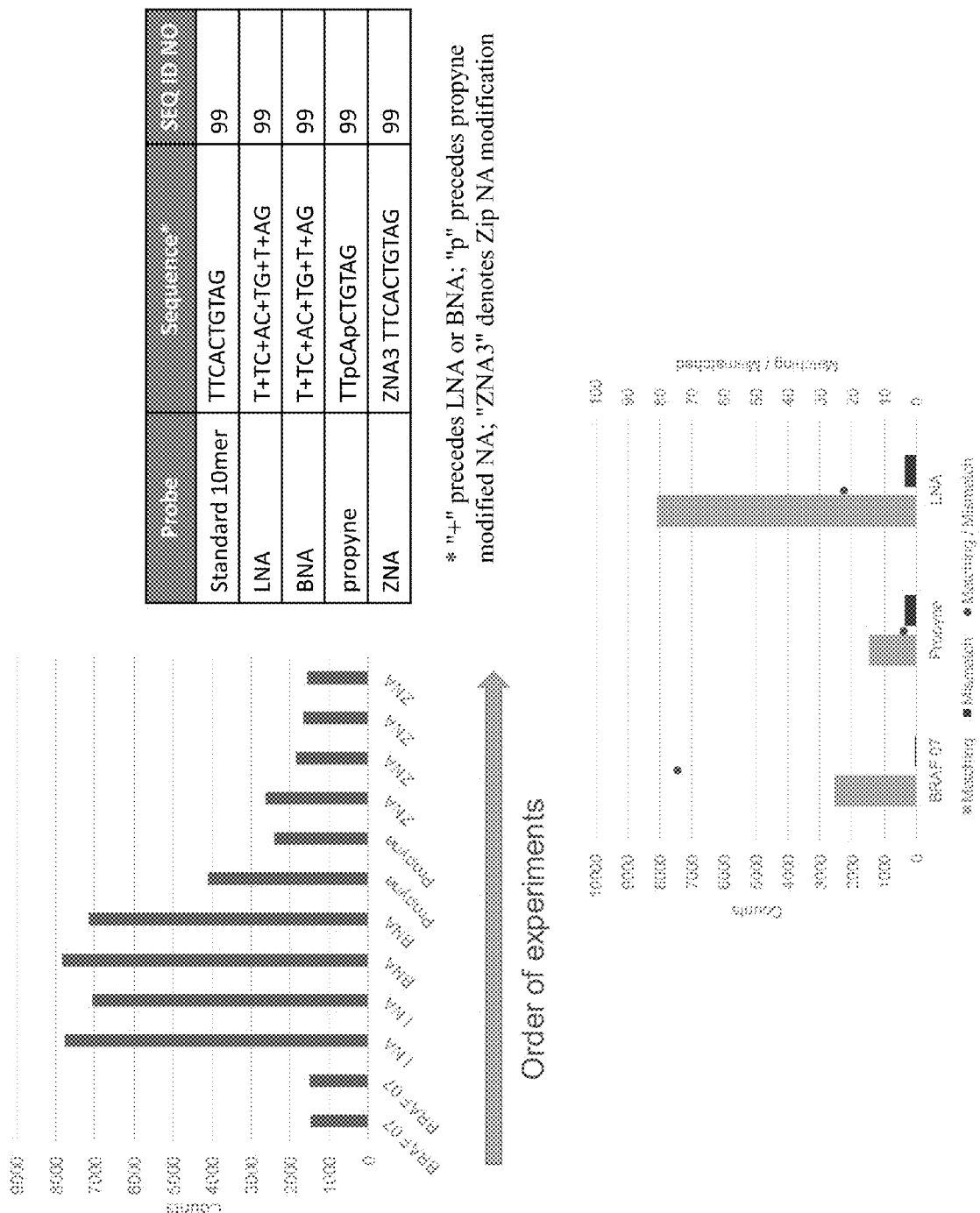
FIG. 25 shows the effect of modified nucleotides and nucleic acid analogue substitutions in exemplary target binding domains of the present disclosure.

Example 14—Effect of Modified Nucleotide and Nucleic Acid Analogue Substitutions in the Target Binding Domain The effect of the substitution of various modified nucleotides and nucleic acid analogues, including locked nucleic acids (LNA), bridged nucleic acids (BNA), propyne-modified nucleic acids, zip nucleic acids (ZNA®), isoguanine and isocytosine, into the target binding domain of sequencing probes was tested as follows. Biotinylated target nucleic acids 50 nucleotides in length were loaded onto a streptavidin cover slide of a prototype sequencing cartridge. Sequencing and reporter probes were then sequentially introduced into the sample chamber and imaged using a Hyb & Seq prototype instrument. The images were processed to compare the counts for each different sequencing probe. Substitutions in the 10 nucleotide (SEQ ID NO: 99) target binding domain of the sequencing probes were made to include LNA, BNA, propyne, and ZNA® bases at the positions shown in FIG. 25. FIG. 25 shows that probes containing LNAs and BNAs showed the largest increase in binding affinity while maintaining specificity, as indicated by the number of counts detected for matching and mismatched targets. These results indicated that LNA or BNA base substitutions can improve base sensitivity without reducing specificity.

Figure 26:
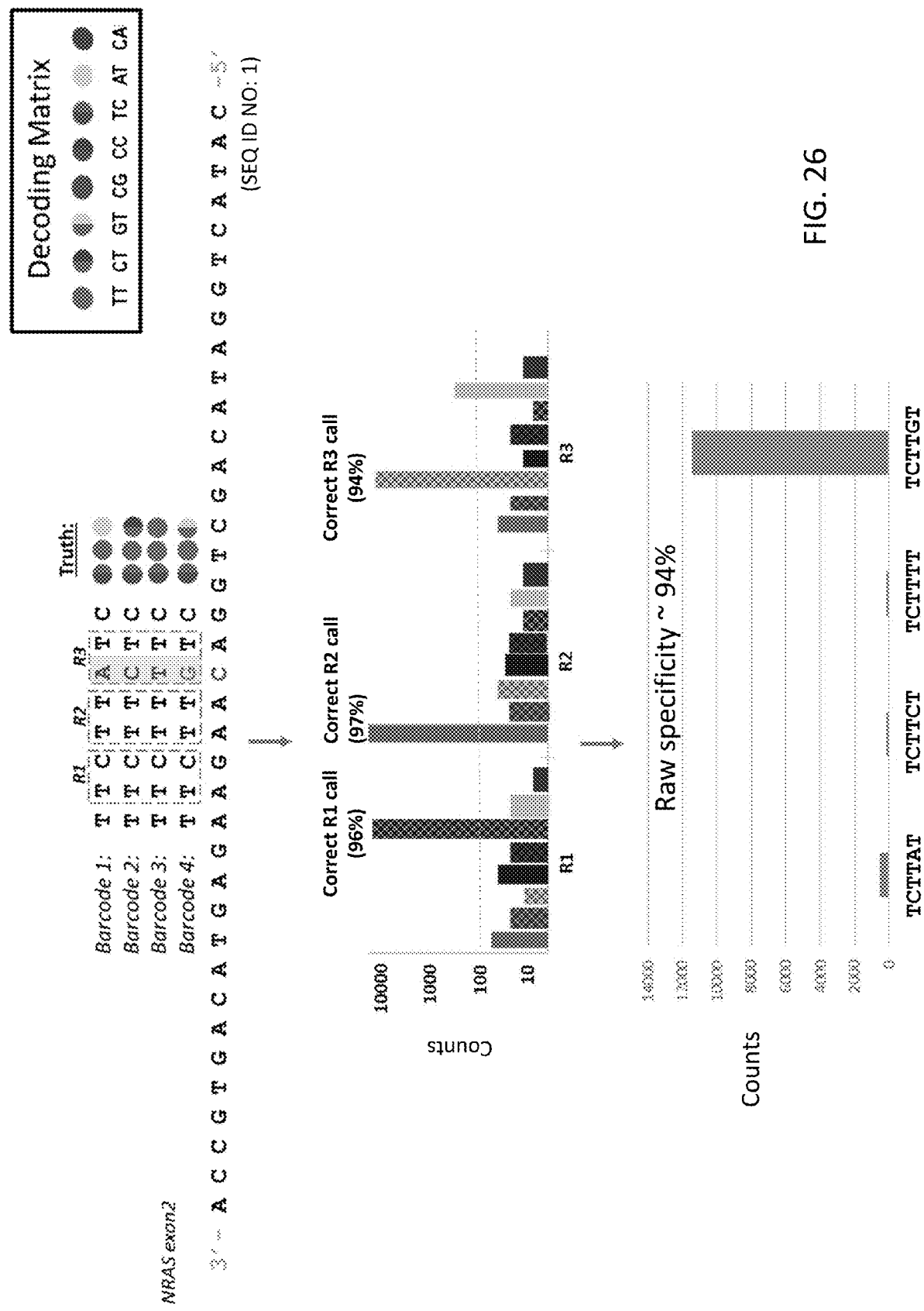
FIG. 26 shows the results from an experiment to quantify the raw accuracy of the sequencing method of the present disclosure

Example 15—Determining Accuracy of the Sequencing Method of the Present Disclosure FIG. 26 depicts the results from an experiment that quantified the raw specificity of the sequencing method of the present disclosure. In this experiment, a sequencing reaction was performed in which a pool of 4 different sequencing probes was hybridized to a target nucleic acid that included a fragment of NRAS exon2 (SEQ ID NO: 1). Each sequencing probe (barcode 1 to 4) had a target binding domain that was identical except that the hexamer of the target binding domain differed at position $b_5$, as depicted in the top panel of FIG. 26. In this example, barcode 4 is the correct sequencing probe. After hybridization of the sequencing probes, reporter probes were sequentially hybridized to each of the three positions of the barcode domain ($R_1$, $R_2$ and $R_3$) and the corresponding fluorescence data recorded. The middle panel of FIG. 26 depicts the number of times each color combination was recorded for the three barcode domain positions and the percentage of the time that the correct combination was recorded. The color combination at $R_1$ was correctly identified 96% of the time, the color combination at $R_2$ was correctly identified 97% of the time and the correct color combination at $R_3$ was correctly identified 94% of the time. As depicted in the bottom panel of FIG. 26, this leads to an overall raw specificity of 94%. The sources of error that could explain the miscalled barcode domain positions include: (a) non-specific binding of reporter probes to the surface of the flow cell and (b) incorrect hybridization of reporter probes. The estimated amount of reporter hybridization errors was approximately 2 to 4%.

Figure 27:
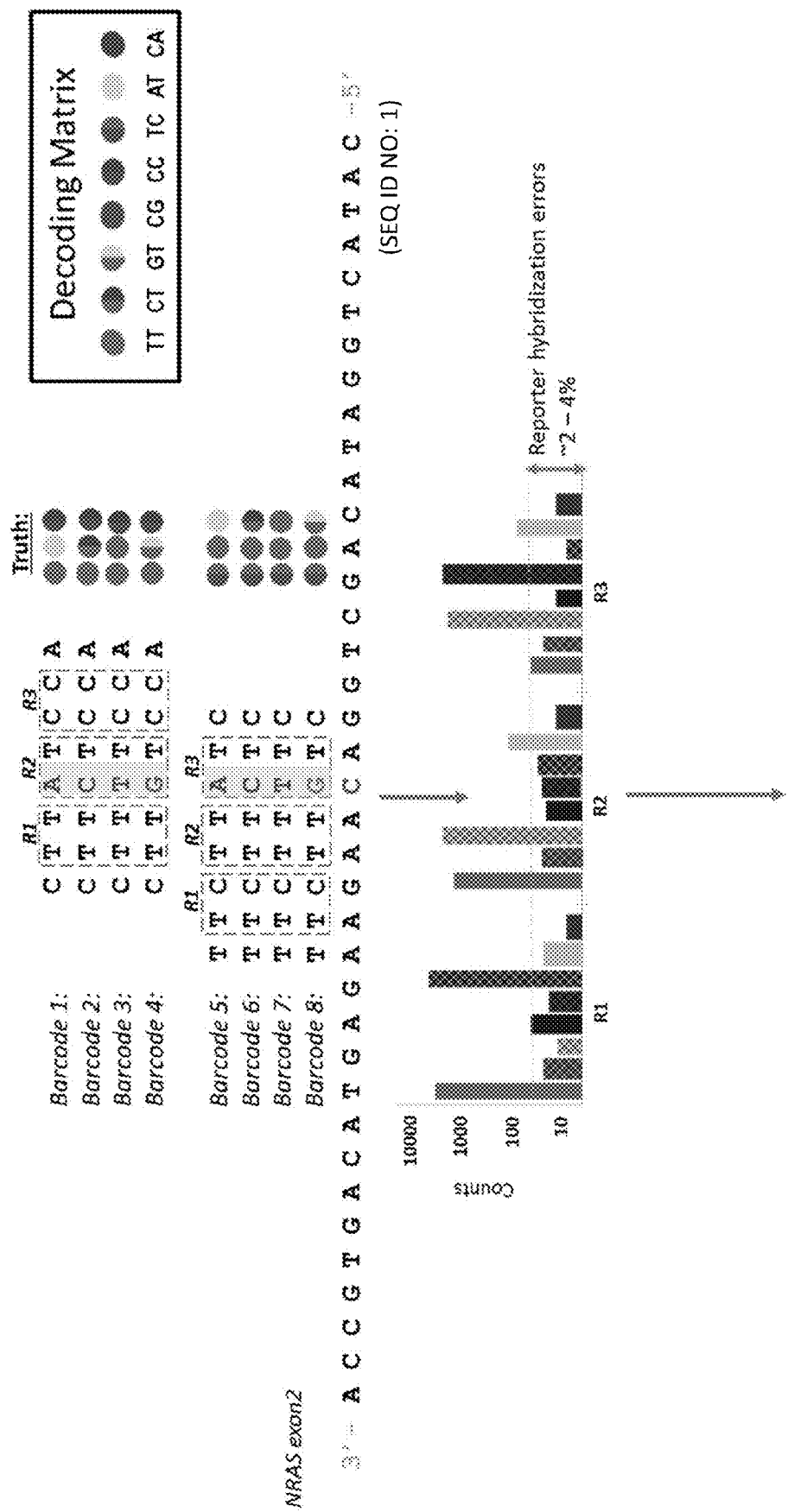
FIG. 27 shows the results from an experiment to determine the accuracy of the sequencing method of the present disclosure when nucleotides in the target nucleic acid are sequenced by more than one sequencing probe.

FIG. 27 shows the results from an experiment to determine the accuracy of the sequencing method of the present disclosure when nucleotides in the target nucleic acid are sequenced by more than one sequencing probe. As shown in the top panel of FIG. 27, the target nucleic acid in this example is a fragment of NRAS exon2 (SEQ ID NO: 1). The particular base of interest is a cytosine (C) that is highlighted in the target nucleic acid. The base of interest will be hybridized to two different sequencing probes, each with a distinct footprint of hybridization to the target nucleic acid. In this example, sequencing probes 1 to 4 (barcode 1 to 4) bind three nucleotides to the left of the base of interest, while sequencing probes 5 to 8 (barcodes 5 to 8) bind 5 nucleotides to the left of the base of interest. The middle panel of FIG. 27 shows the number of times specific color combinations were recorded at each position of the barcode domains of the sequencing probes. After image quantification and using the base calling techniques depicted in FIG. 17, an average accuracy of 98.98% can be recorded.

Example 16: Capturing Target Nucleic Acids Using CRISPR-Based Fragmentation

A target nucleic acid was captured and immobilized on a substrate using a c3 probe complex (described above) and a c5 probe complex (described above) as follows: genomic DNA (gDNA) was fragmented using CRISPR-based fragmentation. A solution comprising c3 probe complexes and c5 probe complexes were incubated mixed with the fragmented gDNA to hybridize the c3 and c5 probe complexes to a target nucleic acid such that the complex depicted in FIG. 34 was formed. The target nucleic acid-capture probe complex was then incubated with a mixture of HiFi Taq ligase and FEN1 at 65° C. The 5'-overhanging flap structure was removed by FEN1 and the 3' end of the target nucleic acid molecule was ligated to the strand of the c5 probe complex that comprises the substrate specific domain. After incubation, the target nucleic acid-capture probe complex was incubated with 20 µl F-like beads for 10 minutes with agitation. The F-like beads were captured with a magnet and washed three times. To elute the target nucleic acid-capture probe complex from the F-like beads, the F-like beads were suspended in 20 µl of USER enzyme mixture and incubated for 15 minutes at 25° C. The beads were removed with a magnet and the resultant supernatant containing the eluted target nucleic acid-capture probe complex was further purified using SPRI beads. 36 µl of SPRI beads were mixed with the supernatant and incubated for 10 minutes at 25° C. The beads were then bound to a magnet and washed twice with 100 µl of 80% ethanol. The ethanol was then removed and the beads allowed to dry for five minutes at 25° C. After drying, the beads were resuspended in 10 µl 0.1×SSPE. The purified nucleic acid-capture probe complex was eluted from the SPRI beads for 10 minutes. After elution, target nucleic acid-capture probe complexes derived from different biological samples were pooled together and added to F beads. The pooled complexes were incubated with F beads for 10 minutes at 25° C. The F beads were washed three times and resuspended in 8 µl. The F-beads were then transferred to a card comprising nucleic acid molecules that were complementary to the substrate specific domain of the c5 probe complexes and that were attached to a substrate. The complementary nucleic acid molecules attached to the substrate were hybridized to the substrate specific domains, thereby immobilizing the target nucleic acid onto the substrate. The substrate was then exposed to UV light to cleave the photo-cleavable linker on the c3 probe complex, thereby releasing the target nucleic acid-capture probe complexes from the F beads.

Example 17—CRISPR-Based Fragmentation of gDNA

The following protocol can be used to fragment genomic DNA using a CRISPR-based fragmentation step. The protocol enables in vitro cleavage of double-stranded, target DNA to generate target nucleic acid molecules that can be used in the methods of the present disclosure.

The following protocol uses a Cas9 RNP complex that contains both multiple single-guide RNAs (sgRNA) and a V3-Cas9 nuclease. In this non-limiting example, the guide RNA contained 17-20 nucleotides corresponding to the target sequence at the 5' end of the molecule that matches exactly the dsDNA that is desired to be cut.

The protocol was performed in an RNase free environment: (1) tubes containing each sgRNA molecule were centrifuged to ensure that a dried RNA pellet was collected at the bottom of the tube. In this example, 154 separate sgRNAs were used to make 154 cuts, resulting in the generation of 77 target nucleic acids; (2) each sgRNA pellet was dissolved in nuclease-free 1× TE Buffer such that a final concentration of 50 μM sgRNA was achieved; (3) all of the sgRNAs were then pooled together by mixing together 5 μl of each sample from step (2).

After the sgRNAs were pooled together, the protocol further comprised: (4) combining the sgRNA and Cas9 enzyme in equimolar amounts set forth in Table 9 and Table 10. To ensure good cleavage efficiency for each cutsite, 1.0 pmol of sgRNA and Cas9 was used for every 1000 ng dsDNA to be cut.

TABLE 9

Amounts per 1 cutsite

| | |
|---|---|
| sgRNA | 1 pmol |
| Cas9 | 1 pmol |
| 10xCas9 buffer | 0.3 μL |
| 100xBSA | 0.1 μL |
| DTT(1M) | 0.2 μL |
| dH2O (add to final volume of 10 μL) | X μL |

TABLE 10

Amounts for 154 cutsites

| | |
|---|---|
| sgRNA1-154(50 μM e.a) | 3.1 μL |
| Cas9 (61 μM) | 2.5 μL |
| 10xCas9 buffer | 0.3 μL |
| 100xBSA | 0.1 μL |
| DTT(1M) | 0.2 μL |
| dH2O | 3.8 μL |

After the sgRNAs and Cas9 enzyme were mixed, the protocol further comprised: (5) incubating the sgRNA-Cas9 mixture for 10 min at 37° C. to allow for formation of the RNP complex; (6) 1000 ng of extracted human genomic DNA (hgDNA) was then mixed with the RNP complexes formed in step (5) at room temperature according to the amounts set forth in Table 11.

TABLE 11

1 ug hgDNA (77 target nucleic acids)

| | |
|---|---|
| NEB3 buffer | 4 μL |
| DTT | 2 μL |
| CRISPR154 | 10 μL |
| hgDNA | 1000 ng |
| ddH$_2$O (add to final volume of 10 μL) | X μL |

After mixing the hgDNA with the RNP complexes, the protocol further comprised: (7) incubating the reaction assembled in step (6) at 37° C. for 60 min; (8) inactivating the CRISPR cleavage by incubating the reaction from step (7) at 70° C. for 10 minutes; and (9) adding 1 μL of Proteinase K (20 mg/mL stock solution to the reaction from step (8) and incubating this mixture at 56° C. for 10 min to release the DNA substrate from the Cas9 endonuclease. Alternatively, 2 μL Qiagen Protease (1.07 AU/mL) to the reaction can be added to the reaction from step (8), followed by an incubation at 37° C. for 30 min, followed by a second incubation at 70° C. for 15 minutes to heat inactivate the Qiagen Protease.

Example 18—Purification of Target Nucleic Acids from DNA that has been Fragmented Using a CRISPR-Based Fragmentation Step and USER-Mediated Cleavage After CRISPR-based fragmentation, the following protocol can be used to capture and purify specific target nucleic acids using the probes and methods of the present disclosure.

Following CRISPR-based fragmentation of DNA extracted from a sample, the fragmented DNA is mixed with capture probes. In this non-limiting example, the fragmented DNA is mixed with two capture probes. The first capture probe comprises a domain that is complementary to the 5' end of a specific target nucleic acid and an affinity moiety. In this example, the affinity moiety is an F-tag. A cleavable moiety is located between the F-tag and the domain that is complementary to the 5' end of the target nucleic acid. In this example, the cleavable moiety is a USER sequence. The second capture probe comprises a domain that is complementary to the 3' end of the target nucleic acid. The second capture probe can optionally include an affinity moiety. 1 nM of capture probes are mixed with 20 fM of the target nucleic acid in 5×SSPE buffer to a final reaction volume of 100 μl.

To hybridize the capture probes to the target nucleic acid, the solution of fragmented DNA and probes is incubated first at 98° C. for 3 minutes, then at 65° C. for 15 minutes and finally at 22° C. until the next step in the protocol.

To capture the target nucleic acid-capture probe complexes following hybridization, the solution of CRISPR-fragmented DNA and capture probes is incubated with F-beads (which are capable of binding to the F-tag located on first capture probe) for 10 minutes at room temperature with rotation or hand mixing. After incubation, the beads are washed three times with 1 mL 0.1×SSPE buffer to remove DNA that is not specifically bound to the beads. The beads are resuspended in 100 μl of 1×SSPE, transferred to a PCR tube, and spun down. The supernatant is removed and the beads are resuspended in 10 μl of USER master mix, which contains 1× Cutsmart buffer and 1 μl of USER enzyme. The beads are incubated in the USER master mix for 15 minutes at room temperature, thereby cleaving the USER sequence in the first capture probe, releasing the target nucleic acid from the beads. The beads are spun down and the supernatant, containing the target nucleic acid, is collected.

To further purify the target nucleic acid, an AMPure purification is performed twice. In an AMPure purification, the supernatant containing the target nucleic acid is mixed with AMPure XP beads (solid phase reversible immobilization beads, SPRI) at a ratio of 1:1.8, sample to beads. This mixture is incubated for 10 minutes to allow binding of the target nucleic acid to the beads. The beads are then washed twice with 200 μl of 75-80% ethanol. The beads are pulled across the ethanol using a magnet twice during each wash. The beads are then dried on the magnet for 5 minutes. The beads are then resuspended with 10 µl of 0.1×SSPE solution and incubated for 10 minutes. Finally, the purified target nucleic acid is eluted from the beads.

Example 19—Purification and Deposition of Target Nucleic Acids from DNA that has been Fragmented Using a CRISPR-Based Fragmentation Step and USER-Mediated Cleavage After CRISPR-based fragmentation, the following protocol can be used to capture, purify and deposit onto a suitable substrate, specific target nucleic acids using the probes and methods of the present disclosure.

Following CRISPR-based fragmentation of DNA extracted from a sample, the fragmented DNA is mixed with capture probes. In this non-limiting example, the fragmented DNA is mixed with the c3 probe complex and c5 complex as depicted in FIG. 34, except that the F-like tag located on the C5 probe is replaced with a G-tag. 1 nM of capture probes, 20 fM of the target nucleic acid, 1 µl of HiFi DNA ligase, and 2 µl of FEN1 enzyme are mixed in 1× HiFi buffer to a final reaction volume of 100 µl.

To hybridize the capture probes to the target nucleic acid, cleave the 5'-overhanging flap structure formed by the target nucleic acid and the c5 probe complex and ligate the 3' end of the target molecule to the strand of the c3 probe that comprises the substrate specific domain, the solution of fragmented DNA and probes is incubated first at 98° C. for 3 minutes, then at 65° C. for 60 minutes and finally at 22° C. until the next step in the protocol. During the last ten minutes of the 65° C. incubation, 10 µl of 5M NaCl is added to bring the salt concentration to 500 mM and help stabilize the hybridization of the capture probes.

To capture the target nucleic acid-capture probe complexes following hybridization, cleavage and ligation, the solution of fragmented DNA and capture probes is incubated with G-beads (which are capable of binding to the G-tag) for 10 minutes at room temperature with rotation or hand mixing. After incubation, the beads are then washed three times with 1 mL 0.1×SSPE buffer to remove DNA that is not specifically bound to the beads. The beads are resuspended in 100 µl of 1×SSPE, transferred to a PCR tube, and spun down. The supernatant is removed and the beads are resuspended in 10 µl of USER master mix, which contains 1× Cutsmart buffer and 1 µl of USER enzyme. The beads are incubated in the USER master mix for 15 minutes at room temperature, thereby cleaving the USER sequence in the first capture probe, releasing the target nucleic acid from the beads. The beads are spun down and the supernatant, containing the target nucleic acid, is collected.

To further purify the target nucleic acid, an AMPure purification is performed twice. In an AMPure purification, the supernatant containing the target nucleic acid is mixed with AMpure XP beads (solid phase reversible immobilization beads, SPRI) at a ratio of 1:1.8, samples to beads. This mixture is incubated for 10 minutes to allow binding of the target nucleic acid to the beads. The beads are then washed twice with 200 µl of 75-80% ethanol. The beads are pulled across the ethanol using a magnet twice during each wash. The beads are then dried on the magnet for 5 minutes. The beads are then resuspended with 10 µl of 0.1×SSPE solution and incubated for 10 minutes. Finally, the purified target nucleic acid is eluted from the beads. The purified target nucleic acid can then be deposited on a substrate capable of binding to the substrate specific domain that was ligated onto the target nucleic acid.

Example 20—Purification of Target Nucleic Acids from DNA that has been Fragmented Using a CRISPR-Based Fragmentation Step First, a 100 µl hybrid-capture reaction is prepared in which pre-fragmented gDNA is mixed with capture probes in 5×SSPE buffer using DEPC-treated/nuclease free water. Prior to adding the pre-fragmented gDNA to the hybrid-capture reaction, the concentration of the pre-fragmented gDNA is measured using the Qubit dsDNA BR Assay Kit (Thermo Scientific). The quantitative range of the Qubit assay is 2-1000 ng. Preferably, 10-100 ng of the gDNA sample should be assayed using the Qubit assay. If the gDNA sample is thought to have a concentration of greater than 1000 ng/µl, the sample should first be diluted to ~10-1000 ng/µl. In total, 100 to 1000 ng of gDNA should be added to the hybrid-capture reaction, preferably 1000 ng.

In this non-limiting example, two capture probes are used for each target nucleic acid to be purified. The first capture probe comprises a domain that is complementary to the 5' end of a specific target nucleic acid and an affinity moiety. In this example, the affinity moiety is an F-tag. The second capture probe comprises a domain that is complementary to the 3' end of the target nucleic acid. The second capture probe can optionally include an affinity moiety. First, a stock solution of 1 µM/probe is prepared. The stock solution is diluted to a 50 nM/probe working solution. 2 µl of the 50 nM/probe working solution is added to the final 100 µl hybrid-capture reaction.

To hybridize the capture probes to the target nucleic acid, the hybrid-capture reaction is incubated at 98° C. for 3 min, followed by incubation at 65° C. for 15 min. After the 65° C. incubation, the reaction can be stored at 22° C. until the next step in the protocol.

F-beads, which are capable of binding the F-tag, are prepared by washing twice with 1 ml of 5×SSPE. After washing, the beads are spun down, the supernatant removed, and the beads resuspended in a buffer comprising 5×SSPE, 60% formamide and 0.1% Tween-20.

Roughly, F-beads are expected to have a binding capacity of 1.25 pmol/µL at 10 mg/ml sample concentrations. It is preferable to using 1.5× the binding capacity of the F-beads, as determined by the total moles of the first capture probe present in the reaction. For example, in a reaction aiming to capture 77 different target nucleic acid, 0.1 pmol of each first probe (corresponding to each target nucleic acid) is used, meaning there is in 7.7 pmol of total first probe. 1.5× of 7.7 pmol is 11.55 pmol, and since the binding capacity of the F-beads is calculated to be 1.25 pmol/µl, 9.24 µL of beads should be used.

After hybridization of the capture probes, the 100 µl hybrid-capture reaction is incubated with 100 µl of resuspended F-beads at room temperature for 10 minute while being rotated. After the capture probe-target nucleic acid complexes are bound to the beads, the beads are washed to remove uncaptured gDNA. To wash the beads, the beads are first concentrated with a magnet, and then washed three times with 1 ml of 0.1×SSPE. After the last wash, 900 µl of the final wash solution is removed and the beads are resuspended in the remaining 100 µl. The resuspended beads are transferred to a clean PCR tube, concentrated using a magnet and the supernatant is removed.

To elute the capture probe-target nucleic acid complexes from the beads, the beads are resuspended in 12 µl of 0.1×SSPE and incubated at 45° C. for 7.5 minutes. After the incubation, the beads are quickly concentrated on a magnet and the 12 µl eluate removed.

The target nucleic acid is furthered purified using two SPRI (AMPure) purifications. The 12 µl eluate is mixed with AMPure beads at a ratio of 1:1.8, eluate to beads, and incubated for 10 minutes at room temperature on a rotator. The beads are then concentrated with a magnet and washed twice with 100 µl of 80% ethanol. The beads are moved across the magnet twice per wash to ensure the ethanol washes the entire bead pellet. After the second ethanol wash, as much ethanol as possible is removed and the beads permitted to dry on the magnet in an uncapped tube for 5 minutes. The beads are then resuspended in 12 µl of 0.1× SSPE and eluted for 10 minutes at room temperature. The beads are concentrated and the eluate removed. After the second SPRI purification, 1 µl 20×SSPE buffer is added to the final eluate to stabilize the capture probe-target nucleic acid complexes.

Example 21—Sequencing of Target Nucleic Acids Using the Sequencing Probes of the Present Disclosure The following is an example that describes the use of two different sequencing probe designs to sequence synthetic target nucleic acids.

The first sequencing probe design, herein referred to as LG-spaced sequencing probes, is shown in FIG. 53. Starting at the 5' end, the sequencing probe comprises a target binding domain. The target binding domain comprises a six nucleotide long (6-mer) sequence ($b_1$-$b_2$-$b_3$-$b_4$-$b_5$-$b_6$) that hybridizes specifically to six complementary nucleotides in a target nucleic acid. This 6-mer sequence is flanked on either side by a degenerate base (N). The sequencing probe also comprises a barcode domain that is covalently attached to the target-binding domain via a double-stranded DNA spacer designated the L-DNA stem. Both the barcode domain and the double-stranded DNA spacer consist entirely of L-DNA, while the target-binding domain consists entirely of D-DNA. The L-DNA stem is 25 nucleotides in length. The barcode domain is 27 nucleotides in length and comprises three attachment regions (designated Spot 1, Spot 2 and Spot 3). Each attachment position comprises 9 nucleotides. The 3' terminal nucleotide of each attachment region is a L-dG nucleotide.

For these experiments, a pool of 512 distinct species of LG-spaced sequencing probes (LG-spaced pool) was designed, with each sequencing probe comprising a unique combination of Spot 1, Spot 2 and Spot 3 nucleic acid sequences. A total of 30 unique, low complexity nucleic acid sequences were designed for the attachment regions, with 10 designated for use in spot 1, 10 designated for use in spot 2 and 10 designated for use in spot 3. Each distinct species of LG-spaced sequencing probe also comprises a different 6-mer sequence in the target binding domain.

Figure 54:
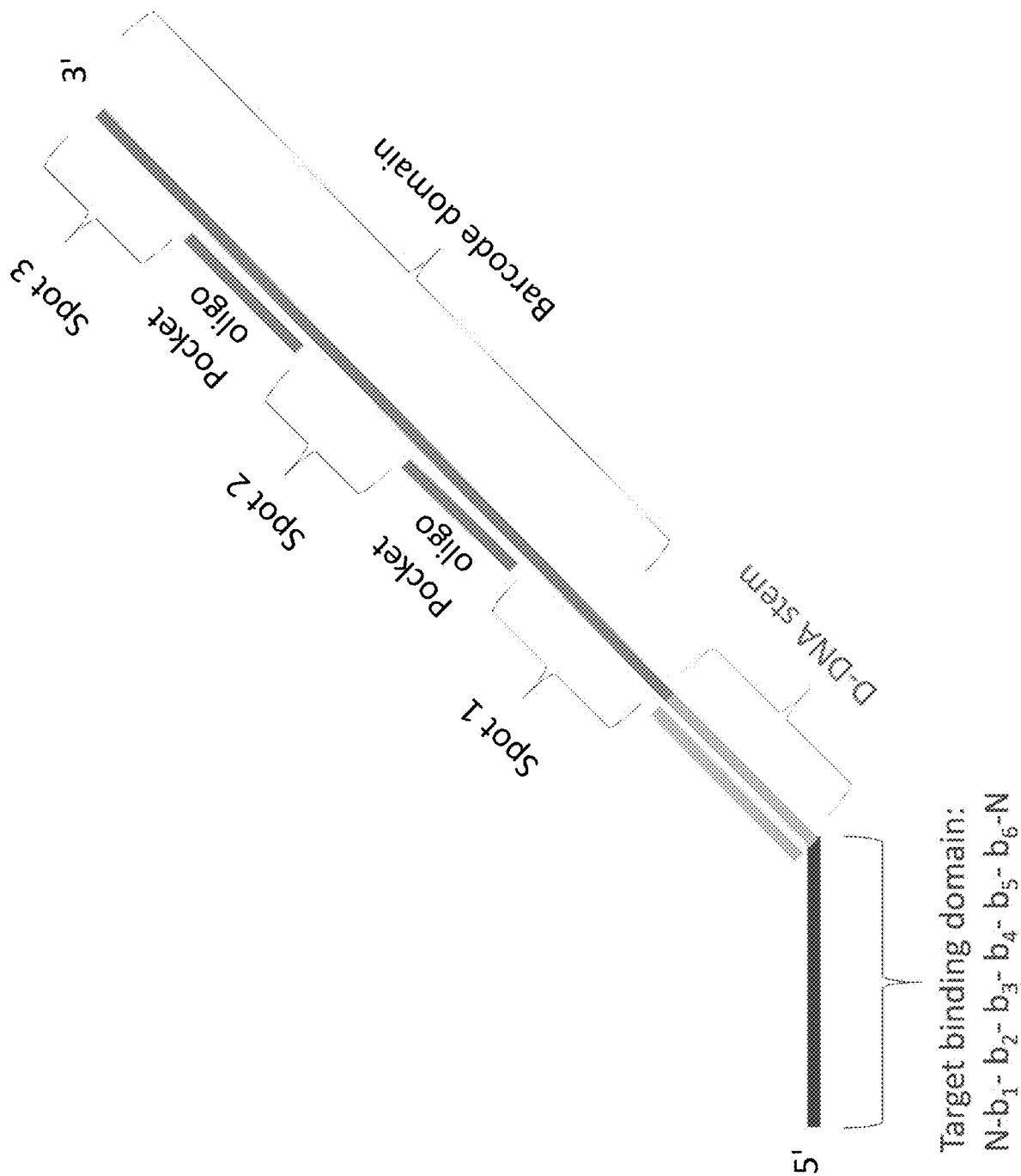
FIG. 54 is a schematic illustration of a sequencing probe of the present disclosure that consists entirely of D-DNA and that comprises pocket oligos located between attachment region 1 (Spot 1) and attachment region 2 (Spot 2) and between attachment region 2 (Spot 2) and attachment region 3 (Spot 3).

The second sequencing probe design, herein referred to as D-pocket sequencing probes, is shown in FIG. 54. Starting at the 5' end, the sequencing probe comprises a target binding domain. The target binding domain comprises a six nucleotide long (6-mer) sequence ($b_1$-$b_2$-$b_3$-$b_4$-$b_5$-$b_6$) that hybridizes specifically to six complementary nucleotides in a target nucleic acid. This 6-mer sequence is flanked on either side by a degenerate base (N). The sequencing probe also comprises a barcode domain that is covalently attached to the target-binding domain via a double-stranded DNA spacer designated the D-DNA stem. The D-DNA stem is 25 nucleotides in length. The barcode domain is 74 nucleotides in length and comprises three attachment regions (designated Spot 1, Spot 2 and Spot 3). Each attachment position comprises 8 nucleotides. Spot 1 and Spot 2 are separated by a double-stranded DNA region that is comprised of the barcode domain hybridized to a 25 nucleotide long pocket oligonucleotide. Spot 2 and Spot 3 are also separated by a double-stranded DNA region that is comprised of the barcode domain hybridized to a 25 nucleotide pocket oligonucleotide. The D-pocket sequencing probe consists entirely of D-DNA.

For these experiments two different pools of 512 distinct species of D-pocket sequencing probes (D-pocket pool 1 and D-pocket pool 3) was designed. Each distinct species of sequencing probe comprised a different 6-mer sequence in the target binding domain.

For these experiments the target-binding domains of the series of sequencing probes in the pools of the D-pocket sequencing probes were identical to the target-binding domains of the series of sequencing probes in the pools of the LG-spaced sequencing probes and the color assignments for each of the reporter attachment positions 1, 2 and 3 were the same between the D-pocket sequencing probes and the LG-spaced sequencing probes. In other words, for each D-pocket sequencing probe there was a corresponding LG-spaced sequencing probe with the same target-binding domain sequence and corresponding 3-color reporter readout.

Figure 55:
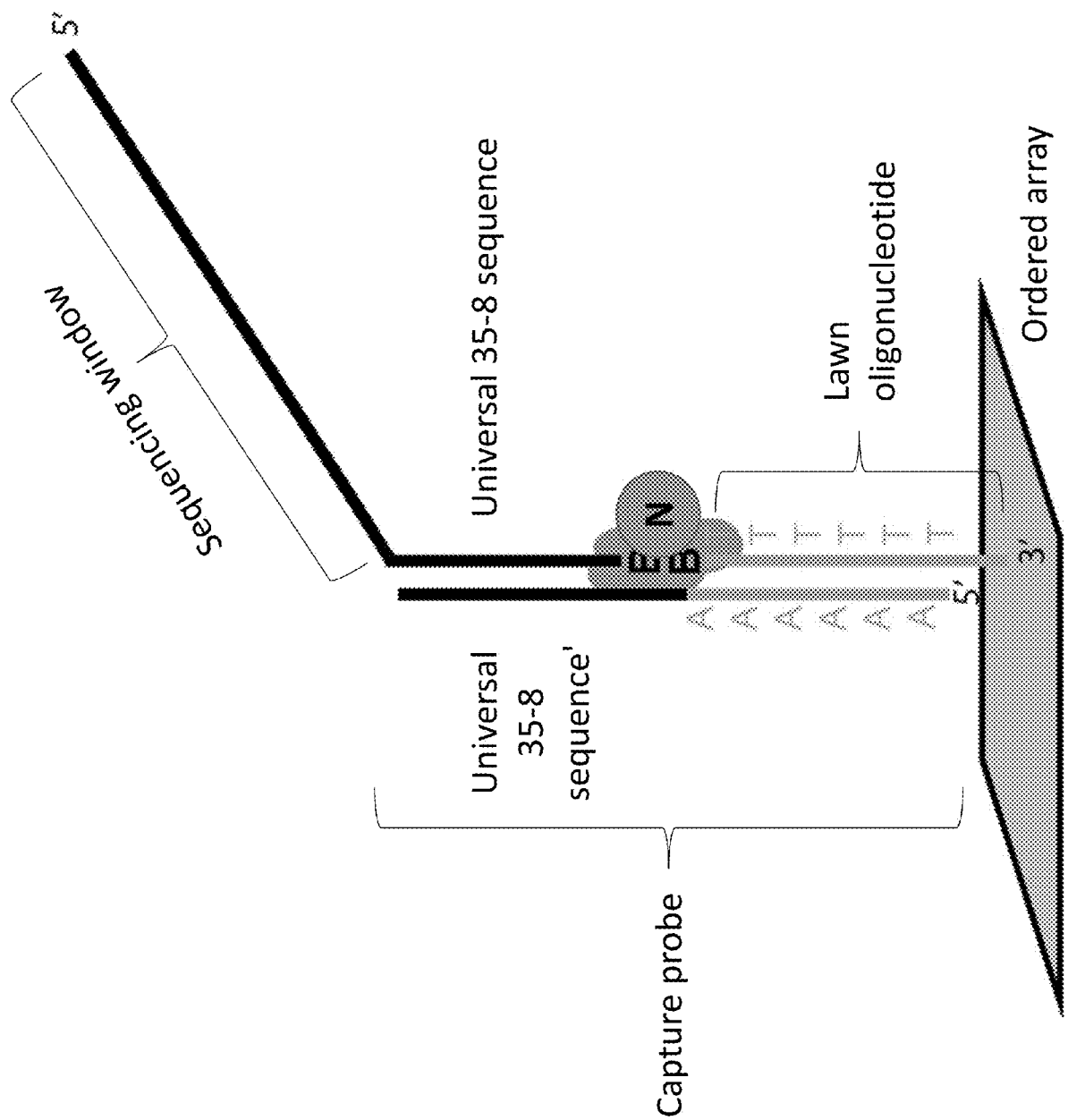
FIG. 55 is a schematic illustration of a synthetic target nucleic acid immobilized onto a solid substrate using a capture probe and a lawn oligonucleotide in combination with a protein lock.

To test the efficiency and accuracy of the LG-spaced and D-pocket sequencing probes, synthetic target nucleic acids were designed. Starting at the 5' end, a synthetic target nucleic acid comprises a single-stranded sequencing window that was 25 nucleotides to 45 nucleotides in length. These sequencing windows comprised both synthetic nucleotide sequences as well as nucleotide sequences from known, human genes such as P53, ALX1, SMO1-1. The sequencing window is followed by a 35 nucleotide long universal sequence herein referred to as the 35-8 sequence. Following the 35-8 sequence is a 3' biotin-TEG modification. The synthetic target nucleic acid consists entirely of D-DNA. A schematic of a synthetic target nucleic acid is shown in FIG. 55.

To capture and immobilize a synthetic target nucleic acid for the following experiments, 70 nucleotide long capture probes were used. The capture probes comprised a sequence complementary to the 35-8 sequence, allowing the capture probes to hybridize to the synthetic target nucleic acids. The sequence complementary to the 35-8 sequence consisted entirely of D-DNA. The capture probe also comprised a 35 nucleotide long poly-L-dA sequence. As shown in FIG. 55, after hybridizing a capture probe to a synthetic target nucleic acid, the capture probe-target nucleic acid complex can be immobilized to a surface that comprises a lawn oligonucleotide comprising a poly-L-dT sequence. Additionally, the lawn oligonucleotide can comprise a biotin molecule. Thus, as shown in FIG. 55, after the poly-L-dA sequence of the capture probe hybridizes to the poly-L-dT sequence of the lawn oligonucleotide, neutravidin can be added to create a protein lock between the synthetic target nucleic acid and the lawn oligonucleotide, as the neutravidin binds both the 3' biotin of the synthetic target nucleic acid and the biotin located on the lawn oligonucleotide.

In the following experiments, synthetic target nucleic acids were hybridized to capture probes and immobilized onto ordered arrays. The ordered arrays contained 200 nm diameter pads functionalized with lawn oligonucleotides. The pitch of the ordered array was 800 nm. A protein lock between the synthetic target nucleic acid and the lawn oligonucleotide was performed by pipetting a 0.2 mg/mL neutravidin solution over the immobilized capture probe-target nucleic acid complex and incubating for 5 minutes. Open neutravidin binding sites were subsequently blocked with dual biotinylated PEG by incubating the immobilized and protein locked target nucleic acids in a 1 μM biotinylated PEG solution for one minute. Finally, any non-protein locked target nucleic acids were removed from the ordered arrays using a low salt (0.0033×SSPE) wash.

Following target nucleic acid immobilization and protein-locking, the pools of sequencing probes were flowed onto the array at a concentration of 200 nM per sequencing probe (in a 3.75×SSPE and 15% formamide buffer) at 8° C. for 1 minute to allow for hybridization of the sequencing probes to the target nucleic acids. After the sequencing probes were hybridized to the target nucleic acids, the sequencing probes were hybridized to reporter probes under buffer conditions of 8.75×SSPE in three sequential rounds of hybridization. The reporter probes in these experiments comprised a UV-cleavable linker between the portion of the reporter probe that binds to an attachment region and the portion comprising detectable labels.

In the first round, a first reporter probe was hybridized to spot 1 of the sequencing probes. After identifying the detectable labels of the first reporter probe hybridized to spot 1, the first reporter probe was cleaved by exposing the sample to UV light, thereby removing the detectable labels. In the second round, a second reporter probe was hybridized to spot 2 of the sequencing probes. After identifying the detectable labels of the second reporter probe hybridized to spot 2, the second reporter probe was cleaved by exposing the sample to UV light, thereby removing the detectable labels. In a final, and third round reporter probe was hybridized to spot 3 of the sequencing probes. After identifying the detectable labels of the third reporter probes hybridized to spot 3, the sequencing probes were de-hybridized from the immobilized synthetic target nucleic acids using a low salt wash (0.0033×SSPE). After de-hybridization, a new pool of sequencing probes can be hybridized to the immobilized synthetic target nucleic acids. These steps constitute one cycle of sequencing.

In a first set of experiments, the LG-spaced pool was used to sequence several different immobilized synthetic target nucleic acids in a 50 cycle sequencing run. In a second set of experiments, the D-pocket pool was used to sequence several different immobilized synthetic target nucleic acids in a 50 cycle sequencing run. The results of these two sets of experiments are shown in Tables 12.

TABLE 12

Sequencing results

| Pool | % barcode efficiency | Clean 3-spotter | Clean 2-spotter | Clean 1-spotter |
|---|---|---|---|---|
| LG-spaced (2044) | 41.1 | 12.3 | 10.4 | 13.9 |
| D-pocket (2073) | 32.0 | 10.1 | 10.0 | 10.2 |

| Pool | Clean Spot 1 efficiency | Clean Spot 2 efficiency | Clean Spot 3 efficiency | Clean % 3-spot readout | % Multicolor Darked | % valid | % invalid |
|---|---|---|---|---|---|---|---|
| LG-spaced (2044) | 76.4 | 70.0 | 65.4 | 29.8 | 11.2 | 86.8 | 13.2 |
| D-pocket (2073) | 74.0 | 69.2 | 63.6 | 31.5 | 5.5 | 91.7 | 8.4 |

Survival Cutoff and Voted

| Pool | % barcode efficiency | Clean 3-spotter | Clean 2-spotter | Clean 1-spotter |
|---|---|---|---|---|
| LG-spaced (2044) | 46.9 | 15.2 | 11.8 | 14.4 |
| D-pocket (2073) | 29.3 | 10.5 | 8.7 | 8.7 |

| Pool | Clean Spot 1 efficiency | Clean Spot 2 efficiency | Clean Spot 3 efficiency | Clean % 3-spot readout | % Multicolor Darked | % valid | % invalid |
|---|---|---|---|---|---|---|---|
| LG-spaced (2044) | 82.3 | 71.7 | 65.4 | 32.5 | 11.6 | 86.9 | 13.1 |
| D-pocket (2073) | 75.6 | 69.9 | 66.8 | 35.9 | 4.6 | 93.5 | 6.5 |

Table 12 shows that the LG-spaced pool displayed an increased barcode efficiency as compared to the D-pocket pool (47% versus 30%). Furthermore, the LG-spaced pool also displayed an increased clean spot 1 efficiency as compared to the D-pocket pool (82% versus 76%). The clean spot 2 and clean spot 3 efficiencies were approximately the same for both the LG-spaced pool and the D-pocket pool.

Figure 56:
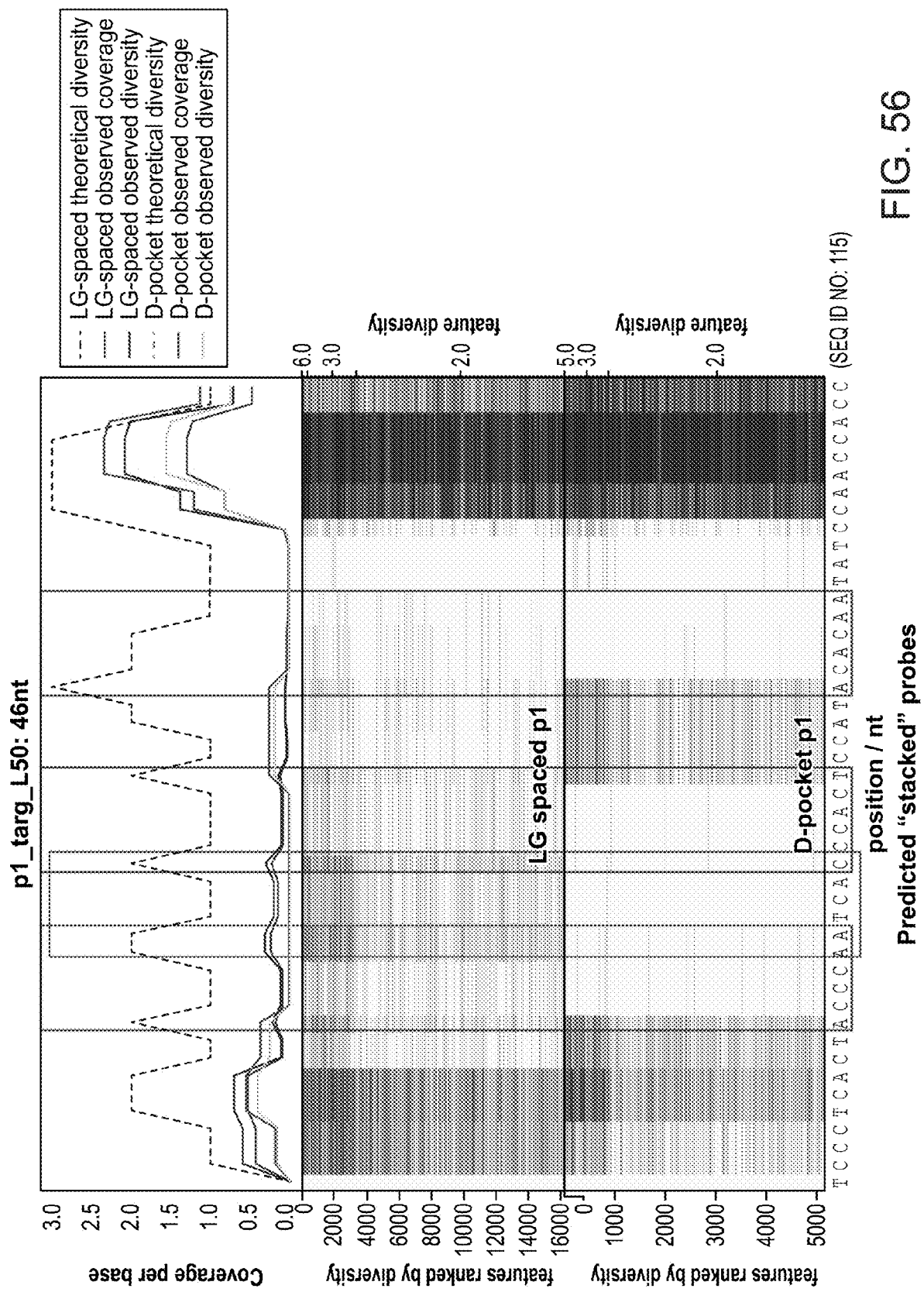
FIG. 56 is a series of charts showing the results of sequencing experiments using LG-spaced sequencing probes and D-pocket sequencing probes of the present disclosure. The x-axis denotes specific nucleotides of the target nucleic acid being sequenced. The top chart shows the theoretical sequencing diversity, observed sequencing diversity and observed sequencing coverage for the LG-spaced and D-pocket sequencing probes. The red boxes denote predicted problematic areas for sequencing.
Figure 57:
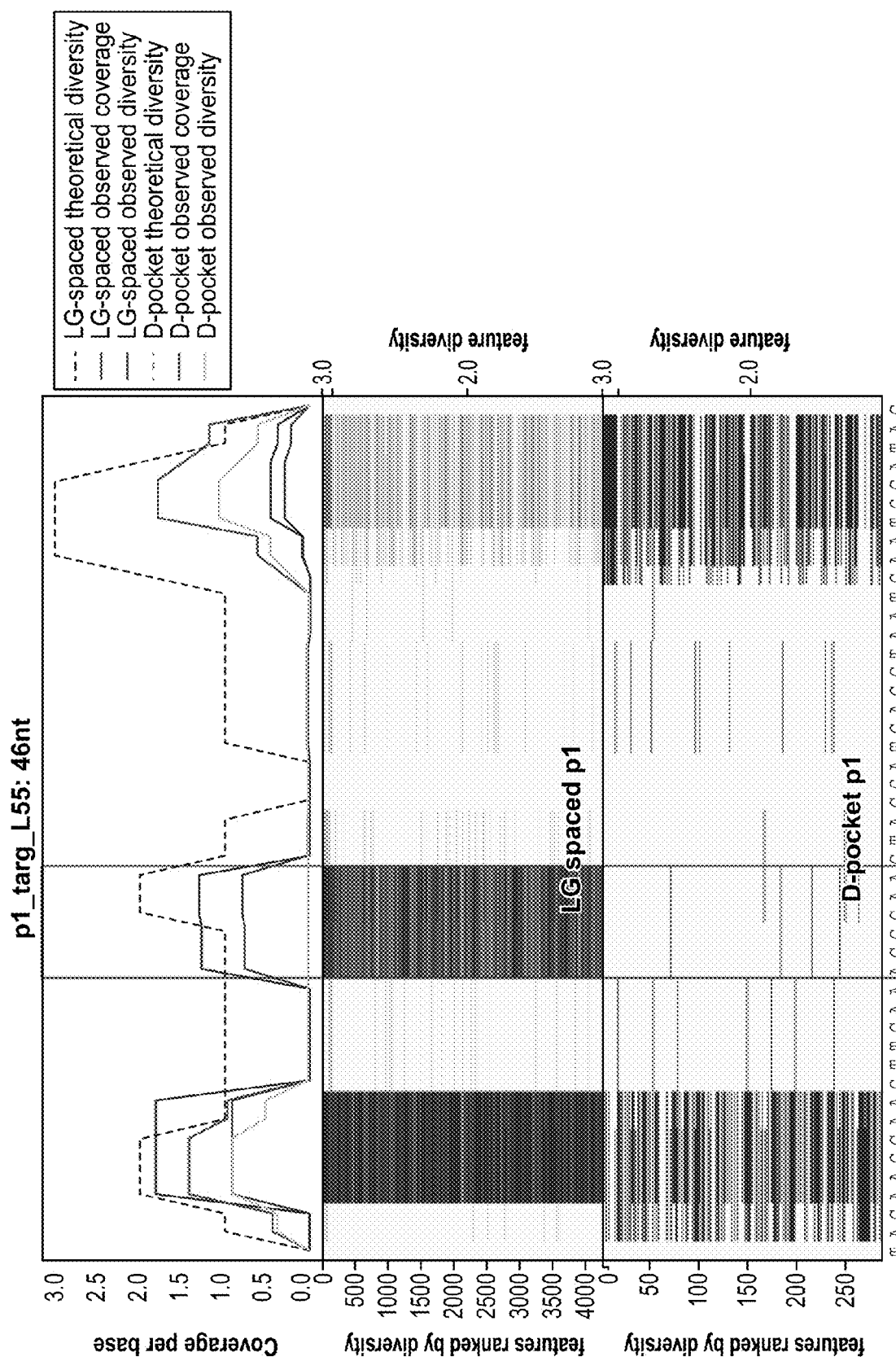
FIG. 57 is a series of charts showing the results of sequencing experiments using LG-spaced sequencing probes and D-pocket sequencing probes of the present disclosure. The x-axis denotes specific nucleotides of the target nucleic acid being sequenced. The top chart shows the theoretical sequencing diversity, observed sequencing diversity and observed sequencing coverage for the LG-spaced and D-pocket sequencing probes. The red boxes denote predicted problematic areas for sequencing.
Figure 58:
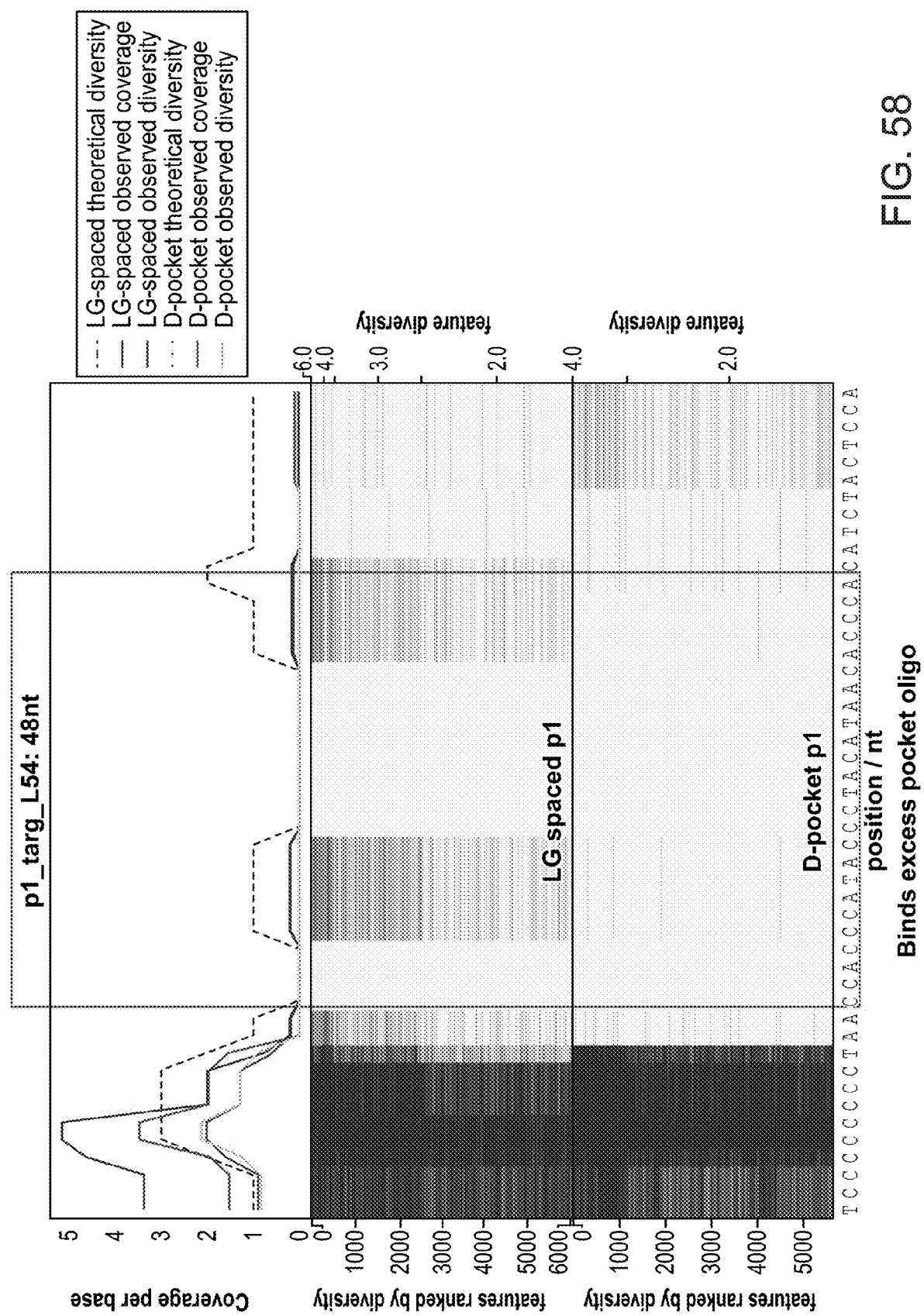
FIG. 58 is a series of charts showing the results of sequencing experiments using LG-spaced sequencing probes and D-pocket sequencing probes of the present disclosure. The x-axis denotes specific nucleotides of the target nucleic acid being sequenced. The top chart shows the theoretical sequencing diversity, observed sequencing diversity and observed sequencing coverage for the LG-spaced and D-pocket sequencing probes. The red boxes denote predicted problematic areas for sequencing.
Figure 59:
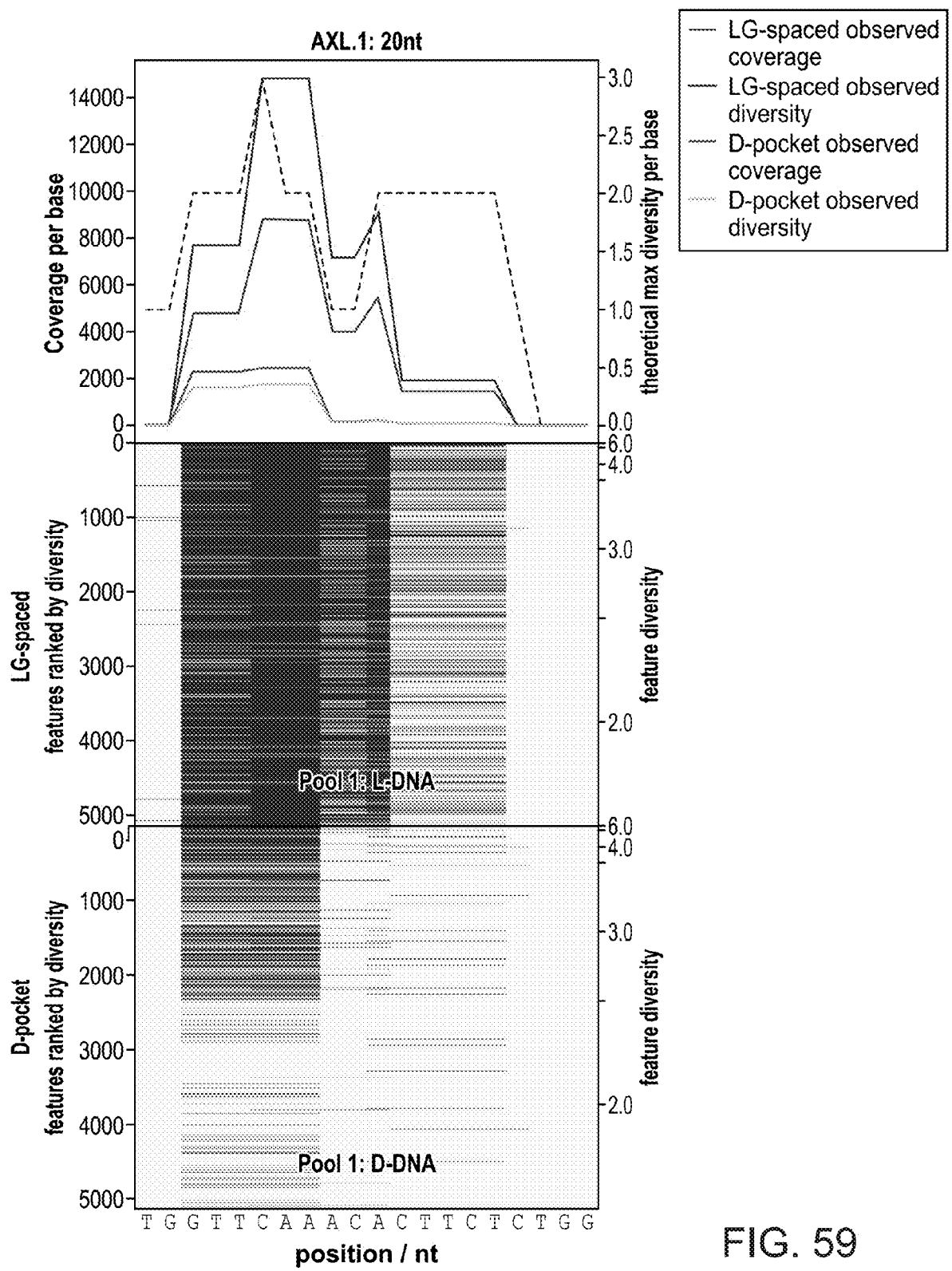
FIG. 59 is a series of charts showing the results of sequencing experiments using LG-spaced sequencing probes and D-pocket sequencing probes of the present disclosure. The x-axis denotes specific nucleotides of the target nucleic acid being sequenced. The top chart shows the observed sequencing diversity and observed sequencing coverage for the LG-spaced and D-pocket sequencing probes.
Figure 60:
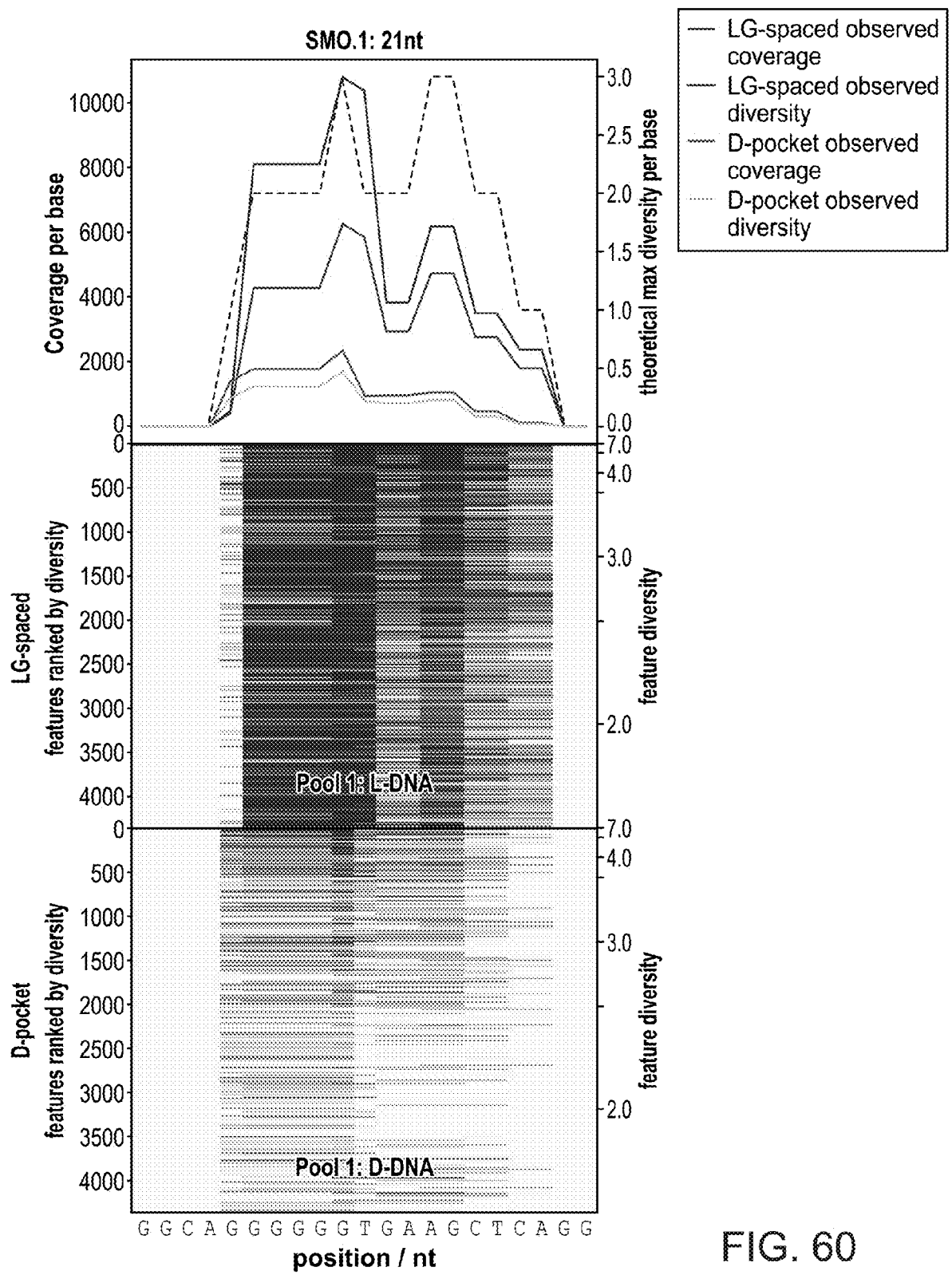
FIG. 60 is a series of charts showing the results of sequencing experiments using LG-spaced sequencing probes and D-pocket sequencing probes of the present disclosure. The x-axis denotes specific nucleotides of the target nucleic acid being sequenced. The top chart shows the observed sequencing diversity and observed sequencing coverage for the LG-spaced and D-pocket sequencing probes.
Figure 61:
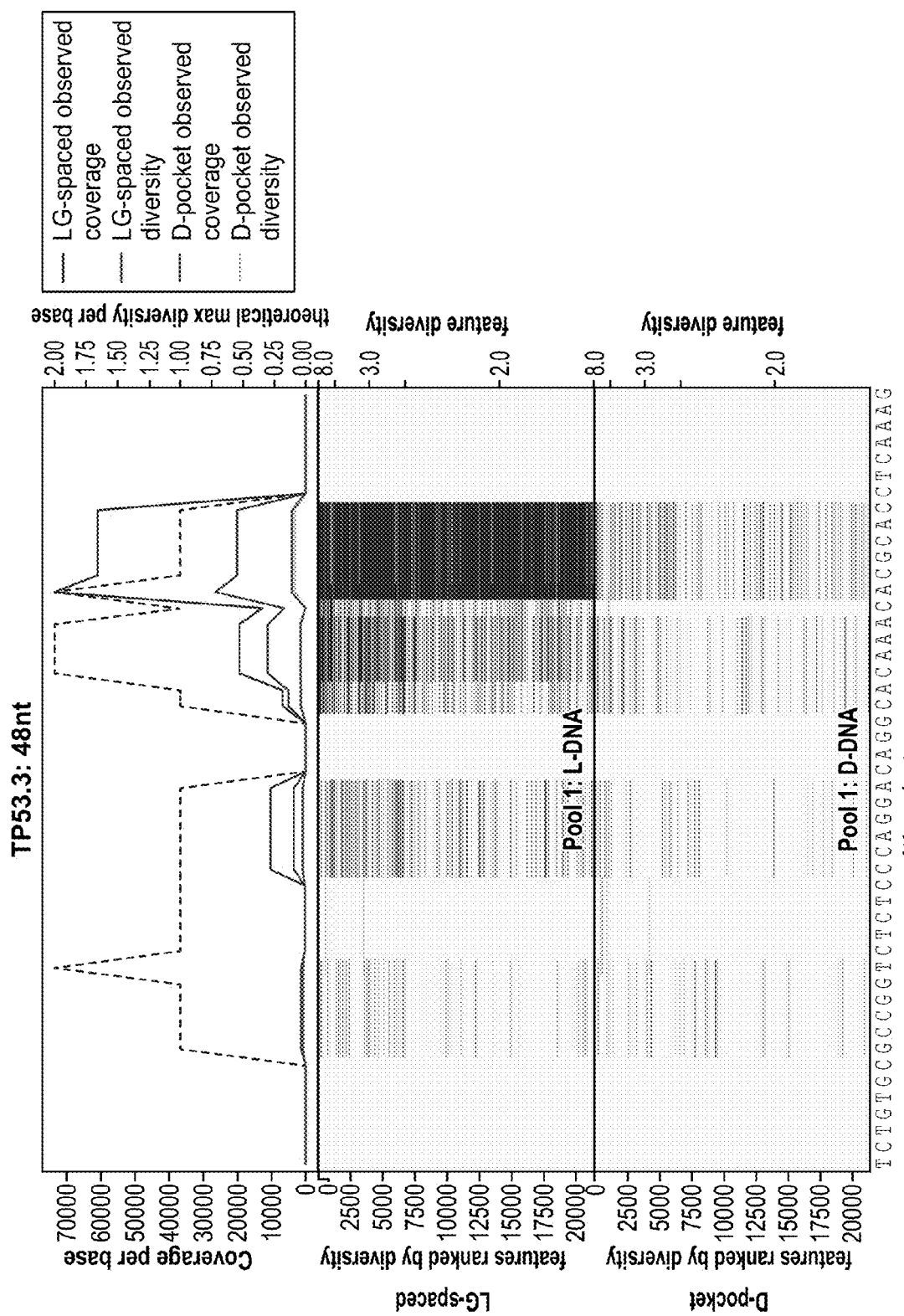
FIG. 61 is a series of charts showing the results of sequencing experiments using LG-spaced sequencing probes and D-pocket sequencing probes of the present disclosure. The x-axis denotes specific nucleotides of the target nucleic acid being sequenced. The top chart shows the observed sequencing diversity and observed sequencing coverage for the LG-spaced and D-pocket sequencing probes.
Figure 63:
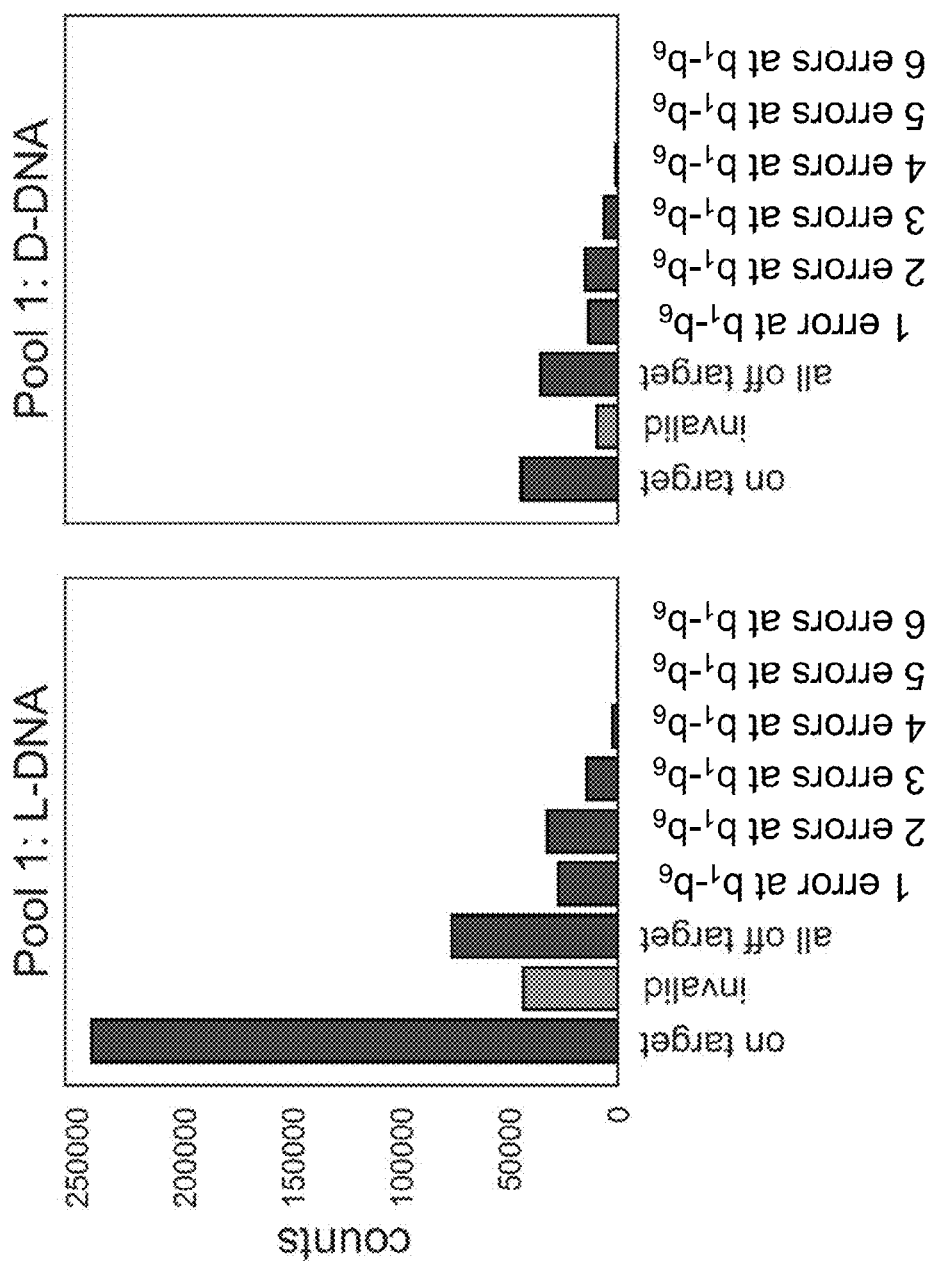
FIG. 63 is a series of graphs showing the total number of on target events, invalid events, off target events, 1 error at $b_1$-$b_6$ events, 2 errors at $b_1$-$b_6$ events, 3 errors at $b_1$-$b_6$ events, 4 errors at $b_1$-$b_6$ events, 5 error at $b_1$-$b_6$ events and 6 errors at $b_1$-$b_6$ events in sequencing experiments using the LG-spaced sequencing probes and the D-pocket sequencing probes of the present disclosure.
Figure 64:
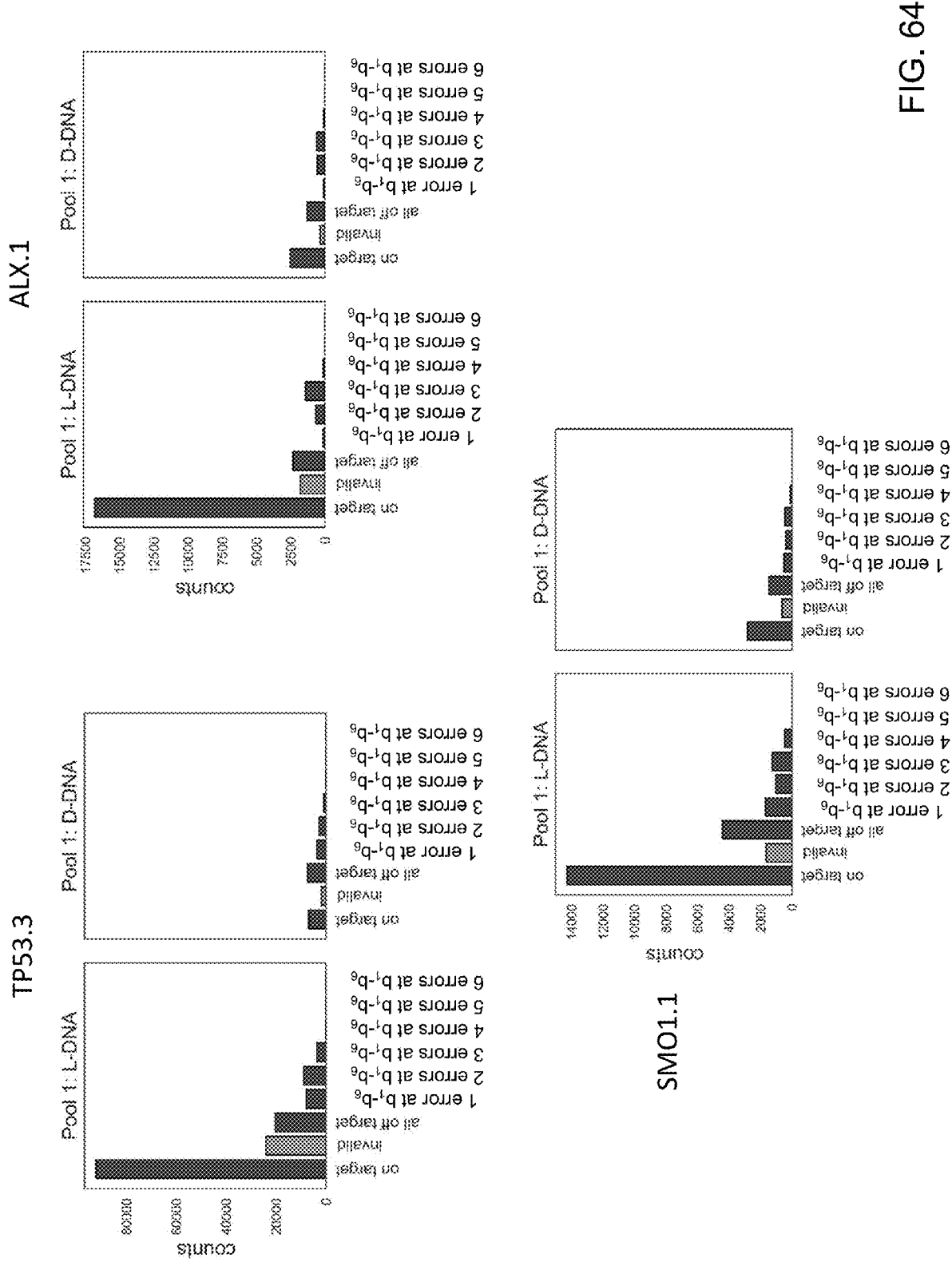
FIG. 64 is a series of graphs showing the total number of on target events, invalid events, off target events, 1 error at $b_1$-$b_6$ events, 2 errors at $b_1$-$b_6$ events, 3 errors at $b_1$-$b_6$ events, 4 errors at $b_1$-$b_6$ events, 5 error at $b_1$-$b_6$ events and 6 errors at $b_1$-$b_6$ events in sequencing experiments using the LG-spaced sequencing probes and the D-pocket sequencing probes of the present disclosure.

Furthermore, FIGS. 56-58 show that the LG-spaced pool and the D-pocket pool showed increased coverage in predicted problematic target areas. In FIGS. 56-58, the bottom x-axis shows the specific nucleotide/position of the target nucleic acid that is being sequenced. The top graph shows the theoretical and observed diversity per base in the LG-spaced and D-pocket sequencing experiments. The sequencing diversity of a base is the number of different distinct probe species that comprise a target binding domain that can hybridize to that specific nucleotide in the target nucleic acid. Thus, the sequencing diversity of a base is a measure of how many distinct sequencing probes can be used to interrogate (e.g. sequence or identify) a single position. Without being bound by theory, the higher the sequencing diversity of a particular base, the higher the expected coverage during multiple sequencing cycles, as there is a greater chance that the base will be bound and sequenced by a probe in each cycle. The top graphs of FIGS. 56-58 also show the observed coverage of each base in the LG-spaced and D-pocket sequencing experiments. The red boxes indicate predicted problematic areas. The LG-spaced sequencing probes showed increased coverage in these problematic areas over the D-pocket sequencing probes, with the LG-spaced sequencing probes in some cases showing coverage in areas where the D-pocket sequencing probes showed no coverage. Moreover, FIGS. 59-61 show sequencing results LG-spaced sequencing probes or the D-pocket sequencing probes. The graphs in FIG. 63 show the total number of on target events, invalid events, off target, and 1/6, 2/6, 3/6, 4/6, 5/6 or 6/6 mismatches at any individual base position $b_1$, $b_2$, $b_3$, $b_4$, $b_5$ and/or $b_6$ of the target binding domain. As shown in FIG. 63, the LG-spaced sequencing probes displayed an on target event to off target event ratio and an on target event to invalid event ratio that were approximately twice that of the D-pocket sequencing probes. As shown in FIG. 64, this increased performance of the LG-spaced sequencing probes is consistent when sequencing a variety of different specific synthetic target nucleic acids.

To directly compare the D-pocket sequencing probes and the LG-spaced sequencing probes, synthetic target nucleic acids were sequenced using a combination of D-pocket and LG-spaced sequencing probes. The D-pocket pool (D-pocket pool 1) was used for the first 50 sequencing cycles. The same immobilized synthetic target nucleic acids were then subsequently sequenced for 50 cycles with the LG-spaced pool. The results from the first 50 cycles using the D-pocket sequencing probes and the last 50 cycles using the LG-spaced sequencing probes were then compared. These results are shown in Table 13.

TABLE 13

Sequencing results

| Pool | % barcode efficiency | Clean 3-spotter | Clean 2-spotter | Clean 1-spotter |
| --- | --- | --- | --- | --- |
| D-pocket (cycles 1-50) | 26.9 | 6.8 | 8.4 | 10.6 |
| LG-spaced (cycles 51-100) | 37.8 | 12.8 | 11.6 | 11.0 |

| Pool | Clean Spot 1 efficiency | Clean Spot 2 efficiency | Clean Spot 3 efficiency | Clean % 3-spot readout | % Multicolor Darked | % valid | % invalid |
| --- | --- | --- | --- | --- | --- | --- | --- |
| D-pocket (cycles 1-50) | 70.0 | 62.6 | 58.0 | 25.4 | 4.2 | 87.3 | 12.7 |
| LG-spaced (cycles 51-100) | 73.3 | 74.5 | 66.7 | 33.9 | 6.4 | 86.2 | 13.8 | from more experiments using the LG-spaced sequencing probes and the D-pocket sequencing probes. As shown in FIG. 59-61, both the observed sequencing coverage and the observed sequencing diversity is increased when LG-spaced sequencing probes are used as compared to when D-pocket sequencing probes are used.

Figure 62:
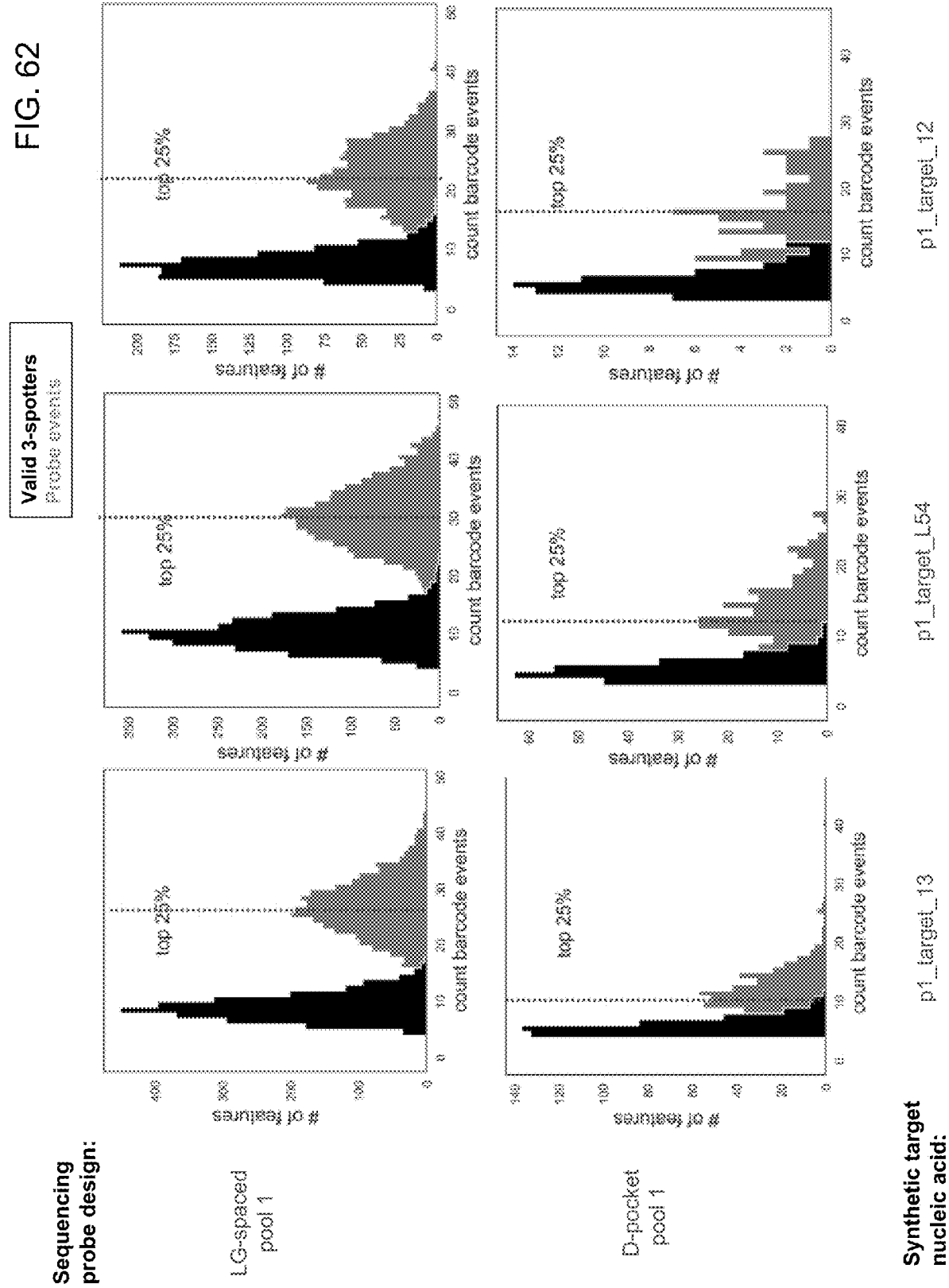
FIG. 62 is a series of histograms showing the total number of barcode events and the number of valid, 3-spot readouts in sequencing experiments using the LG-spaced sequencing probes and the D-pocket sequencing probes of the present disclosure.

More experimental results comparing the performance of the LG-spaced sequencing probes and D-pocket sequencing probes are shown in FIG. 62. The x-axis of each histogram in FIG. 62 denotes the number of observed barcode events (i.e. some form of detectable signal) recorded in the experiments. The black segments of the histogram specifically denote valid, 3-spot readout (i.e. where each of the three attachment regions of a sequencing probe were validly identified). The Y-axis denotes the number of features on the array (i.e. individual, immobilized target nucleic acids) that displayed the corresponding number of barcode events for a particular target. FIG. 62 shows that the LG-spaced pool exhibited an increased number of total barcode events and valid 3-spot readouts as compared to the D-pocket pool.

More experimental results comparing the performance of the LG-spaced sequencing probes and D-pocket sequencing probes are shown in FIG. 63. In total, 20 different types of synthetic target nucleic acids were sequenced using the Table 13 shows that the LG-spaced pool displayed an increased barcode efficiency, clean spot 1 efficiency, clean spot 2 efficiency, clean spot 3 efficiency and clean 3-spot readout as compared to the D-pocket pool.

Figure 65:
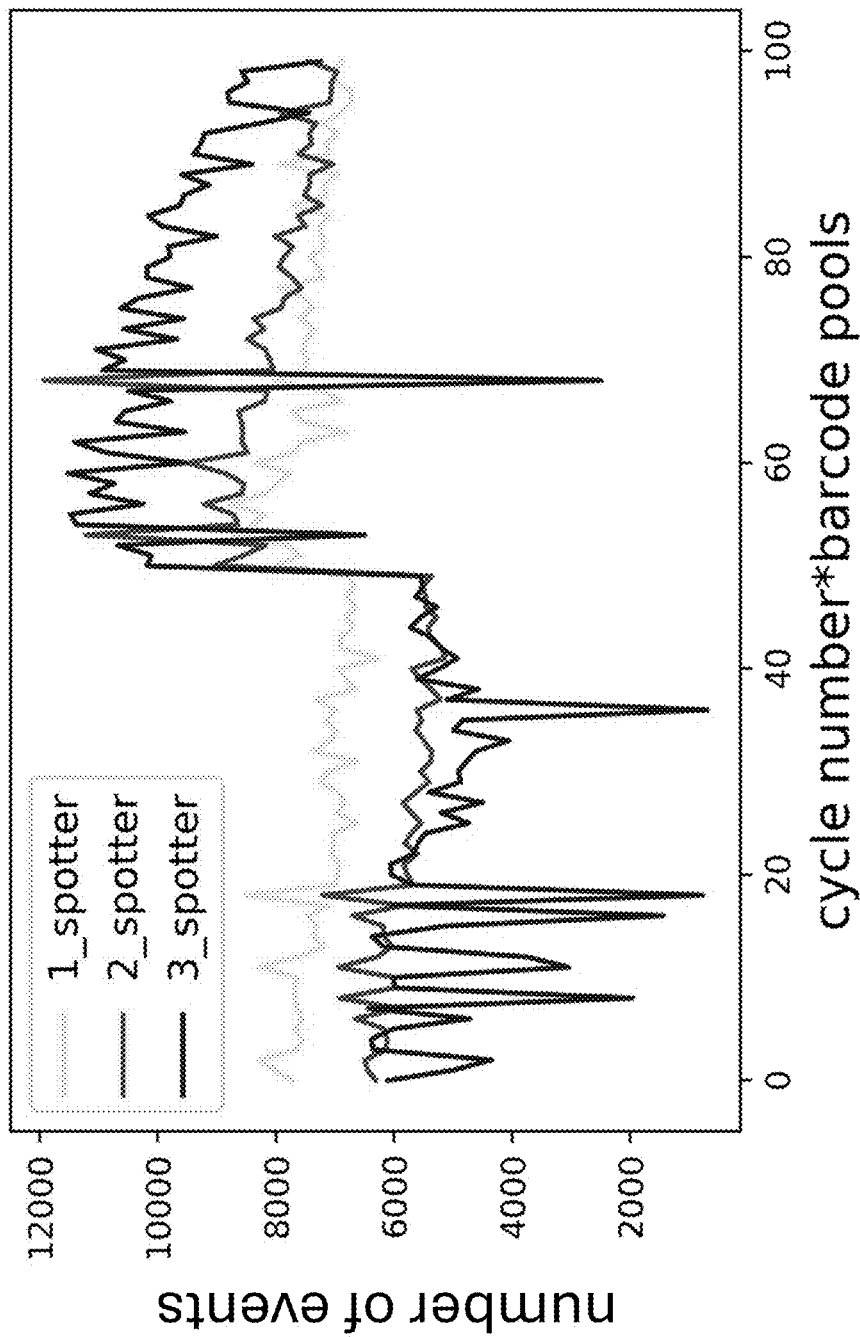
FIG. 65 is a chart showing the number of 1 spotter (only one out of a possible three reporter probes are successfully recorded), 2 spotter (only two out of a possible three reporter probes are successfully recorded) and 3 spotter (all three possible reporter probes are successfully recorded) events in each cycle of a sequencing experiments using the D-pocket sequencing probes (cycles 1-50) and LG-spaced sequencing probes (cycles 51-100) of the present disclosure.
Figure 66A:
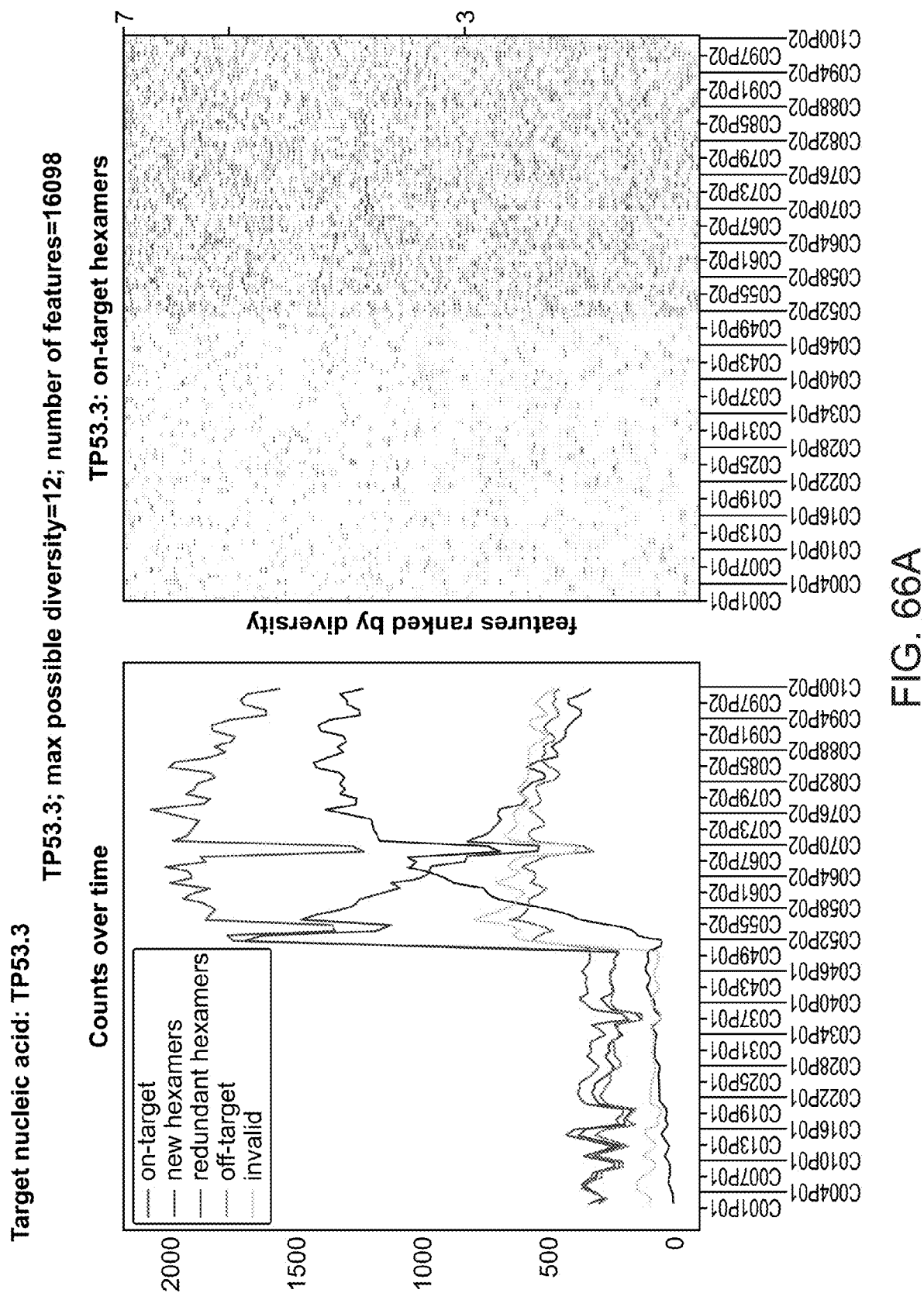
Figure 66D:
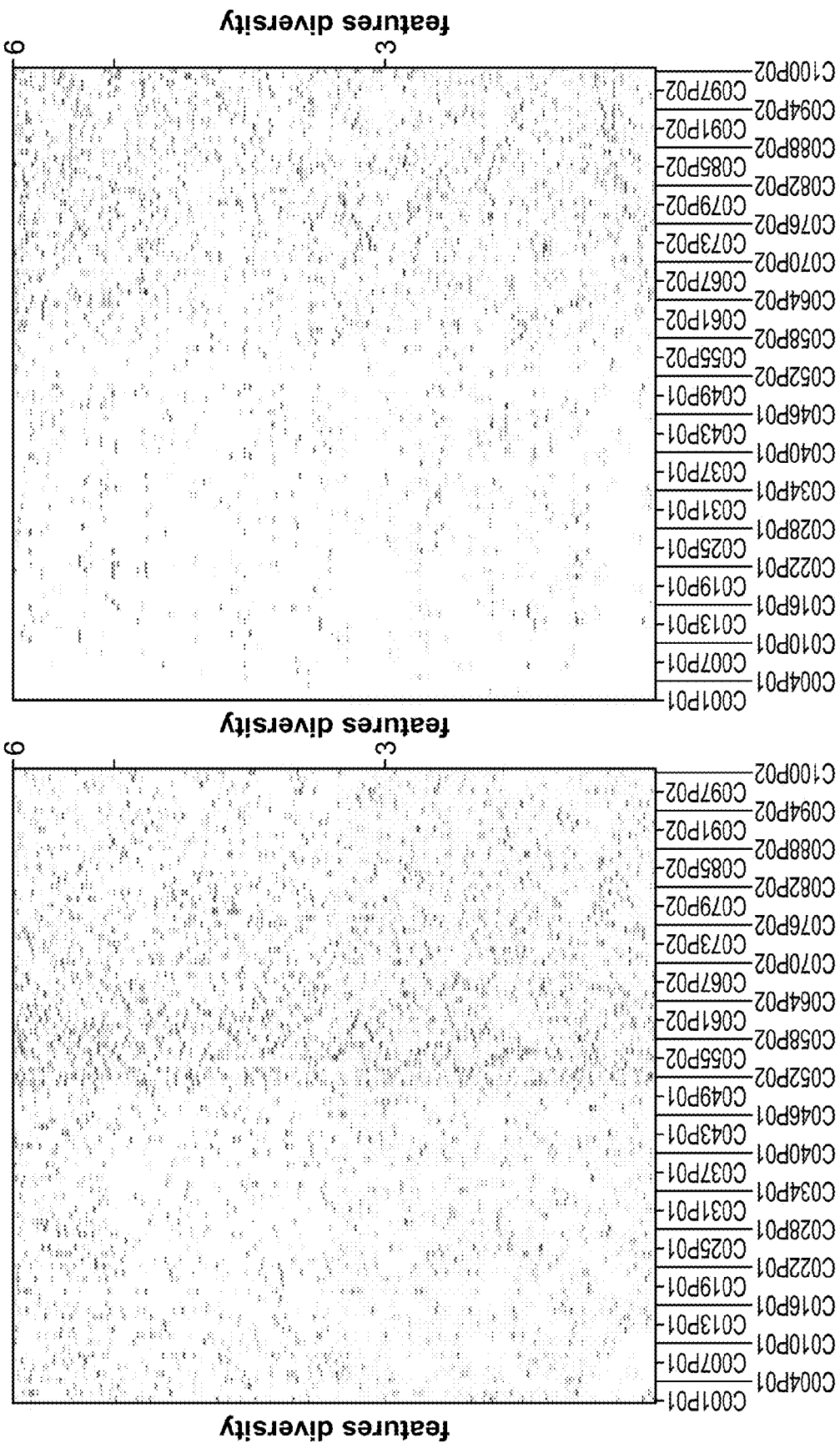

Furthermore, FIG. 65 shows that number of 1 spotter (only one out of a possible three reporter probes are successfully recorded), 2 spotter (only two out of a possible three reporter probes are successfully recorded) and 3 spotter (all three possible reporter probes are successfully recorded) events per cycle. As shown in FIG. 65, the number of 1 spotter, 2 spotter and 3 spotter events all increase starting at cycle 51 (corresponding to the switch to LG-spaced sequencing probes). In particular, the largest increase occurs in the number of 3 spotter events.

FIGS. 66A-66D show the number of on-target, new hexamer, redundant hexamer, off-target and invalid events recorded in each cycle of the experiment described above. On-target events are events in which a sequencing probe correctly bound to the target nucleic acid and all three reporter probes were successfully and correctly identified. A new hexamer event is an event in which a new hexamer is identified/sequenced in a single immobilized target nucleic acid, wherein that particular hexamer had not been identified in previous cycles. A redundant hexamer event is an event in which a particular hexamer is identified again in a single immobilized target nucleic acid. Off-target and invalid events are events in which errors occur in the hybridization and/or detection of the sequencing and reporter probes. As shown in the leftmost panels of FIGS. 66A-66D, the number of on-target, new hexamer and redundant hexamer events all increase starting at cycle 51 (corresponding to the switch to LG-spaced sequencing probes). Accordingly, the number of new hexamer events decreases between cycles 51-100 as there are fewer hexamers in each successive cycle that have not yet been identified in the target nucleic acids, and a corresponding increase is seen in the number of redundant hexamer events.

In another set of experiments a single LG-spaced pool and two D-pocket pools (D-pocket pool 1 and D-pocket pool 3) were used to sequence immobilized synthetic target nucleic acids. The LG-spaced pool was used for the first 50 sequencing cycles. The same immobilized synthetic target nucleic acids were then subsequently sequenced for 100 cycles with D-pocket pool 1 and D-pocket pool 3. The two pools were alternated: D-pocket pool 1 was used for cycle 51, D-pocket pool 3 was used for cycle 52, D-pocket pool 1 was used for cycle 53 and so on and so forth. The results from the 150 cycles of sequencing are shown in Table 14.

TABLE 14

| | Sequencing results | | | |
|---|---|---|---|---|
| Pool | % barcode efficiency | Clean 3-spotter | Clean 2-spotter | Clean 1-spotter |
| LG-spaced pool 1 (cycles 1-50) | 36.6 | 11.3 | 12.4 | 11.7 |
| D-pocket pool 1 (odd numbered cycles from 51-100) | 13.1 | 2.8 | 4.1 | 5.9 |
| D-pocket pool 3 (even numbered cycles from 51-100) | 11.8 | 2.6 | 3.7 | 5.4 |

| Pool | Clean Spot 1 efficiency | Clean Spot 2 efficiency | Clean Spot 3 efficiency | Clean % 3-spot readout | % Multicolor Darked | % valid | % invalid |
|---|---|---|---|---|---|---|---|
| LG-spaced pool 1 (cycles 1-50) | 66.6 | 69.9 | 67.0 | 30.9 | 3.3 | 88.1 | 12.0 |
| D-pocket pool 1 (odd numbered cycles from 51-100) | 64.2 | 58.4 | 55.0 | 21.4 | 1.8 | 89.5 | 10.6 |
| D-pocket pool 3 (even numbered cycles from 51-100) | 64.1 | 58.3 | 56.1 | 21.8 | 2.0 | 88.7 | 11.3 |

The results shown in Table 14 demonstrate that the LG-spaced pool displayed an increased barcode efficiency, clean spot 1 efficiency, clean spot 2 efficiency, clean spot 3 efficiency and clean 3-spot readout as compared to the D-pocket pools.

Taken together the results described above demonstrate that both the LG-spaced sequencing probes and the D-pocket sequencing probes can be used to interrogate an immobilized target nucleic acid, with LG-spaced probes showing increased coverage, efficiency and valid barcode events as compared to the D-pocket sequencing probes.

What is claimed is:

1. A probe comprising:
a target binding domain and a barcode domain;
wherein the target binding domain is at least 12 nucleotides in length;
wherein the barcode domain comprises a synthetic backbone, the barcode domain comprising at least two attachment positions, each attachment position comprising at least one attachment region comprising at least one nucleic acid sequence that hybridizes to a complementary nucleic acid molecule, and wherein the synthetic backbone comprises L-DNA,
wherein each of the at least two attachment positions has a different nucleic acid sequence,
wherein the at least two attachment positions correspond to the sequence of the target binding domain,
wherein said nucleic acid sequence of each position of the at least two attachment positions determines the identity of the target nucleic acid that is bound by said target binding domain, and
wherein each nucleotide of the at least one nucleic acid sequence of each attachment region is L-DNA.

2. The probe of claim 1, wherein the synthetic backbone is single-stranded and is about 10 nucleotides to about 100 nucleotides in length.

3. The probe of claim 1, wherein the barcode domain comprises:
a) at least three attachment positions; or
b) at least four attachment positions.

4. The probe of claim 1, wherein each attachment position in the barcode domain comprises one attachment region, wherein the at least one nucleic acid sequence of each attachment position in the barcode domain is:
a) about 6 to about 20 nucleotides in length;
b) about 9 nucleotides in length;
c) about 12 nucleotides in length;
d) about 14 nucleotides in length; or
e) about 16 nucleotides in length.

5. The probe of claim 1, wherein each nucleotide of the at least 12 nucleotides of the target binding domain is D-DNA.

6. A method for identifying the presence of a target nucleic acid in a sample comprising:
(1) hybridizing a target binding domain of the probe of claim 1 to the target nucleic acid;
(2) hybridizing a first complementary nucleic acid molecule comprising at least one first detectable label and at least one second detectable label to a first attachment position of the at least two attachment positions of the barcode domain;
(3) identifying the at least one first and the at least one second detectable label of the first complementary nucleic acid molecule hybridized to the first attachment position;
(4) removing the at least one first and the at least one second detectable label hybridized to the first attachment position;
(5) hybridizing a second complementary nucleic acid molecule comprising at least one third detectable label and at least one fourth detectable label to a second attachment position of the at least two attachment positions of the barcode domain;

(6) identifying the at least one third and the at least one fourth detectable label of the second complementary nucleic acid molecule hybridized to the second attachment position, and (7) determining the presence of the target nucleic acid based on at least the identity of each of the identified detectable labels.

7. The method of claim 6, wherein the barcode domain of the probe comprises at least three attachment positions or at least four attachment positions, wherein the method further comprises, prior to step (7):

repeating steps (4) to (6) until each attachment position in the barcode domain has been bound by a complementary nucleic acid molecule comprising two detectable labels, and the two detectable labels of the bound complementary nucleic acid molecule have been detected.

8. The method of claim 6, wherein the first and second detectable labels have the same emission spectrum or have different emission spectra.

9. The method of claim 6, wherein the third and fourth detectable labels have the same emission spectrum or have different emission spectra.

10. The method of claim 6, wherein at least the first complementary nucleic acid molecule comprises a cleavable linker.

11. The method of claim 10, wherein the cleavable linker is a photocleavable linker.

12. The method of claim 10, wherein each complementary nucleic acid molecule comprises a cleavable linker.

13. The method of claim 7, wherein the first complementary nucleic acid molecule comprises a reporter probe comprising a primary nucleic acid, wherein the primary nucleic acid molecule comprises at least two domains, a first domain that hybridizes to the first attachment position of the barcode domain and a second domain that is hybridized to six secondary nucleic acid molecules, wherein each of the secondary nucleic acid molecules is hybridized to five tertiary nucleic molecules, wherein each of the tertiary nucleic acid molecules comprises a detectable label.

14. The method of claim 13, wherein the primary nucleic acid molecule comprises a cleavable linker located between the first domain and the second domain.

15. The method of claim 14, wherein the cleavable linker is a photocleavable linker.

16. The method of claim 13, wherein each of the secondary nucleic acid molecules comprises at least two domains, a first domain that hybridizes to the second domain of the primary nucleic acid molecule and a second domain that hybridizes to the five tertiary nucleic acid molecules, wherein each of the secondary nucleic acid molecules comprises a cleavable linker located between the first domain and the second domain.

17. The method of claim 16, wherein the cleavable linker is a photocleavable linker.

18. The method of claim 13, wherein removing the at least one first and the at least one second detectable label hybridized to the first attachment position comprises cleaving the cleavable linker between the first domain and the second domain of the primary nucleic acid molecule.

19. The method of claim 16, wherein removing the at least one first and the at least one second detectable label hybridized to the first attachment position comprises cleaving the cleavable linkers between the first domains and the second domains of the secondary nucleic acid molecules.

* * * * *